United States Patent [19]

Luly et al.

[11] Patent Number: 5,708,002

[45] Date of Patent: Jan. 13, 1998

[54] MACROCYCLIC IMMUNOMODULATORS

[75] Inventors: Jay R. Luly; Megumi Kawai; Yat Sun Or; Paul Wiedeman, all of Libertyville; Rolf Wagner, Gurnee, all of Ill.

[73] Assignee: Abbott Laboratories, Abbott Park, Ill.

[21] Appl. No.: 734,793

[22] Filed: Oct. 23, 1996

Related U.S. Application Data

[60] Continuation of Ser. No. 531,534, Sep. 21, 1995, which is a division of Ser. No. 149,416, Nov. 9, 1993, Pat. No. 5,457,111, which is a continuation-in-part of Ser. No. 32,958, Mar. 17, 1993, abandoned, which is a continuation-in-part of PCT/US92/07600, Sep. 8, 1992, which is a continuation-in-part of Ser. No. 755,208, Sep. 5, 1991, abandoned.

[51] Int. Cl.$^6$ .................. A61K 31/395; C07D 498/16
[52] U.S. Cl. .................. 514/291; 514/211; 540/456
[58] Field of Search .................. 540/456; 514/291, 514/411

[56] References Cited

U.S. PATENT DOCUMENTS

| | | |
|---|---|---|
| 4,894,366 | 1/1990 | Okuhara et al. .................. 540/456 |
| 5,064,835 | 11/1991 | Bochis et al. .................. 540/456 |
| 5,149,701 | 9/1992 | Shafiee et al. .................. 540/456 |
| 5,162,334 | 11/1992 | Goulet et al. .................. 540/456 |
| 5,189,042 | 2/1993 | Goulet et al. .................. 540/456 |
| 5,208,228 | 5/1993 | Ok et al. .................. 540/456 |
| 5,262,533 | 11/1993 | Sinclair et al. .................. 540/456 |

FOREIGN PATENT DOCUMENTS

| | | | |
|---|---|---|---|
| 8010891 | 1/1992 | Australia | 540/456 |
| 0323042 | 7/1989 | European Pat. Off. | 540/456 |
| 0358508 | 3/1990 | European Pat. Off. | 540/456 |
| 0402931 | 12/1990 | European Pat. Off. | 540/456 |
| 0427680 | 5/1991 | European Pat. Off. | 540/456 |
| 0465426 | 1/1992 | European Pat. Off. | 540/456 |
| 0480623 | 4/1992 | European Pat. Off. | 540/456 |
| 2245891 | 1/1992 | United Kingdom | 540/456 |
| 2246568 | 2/1996 | United Kingdom | 540/456 |
| 9015805 | 12/1990 | WIPO | 540/456 |
| 9102736 | 3/1991 | WIPO | 540/456 |
| 9104025 | 4/1991 | WIPO | 540/456 |
| 9113889 | 9/1991 | WIPO | 540/456 |
| 9113899 | 9/1991 | WIPO | 540/456 |
| 9200313 | 1/1992 | WIPO | 540/456 |
| 9218506 | 10/1992 | WIPO | 540/456 |
| 9304679 | 3/1993 | WIPO | 540/456 |
| 9304680 | 3/1993 | WIPO | 540/456 |
| WO93/04680 | 3/1993 | WIPO | A61K 31/395 |
| 9421644 | 9/1994 | WIPO | 540/456 |

*Primary Examiner*—Robert T. Bond
*Attorney, Agent, or Firm*—Gregory W. Steele

[57] ABSTRACT

Immunomodulatory macrocyclic compounds having the formula

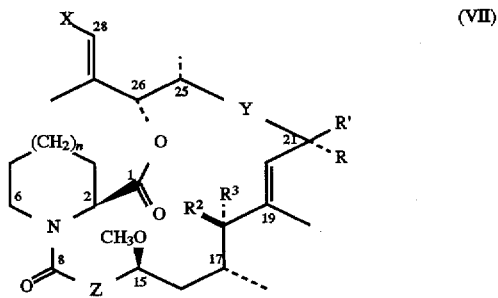

(VII)

and pharmaceutically acceptable salts, esters, amides and prodrugs thereof, wherein X is selected from one of the formulae

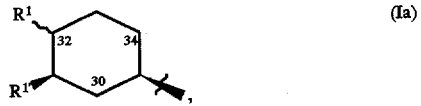

(Ia)

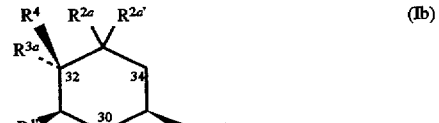

(Ib)

and

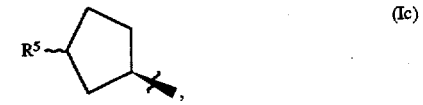

(Ic)

as well as pharmaceutical compositions containing the same.

7 Claims, No Drawings

MACROCYCLIC IMMUNOMODULATORS

This application is a Continuation of application Ser. No. 08/531,534 filed Sep. 21, 1995, which is a Division of Ser. No. 08/149,416 filed Nov. 9, 1993, now U.S. Pat. No. 5,457,111, which is a CIP of Ser. No. 08/032,958 filed Mar. 17, 1993 ABN, which is a CIP of PCT/US92/07600 filed Sep. 8, 1992, which is a CIP of Ser. No. 07/755,208 filed Sep. 5, 1991 ABN

FIELD OF THE INVENTION

The present invention relates to novel chemical compounds having immunomodulatory activity, and in particular to macrolide immunosuppressants. More particularly, the invention relates to semisynthetic analogs of ascomycin and FK-506, means for their preparation, pharmaceutical compositions containing such compounds and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Unsatisfactory side-effects associated with cyclosporine, however, such as nephrotoxicity, have led to a continued search for immunosuppressant compounds having improved efficacy and safety.

Recently, several classes of macrocyclic compounds having potent immunomodulatory activity have been discovered. Okuhara et al., in European Patent Application No. 184162, published Jun. 11, 1986, disclose a number of macrocyclic compounds isolated from the genus Streptomyces. Immunosuppressant FK-506, isolated from a strain of *S. tsukubaensis*, is a 23-membered macrocyclic lactone represented by formula 1a, below. Other related natural products, such as FR-900520 (1b) and FR-900523 (1c), which differ from FK-506 in their alkyl substituent at C-21, have been isolated from *S. hygroscopicus yakushimnaensis*. Yet another analog, FR-900525, produced by *S. tsukubaensis*, differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monaghan, R. L., et al., on the other hand, describe the use of ascomycin as an immunosuppressant in European Patent Application No. 323865, published Jul. 12, 1989.

Although the immunosuppressive activity of FK-506 has been clinically confirmed, toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

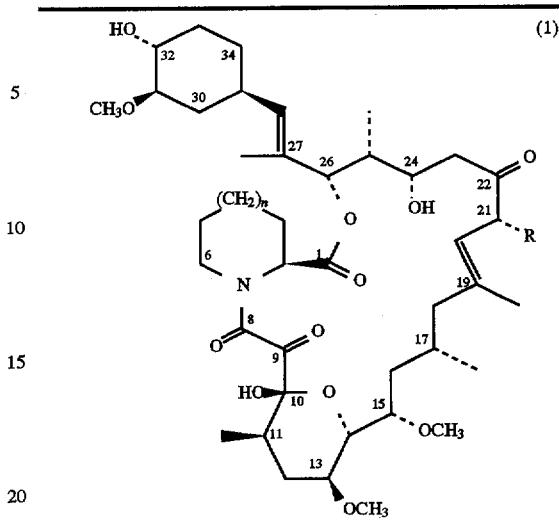

1(a): FK-506    R = CH$_2$CH=CH$_2$; n = 1
1(b): FR-900520   R = CH$_2$CH$_3$; n = 1
1(c): FR-900523   R = CH$_3$; n = 1
1(d): FR-900525   R = CH$_2$CH=CH$_2$; n = 0

Fermentation products of FK-type compounds include C-21-epi derivatives of FK-506; a 31-demethylated derivative of FK-506; 31-oxo-FK-506; and compounds derived from FK-506, FR-900523 and FR-900525 which are characterized by the introduction of hydroxy-protecting groups, formation of a double bond by elimination of water between carbons 23 and 24, oxidation of the hydroxy group at carbon 24 to the ketone, and reduction of the allyl side-chain at carbon 21 via hydrogenation. Other published derivatives include those derived from FK-506 and FR-900520 where the lactone ring is contracted to give a macrocyclic ring containing two fewer carbons.

Several microbial transformations of FK-type compounds at carbon 13 have been published, such as the microbial demethylation of FR-900520 to form the bis-demethylated 13,31-dihydroxy ring-rearranged derivative of FR-900520; the microbial monodemethylation of FK-506 and FR-900520, respectively; and the microbial demethylation of FR-900520 at C-31, as well as a number of other macrocyclic microbial transformation products.

Numerous chemical modifications of the FK-type compounds have been attempted. These include the preparation of small synthetic fragments of FK-type derivatives; a thermal rearrangement of a variety of derivatives of FK-506 which expands the macrocyclic ring by two carbons; and modifications which include methyl ether formation at C-32 and/or C-24, oxidation of C-32 alcohol to the ketone, and epoxide formation at C-9.

Although some of these modified compounds exhibit immunosuppressive activity, the need remains for macrocyclic immunosuppressants which do not have the serious side effects frequently associated with immunosuppressant therapy. Accordingly, one object of the invention is to provide novel semisynthetic macrolides which possess the desired immunomodulatory activity but which may be found to minimize untoward side effects.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient, one of the above compounds. Yet another object of the invention is to provide a method of treating a variety of disease states, including post-transplant tissue rejection and autoimmune disfunction.

SUMMARY OF THE INVENTION

In one aspect of the present invention are disclosed compounds having the formula

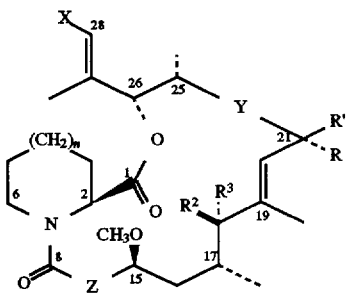

(VII)

and pharmaceutically acceptable salts, esters, amides and prodrugs thereof. In formula VII, n is zero or one, and R and R' are chosen such that one of R and R' is hydrogen and the other is selected from the group consisting of methyl, ethyl, 2-hydroxyethyl, propyl, cyclopropylmethyl, 2-oxopropyl, 2-ethanal, allyl, —$CH_2CH_2OC(O)R^{10}$ where $R^{10}$ is aryl, —$CH_2C(O)R^{12}$, —$CH_2C(O)N(R^{14'})(CH_2)_m CH(R^{16'})C(O)R^{12}$, —$CH_2C(O)N(R^{14'})(CH_2)_m CH(R^{16'})C(O)N(R^{14''})(CH_2)_{m'} CH(R^{16''})C(O)R^{12}$, —$CH_2C(O)N(R^{14'})(CH_2)_m CH(R^{16'})C(O)N(R^{14''})(CH_2)_{m'} \cdot CH(R^{16''})C(O)N(R^{14'''})(CH_2)_{m''} \cdot CH(R^{16'''})C(O)R^{12}$ and —$CH_2CH_2OR^{14}$.

In these formulae, m, m' and m" are independently zero to six; $R^{14'}$, $R^{14''}$ and $R^{14'''}$ are independently selected from hydrogen, loweralkyl, arylalkyl, cycloalkyl and cycloalkylalkyl; and $R^{16}$, $R^{16'}$ and $R^{16''}$ are independently selected from hydrogen, loweralkyl, hydroxyloweralkyl, carboxyalkyl, thioloweralkyl, thioalkoxyalkyl, guanidinoalkyl, aminoalkyl, arylalkyl and, if m, m' and m" are other than zero, amino or amidoalkyl; or, taken together, one or more of $R^{14'}$ and $R^{16}$, $R^{14''}$ and $R^{16'}$, and $R^{14'''}$ and $R^{16''}$ are —$(CH_2)_p$— where p is two to five. $R^{12}$ in the above is selected from (i) hydroxy, (ii) —$OR^{13}$ where $R^{13}$ is loweralkyl, cycloalkyl, cycloalkylalkyl, arylalkyl or mono- di- tri- or perhalogenated alkyl, (iii) —$NR^{14}R^{15}$, (iv) aryl substituted by $R^{301}$, $R^{302}$ and $R^{303}$, (v) heterocyclic substituted by $R^{301}$, $R^{302}$ and $R^{303}$, (vi) mono-, di-, tri-, or perhalogenated alkyl, (vii) —$N(R^8)NR^6R^7$, (viii) —$Si(R^{11})_3$, where each $R^{11}$ is independently selected from loweralkyl, arylalkyl substituted by $R^{301}$, $R^{302}$ and $R^{303}$, and aryl substituted by $R^{301}$, $R^{302}$ and $R^{303}$, (ix) —$Sn(R^{11})_3$, (x) —$P(R^{11})_2$ and (xi) —$R^{14}$.

The above substituents $R^{301}$, $R^{302}$ and $R^{303}$ are independently selected from the group consisting of hydrogen; —($C_1$-to-$C_7$ alkyl); —($C_2$-to-$C_6$ alkenyl); halogen; —$(CH_2)_m NR^8R^{8'}$; —CN; —CHO; mono-, di-, tri-, or perhalogenated alkyl; —$S(O)_s R^8$ where s is zero, one or two; —$C(O)NR^8R^{8'}$; —$(CH_2)_m OR^8$; —$CH(OR^{12'})(OR^{12''})$, where $R^{12'}$ and $R^{12''}$ are independently —($C_1$-to-$C_3$ alkyl) or, taken together, form an ethylene or propylene bridge; —$(CH_2)_m OC(O)R^8$; —$(CH_2)_m C(O)OR^8$; —$OR^{11'}$, where $R^{11'}$ is selected from (i) —$PO(OH)O^-M^+$, wherein $M^+$ is a proton or a positively charged inorganic or organic counterion, (ii) —$SO_3^-M^+$, and (iii) —$C(O)(CH_2)_m C(O)O^-M^+$; —$S(O)_t NR^8R^{8'}$, where t is one or two; —$NO_2$; —$N_3$; and guanidino optionally substituted by loweralkyl, aryl, acyl, arylsulfonyl, alkoxycarbonyl, arylalkoxycarbonyl, aryloxycarbonyl and alkylsulfonyl; or, taken together, any two of adjacent $R^{301}$, $R^{302}$ and $R^{303}$ form a carbocyclic or heterocyclic ring having 5, 6, or 7 ring atoms which optionally includes one or two additional heteroatoms independently selected from the group consisting of —O—, —$S(O)_s$— where s is zero, one or two, and —$NR^8$—. The substituents $R^{301}$, $R^{302}$ and $R^{303}$ are subject to the further limitation that each may comprise no more than twenty non-hydrogen atoms.

The above substituents $R^6$ and $R^7$ are independently selected from the group consisting of hydrogen; aryl substituted by $R^{301}$, $R^{302}$ and $R^{303}$; heterocyclic substituted by $R^{301}$, $R^{302}$ and $R^{303}$; $C_1$-to-$C_{10}$ alkyl; $C_3$-to-$C_{10}$ alkenyl; $C_3$-to-$C_{10}$ alkynyl; $C_3$-to-$C_{10}$ cycloalkyl; $C_4$-to-$C_{10}$ cycloalkenyl; $C_6$-to-$C_{10}$ bicycloalkyl; and $C_6$-to-$C_{10}$ bicycloalkenyl. Each of the $C_1$-to-$C_{10}$ alkyl, $C_3$-to-$C_{10}$ alkenyl, $C_3$-to-$C_{10}$ alkynyl, $C_3$-to-$C_{10}$ cycloalkyl, $C_4$-to-$C_{10}$ cycloalkenyl, $C_6$-to-$C_{10}$ bicycloalkyl and $C_6$-to-$C_{10}$ bicycloalkenyl groups may be optionally substituted with between one and five radicals selected from —$R^8$, —$R^{8'}$, —$OR^8$, —$S(O)_s R^8$, —$S(O)_t NR^8R^{8'}$, —$NR^8R^{8'}$, —$SO_3H$, =$NOR^8$, —$R^{399}$ and —$R^{400}$. $R^{399}$ is selected from the group consisting of hydroxyl; —C(O)OH; —$C(O)OR^8$; —($C_3$-to-$C_7$ cycloalkyl); oxo; thiooxo; epoxy; halogen; —CN; —$N_3$; —$NO_2$; —$OR^{11'}$; —$OR^{12'}$; —$OR^{12''}$; and guanidino optionally substituted by hydrogen, loweralkyl, aryl, acyl, arylsulfonyl, alkoxycarbonyl, arylalkoxycarbonyl, aryloxycarbonyl and alkylsulfonyl. $R^{400}$ is selected from the group consisting of aryl substituted by $R^{301}$, $R^{302}$ and $R^{303}$; —Q-aryl where aryl is substituted by $R^{301}$, $R^{302}$ and $R^{303}$; heterocyclic substituted by $R^{301}$, $R^{302}$ and $R^{303}$; —Q-heterocyclic where heterocyclic is substituted by $R^{301}$, $R^{302}$ and $R^{303}$; biaryl substituted by $R^{301}$, $R^{302}$ and $R_{303}$; —Q-biaryl where biaryl is substituted by $R^{301}$, $R^{302}$ and $R^{303}$; -aryl-Q-aryl' where aryl and aryl' are the same or different and are independently substituted by $R^{301}$, $R^{302}$ and $R^{303}$; -aryl-Q-heterocyclic where heterocyclic and aryl are independently substituted by $R^{301}$, $R^{302}$ and $R^{303}$; -heterocyclic-Q-aryl where heterocyclic and aryl are independently substituted by $R^{301}$, $R^{302}$ and $R^{303}$; -heterocyclic-aryl where heterocyclic and aryl are independently substituted by $R^{301}$, $R^{302}$ and $R^{303}$; and -aryl-heterocyclic where heterocyclic and aryl are independently substituted by $R^{301}$, $R^{302}$ and $R^{303}$. The divalent radical —Q— is selected from the group consisting of —($C_1$-to-$C_6$ alkyl)—, —($C_2$-to-$C_6$ alkenyl)—, —($C_2$-to-$C_6$ alkynyl)—, —$(CH_2)_m O$—, —$O(CH_2)_m$—, —$N(R^8)C(O)$—, —$C(O)N(R^8)$—, —$S(O)_s$—, —$N(R^8)$—, —$N(R^8)S(O)_t$—, —$S(O)_t N(R^8)$—, —C(O)—, —NN—, —CHN—, —NCH—, —ONCH— and —CHNO—.

Alternatively, —$NR^6R^7$ may be a 3-to 7-membered heterocyclic ring optionally substituted with between one and five compatible radicals independently selected from the group consisting of —$R^8$, —$R^{8'}$, —$(CH_2)_m OR^8$, —$S(O)_s R^8$, —$S(O)_t NR^8R^{8'}$, —$NR^8R^{8'}$, —$SO_3H$, —$R^{399}$ and —$R^{400}$. The heterocyclic ring can optionally include up to two additional heteroatoms independently selected from the group consisting of —O—, —$S(O)_s$— where s is zero, one or two, and —$NR^8$—.

The above substituents $R^8$ and $R^{8'}$ are independently selected from the group consisting of hydrogen; aryl substituted by $R^{301}$, $R^{302}$ and $R^{303}$; heterocyclic substituted by $R^{301}$, $R^{302}$ and $R^{303}$; and —($C_1$-to-$C_6$ alkyl), —($C_3$-to-$C_6$ alkenyl), —($C_3$-to-$C_6$ alkynyl), —($C_3$-to-$C_{10}$ cycloalkyl), —($C_4$-to-$C_{10}$ cycloalkenyl), —($C_6$-to-$C_{10}$ bicycloalkyl) and —($C_6$-to-$C_{10}$ bicycloalkenyl). Each of the —($C_1$-to-$C_6$ alkyl), —($C_3$-to-$C_6$ alkenyl), —($C_3$-to-$C_6$ alkynyl), —($C_3$-to-$C_{10}$ cycloalkyl), —($C_4$-to-$C_{10}$ cycloalkenyl), —($C_6$-to- $C_{10}$ bicycloalkyl) and —($C_6$-to-$C_{10}$ bicycloalkenyl) groups may optionally be substituted with between one and three radicals selected from halogen, hydroxy, mono- or dialkylamino, carboxyl, carboxamido, thiol, alkylthioether, alkylether, guanidino, alkoxycarbonyl, arylalkoxycarbonyl, alkoxycarbonylamino, acylamino, arylalkyloxycarbonylamino, aryloxycarbonylamino, acylguanidino, arylsulfonylguanidino, alkoxycarbonylguanidino, amino, arylalkyloxycarbonylguanidino, aryloxycarbonylguanidino, N-alkylcarboxamido, N,N-dialkylcarboxamido, N-axylcarboxamido, N,N-diarylcarboxamido, —$OSO_2R^{11}$, oxo, epoxy, arylether, arylthioether, arylalkylether, arylalkylthioether, (heterocyclic)ether, (heterocyclic) thioether, (heterocylic)alkylether, (heterocyclic) alkylthioether, aryl, heterocyclic, —$SO_3H$, —$S(O)_s$ $NR^{16}R^{16''}$ and —$S(O)_sR^{14'}$ in which any aryl or heterocyclic moiety may be optionally and independently substituted by $R^{301}$, $R^{302}$ and $R^{303}$.

Alternatively, —$NR^8R^{8'}$ may be a 3-to 7-membered heterocyclic ring which optionally includes up to two additional heteroatoms independently selected from the group consisting of —O—, —$S(O)_s$— and —$NR^8$—. Heterocyclic rings which are representative of —$NR^8R^{8'}$ include aziridine, morpholine, thiomorpholine, thiomorpholine-oxide, thiomorpholine dioxide, piperidine, pyrrolidine and piperazine.

In the above, $R^{14}$ and $R^{15}$ are independently selected from the group consisting of hydrogen; —$R^{400}$; and —($C_1$-to-$C_{10}$ alkyl), —($C_3$-to-$C_{10}$ cycloalkyl), —($C_4$-to-$C_{10}$ cycloalkylalkyl), —($C_3$-to-$C_{10}$ alkenyl), —($C_5$-to-$C_{10}$ cycloalkenyl), —($C_6$-to-$C_{10}$ cycloalkylalkenyl), —($C_3$-to-$C_{10}$ alkynyl), —($C_6$-to-$C_{10}$ cycloalkylalkynyl), —($C_6$-to-$C_{10}$ bicycloalkyl) and —($C_6$-to-$C_{10}$ bicycloalkenyl), each optionally substituted with up to six radicals independently selected from the group consisting of $R^6$, $R^7$, —$(CH_2)_mOR^6$, —$NR^6R^7$, —$C(O)OR^6$, —$SO_3H$, —$S(O)_sR^6$, —$S(O)_t$ $NR^6R^7$, =$NOR^6$, $R^{399}$ and $R^{400}$. Alternatively, the group —$NR^{14}R^{15}$ may also be a 3- to 7-membered heterocyclic ring which optionally includes up to two additional heteroatoms independently selected from the group consisting of —O—, —$S(O)_s$— and —$NR^8$—. This heterocycle is optionally and independently substituted with between one and five compatible radicals independently selected from the group consisting of $R^6$, $R^7$, —$(CH_2)_mOR^6$, —$NR^6R^7$, —$C(O)OR^6$, —$SO_3H$, —$S(O)_sR^6$, —$S(O)_tNR^6R^7$, =$NOR^6$, —$R^{399}$ and —$R^{400}$.

Alternatively, one of R and R', taken together with one of $R^{35}$ and $R^{36}$ (described below), forms a C-21/C-22 bond and the other of R and R', taken together with the other of $R^{35}$ and $R^{36}$, is a heterocycle-forming group having a formula selected from —$N(R^{63})CH$=$CH$— and —$OC(R^{64})$=$CH$— where the heteroatom in each instance is connected to C-22, $R^{63}$ is selected from hydrogen, loweralkyl, arylalkyl and aryl, and $R^{64}$ is hydrogen or loweralkyl.

$R^2$ and $R^3$ in the above are independently chosen from among hydrogen, —$OR^{14}$ and halogen or, taken together, may be oxo or thiooxo. Each of $R^2$ and $R^3$ may also be hydroxy, provided that the other of $R^2$ or $R^3$ is hydrogen.

X in formula VII is a group having one of the following subformulae:

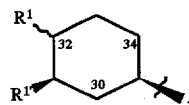 (Ia)

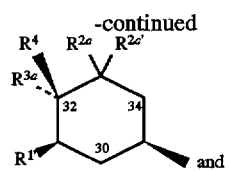 (Ib)

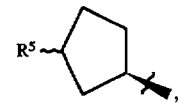 (Ic)

in which $R^1$ and $R^{1'}$ are independently selected from the group consisting of (a) hydrogen; (b) halogen; (c) triflate; (d) mesylate; (e) tosylate; (f) benzenesulfonate; (g) azide; (g') cyanate; (h) —$OC(S)OR^{11}$; (i) —$OC(O)R^{19}$, wherein $R^{19}$ is selected from (i) hydrogen, (ii) loweralkyl, (iii) arylalkyl, (iv) aminoalkyl, (v) aryl and (vi) an alpha-carbon with an optionally protected alpha-amino, and appended side-chain of a standard alpha-amino acid; (j) a carbamoyl derivative selected from (i) —$OC(O)NR^{14}R^{15}$, (ii) —$OC(O)NHR^{400}$, (iii) —$OC(O)NHNR^{14}R^{15}$, (iv) —$OC(O)NHNHR^{400}$, (v) —$OC(O)NHNHC(O)NR^{14}R^{15}$, (vi) —$OC(O)NHNHC$ (=$NH$)$NR^{14}R^{15}$, (vii) —$OC(O)NHNHC(O)R^{19}$ and (viii) —$OC(O)NHOR^{11}$; (k) —$OC(O)OR^{400}$; (l) —$OP(O)$ $(OR^{11})_2$; (m) —$OR^{11}$; (m') —$OR^{14}$; (n) —$O(CH_2)_jC(O)R^{12}$, where j is one to five; (n') —$O(CH_2)_mS(O)_sR^2$; (o) —$O(CH_2)_jC(O)N(R^{14'})(CH_2)_mCH(R^{16'})C(O)R^{12}$; (p) —$O(CH_2)_jC(O)N(R^{14'})(CH_2)_mCH(R^{16'})C(O)N(R^{14''})$ $(CH_2)^{m'}CH(R^{16'})C(O)R^{12}$; (q) —$O(CH_2)_jC(O)N(R^{14'})$ $(CH_2)_mCH(R^{16'})C(O)N(R^{14''})(CH_2)_mCH(R^{16'})C(O)N(R^{14'''})$ —$(CH_2)_mCH(R^{16'})C(O)R^{12}$; (r) —$SR^{17}$, where $R^{17}$ is selected from hydrogen, loweralkyl, aryl substituted by $R^{301}$, $R^{302}$ and $R^{303}$, and arylalkyl substituted by $R^{301}$, $R^{302}$ and $R^{303}$; (r') —$SR^{400}$; (s) —$SC(O)R^{11}$; (t) —$P(O)(OR^{11})_2$; (u)1-tetrazolyl; (u')2-tetrazolyl; (v) —$NHC$(=$NH$)$NH_2$; (w) —$C$(=$NH$)$NH_2$; (w') —$OC$(=$NH$)$CCl_3$; (x) —O-(hydroxyl protecting group); (x') —O-tert-butyldimethylsilyl; (y) —$HNSR^{11}$; (z) —$NR^{17}S(O)_2R^{11}$; (aa) —$NR^{14}R^{15}$; (bb) —$NR^{17}C(O)NHR^{18}$, where $R^{18}$ is selected from hydrogen, loweralkyl, arylalkyl substituted by $R^{301}$, $R^{302}$ and $R^{303}$, aryl substituted by $R^{301}$, $R^{302}$ and $R^{303}$, —$NR^{14}R^{17}$ and —$NR^{14}R^{14''}$; (cc) —$NR^{17}C(O)OR^{11}$; (dd) —$NHP(O)(OR^{11})_2$; (ee) a group having the formula

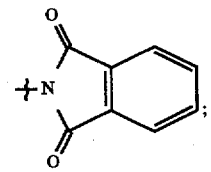 (Ie)

(ff) a group having the formula

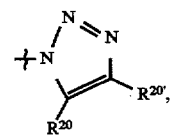 (If)

where $R^{20}$ and $R^{20'}$ are independently selected from the group consisting of hydrogen, aryl, cyano, trifluoromethyl, —$C(O)$—O-loweralkyl and —$C(O)$-loweralkyl or, alternatively, where $R^{20}$ and $R^{20'}$, taken together, form an aromatic ring optionally substituted by $R^{301}$, $R^{302}$ and $R^{303}$; (gg) a group having the formula

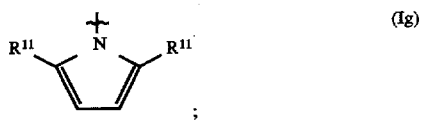

(Ig)

(hh) —OCH(R¹⁴)C(heterocyclic)=CHR¹⁵; (ii) hydroxy; (jj) —O(CH₂)ᵢCN; (kk) —O(CH₂)ᵢC(=NOR¹⁴)R¹²; (ll) —O(CH₂)ᵢC(=N⁺(O⁻)R¹⁴)R¹², with the proviso that R¹⁴ may not be hydrogen; (mm) —O(CH₂)ᵢC(=NOR¹⁴)R¹⁵; (nn) —O(CH₂)ᵢC(=N⁺(O⁻)R¹⁴)R¹⁵, with the proviso R¹⁴ may not be hydrogen; and (oo) —OC(O)O(CH₂)ᵢC(O)NR¹⁴R¹⁵.

R²ᵃ in subformula Ib is hydrogen or trifluoromethylcarbonyl or, taken together with R²ᵃ', forms a diazo group or, taken together with one of R³ᵃ and R⁴, forms a C-32/C-33 bond.

R²ᵃ' in subformula Ib is hydrogen or, taken together with R²ᵃ, forms a diazo group.

R³ᵃ and R⁴ in subformula Ib are chosen such that (a) both are thioloweralkoxy, thioaryloxy or thioarylalkoxy; (b) one of R³ᵃ and R⁴ is selected from hydrogen, hydroxy and a C-32/C-33 bond formed with R²ᵃ, and the other of R³ᵃ and R⁴ is hydrogen or R¹¹; or (c) taken together, R³ᵃ and R⁴ form a group selected from (i) oxo, (ii) =NR⁴⁸ where R⁴⁸ is selected from arylalkoxy, hydroxy, —O(CH₂)ᵢCOOH where f is one to five, —NHC(O)OR³⁹ where R³⁹ is loweralkyl, and —NHS(O)₂R⁴⁰ where R⁴⁰ is aryl, (iii) =NOR²²² or =N⁺(O⁻)R²²², where R²²² is loweralkyl, aryl, —SO₂-(loweralkyl) or —SO₂-(aryl), and (iv) a thioketal-forming moiety having the formula —S—(CH₂)ᵣ—S— where r is two or three.

R⁵ in subformula Ic is selected from the group consisting of formyl and —CH₂OR¹, where R¹ is as defined above.

Y in formula VII is a group selected from the subformulae

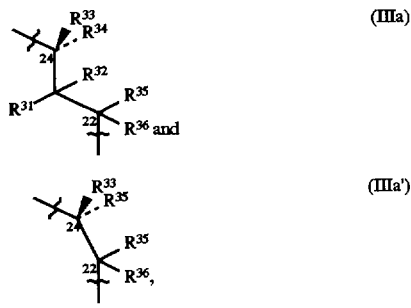

in which R³¹ and R³² are chosen such that one of R³¹ and R³² is hydrogen and the other is independently selected from the group consisting of (i) hydrogen, (ii) hydroxy, (iii) —R¹⁷, (iv) —C(O)R¹¹ and (v) —CH(R¹¹)NHR¹⁷. Alternatively R³¹ and R³², taken together, form a diazo group; or, taken together with one of R³³ and R³⁴, one of R³¹ and R³² forms a C-23/C-24 bond and the other is selected from hydrogen, alkyl, —C(O)NHR⁶¹, —S(O)₂R⁶¹ and —C(O)OR⁶¹, where R⁶¹ is hydrogen, aryl or loweralkyl; or, taken together with one of R³³ and R³⁴, one of R³¹ and R³² forms a group having the formula (in C-23 to C-24 orientation) —CH(R¹¹)NHCH(C(O)OR¹¹)—; or, taken together with one of R³⁵ and R³⁶, one of R³¹ and R³² forms a C-22/C-23 bond and the other is selected from hydrogen, alkyl, —C(O)NHR⁶¹, —S(O)₂R⁶¹ and —C(O)OR⁶¹; or R³¹ and R³², together with carbon atom C-23 to which they are attached, may be absent and replace by a C-22/C-24 bond, as shown in subformula IIIa', above.

One or both of R³¹ and R³² may also, when taken together with one or both of R³³ and R³⁴ and the carbon atoms to which they are attached, form (i) a fused indole group wherein the nitrogen atom is adjacent to C-24, (ii) a fused, optionally unsaturated, 5-membered heterocyclic group wherein one of the two ring members adjacent to C-23 and C-24 is oxygen, the other adjacent ring member is —CHR¹⁷— or =CR¹⁷—, and the remaining ring member is =N— or —NR¹¹—; or (iii) a fused pyrrole. Furthermore, taken together with R³⁵ and R³⁶ and the carbon atoms to which they are attached, R³¹ and R³² may form (i) a fused indole group wherein the nitrogen atom is adjacent to C-22 or (ii) a fused furan ring wherein the oxygen atom is adjacent to C-22.

R³⁵ and R³⁶ in subformulae IIIa and IIIa' are chosen such that both are loweralkoxy; or that one of R³⁵ and R³⁶ is hydrogen and the other is selected from hydroxy, amino, —NHR¹⁷, —OC(O)R¹¹, —OC(O)O-(benzyl) and —NHNH-(tosyl); or (in subformula IIIa), taken together with one of R³¹ and R³², one of R³⁵ and R³⁶ forms a C-22/C-23 bond and the other is hydrogen or hydroxy; or (in subformula IIIa'), taken together with one of R³³ and R³⁴ when C-23 is absent, one of R³⁵ and R³⁶ forms a C-22/C-24 bond and the other is hydrogen or hydroxy; or, taken together with one of R³³ and R³⁴, one of R³⁵ and R³⁶ forms a group having the formula —OC(CH₃)₂O—; or, taken together, R³⁵ and R³⁶ form an oxo group or =NR³⁸ where R³⁸ is selected from (i) arylalkoxy, (ii) hydroxy, (iii) —OCH₂COOH, (iv) —OCH₂CHCH₂, (v) —NHC(O)OR³⁹ and (vi) —NHS(O)₂R⁴⁰. Alternatively, taken together with R and R', R³⁵ and R³⁶ may form a C-21/C-22 bond and a heterocycle-forming group as described above or, taken together with R³¹ and R³², R³⁵ and R³⁶ may form an indole or furan group as described above. As a further alternative, when taken together with either or both of R³³ and R³⁴ and intervening carbon atoms C-22, C-23 and C-24, R³⁵ and R³⁶ may form a fused, heterocyclic group selected from either (i) a five- or six-membered, unsaturated group which comprises a heteroatom selected from N, O and S, optionally comprises a second heteroatom selected from N, O and S with the proviso that when two heteroatoms are present, at least one is N, and is optionally substituted with loweralkyl, aryl, arylalkyl, amido, formyl, —C(O)OR¹¹ or —C(O)R⁴¹ where R⁴¹ is loweralkyl, or (ii) a seven-membered, optionally unsaturated group having fused thereto a phenyl group optionally substituted with loweralkyl, alkoxy or halogen, wherein the ring member adjacent to C-22 is =N— and the ring member adjacent to C-24 is O or S.

R³³ and R³⁴ in subformulae IIIa and IIIa' are chosen such that (i) one of R³³ and R³⁴ is hydrogen and the other is selected from hydrogen, hydroxy, amino, —OR¹¹, —ONO₂, —OC(O)NHR¹⁷, —C(O)R¹¹, —C(R¹¹)NHR¹⁷ and —O-(hydroxyl protecting group); (ii) one of R³³ and R³⁴ is hydrogen and the other forms, with one of R³¹ or R³², a group having the formula —CH(R¹¹)NHCH(C(O)OR¹¹)— or, with one of R³⁵ and R³⁶, a group having the formula —OC(CH₃)₂O—; or (iii) one of R³³ and R³⁴ forms a C-23/C-24 bond (or, when C-23 is absent, a C-22/C-24 bond) and the other is selected from hydrogen, hydroxy and loweralkoxy. Alternatively, when taken together, R³³ and R³⁴ may form an oxo group or, taken together with one or more of R³¹, R³², R³⁵ and R³⁶ and the intervening carbon atoms, one or both of R³³ and R³⁴ form a group selected from (i) indole, where the nitrogen atom is adjacent to C-24, (ii) furan, with the oxygen atom attached to C-24, or (iii) a heterocyclic group, as described above.

Z in formula VII is selected from groups having the subformulae

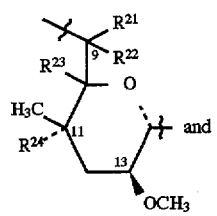

(IIa)

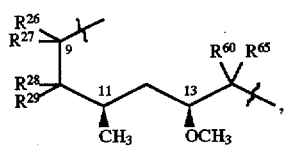

(IIb)

wherein $R^{21}$ and $R^{22}$ are chosen such that (i) one of $R^{21}$ and $R^{22}$ is hydrogen and the other is selected from hydrogen, loweralkyl, arylalkyl, aryl, halogen, triflate, mesylate, tosylate, benzenesulfonate, azide, amine, acetate, $-NR^{17}R^{18}$, $-OC(O)R^{19}$, $-NR^{17}S(O)_2R^{18}$, $-NR^{17}C(O)R^{18}$, and groups having the formulae

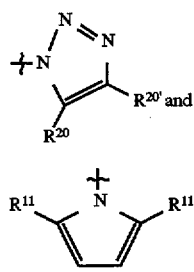

(If)

(Ig)

or, taken together with $R^{23}$, forms a C-9/C-10 bond. Alternatively, one of $R^{21}$ and $R^{22}$ may be hydroxy and the other selected from hydrogen, loweralkyl, arylalkyl and aryl; or one of $R^{21}$ and $R^{22}$ may be selected from hydrogen, loweralkyl and arylalkyl and the other, taken together with $R^{23}$ and the carbon atoms to which they are attached, may form a fused, five-membered heterocyclic group wherein the two ring members adjacent to C-9 and C-10 are oxygen and the remaining ring member is selected from $-C(O)-$ and $-C(S)-$; or one of $R^{21}$ and $R^{22}$ may be selected from hydrogen, loweralkyl and arylalkyl and the other, taken together with $R^{23}$ and the carbon atoms to which they are attached, may form a fused, five-membered heterocyclic group wherein the two ring members adjacent C-9 and C-10 are oxygen and the remaining ring member is $-P(O)(R^{25})-$ where $R^{25}$ is loweralkyl, arylalkyl, loweralkoxy, amino or loweralkylamino.

As a further alternative, $R^{21}$ and $R^{22}$, when taken together, may form a group selected from oxo, oxime and $-O-CH_2-$; or $R^{21}$ and $R^{22}$, taken together with the carbon to which they are attached, may be absent and C-8 attached directly to C-10.

$R^{23}$ in subformula IIa is selected from the group consisting of hydroxy, halogen, amino, loweralkylamino, arylalkylamino, loweralkoxy and arylalkoxy or, taken together with one of $R^{21}$ and $R^{22}$, forms a C-9/C-10 bond or, taken together with $R^{24}$, forms a C-10/C-11 bond.

$R^{24}$ in subformula IIa is hydrogen or, taken together with $R^{23}$, forms a C-10/C-11 bond.

$R^{26}$, $R^{27}$, $R^{28}$ and $R^{29}$ in subformula IIb are chosen such that (i) one of $R^{28}$ and $R^{29}$ is hydroxy and the other is $-COOH$ or $-C(O)O$-loweralkyl, and (ii) $R^{26}$ and $R^{27}$ and the carbon to which they are attached are absent and C-8 is directly attached to C-10; or, taken together, $R^{26}$ and $R^{27}$ are oxo while one of $R^{28}$ and $R^{29}$ is hydroxy and the other forms a C-2/C-10 bond; or, taken together, $R^{26}$ and $R^{28}$ form a bond and $R^{27}$ and $R^{29}$ form a group having the formula $-U-C(R^{11})=N-$ in which U is adjacent to C-9 and is selected from $-O-$, $-S-$ and $-NH-$; or $R^{26}$ and $R^{28}$ are each hydroxy and $R^{27}$ and $R^{29}$, taken together, form a group having the formula $-CH_2-C(CH_2)-CH_2-$.

Alternatively, $R^{26}$, $R^{27}$, $R^{28}$ and $R^{29}$, when taken together with the carbon atoms to which they are attached, may form either (i) a fused naphthalene group wherein the atoms adjacent to C-9 and C-10 are substituted by cyano groups, or (ii) a fused, mono-, bi- or tricyclic heterocyclic aromatic group comprising fused, six-membered rings, which has between one and three nitrogen heteroatoms and is optionally substituted with up to six groups selected from amino, halogen, loweralkyl and loweralkoxy.

$R^{60}$ and $R^{65}$ in subformula IIb are chosen such that $R^{65}$ is hydrogen and $R^{60}$ is selected from the group consisting of (i) hydrogen, (ii) hydroxy and (iii) $-OC(O)R^{19}$ or, taken together, $R^{60}$ and $R^{65}$ may form an oxo group.

When examined for immunomodulatory activity using a common in vitro biological assay, the compounds of the invention are seen to be potent immunosuppressant agents. Consequently, it is expected that the compounds may be found to possess immunosuppressive, antimicrobial, antifungal, antiviral, antiinflammatory, and antiproliferative activity, as well as the ability to reverse chemotherapeutic drug resistance.

Accordingly, in another aspect of the present invention are disclosed pharmaceutical compositions comprising a compound of the invention in combination with a pharmaceutically acceptable carrier. Suitable carriers and methods of formulation are also disclosed.

In a further aspect of the present invention are disclosed processes for the preparation of the above compounds, synthetic intermediates useful in the preparations of these and other immunomodulator derivatives of ascomycin, and methods of immunomodulatory treatment by the administration of a therapeutically effective amount of a compound of the invention to a patient in need of such treatment.

DETAILED DESCRIPTION OF THE INVENTION

The compounds of the present invention are formed by modification of FR-900520 (ascomycin) or one of its congeners (such as FK-506, etc.) in one or more of three general regions. Accordingly, representative compounds of the invention may be categorized as belonging to one of several classes, depending on the number of modifications present. Singly-modified compounds, i.e., those in which two of the three general regions remain unchanged over the parent molecule, are encompassed by the formulae

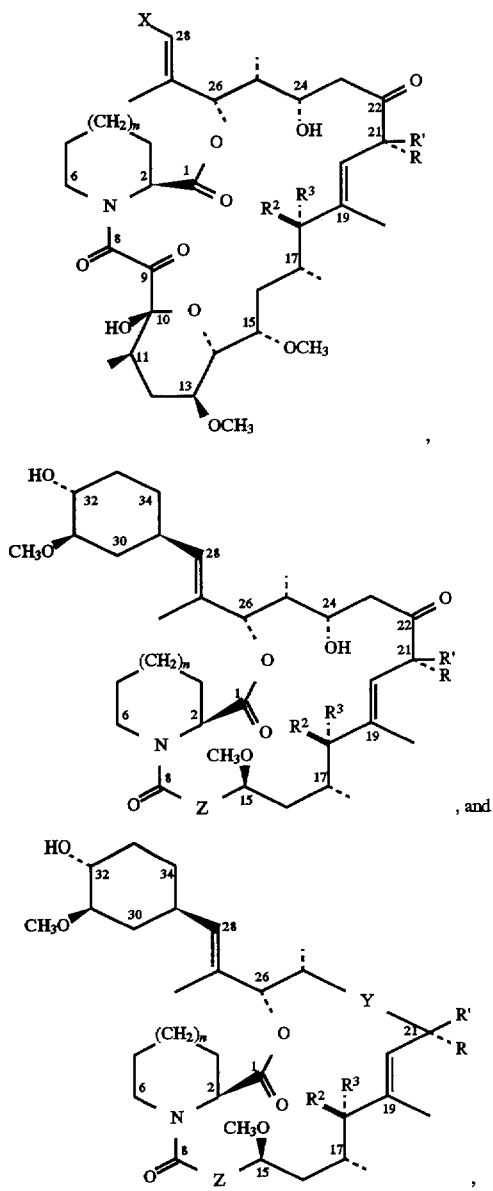

(I)

(II)

(III)

and the pharmaceutically acceptable salts, esters, amides and prodrugs thereof, wherein each of the substituents is as defined above. Among the compounds characterized by formula I are the most preferred compounds of the present invention, including that of Example 510 below which is regarded as the best mode hereof; other compounds which are similarly desirable are those of Examples 4, 5, 6, 11, 14b, 30, 208, 209, 393, 394, 504, 505, 508 and 509. Also among the compounds of formula I are preferred derivatives useful as intermediates in the synthesis of other immunomodulators, including especially compounds in which X is a group of the formula

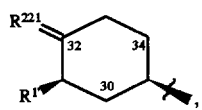

(Ib')

wherein $R^{221}$ is selected from $=NOR^{222}$ and $=N^+(O^-)R^{222}$. In these intermediates, $R^{222}$ is chosen from among loweralkyl, aryl, —SO$_2$-(loweralkyl) and —SO$_2$-(aryl). Other preferred intermediates include compounds of formula I where X is a group of subformula Ia, in which R' (R-configuration) is —OC(O)O-(p-nitrophenyl) and $R^{1'}$ is —OCH$_3$.

On the other hand, doubly-modified analogs of ascomycin which are representative of the compounds of the invention may be described by the formulae

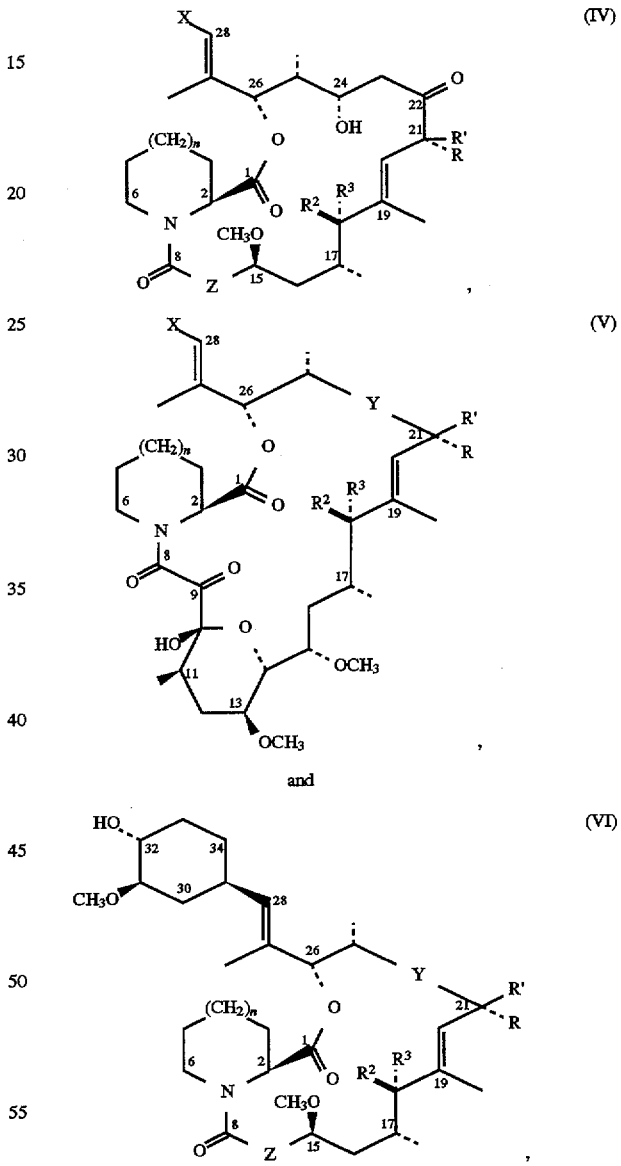

(IV)

(V)

and (VI)

and the pharmaceutically acceptable salts, esters, amides and prodrugs thereof, wherein each of the substituents again are as previously defined. Among these doubly-modified compounds are those in which a direct bond is formed between carbon atoms C-2 and C-10, represented by the structural formula

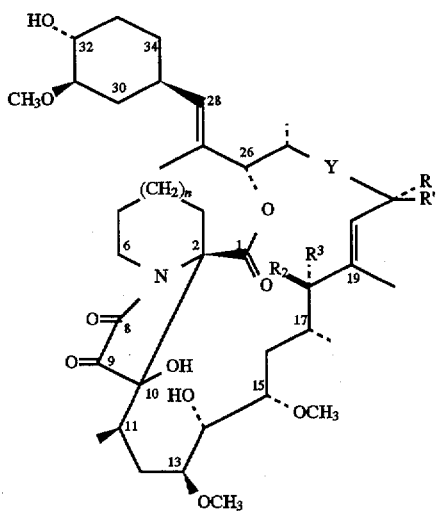

(VIII)

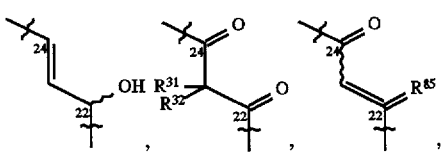
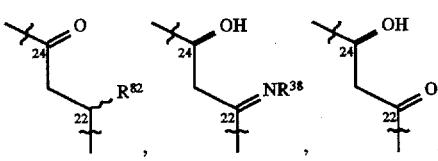
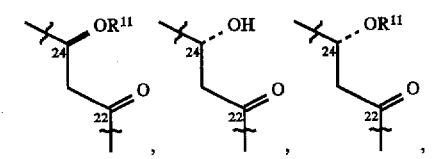
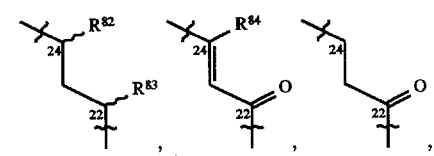
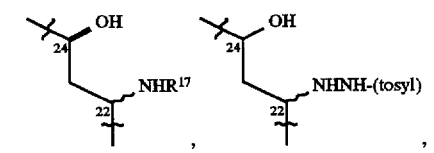

Multiple modifications are also possible by the careful selection of syntheses from those disclosed herein as well as by the use of other synthetic methods known to those skilled in the art, and result in the compounds belonging to the representative class encompassed by formula VII, above.

The compounds of formulae (I), (IV), (V) and (VII) are subject to a limitation on the values of $R^1$ and $R^{1'}$ when each of the following conditions are met:

a) $R^1$ and $R^{1'}$ are in the trans stereochemical orientation, b) $R^{35}$ and $R^{36}$, taken together, are an oxo group, c) $R^{31}$ and $R^{32}$ are hydrogen, and $R^{33}$ and $R^{34}$ are chosen such that one of $R^{33}$ and $R^{34}$ is hydrogen and the other is selected from the group consisting of hydrogen, hydroxy, —OCOR$^8$ and —OSi(R$^{11}$)$_3$, where each $R^{11}$ is independently selected from the previously disclosed definition, or, alternatively, $R^{31}$ is hydrogen and $R^{32}$, taken together with one of $R^{33}$ and $R^{34}$, forms a C-23/C-24 bond, and the other of $R^{33}$ and $R^{34}$ is selected from the group consisting of hydrogen, hydroxy, —OCOR$^8$ and —OSi(R$^{11}$)$_3$, and d) R' is hydrogen and R is chosen from the group consisting of hydrogen, methyl, ethyl, allyl, propyl, 2-hydroxyethyl, cyclopropylmethyl, 2-oxopropyl and 2-ethanalyl.

In this sole instance, $R^1$ and $R^{1'}$ may not be selected from the group consisting of:

(a) —O(CH$_2$)$_j$C(O)R$_{12}$, where j is one to five,
(b) —O(CH$_2$)$_m$S(O)$_s$R$^{12}$,
(c) —O(CH$_2$)$_j$CN,
(d) —O(CH$_2$)$_j$C(=NOR$^{14}$)R$^{12}$,
(e) —O(CH$_2$)$_j$C(=N$^+$(O$^-$)R$^{14}$)R$^{12}$,
(f) —O(CH$_2$)$_j$C(=NOR$^{14}$)R$^{15}$,
(g) —O(CH$_2$)$_j$C(=N$^+$(O$^-$)R$^{14}$)R$^{15}$,
(h) —OC(O)O(CH$_2$)$_j$C(O)NR$^{14}$R$^{15}$,
(i) —O(CH$_2$)$_j$NR$^6$C(O)OR$^{14}$,
(j) —O(CH$_2$)$_j$NR$^6$C(O)NR$^{14}$R$^{15}$,
(k) —O(CH$_2$)$_j$NR$^6$C(O)NR$^7$NR$^{14}$R$^{15}$,
(l) —O(CH$_2$)$_j$NR$^6$C(O)R$^{14}$, and
(m) —O(CH$_2$)$_j$NR$^6$C(O)OC(O)R$^{14}$, and instead must be chosen from the remaining substituents previously described.

Representative and preferred compounds of the invention include those encompassed within formulae III, V, VI, VII and VIII wherein Y is selected from the group consisting of

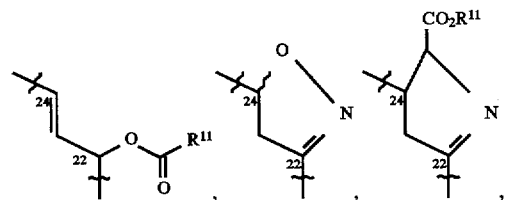
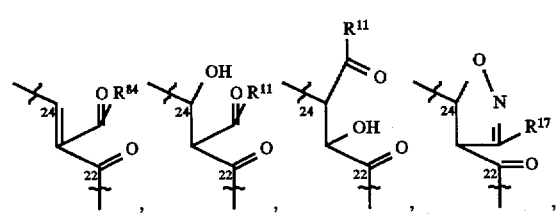
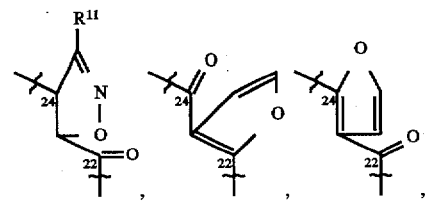
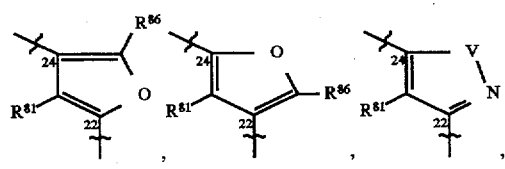

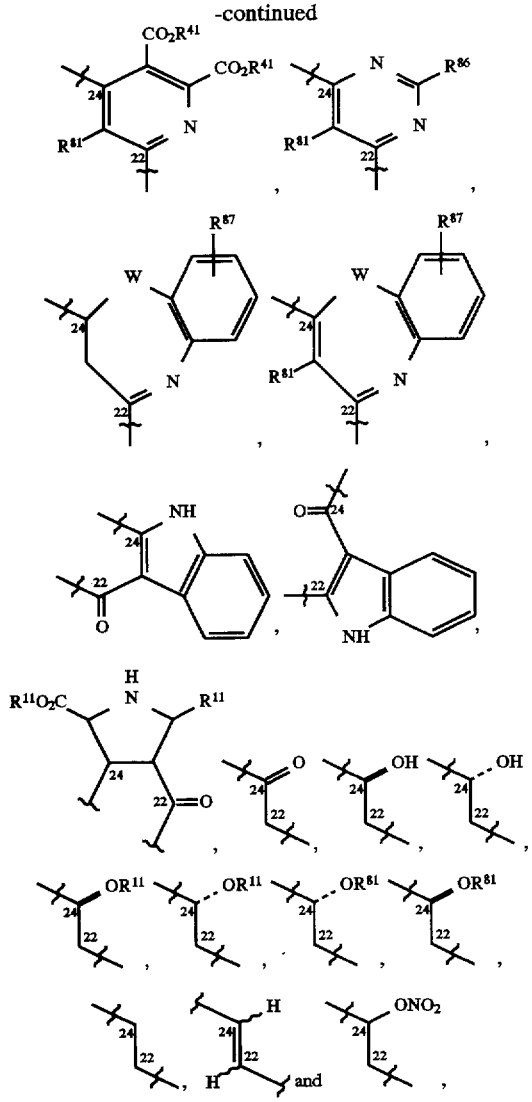

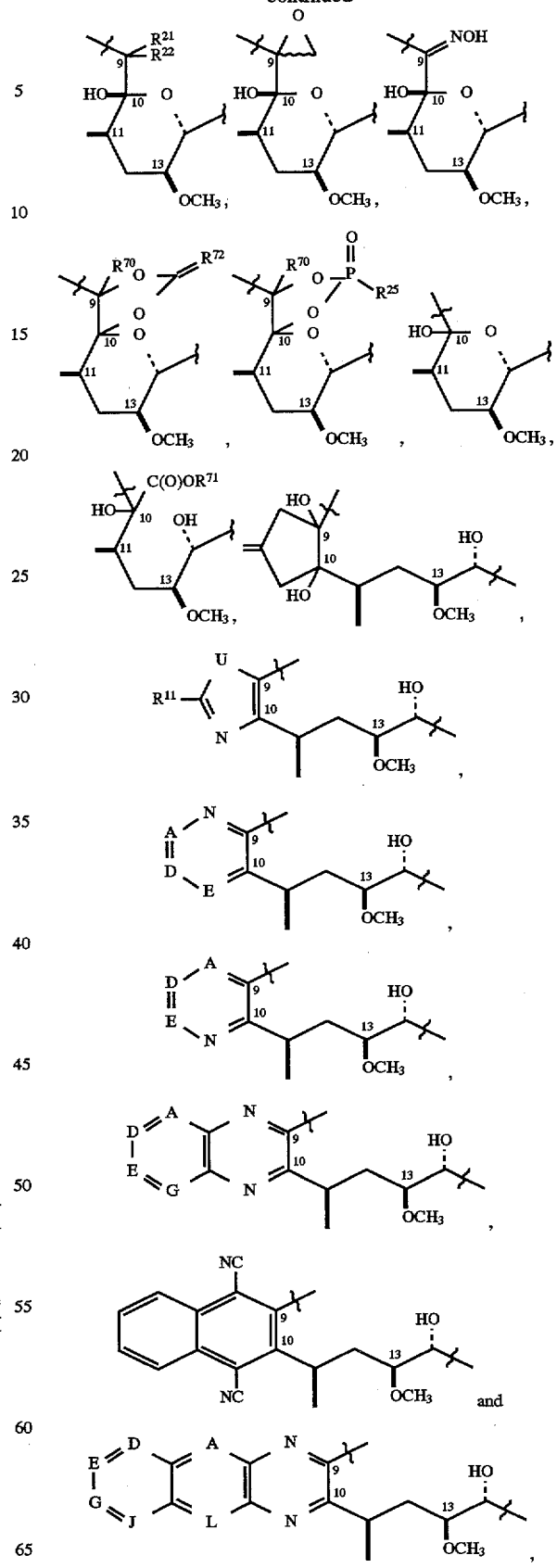

wherein $R^{11}$, $R^{17}$, $R^{31}$, $R^{32}$, $R^{38}$ and $R^{41}$ are as previously defined; $R^{81}$ is selected hydrogen, alkyl, —C(O)NHR$^{61}$, —S(O)$_2$R$^{61}$ and —C(O)OR$^{61}$; $R^{82}$ and $R^{83}$ are independently selected from hydroxy and amino; $R^{84}$ is hydrogen, hydroxy or loweralkoxy $R^{85}$ is hydrogen or hydroxy; $R^{86}$ is selected from hydrogen, loweralkyl, aryl, arylalkyl, amido, formyl, —C(O)R$^{41}$ and —C(O)OR$^{41}$; $R^{87}$ is selected from hydrogen, halogen, alkoxy and loweralkyl; V is selected from oxygen, —N(R$^{86}$)— and —NC(O)R$^{86}$—; and W is oxygen or sulfur.

Other representative compounds of the invention include those encompassed within formulae II, IV, VI and VII wherein Z is selected from the group consisting of

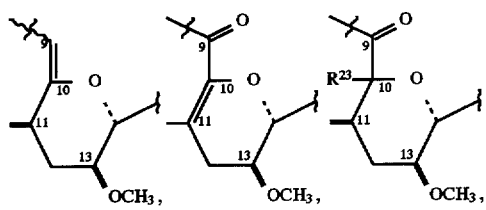

wherein $R^{11}$, $R^{21}$, $R^{22}$, $R^{23}$ and U are as previously defined; $R^{70}$ is hydrogen, loweralkyl or arylalkyl; $R^{71}$ is hydrogen or loweralkyl; $R^{72}$ is oxygen or sulfur; and A, D, E, G, J and L are selected from nitrogen, carbon and —C($R^{73}$)— where $R^{73}$ is amino, halogen, loweralkyl or loweralkoxy.

Throughout the specification and claims, it is intended that when a variable such as $R^{11}$, $R^{21}$, m and n occurs more than once in a structural formula, its value is chosen independently at each occurrence.

As used throughout this specification and in the appended claims, the following terms have the meanings specified:

The term "acyl" as used herein refers to an aryl or alkyl group, as defined below, appended to a carbonyl group including, but not limited to, acetyl, pivaloyl, benzoyl and the like.

The term "acylamino" as used herein refers to an acyl group, as defined above, appended to an amino group including, but not limited to, acetylamino, pivaloylamino, benzoylamino and the like.

The term "acylguanidino" as used herein refers to an acyl group, as defined above, appended to a nitrogen of a guanidino radical in one of three ways: HN(acyl)C(NH)NH— or $H_2$NC(NH)N(acyl)- or (acyl)NC($NH_2$)HN—.

The term "alkenyl" as used herein refers to straight or branched chain groups of 2 to 12 carbon atoms containing one or more carbon-carbon double bonds including, but not limited to ethenyl, 1-propenyl, 2-propenyl, 2-methyl-1-propenyl, 1-butenyl, 2-butenyl and the like.

The terms "alkoxy", "alkylether" and "loweralkoxy" as used herein refer to a loweralkyl group, as defined below, attached to the remainder of the molecule through an oxygen atom including, but not limited to, methoxy, ethoxy, isopropoxy, n-butoxy, sec-butoxy, isobutoxy, tert-butoxy and the like.

The term "alkoxycarbonyl" as used herein refers to an alkoxy group, as defined above, attached via a carbonyl group including, but not limited to, methyloxycarbonyl, ethyloxycarbonyl, tert-butyloxycarbonyl, cyclohexyloxycarbonyl and the like.

The term "alkoxycarbonylamino" as used herein refers to an alkoxycarbonyl group, as defined above, appended to an amino group including, but not limited to, methyloxycarbonylamino, tert-butyloxycarbonylamino and the like.

The term "alkoxycarbonylguanidino" as used herein refers to an alkoxycarbonyl group, as defined above, appended to a nitrogen of a guanidino radical in one of three ways: HN(alkoxycarbonyl)C(NH)HN—, $H_2$NC(NH)N(alkoxycarbonyl)- or (alkoxycarbonyl)NC($NH_2$)HN—.

The term "alkyl" as used herein refers to a monovalent straight chain or branched chain group of 1 to 12 carbon atoms including, but not limited to, methyl, ethyl, n-propyl, isopropyl, n-butyl, sec-butyl, isobutyl, tert-butyl and the like.

The terms "alkylamino" and "loweralkylamino" as used herein refers to a group having the structure —NH-(loweralkyl), where the loweralkyl portion is as defined below. Alkylamino and loweralkylamino groups include, for example, methylamino, ethylamino, isopropylamino and the like.

The term "alkylsulfonyl" as used herein refers to an alkyl group, as defined above, attached via a sulfur dioxide diradical including, but not limited to, methanesulfonyl, camphorsulfonyl and the like.

The terms "alkylthioether", "thioalkoxy" and "thiolower-alkoxy" as used herein refer to a loweralkyl group, as previously defined, attached via a sulfur atom including, but not limited to, thiomethoxy, thioethoxy, thioisopropoxy, n-thiobutoxy, sec-thiobutoxy, isothiobutoxy, tert-thiobutoxy and the like.

The term "alkynyl" as used herein refers to straight or branched chain groups of 2 to 12 carbon atoms containing a carbon-carbon triple bond including, but not limited to acetylenyl, propargyl, and the like.

The term "amidoalkyl" as used herein refers to a group having the structure —$NR^{101}C(O)R^{102}$ appended to a loweralkyl group, as previously defined. The groups $R^{101}$ and $R^{102}$ are independently selected from hydrogen, lower alkyl, aryl, arylalkyl, and halosubstituted alkyl. Additionally, $R^{101}$ and $R^{102}$, taken together, may optionally be —$(CH_2)_{aa}$— where aa is an integer of from 2 to 6.

The term "aminoalkyl" as used herein refers to a group having the structure —$NR^{103}R^{104}$ appended to a loweralkyl group, as previously defined. The groups $R^{103}$ and $R^{104}$ are independently selected from hydrogen, lower alkyl, aryl and arylalkyl. Additionally, $R^{103}$ and $R^{104}$, taken together, may optionally be —$(CH_2)_{bb}$— where bb is an integer of from 2 to 6.

The terms "aryl" and "aryl'" as used herein refers to carbocyclic aromatic groups including, but not limited to, phenyl, 1- or 2-naphthyl, fluorenyl, (1,2)-dihydronaphthyl, (1,2,3,4)-tetrahydronaphthyl, indenyl, indanyl and the like, substituted by $R^{301}$, $R^{302}$ and $R^{303}$.

The terms "arylalkoxy" and "arylalkylether" as used herein refer to an arylalkyl group, as defined below, attached to the parent molecular moiety through an oxygen atom. Arylalkoxy includes, but is not limited to, benzyloxy, 2-phenethyloxy, 1-naphthylmethyloxy and the like.

The term "arylalkoxycarbonyl" as used herein refers to an arylalkoxy group, as defined above, attached via a carbonyl group including, but not limited to, benzyloxycarbonyl, 9-fluorenylmethyloxycarbonyl and the like.

The term "arylalkoxycarbonylamino" as used herein refers to an arylalkoxycarbonyl group, as defined above, appended to an amino group including, but not limited to, benzyloxycarbonylamino, 9-fluorenylmethyloxycarbonylamino and the like.

The term "arylalkoxycarbonylguanidino" as used herein refers to an arylalkoxycarbonyl group, as defined above, appended to a nitrogen of a guanidino radical in one of three ways: HN(arylalkoxycarbonyl)C(NH)HN—, $H_2$NC(NH)N(arylalkoxycarbonyl)- or (arylalkoxycarbonyl)NC($NH_2$)HN—.

The term "arylalkyl" as used herein refers to an aryl group, as previously defined, appended to an alkyl group including, but not limited to, benzyl, 1- and 2-naphthylmethyl, halobenzyl, alkoxybenzyl, hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The term "arylalkylamino" as used herein refers to a group having the structure —NH-(arylalkyl), where the arylalkyl portion is as previously defined. Examples of arylalkylamino groups include benzylamino, 1-phenylethylamino and the like.

The terms "arylalkylthioether" and "thioarylalkoxy" as used herein refer to an arylalkyl group, as previously defined, attached via a sulfur atom.

The term "arylamino" as used herein refers to an aryl group, as defined above, appended to an amino group including, but not limited to, anilino, naphthylamino and the like.

The terms "arylether" and "aryloxy" as used herein refer to an aryl group, as previously defined, attached to the parent molecular moiety through an oxygen atom. Aryloxy includes, but is not limited to, phenoxy, 1-naphthoxy, 2-naphthoxy and the like.

The term "aryloxycarbonyl" as used herein refers to an aryloxy group, as defined above, attached via a carbonyl group including, but not limited to, phenyloxycarbonyl.

The term "aryloxycarbonylamino" as used herein refers to an aryloxycarbonyl group, as defined above, appended to an amino group including, but not limited to, phenyloxycarbonylamino.

The term "aryloxycarbonylguanidino" as used herein refers to an aryloxycarbonyl group, as defined above, appended to a nitrogen of a guanidino moiety in one of three ways: HN(aryloxycarbonyl)C(NH)HN—, $H_2$NC(NH)N(aryloxycarbonyl)- or (aryloxycarbonyl)NC($NH_2$)HN—.

The term "arylsulfonyl" as used herein refers to an aryl group, as defined above, attached via a sulfur dioxide diradical including, but not limited to p-toluenesulfonyl, benzenesulfonyl and the like.

The term "arylsulfonylguanidino" as used herein refers to an arylsulfonyl group, as defined above, bonded to a nitrogen of a guanidino radical in one of three ways:

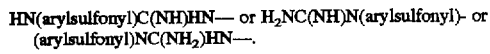
HN(arylsulfonyl)C(NH)HN— or $H_2$NC(NH)N(arylsulfonyl)- or (arylsulfonyl)NC($NH_2$)HN—.

The terms "arylthioether" and "thioaryloxy" as used herein refer to an aryl group, as defined above, attached via a sulfur atom.

The term "biaryl" as used herein refers to a first aryl group, as defined above, substituted with a second aryl group which may the same as or different than the first, such that the two are connected by a single carbon-carbon bond.

The term "carboxamido" as used herein refers to an amino group attached via a carbonyl group and having the formula $H_2$NC(O)—.

The term "carboxyalkyl" as used herein refers to a carboxyl group, —$CO_2$H, appended to a loweralkyl group, as previously defined.

The term "cycloalkenyl" as used herein refers to cyclic groups of 5 to 10 carbons possessing one or more carbon-carbon double bonds including, but not limited to, cyclopentenyl, cyclohexenyl, 1,3,3-trimethylcyclohexenyl and the like, in which the point of attachment can occur at any available valency on the carbocylic ring.

The term "cycloalkyl" as used herein refers to cyclic groups of 3 to 8 carbons including, but not limited to, cyclopropyl, cyclobutyl, cyclopentyl, cyclohexyl and the like.

The term "cycloalkylalkenyl" as used herein refers to cycloalkyl, as defined above, appended to an alkenyl group, as defined above.

The term "cycloalkylalkyl" as used herein refers to a cycloalkyl group appended to a lower alkyl group including, but not limited to, cyclohexylmethyl and cyclohexylethyl.

The term "cycloalkylalkynyl" as used herein refers to cycloalkyl, as defined above, appended to an alkynyl group, as defined above.

The term "guanidinoalkyl" as used herein refers to a group of the structure —$NR^{105}$C(=$NR^{106}$)$NHR^{107}$ appended to a loweralkyl group, as previously defined. $R^{105}$, $R^{106}$, and $R^{107}$ are independently selected from hydrogen, lower alkyl, heterocyclic, aminoalkyl and aryl. Alternatively, $R^{106}$, and $R^{107}$, taken together, may optionally be —$(CH_2)_{cc}$— wherein cc is an integer of from 2 to 6.

The terms "halo" and "halogen" as used herein refer to an atom selected from fluorine, chlorine, bromine and iodine.

The term "heterocyclic" as used herein, except where otherwise specified, refers to any aromatic or non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 3 double bonds, (ii) the nitrogen and sulfur heteroatoms as well as the carbon atoms may optionally be oxidized by unsaturation and/or substitution by hydroxy, thiol, oxo or thiooxo, (iii) the nitrogen heteroatom may optionally be quaternized, (iv) any of the above heterocyclic rings may be fused to a benzene ring, and (v) any carbon or heteroatom with suitable valence may bear a substituent selected from $R^{301}$, $R^{302}$ and $R^{303}$. Representative heterocycles include, but are not limited to, pyrrolyl, pyrrolidinyl, pyrazolyl, pyrazolinyl, pyrazolidinyl, cytosinyl, thiocytosinyl, imidazolyl, imidazolinyl, imidazolidinyl, pyridyl, piperidinyl, pyrazinyl, piperazinyl, pyrimidinyl, pyridazinyl, xanthenyl, xanthonyl, xanthopterinyl, oxazoyl, oxazolidinyl, thiouracilyl, isoxazolyl, isoxazolidinyl, morpholinyl, indolyl, quinolinyl, uracilyl, urazolyl, uricyl, thiazolyl, thiazolidinyl, isothiazolyl, isothiazolidinyl, isoquinolinyl, thyminyl, benzimidazolyl, benzothiazolyl, benzoxazolyl, furyl, thienyl and benzothienyl.

The term "(heterocyclic)alkyl" as used herein refers to a heterocyclic group appended to an alkyl group, as previously defined.

The term "(heterocyclic)alkylether" as used herein refers to a (heterocyclic)alkyl moiety, as defined above, attached via an oxygen atom.

The term "(heterocyclic)alkenyl" as used herein refers to a heterocyclic group appended to an alkenyl group, as previously defined.

The term "(heterocyclic)alkylthioether" as used herein refers to a (heterocyclic)alkyl moiety, as defined above, attached via a sulfur atom.

The term "(heterocyclic)alkynyl" as used herein refers to a heterocyclic group appended to an alkynyl group, as previously defined.

The term "(heterocyclic)ether" as used herein refers to a heterocyclic moiety, as defined above, attached via an oxygen atom.

The term "(heterocyclic)thioether" as used herein refers to a heterocyclic moiety, as defined above, attached via a sulfur atom.

The terms "hydroxyalkyl" and "hydroxyloweralkyl" as used herein refer to —OH appended to a loweralkyl group, as defined below.

The term "hydroxy-protecting group" as used herein refers to those groups which are known in the art to protect a hydroxyl group against undesirable reaction during synthetic procedures and to be selectively removable including, but not limited to, methylthiomethyl, tert-dimethylsilyl, tert-butyldiphenylsilyl, acyl substituted with an aromatic group and the like.

The term "loweralkyl" as used herein refers to an alkyl group, as defined above, of 1 to 8 carbon atoms.

The terms "monoalkylamino" and "dialkylamino" refer respectively to one and two alkyl or cycloalkyl groups, as defined above, appended to an amino group including, but not limited to, methylamino, isopropylamino, cyclohexylamino, dimethylamino, N,N-methylisopropylamino; bis-(cyclohexyl)amino and the like.

The term "N-alkylcarboxamido" as used herein refers to an alkylamino group, as defined above, attached via a carbonyl group and having the formula HN(alkyl)C(O)—.

The term "N-arylcarboxamido" as used herein refers to an arylamino group, as defined above, attached via a carbonyl group and having the formula HN(aryl)C(O)—.

The terms "naturally occuring amino acid" and "standard amino acid" refer to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

The term "N,N-dialkylcarboxamido" as used herein refers to an amino group substituted with two alkyl groups, as defined above, wherein the two alkyl groups need not be identical, attached via a carbonyl group and having the formula N(alkyl)(alkyl')C(O)—.

The term "N,N-diarylcarboxamido" as used herein refers to an amino group substituted with two aryl groups, as defined above, wherein the two aryl groups need not be identical, attached via a carbonyl group and having the formula N(aryl)(aryl')C(O)—.

The term "N-terminal protecting group" as used herein refers to those groups known in the art to protect the N-terminus against undesirable reactions during synthetic procedures or to prevent the attack of exopeptidases on the final compounds or to increase the solubility of the final compounds and includes, but is not limited to acyl, acetyl, pivaloyl, ten-butylacetyl, tert-butyloxycarbonyl (Boc), carbobenzyloxycarbonyl (Cbz), and benzoyl groups. Other such groups are described by Gross, E. and Meienhofer, J. in "The Peptides", Volume 3; Academic Press, 1981.

The term "oxo" as used herein refers to an oxygen atom forming a carbonyl group.

The term "thioalkoxyalkyl" as used herein refers to a thioalkoxy group, as defined above, appended to a lower-alkyl group.

The term "thioloweralkyl" as used herein refers to a loweralkyl group, as defined above, attached via a sulfur atom.

The term "thiooxo" as used herein refers to a sulfur atom forming a thiocarbonyl group.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge, et at., "Pharmaceutical Salts," *J. Pharm. Sci.*, 66:1–19 (1977) which is incorporated herein by reference.)

Examples of pharmaceutically acceptable, non-toxic esters of the compounds of this invention include $C_1$ to $C_6$ alkyl esters wherein the alkyl group is a straight or branched chain. Acceptable esters also include $C_5$ to $C_7$ cycloalkyl esters as well as arylalkyl esters such as, but not limited to benzyl. $C_1$ to $C_{-4}$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$ to $C_6$ alkyl primary amides and $C_1$ to $C_2$ dialkyl secondary amides are preferred. Amides of the compounds of the invention may be prepared according to conventional methods.

The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexylcarbodiimede) method, the active ester method (p-nitrophenyl ester method, N-hydroxysuccinic acid imide ester method, cyanomethyl ester method and the like), the Woodward reagent K method, the DCC-HOBT (1-hydroxy-benzotriazole) method and the like. Classical methods for amino acid condensation reactions are described in "Peptide Synthesis" Second Edition, M. Bodansky, Y. S. Klausner and M. A. Ondetti (1976).

As in conventional peptide synthesis, branched chain amino and carbonyl groups at alpha and omega positions in amino acids may be protected and deprotected if necessary. The protecting groups for amino groups which can be used involve, for example, benzyloxycarbonyl (Z), o-chlorobenzyloxycarbonyl ((2-Cl)Z)), p-nitrobenzyloxycarbonyl (Z(NO₂)), p-methoxybenzyloxycarbonyl (Z(OMe)), t-amyloxycarbenyl (Aoc), isobornealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt) and dimethylphosphino-thioyl (Mpt).

The examples for protecting groups for carboxyl groups involve, for example, benzyl ester (OBzl), cyclohexyl ester, 4-nitrobenzyl ester (OBzlNO₂), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (NG) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethyl-benzenesulfonyl (Mts) and the like; the thiol group in cysteine may be protected with benzyl, p-methoxybenzyl, triphenylmethyl, acetamidomethyl, ethylcarbamyl, 4-methylbenzyl (4-MeBzl), 2,4,6-trimethylbenzyl (Tmb) and the like; and the hydroxy group in serine may be protected with benzyl (Bzl), t-butyl, acetyl, tetrahydropyranyl (THP) and the like.

Numerous asymmetric centers exist in the compounds of the present invention. Except where otherwise noted, the present invention contemplates the various stereoisomers and mixtures thereof. Accordingly, whenever a bond is represented by a wavy fine, it is intended that both steric orientations are intended.

The potent immunomodulatory activity, which compounds of the instant invention demonstrate in common in vitro biological assays, suggest that these compounds possess immunosuppressive, antimicrobial, antifungal, antiviral, antiinflammatory and antiproliferative activity, and possess the ability to reverse chemotherapeutic drug resistance. As agents which block T-cell activation, a prerequisite for HIV proliferation, the compounds may be useful as prophylactics for the prevention of HIV replication. While the compounds of the invention would be useful when used alone, combination therapy with other immunosuppressants, such as, FK506, rapamycin, cyclosporin A, picibanil, mycophenolic acid, azathioprine, prednisolone, cyclophosphamide, brequinar and leflunomide, would also be expected to be beneficial.

As immunosuppressants, the compounds of the present invention are useful when administered for the prevention of immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation. The regulation of the immune response by the compounds of the invention would also find utility in the treatment of autoimmune diseases, such as rheumatoid arthritis, systemic lupus erythematosus, Hashimoto's thyroiditis, multiple sclerosis, myasthenia gravis, type I diabetes, uveitis, allergic encephalomyelitis, glomerulonephritis, and the like; and further infectious diseases caused by pathogenic microorganisms, such as HIV. In the particular cases of HIV-1, HIV-2 and related retroviral strains, inhibition of T-cell mitosis would suppress the replication of the virus, since the virus relies upon the host T-cell's proliferative functions to replicate.

Further uses include the treatment and prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; reversible obstructive airway disease, which includes conditions such as asthma (for example, bronchial asthma, allergic asthma, intrinsic asthma, extrinsic asthma and dust asthma), particularly chronic or inveterate asthma (for example, late asthma and airway hyperresponsiveness), bronchitis and the like; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by the compounds of the invention.

Other treatable conditions would include but are not limited to ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastro-intestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia seniiis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, vital hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, anti-inflammatory activity, and so on.

Additionally, some compounds also possess FK-506 antagonistic properties, and are thus useful in the treatment of immunodepression or a disorder involving immunodepression. Examples of disorders involving immunodepression include AIDS, cancer, senile dementia, trauma (including wound healing, surgery and shock), chronic bacterial infection, and certain central nervous system disorders. The immunodepression to be treated may be caused by an overdose of an immunosuppressive macrocyclic compound, for example derivatives of 12-(2-cyclohexyl-1-methylvinyl)-13,19,21,27-tetramethyl-11,28-dioxa-4-azatricyclo [22.3.1.0$^{4,9}$] octacos-18-ene such as FK-506, or rapamycin. Overdosing of such medicants by patients is quite common upon their realizing that they have forgotten to take their medication at the prescribed time and can lead to serious side effects.

A further situation in which the compounds of the present invention may be used to treat immunosuppression is in vaccination. It is sometimes found that the antigen introduced into the body for the acquisition of immunity from disease also acts as an immunosuppressive agent, and therefore antibodies are not produced by the body and immunity is not acquired. By introducing a compound of the present invention into the body (as in a vaccine), the undesired immunosuppression may be overcome and immunity acquired.

The compounds of the present invention may also find utility in the chemosensitization of drug resistant target cells. Cyclosporin A and FK-506 are known to be effective modulators of P-glycoprotein, a substance which binds to and inhibits the action of anticancer drugs; by inhibiting P-glycoprotein, they are capable of increasing the sensitivity of multidrug resistant (MDR) cells to chemotherapeutic agents. It is believed that the compounds of the invention may likewise be effective at overcoming resistance expressed to clinically useful antitumour drugs such as 5-fluorouracil, cisplatin, methotrexate, vincristine, vinblastine and adriamycin, colchicine and vincristine.

Further, it has recently been shown that the steroid receptor-associated heat shock proteins, hsp56 or hsp59, belong to the FK506 family of immunophilin proteins. The ability of a steroid receptor-associated heat shock protein to bind the immunosuppressive macrolide FK506 may suggest that the steroid receptor and immunophilin signal transduction pathways are functionally interrelated. The combined treatment of compounds of the present invention and low concentrations of a steroid ligand (e.g. progesterone, dexamethasone) may result in a significant enhancement of target gene expression over that seen in response to ligand alone. Thus, the compounds of the present invention may potentiate steroid-mediated transactivation.

Aqueous liquid compositions of the present invention may be particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation.

When used in the above or other treatments, a therapeutically effective amount of one of the compounds of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat gastrointestinal disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required for to achieve the desired therapeutic effect and to gradually increase the dosage until the desired effect is achieved.

The total daily dose of the compounds of this invention administered to a human or lower animal may range from about 0.001 to about 3 mg/kg/day. For purposes of oral administration, more preferable doses may be in the range of from about 0.005 to about 1.5 mg/kg/day. If desired, the effective daily dose may be divided into multiple doses for purposes of administration; consequently, single dose compositions may contain such amounts or submultiples thereof to make up the daily dose.

The pharmaceutical compositions of the present invention comprise a compound of the invention and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

The compounds of the invention may be prepared using one or more of the processes which follow. The starting materials for use in these processes are preferably one of the macrolides isolated from culture media obtained in accordance with known methods by fermentation of microorganisms of the genus Streptomyces, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on Apr. 27, 1989 with the Agricultural Research Culture Collection International Depository, Peoria, Ill. 61604, USA under the provisions of the Budapest Treaty, under deposit No. NRRL 18488. The macrolide FR-900520 (European Patent Application 0184162), also known as ascomycin, may be prepared in accordance to the published methods of (i) H. Hatanaka, M. Iwami, T. Kino, T. Goto and M. Okuhara, FR-900520 and FR-900523, *Novel immunosuppressants isolated from A streptomyces. I. Taxonomy of the producing strain.* J. Antibiot., 1988. XLI(11), 1586–1591; (ii) H. Hatanaka, T. Kino, S. Miyata, N. Inamura, A. Kuroda, T. Goto, H. Tanaka and M. Okuhara, FR-900520 and FR-900523, *Novel immunosuppressants isolated from A streptomyces. II. Fermentation, isolation and physico-chemical and biological characteristics.* J. Antibiot., 1988. XLI(11), 1592–1601; (iii) T. Arai, Y. Koyama, T. Suenaga and H. Honda, *Ascomycin, An Antifungal Antibiotic.* J. Antibiot., 1962. 15(231-2); and (iv) T. Arai in U.S. Pat. No. 3,244,592. One or more of the processes discussed below may be then employed to produce the desired compound of the invention.

Such processes comprise:

(a) producing a compound of formulae I–VIII, which contains a CH—OR group, by selective activation of a selected CH—OH group in a corresponding compound wherein —OR is a leaving group which is easily displaced by nucleophilic attack.

(b) producing a compound of formulae I–VIII, which contains a CH—$N_3$ group, by selective displacement of an —OR group in a corresponding compound.

(c) producing a compound of formulae I–VIII, which contains a CH—$NH_2$ group, by selective reduction of a CH—$N_3$ group in a corresponding compound.

(d) producing a compound of formula I–VIII, which contains a R'–NR" COR group, by selective acylation of a R'—NR" H group in a corresponding compound wherein R is selected from hydrogen, aryl, arylalkyl, alkyl, heterocyclic, heterocyclic alkyl, cycloalkyl, and cycloalkylalkyl such that R' and/or R" represent(s) a radical derived from formula I–VIII; or R' and R" are $R^{14}$ and $R^{15}$ respectively, as defined above, and R is a radical as described in connection with formulae I–VIII.

(e) producing a compound of formulae I–VIII, which contains a CH—$NR_1R_2$ group, by selective alkylation of a CH—$NH_2$ group in a corresponding compound wherein $R_1$ and $R_2$ are independently selected from hydrogen, aryl, arylalkyl, alkyl, heterocyclic, heterocyclic alkyl, cycloalkyl, and cycloalkylalkyl.

(f) producing a compound of formulae I–VIII, which contains a CH—NHC(=X)NH—R group, by selective urea or thiourea formation from a CH—$NH_2$ group in a corresponding compound wherein R is selected from hydrogen, aryl, arylalkyl, alkyl, heterocyclic, heterocyclic alkyl, cycloalkyl, and cycloalkylalkyl, and X is oxygen or sulfur.

(g) producing a compound of formulae I–VIII, which contains a CH—NH—$SO_2R$ group, by selective sulfonylation of a CH—$NH_2$ group in a corresponding compound wherein R is selected from aryl, arylalkyl, alkyl, cycloalkyl, cycloalkylalkyl, heterocyclic alkyl and heterocyclic.

(h) producing a compound of formulae I–VIII, which contains a CH—NH—C(=O)OR group, by selective carbamate formation from a selected CH—$NH_2$ group in a corresponding compound wherein R is selected from aryl, cycloalkyl, cycloalkyl alkyl, alkyl, heterocyclic alkyl, heterocyclic and arylalkyl.

(i) producing a compound of formulae I–VIII, which contains a CH—NH—C(=NH)$NH_2$ group, by selective guanidinium formation from a CH—$NH_2$ group in a corresponding compound.

(j) producing a compound of formulae I–VIII, which contains a CH—NH—SR group, by selective sulfenylation of a CH—$NH_2$ group in a corresponding compound wherein R is selected from aryl, arylalkyl, alkyl, cycloalkyl, cycloalkylalkyl, heterocyclic alkyl and heterocyclic.

(k) producing a compound of formulae I–VIII, which contains a CH—X group, by selective halogenation of a CH—OH group in a corresponding compound wherein X is selected from chlorine, bromine, fluorine and iodine.

(l) producing a compound 6f formulae I–VIII, which contains a CH—P(O)(OR)$_2$ group, by selective phosphonic acid ester formation of a CH—X group in a corresponding compound wherein R is selected from alkyl, arylalkyl, and aryl.

(m) producing a compound of formulae I–VIII, which contains a CH—OP(O)(OR)$_2$ group, by selective phosphorylation of a CH—OH group in a corresponding compound wherein R is selected from alkyl, arylalkyl, and aryl.

(n) producing a compound of formulae I–VIII, which contains a CH—S—R group, by selective thioether formation from a CH—OH group in a corresponding compound wherein R is selected from cycloalkyl, cycloalkyl alkyl, heterocyclic, heterocylic alkyl, alkyl, arylalkyl, and aryl.

(o) producing a compound of formulae I–VIII, which contains a CH—O—C(=S)—OR group, by selective aryl- or alkyloxythiocarbonylation of a CH—OH group in a corresponding compound wherein R is selected from cycloalkyl, cycloalkyl alkyl, heterocyclic, heterocylic alkyl, alkyl, arylalkyl, and aryl.

(p) producing a compound of formulae I–VIII, which contains one or more CH—O—R groups, by selective ether formation of one or more CH—OH groups in a corresponding compound wherein R is selected from cycloalkyl, cycloalkylalkyl, heterocyclic, (heterocylic) alkyl, (heterocyclic)alkenyl, (heterocyclic)alkynyl, alkyl, arylalkyl, aryl, loweralkoxycarbonylalkyl, arylalkoxycarbonylalkyl, arylalkylcarbonylalkyl, trialkylsilylcarbonylalkyl, trialkylstannylcarbonylalkyl, amidocarbonylalkyl, alkylamidocarbonylalkyl, dialkylamidocarbonylalkyl, arylamidocarbonylalkyl and heterocyclicamidocarbonylalkyl.

(q) producing a compound of formulae I–VIII, which contains a CH—(substituted)phthalimide group, by selective cyclic imide formation using a CH—NH$_2$ group in a corresponding compound.

(r) producing a compound of formulae I–VIII, which contains a CH—NH—P(=Y)R$_2$ group, by selective phosphinamide formation from a CH—NH$_2$ group in a corresponding compound wherein R is phenyl, or substituted phenyl and Y is oxygen or sulfur.

(s) producing a compound of formulae I–VIII, which contains CH—N—P(=Y)(OR)$_2$ group, by selective phosphoramide formation from a CH—NH$_2$ group in a corresponding compound wherein R is phenyl, arylalkyl, or substituted phenyl and Y is oxygen or sulfur.

(t) producing a compound of formulae I–VIII, which contains a CH$_2$ group, by selective deoxygenation of a CH—O—C(=S)—OR group in a corresponding compound.

(u) producing a compound of formulae I–VIII, which contains a C(OH)=CH—(=O) or a C(=O)—CH$_2$—C(=O) group, by selective oxidation of a CH(OH)—CH$_2$—C(=O) group in a corresponding compound.

(v) producing a compound of formulae I–VIII, which contains a C(=O)—CR$_1$R$^2$—C(=O) group, by selective alkylation of a C(OH)=CH—C(=O) or a C(=O)—CH$_2$—C(=O) group in a corresponding compound wherein R$_1$ and R$_2$ are independently selected from hydrogen, aryl, cycloalkyl, cycloalkyl alkyl, alkyl, heterocyclic alkyl, heterocyclic and arylalkyl, but both cannot be hydrogen.

(w) producing a compound of formulae I–VIII, which contains a C(=O)—CR$_1$R$_2$—C(=O) group, by selective halogenation of a C(OH)=CH—C(=O) or a C(=O)—CH$_2$—C(=O) group in a corresponding compound wherein R$_1$ and R$_2$ are independently selected from fluorine, chlorine, bromine and iodine.

(x) producing a compound of formulae I–VIII, which contains a C(=O)—CH(OH)—C(=O) group, by selective oxidation of a C(OH)=CH—C(=O) or a C(=O)—CH$_2$—C(=O) group in a corresponding compound.

(z) producing a compound of formulae I–VIII, which contains a C(=O)—C(N$_2$)—C(=O) group, by selective diazotization of a C(OH)=CH—C(=O) or a C(=O)—CH$_2$—C(=O) group in a corresponding compound.

(aa) producing a compound of formulae I–VIII, which contains a C(=CH—R)—CH$_2$—C(=O) group, by selective olefination of a C(OH)=CH—C(=O) or a C(=O)—CH$_2$—C(=O) group in a corresponding compound wherein R is selected from lower alkyl and arylalkyl.

(bb) producing a compound of formulae I–VIII, which contains a C(OCOR)=CH—C(=O) group, by selective O-acylation of a C(OH)=CH—C(=O) or a C(=O)—CH$_2$—C(=O) group in a corresponding compound wherein R is selected from aryl, cycloalkyl, cycloalkyl alkyl, alkyl, heterocyclic alkyl, heterocyclic and arylalkyl.

(cc) producing a compound of formulae I–VIII, which contains a C(NH—R)=CH—C(=O) group, by selective amination of a C(OH)=CH—C(=O) or a C(=O)—CH$_2$—C(=O) group in a corresponding compound wherein R is selected from alkylamine, arylalkylamine, arylamine and amino acid derivatives.

(dd) producing a compound of formulae I–VIII, which contains C(O)—C(=CH—R)—C(=O) group, by selective alkylidene formation of a C(OH)=CH—C(=O) or a C(=O)—CH$_2$—C(=O) group in a corresponding compound wherein R is selected from hydrogen, aryl, cycloalkyl, cycloalkyl alkyl, alkyl, heterocyclic alkyl, heterocyclic and arylalkyl.

(ee) producing a compound of formulae I–VIII, which contains a carbon-carbon double bond, by elimination of HL from a corresponding compound, where L is a leaving group.

(ff) producing a compound of formulae I–VIII, which contains a quinoxaline, benzoquinoxaline, pyrazino[2,3-d]pyridazine, pyrido[3,4-b]pyrazine, or a pteridine by condensation of a 1,2-dicarbonyl or masked 1,2-dicarbonyl groups of a corresponding compound with an appropriate aromatic diamine.

(gg) producing a compound of formulae I–VIII, which contains one or more hydroxyl groups, by selective reduction of one or more C=O groups of a corresponding compound.

(hh) producing a compound of formulae I–VIII, which contains one dihydrobenzo[1,5]thiazepine, by reaction of an alpha, beta-unsaturated ketone of a corresponding compound with an appropriate 2-aminothiophenol.

(ii) producing a compound of formulae I–VIII, which contains one or more carbonyl groups, by selective oxidation of one or more hydroxyl groups of a corresponding compound.

(jj) producing a compound of formulae I–VIII, by selective reaction of one of the carbonyl groups of a corresponding compound and dithiols.

(kk) producing a compound of formulae I–VIII, which contains an oxime group, by selective reaction of one of the carbonyl groups of a corresponding compound with hydroxyl amine or O-alkylated hydroxyl amines.

(ll) producing a compound of formulae I–VIII, which contains a pyrazole system, by condensation of a 1,3-dicarbonyl group of a corresponding compound and appropriate hydrazines.

(mm) producing a compound of formulae I–VIII, which contains a substituted pyrimidine system, by condensation of the 1,3-dicarbonyl group of a corresponding compound with appropriate amidines, guanidines, isoureas, ureas and thioureas.

(nn) producing a compound of formulae I–VIII, which contains a furan system, by reaction of the 1,3-dicarbonyl group of a corresponding compound with appropriate diazoacetic esters or diazomethyl ketones.

(oo) producing a compound of formulae I–VIII, which contains an isoxazole system, by condensation of the 1,3-dicarbonyl group of a corresponding compound with hydroxyl amine.

(pp) producing a compound of formulae I–VIII, which contains a pyridine system, by condensation of the 1,3-dicarbonyl group of a corresponding compound with appropriate malonic acid derivatives or cyanoacetic acid derivatives.

(qq) producing a compound of formulae I–VIII, which contains a benzo[1,5]thiazepine, benzo[1,5]oxazepine or benzo[1,5]diazepine system, by condensation of the 1,3-dicarbonyl group of a corresponding compound with appropriate 2-aminothiophenols, 2-aminophenols, and 1,2-aromatic diamines.

(rr) producing a compound of formulae I–VIII, which contains a keto-substituted furan system, by reaction of the 1,3-dicarbonyl group of a corresponding compound with appropriate aldehydes, and enol ethers.

(ss) producing a compound of formulae I–VIII, which contains a substituted phenyl group, by C-arylation of a 1,3-dicarbonyl group of a corresponding compound with appropriate 1-halo-2-nitro-aromatics.

(uu) producing a compounds of formulae I–VIII, which contains a 2-isoxazoline, by nitrile oxide 1,3-dipolar cycloaddition to an enone.

(zz) producing a compound of formulae I–VIII, which contain either a beta-hydroxy ketone or an alpha, beta-enone, by reductive hydrolysis of a corresponding 2-isoxazoline and subsequent separation of the two compounds.

(eee) producing a compound of formulae I–VIII, which contains a hydrazone, by selective hydrazone formation with a corresponding ketone.

(fff) producing a compound of formulae I–VIII, which contains either an alpha-hydroxy, beta-keto acid or ester, by selective nucleophilic addition and subsequent benzilic acid type rearrangement of a corresponding compound containing a tricarbonyl moiety.

(ggg) producing a compound of formulae I–VIII, which contains a 1,2-dicarbonyl system, by selective oxidative cleavage of a benzilic acid rearrangement product which has been derived from a corresponding compound.

(hhh) producing a compound of formulae I–VIII, which contains an allylic alcohol, by selective reduction of a corresponding enone.

(iii) producing a compound of formulae I–VIII, which contains an epoxide, by selective addition of the carbene arising from diazomethane across an activated carbonyl.

(jjj) producing a compound of formulae I–VIII, which contains a carboxylic acid, by selective ester cleavage in a corresponding compound.

(kkk) producing a compound of formulae I–VIII, which contains a substituted or unsubstituted carboxamide, by selective condensation of the corresponding amine with a corresponding carboxylic acid.

(lll) producing a compound of formulae I–VIII, which contains a 24R-hydroxyl substituent, by selective inversion of the naturally occurring 24S configuration.

(mmm) producing a compound of formulae I–VIII, which contains an alkyloxycarbonyl hydrazone, by selective condensation of an alkyl carbazate with a corresponding compound of formulae I–VIII, having a ketone.

(nnn) producing a compound of formulae I–VIII, which contains a C-33-alkylcarbonyl or polyhaloalkylcarbonyl substituent, by selective C-acylation of 32-oxo-ascomycin or a related analog.

(ooo) producing a compound of formulae I–VIII, which contains a 33-diazo moiety, by selective diazotization of a derivative of 32-oxo-ascomycin or a related analog.

(ppp) producing a compound of formulae I–VIII, which contains one thiazole, by condensation of an alpha substituted carbonyl or an alpha substituted masked carbonyl group of a corresponding compound with an appropriate thioamide, thiourea or with dithiocarbamic acid derivatives, where the alpha substituent L is a leaving group.

(qqq) producing a compound of formulae I–VIII, which contains one imidazole, by condensation of an alpha substituted carbonyl or an alpha substituted masked carbonyl group of a corresponding compound with an appropriate amidine, isourea or guanidine, where the substituent L is a leaving group.

(rrr) producing a compound of formulae I–VIII, which contains one oxazole, by condensation of an alpha substituted carbonyl or an alpha substituted masked carbonyl group of a corresponding compound with an appropriate amide, where the substituent L is a leaving group.

(sss) producing a compound of formulae I–VIII, which contains a tertiary alcohol, by selective addition of a Grignard reagent or an organometallic reagent to a carbonyl moiety of a corresponding compound.

(ttt) producing a compound of formulae I–VIII, which contains one pyrrole, by cyclization of an appropriate gamma-amino alpha hydroxy carbonyl or a masked gamma-amino alpha hydroxy carbonyl of a corresponding compound prepared by process (sss).

(uuu) producing a compound of formulae I–VIII, which contains one pyrazine, by condensation of a 1,2-dicarbonyl or masked 1,2-dicarbonyl group of a corresponding compound with an appropriate 1,2-diamine in the presence of an oxidizing agent.

(vvv) producing a compound of formulae I–VIII, which contains one pyridine, by condensation of a 1,5-dicarbonyl group prepared by process (sss) of a corresponding compound with ammonia.

(www) producing a compound of formulae I–VIII, which contains one pyridazine, by condensation of a 1,4-dicarbonyl group prepared by process (sss) of a corresponding compound with hydrazine.

(xxx) producing a compound of formulae I–VIII, which contains a 1,2-thiocarbonate, by reacting a 1,2-diol of a corresponding compound with thiocarbonyldiimidazole or an appropriately activated thiocarbonate.

(yyy) producing a compound of formulae I–VIII, which contains a 1,2-carbonate, by reacting a 1,2-diol of a corresponding compound with carbonyldiimidazole, triphosgene, phosgene or an appropriately activated carbonate.

(zzz) producing a compound of formulae I–VIII, which contains a 1,2-phosphonate group, by reacting a 1,2-diol of a corresponding compound with an appropriate alkoxyphosphonyl dichloride.

(aaaa) producing a compound of formulae I–VIII, which contains an olefin, by reduction of a 1,2-thiocarbonate prepared by process (xxx) of a corresponding compound.

(bbbb) producing a compound of formulae I–VIII, which contains a $CH_2$ group, by selective reduction of a 1,2-dicarbonyl or masked 1,2-dicarbonyl group of a corresponding compound.

(cccc) producing a compound of formulae I–VIII, which contains an indole group, by selective reduction and condensation of a 2-(o-nitrophenyl)-1,3-diketone [prepared by process (ss)] of a corresponding compound.

(dddd) producing a compound of formulae I–VIII, which contains a substituted triazole group, by cycloaddition of a CH—$N_3$ group in a corresponding compound with appropriate acetylene analogues.

(eeee) producing a compound of formulae I–VIII, which contains a substituted pyrrole group, by reaction of a CH—$NH_2$ group in a corresponding compound with appropriate dicarbonyl compounds.

(ffff) producing a compound of formulae I–VIII, which contains one ethanalyl group, first by selective oxidation of the double bond of an allyl group to a vicinal diol, followed by oxidative cleavage of the diol in a corresponding compound, (gggg) producing a compound of formulae I–VIII, which contains one carboxymethyl group, by selective oxidation of an ethanalyl group in a corresponding compound, (hhhh) producing a compound of formulae I–VIII, which contains one alkyl carboxymethyl group, by esterification of a carboxymethyl group in a corresponding compound, (iiii) producing a compound of formulae I–VIII, which contains one cyclopropylmethyl group, by selective cyclopropanation of the double bond of an allyl group in a corresponding compound, (jjjj) producing a compound of formulae I–VIII, which contains one pyrrole, by reaction of a 1,4-dicarbonyl group with amines in a corresponding compound, (kkkk) producing a compound of formulae I–VIII, which contains one furan, by cyclization of a 1,4-dicarbonyl group in a corresponding compound, (llll) producing a compound of formulae I–VIII, which contains one methyl ketone, by selective oxidation of the double bond of an allyl group in a corresponding compound, (mmmm) producing a compound of formulae I–VIII, which contains a cyano group by Beckmann fragmentation of an oxime derivative of an alpha-methoxy cyclohexanone in a corresponding compound, (nnnn) producing a compound of formulae I–VIII, which contains a hydrazide, by reduction of the corresponding hydrazone, (oooo) producing a compound of formulae I–VIII, which contains an amine, by reduction of the corresponding oxime, (pppp) producing a compound of formulae I–VIII, which contains an alpha,beta-saturated ketone, by reduction of the corresponding alpha, beta-unsaturated enone, (qqqq) producing a compound of formulae I–VIII, which contains an isoxazoline, by treatment of a beta-hydroxy oxime with a dehydrating reagent, (rrrr) producing a compound of formulae I–VIII, which contains an beta-hydroxy carbonyl, by treatment of a carbonyl with a base in the presence of another carbonyl moiety, (ssss) producing a compound of formulae I–VIII, which contains a cyclic imine, by treatment of an enone system with a glycine imine in the presence of base resulting in first Michael addition at the beta-carbon and subsequent imine formation upon aqueous workup, (tttt) producing a compound of formulae I–III, which contains a substituted pyrrole, by treatment of an enone with a glycine imine in the presence of an appropriate catalyst to induce a 1,3-dipolar cycloaddition, (uuuu) producing a compound of formulae I–VIII, which contains a beta-keto carboxylic acid, ester or amide, by decomposition with light or heat of an alpha diazoketone, and (vvvv) producing a compound of formulae I–VIII which contains a ketone, a product of decarboxylation of a beta-keto carboxylic acid, by heating.

(xxxx) producing a compound of formulae I–VIII, which contains a group —$CHOC(O)NR^{14}R^{15}$, —$CHOC(O)NHR^{400}$, —$CHOC(O)NHNR^{14}R^{15}$, —$CHOC(O)NHNHR^{400}$, —$CHOC(O)NHNHC(O)NR^{14}R^{15}$, —$CHOC(O)NHNHC(O)R^{19}$, —$CHOC(O)NHOR^{11}$ or —$CHOC(O)NHNHC(NH)NR^{14}R^{15}$, by selective carbamate formation from a selected —CHOH group in a corresponding compound and a selected group $R^{11}$, $R^{14}$, $R^{15}$, $R^{19}$, or $R^{400}$ from an appropriate compound.

(yyyy) producing a compound of formulae I–VIII, which contains a —$CHOC(O)OR^{400}$, by selective aryl-, heterocyclic-, or alkyloxycarbonylation of a —CHOH group in a corresponding compound.

(zzzz) producing a compound of formula I–VIII, which contains an allylic hydroxyl group, by selective oxidation of an allylic methylene group in a corresponding compound.

In process (a), suitable reagents for activation of an alcohol include acetic anhydride, trifluoromethanesulfonic anhydride (triflic anhydride), methanesulfonyl chloride (mesyl chloride), p-toluenesulfonyl chloride (tosyl chloride), trifluoroacetic anhydride, trifluoroacetyl chloride, methoxysulfonyl fluoride (magic methyl), o-nitrobenzenesulfonyl chloride, 1-methyl-2-fluoropyridinium salt and the like.

The activation may be carried out in a solvent which does not adversely affect the reaction (e.g., diethylether, dichloromethane, tetrahydrofuran, chloroform or N,N-dimethylformamide or a mixture thereof). The reaction may require cooling or heating, depending on the activation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, lutidine, picoline, 4-N, N-dimethylaminopyridine, etc.), quinoline, and the like, preferably in the presence of organic bases such as triethylamine or pyridine.

The activation may also be carried out using a starting material having an opposite configuration at a carbon center. In this situation, the following two additional steps are required to yield a starting material having an epimeric hydroxyl moiety, i.e. (1) the alcohol is oxidized to its corresponding ketone, (2) the obtained ketone is reduced under selective conditions. Both chiral centers having either [R]- or [S]-configuration can be obtained selectively and separately.

In process (b), suitable azide reagents include well-established alkali metal azides such as sodium or lithium azides (NaN$_3$ or LiN$_3$) in the presence or absence of crown ethers, more reactive tetraalkylammonium azides (Danishefski, S. J.; DeNinno, M. P.; Chen, S.-H. *J. Am. Chem. Soc.* 1988, 110, 3929), a copper-assisted azide reaction (Yamamoto, Y.; Asao, N. *J. Org. Chem.* 1990, 55, 5303) and a hydrogen azide-amine system (Saito, S.; Yokoyama, H.; Ishikawa, T.; Niwa, N.; Moriwake, T. *Tetrahedron Lett.* 1991, 32, 663; Saito, S.; Takahashi, N.; Ishikawa, T.; Moriwake, T. *Tetrahedron Lett.* 1991, 32, 667). The azide displacement reaction may be carried out in a solvent which does not adversely affect the reaction (e.g. chloroform, dichloromethane, tetrahydrofuran, pyridine, dimethylsulfoxide, N,N-dimethylformamide, hexamethylphosphoramide, etc. or a mixture thereof). The reaction may be conducted above, at, or below ambient temperature.

In process (c), the reduction may be carried out catalytically using hydrogen. Suitable catalysts include, but are not limited to platinum catalysts (e.g. platinum oxide, platinum black), palladium catalysts (e.g. palladium oxide, palladium on charcoal, palladium black, palladium hydroxide on charcoal, palladium on calcium carbonate poisoned with lead, palladium on barium carbonate with quinoline), nickel catalysts (e.g. nickel oxide, Raney nickel), rhodium catalysts (e.g. rhodium on alumina). Reduction may also be carried out using metal reducing reagents (see Review; Scriven, E. F. V.; Turnbull, K. *Chem Rev.* 1988, 88, 321; Patai, S., Ed., "*The Chemistry of the Azido Group*," Interscience Publishers, New York, 1971; Scriven, E. F. V., Ed., "*Azides and Nitrenes Reactivity and Utility*," Academic Press, Inc., New York, 1984) such as sodium borohydride under phase-transfer conditions, borohydride supported on an ion exchange resin, lithium aluminum hydride and the like, furthermore, 1,3-propanedithiol-triethylamine method (Bayley, H.; Staudring, D. N.; Knowles, J. R. *Tetrahedron Lett.* 1978, 3633), triphenylphosphine (Vaultier, M.; Knouzi, N.; Carrie, R. *Tetrahedron Lett.* 1983, 24, 763), and sodium tellurium hydride (Suzuki, H.; Takaoka, K. *Chem Lett.* 1984, 1733).

The reduction may be carried out in a solvent which does not adversely affect the reaction (e.g., alcohols, water, acetone, dichloromethane, tetrahydrofuran, pyridine or N,N-dimethylformamide or a mixture thereof). The reaction may be conducted above, at, or below ambient temperature.

In process (d), suitable N-acylations may be carried out using the methods of symmetric carboxylic acid anhydrides, carboxylic acid halides, mixed carbonic-carboxylic anhydrides, active esters (p-nitrophenylester, trichlorophenyl ester, pentafluorophenyl ester, N-hydroxysuccinimide, cyanoethyl and the like), and carboxylic acid with suitable condensing reagents such as DCC (N,N-dicyclohexylcarbodiimide and its related condensing agents), DCC-HOBt (N,N-dicyclohexylcarbodiimide-1-hydroxybenzotriazole), Woodward reagent K method, N,N-carbonyldiimidazole and phosphonium containing reagents (e.g. benzotriazolyloxytris[dimethylamino]phosphonium hexafluorophosphate, N,N-bis[2-oxo-3-ox-azolidinyl] phosphorodiamidic chloride, diethylphosphorobromidate, diphenylphosphoryl azide, bromo tris[dimethylamino] phosphonium hexafluorophosphate, and the like). Suitable reagents for amide formation include, but are not limited to formyl derivatives, acetyl halides (chloroacetyl, trichloroacetyl, o-nitrophenylacetyl, o-nitrophenoxyacetyl, acetoacetyl, [N'-dithiobenzyloxycarbonylamino]acetyl and the like), and substituted propionyl derivatives (3-phenylpropionyl, isobutyryl, picolinoyl, and the like). Other groups may be found in volume 3 of *The Peptides* Gross, E. and Meinhofer, J. Academic Press, 1981 and *Protective Groups in Organic Synthesis* Greene, T. W. John Wiley & Sons, New York, Chapter 7, 1981. Typically used coupling conditions are described by Gross, E.; Meinhofer, J. "*The Peptides*" vol. 3, Academic Press, 1981. The N-acylation may be carried out in a solvent which does not adversely affect the reaction (e.g. acetone, dichloromethane, chloroform, tetrahydrofuran, N,N-dimethylformamide, dimethylsulfoxide, diethylether, and the like, or a mixture thereof). The reaction may be conducted above, at, or below ambient temperature. Alternatively, metal salts may be formed from the desired amines and then condensed with an ester which may or may not be activated. These salts may be formed by treatment of the neutral amine with trialkylaluminums (see J. I. Levin, E. Turos, S. M. Weinreb *Synthetic Communications* 1982, 12, 989–993), Sn[N(Si(CH$_3$)$_3$)]$_2$ (See W. Wang, E. J. Roskamp *J. Org. Chem.* 1992, 57, 6101–6103), or with Grignard reagents. For other methods, see A. Solladie-Cavallo, M. Bencheqroun *J. Org. Chem.* 1992, 57, 5831–5834 as well as footnotes 2, 3, 4, 5, 6 and 7 therein.

In process (e), N-alkylations may be carried out using aldehydes or ketones-followed by reduction of the initially formed iminium ion {The following reagents can be used for the reduction; sodium cyanoborohydride-boron trifluoride or the reducing reagents cited in process (c)}, corresponding halides in the presence of bases listed in process (a), or lithium dialkyl cuprate (King, F. E.; King, T. J.; Muir, I. H. M. *J. Chem. Soc.* 1946, 5; Yamamoto, H.; Maruoka, K. *J. Org. Chem.* 1980, 45, 2739). Suitable reagents for N-alkylation include, but are not limited to benzyl halide, 3,4-dimethoxybenzyl halide, nitrobenzyl halide, di(p-methoxyphenyl)methyl halide, triphenylmethyl halide, and the like. Other groups may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-alkylation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (f), urea formation may be carried out from the following reactions; reaction with silicon tetraisocyanate or silicon tetraisothiocyanate (Neville, R. G.; McGee, J. J. *Can. J. Chem.* 1963, 41, 2123), reaction with N,N-carbonyldiimidazole or N,N-thiocarbonyldiimidazole, followed by N-substituted primary or secondary amines or ammonia (Staab, H. A.; Wendel, K. *Org. Synth.* 1968, 48, 44), and reaction with phosgene or thiophosgene in the presence of tert-amine, followed by N-substituted primary or secondary amines or ammonia. The ureido formation may be carried out in a solvent which does not adversely affect the reaction (e.g. acetone, toluene, dichloromethane, tetrahydrofuran, pyridine, N,N-dimethylformamide, etc. or a mixture thereof). The reaction may be conducted above, at, or below ambient temperature.

In process (g), N-sulfonylation may be carried out using substituted sulfonylhalides in the presence of suitable tert-amines such as trialkylamine, pyridine, and the like (Remers, W. A.; Roth, R. H.; Gibs, G. J.; Weiss, M. J. *J. Org.*

*Chem.* 1971, 36, 1232). Suitable reagents include, but are not limited to benzenesulfonyl halide, p-methyoxybenzenesulfonyl halide, 2,4,6-trimethylbenzenesulfonyl halide, toluenesulfonyl halide, benzylsulfonyl halide, p-methoxybenzylsulfonyl halide, trifluoromethylsulfonyl halide, phenacylsulfonyl halide, and the like. Some other representative groups may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-aryl- or alkylsulfonylation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (h), N-carbamate formations may be carried out using common protecting groups for amino group such as, but not limited to methylcarbamates (cyclopropylmethyl, 9-fluorenylmethyl, and the like), substituted ethylcarbamates (2,2,2-trichloroethyl, 2-phosphonoethyl, 2-methylthioethyl, and the like), substituted propyl and isopropylcarbamates (1,1-dimethylpropynyl, 1-methyl-1-(4-biphenylyl)ethyl, tert-butyl, phenyl, p-nitrobenzyl, 8-quinolyl, N-hydroxypiperidinyl, benzyl, dimethoxybenzyl, 9-anthrylmethyl, 1-adamantyl, cyclohexyl, tert-amyl, cinnamoyl, isobutyl, N'p-phenylaminothiocarbonyl, N'-piperidinylcarbonyl, diphenylmethyl, and the like). Preparations of N-carbamates and other groups may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-carbamate formation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (i), N-guanidium formation may be carried out using several common reagents such as 1-guanyl-3,5-dimethylpyrazole (Salvadori, S.; Sarto, G. P.; Tomatis, R. *Eur. J. Med. Chem. Chim. Ther.* 1983, 18, 489), O-methylisourea (Van Nispen, J. W.; Tesser, G. I.; Nivard, R. *J. F. Int. J. Peptide Protein Res.* 1977, 9, 193), and thiourea sulfonylate (Maryanoff, C. A.; Stanzione, R. C.; Plampin, J. N.; Mills, J. E. *J. Org. Chem.* 1986, 51, 1882). The N-guanidinium formation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (j), N-sulfenamides may be prepared from an amine and a sulfenyl halide (Davis, F. A.; Nadir, U. K. *Org. Prep. Proc. Int.* 1979, 11, 33; Kobayashi, T.; Iino, K.; Hiraoka, T. *J. Am. Chem. Soc.* 1977, 99, 5505; Zervas, L.; Borovas, D.; Gazis, E. *J. Am. Chem. Soc.* 1963, 85, 3660). Suitable reagents include, but are not limited to benzenesulfenyl halide, o-nitrobenzenesulfenyl halide, 2,4-dinitrosulfenyl halide, pentachlorobenzenesulfenyl halide, 2-nitro-4-methoxybenzenesulfenyl halide, triphenylmethyl-sulfenyl halide, and the like. Other groups may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-sulfenylation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (k), suitable halogenation reagents include, but are not limited to triphenylphosphine with halogens (Verheyden, J. P. H.; Moffatt, J. G. *J. Am. Chem. Soc.* 1964, 86, 2093; Bergman, R. G. ibid., 1969, 91, 7405; Hrubiec, R. T.; Smith, M. B. *J. Org. Chem.*, 1983, 48, 3667), triphenylphosphine with cyanogen halides (Horner, L.; Oediger, H.; Hoffmann, H. *Annalen Chem.* 1959, 626, 26), triphenylphosphine with carbon tetrahalides (Hooz, J.; Gilani, S. S. H. *Can. J. Chem.* 1968, 46, 86; *Chem. Commun.* 1968, 1350), triphenylphosphine with NBS (N-bromosuccinimide) (Schweizer, E. E.; Creasy, W. S.; Light, K. K.; Shaffer, E. T. *J. Org. Chem.* 1969, 34, 212), and triphenylphosphine with hexachloroacetone (Magid, R. M.; Stanley-Fruchey, O.; Johnson, W. L. *Tetrahedron Lett.* 1977, 2999; Magnid, R. M.; Stanley-Fruchey, O.; Johnson, W. L.; Allen, T. G. *J. Org. Chem.* 1979, 44, 359). The halogenation may also be accomplished by other reagents such as mono- or tri-alkylsilyl halides with or without sodium halides (Olah, G. A.; Husain, A.; Singh, B. P.; Mehrota, A. K. *J. Org. Chem.* 1983, 48, 3667; Balme, G.; Fournet, G.; Gore, J. *Tetrahedron Lett.* 1986, 27, 1907), polymer bound trimethylsilyl derivatives (Cainelli, G.; Contento, M.; Manescalchi, F.; Plessi, L.; Panunzio, M. *Synthesis* 1983, 306; Imamoto, T.; Matsumoto, T.; Kusumoto, T.; Yokoyama, M. *Synthesis* 1983, 460), N,N-dichlorophosphoramidic dichloride (*Chem. Lett.* 1978, 923), phosphorus trihalide-zinc halide (Anderson, Jr. A. G.; Owen, N. E. T.; Freenor, F. J.; Erickson, D. *Synthesis* 1976, 398), diethylaminosulfur trifluoride (Middleton, W. J. *J. Org. Chem.* 1975, 40, 574), triphenoxyphosphonium alkyl halide (Rydon, H. N. *Org. Synth.* 1971, 51, 44; Verheyden, J. P. H.; Moffatt, J. G. *J. Org. Chem.* 1972, 37, 2289), and the like.

The halogenation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (l), phosphonic acid ester formation may be carried out using Michaelis-Arbuzov reactions (Bhattacharya, A. K.; Thyagarajan, G. *Chem. Rev.* 1981, 81, 415; Bauer, G.; Haegele, G. *Angew. Chem. Int. Ed. Engl.* 1977, 16, 477).

The phosphonic acid ester formation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (m), phosphorylation may be carried out using, but is not limited to the 2-halo-2-oxo-1,3,2-dioxaphospholane-triethylamine reaction (Chandrarakumar, N. S.; Hajdu, J. *J. Org. Chem.* 1983, 48, 1197). The phosphorylation may be carried out in a solvent which does not adversely affect the reaction (e.g., benzene, toluene, acetone, dichloromethane, tetrahydrofuran or N,N-dimethylformamide or a mixture thereof). Further, the reaction is preferably conducted in the presence of organic or inorganic bases, as described in process (a), preferably in the presence of organic bases such as triethylamine, pyridine etc. The reaction may be conducted above, at, or below ambient temperature, more preferably from 0° to 50° C.

In process (n), thioether formation may be carried out using, but is not limited to aryl- or alkylmercaptan in the presence of suitable tert-amines such as trialkylamine, pyridine, and the like. The reaction may also be carried out by a metal-catalyzed thioether formation (Guindon, Y;

Frenette, R; Fortin, R.; Rokach, J. *J. Org. Chem.* 1983, 48, 1357), alkali metal salts of aryl- or alkylmercaptans with a compound of formulae I–VIII which contains CH—OR group (OR is the leaving group). The alkali metal may be selected from sodium, potassium, lithium, and cesium. The thioether formation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (o), aryl- or alkyloxythiocarbonylation may be carried out using aryl- or alkyloxythiocarbonylchloride or corresponding halides in the presence of suitable tert-amines such as trialkylamine, pyridine, and the like. The aryl- or alkylthiocarbonylation may be carried out in a solvent which does not adversely affect the reaction (e.g. acetone, dichloromethane, tetrahydrofuran, pyridine, N,N-dimethylformamide etc. or a mixture thereof). The reaction may be conducted above, at, or below ambient temperature.

In process (p), ether formation may be carried out using, for example, aryl-, arylalkyl-, (heterocyclic)alkyl-, (heterocyclic)alkenyl-, (heterocyclic)alkynyl-, loweralkoxycarbonylalkyl-, arylalkoxycarbonylalkyl-, arylalkylcarbonylalkyl-, trialkylsilylcarbonylalkyl-, trialkylstannylcarbonylalkyl-, amidocarbonylalkyl-, alkylamidocarbonylalkyl-, dialkylamidocarbonylalkyl-, arylamidocarbonylalkyl-, alkylamidocarbonylalkyl-, heterocyclicamidocarbonylalkyl-, heterocyclic or alkylhalides in the presence of KY-zeolite (Onaka, M.; Kawai, M.; Izumi, Y. *Chem. Lett.* 1983, 1101), polymeric materials (Kimura, Y.; Kirszensztejn, P.; Regen, S. L. *J. Org. Chem.* 1983, 48, 385), nickel-catalysis (Camps, F.; Coll, J.; Moreto, J. M. *Synthesis* 1982, 186; Yamashita. *Synthesis* 1977, 803), arylalkyl-O-p-toluenesulfonate (Dewick, P.M. *Synth. Commun.* 1981, 11, 853), potassium or sodium alkoxides (Bates, R. B.; Janda, K. D. *J. Org. Chem.* 1982, 47, 4374), pyridine or other bases (*Chem. Lett.* 1978, 57), tetraalkylammonium halide (Miller, J. M.; So, K. H.; Clark, J. H. *Can. J. Chem.* 1979, 1887), mercury perchlorate (McKillop, A.; Ford, M. E. *Tetrahedron* 1974, 30, 2467), silver triflate or silver oxide (Kuhn, R.; Löw, I.; Trischmann, H. *Chem. Ber.* 1957, 90, 203. Croon, I.; Lindberg, B. *Acta Chem. Scand.*, 1959, 13, 593) or a phase transfer catalyst (McKillop, A.; Fiaud, J.-C.; Hug, R. P. *Tetrahedron* 1974, 30, 1379). The ether formation may also be carried out with dialkyl- or diarylphosphoric acid in the presence of p-toluenesulfonic acid (Kashman, Y. *J. Org. Chem.* 1972, 37, 912), or with diazo compounds with tin(II) chloride (Christensen, L. F.; Broom, A. D. *J. Org. Chem.* 1972, 37, 3398). Additionally, ether formation may be accomplished with a suitable trichloroacetimidate in the presence of an acid catalyst (Wessel, H. P.; Iversen, T.; Bundle, D. R. *J. Chem. Soc. Perk Trans.* 1985, 1, 2247.) The ether formation may be carried out in a solvent which does not adversely affect the reaction (e.g. acetone, dichloromethane, tetrahydrofuran, pyridine, N,N-dimethylformamide, ether, cyclohexane, etc. or a mixture thereof). The reaction may be conducted above, at, or below ambient temperature.

More specifically, O-alkylation may be carried out using bromoacetic acid derivatives, iodoacetic acid derivatives, trifluoromethanesulfonyloxy acetic acid derivatives, chlorobromo- or iodomethanesulfonic acid derivatives, chlorobromo- or iodoacetyltrimethylsilane and the like in the presence of an appropriate base such as triethylamine, potassium fluoride or silver(I) oxide. The reaction is performed in an inert solvent such as N,N-dimethylformamide, acetonitrile or dichloromethane, preferably between −50° C. and 80° C. Alternatively, alkylation can be carried out using alkyl diazoacetates in the presence of a metal catalyst, for example $Rh(OAc)_2$ in an inert solvent such as dichloromethane preferably between −20° C. and 80° C.

In process (q), N-cyclic imide formations may be carried out using phthalic anhydride (Sasaki, T.; Minamoto, K.; Itoh, H. *J. Org. Chem.* 1978, 43, 2320), o-methoxycarbonylbenzoyl chloride with trialkylamine (Hoogwater, D. A.; Reinhoudt, D. N.; Lie, T. S.; Gunneweg, J. J.; Beyerman, H. C. *Recl. Trav. Chim. Pays-Bas.* 1973, 92, 819), or N-ethoxycarbonylphthalimide (Nefkens, G. H. L.; Tesser, G. I.; Nivard, R. J. F. *Recl. Trav. Chim. Pays-Bas.* 1960, 79, 688). Other groups and reagents may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-cyclic imide formation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (r), N-phosphinamide formation may be carried out using, but is not limited to phosphinyl chloride with N-methylmorpholine (Kenner, G. W.; Moore, G. A.; Ramage, R. *Tetrahedron Lett.* 1976, 3623). Suitable reagents include, but are not limited to diphenylphosphinyl chloride, dimethyl- or diphenylthiophosphinyl chloride, dibenzyl- or diphenylphosphinyl chloride. Other groups and conditions may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-phosphinamide formation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (s), N-phosphoramide formation may be carried out using, but is not limited to diphenylphosphoryl chloride with a tert-amine-base (Adams, E.; Davis, N. C.; Smith, E. L. *J. Biol Chem.* 1952, 199, 845), and triethylbenzylammonium chloride (Zwierzak, A. *Synthesis* 1975, 507; Zwierzak, A.; Piotrowicz, J. B. *Angew. Chem. Int. Ed. Engl.* 1977, 16, 107). Suitable reagents include, but are not limited to diphenylphosphoryl chloride, dimethyl- or diphenylthiophosphoryl chloride, dibenzyl- or diphenylphosphoryl chloride. Other groups and conditions may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-phosphinamide formation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (t), deoxygenation may be carried out using, but is not limited to phenoxythiocarbonyl derivative with tributyltin hydride and 2,2-azobis-2-methylpropionitrile (AIBN) (Robins, M. J.; Wilson, J. S.; Hansske, F. *J. Am. Chem. Soc.* 1983, 105, 4059; Barton, D. H. R.; McCombie, S. W. *J. Chem. Soc., Perkin Trans. I* 1975, 1574), or a phenyldithiocarbonyl derivative with tributyltin hydride and AIBN (Hayashi, T.; Iwaoka, T.; Takeda, N.; Ohki, E. *Chem. Pharm. Bull.* 1978, 26, 1786). The deoxygenation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (u), suitable oxidizing reagents include activated dialkyl sulfoxides (e.g. dimethylsulfoxide, methylethylsulfoxide) (Mancuso, A. J.; Swern, D. *Synthesis* 1981, 165), organo chromates [e.g. pyridinium chlorochromate (Corey, E. J.; Suggs, J. W. *Tetrahedron Lett.* 1975, 2647; Corey, E. J.; Boger, D. L. *Tetrahedron Lett.* 1978, 2461), pyridinium dichromate (Corey, E. J.; Schmidt, G. *Tetrahedron Lett.* 1979, 5, 399), Collins reagent (Collins, J. C.; Hess, W. W.; Frank, F. J. *Tetrahedron Lett.* 1968, 3363)], tetrapropylammonium perruthenate (Griffith, W. P.; Ley, S. V.; Whitcombe, G. P.; White, A. D. *Chem. Commun.* 1987, 1625; Griffith, W. P. *Aldrichimica Acta.* 1990, 23, 13), and the like. The oxidation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (v), suitable alkylating reagents include, but are not limited to aldehydes and ketones in the presence of reducing agents (Hrubowchak, D. M.; Smith, F. X. *Tetrahedron Lett.* 1983, 24, 4951), alkyl-, aryl, or arylalkyl halides (Shono, T.; Kashimura, S.; Sawamura, M.; Soejima, T. *J. Org. Chem.* 1988, 53, 907). In the case that the reaction is conducted in the presence of an organic or inorganic bases such as an alkaline earth metal (e.g. calcium, balium, magnesium, thallium etc.), an alkali metal hydride (e.g. sodium hydride, lithium hydride, etc.), an alkali metal hydroxide (e.g. sodium hydroxide, potassium hydroxide, etc.), an alkali metal carbonate (e.g. sodium carbonate, potassium carbonate, etc.), an alkali metal hydrogen carbonate (e.g. sodium hydrogen carbonate, potassium hydrogen carbonate, etc.), an alkali metal alkoxide (e.g. sodium methoxide, sodium ethoxide, thallium ethoxide, potassium tert-butoxide, etc.), an alkali metal alkanoic acid (e.g. sodium acetate, etc.), a trialkylamine (e.g. triethylamine, trimethylamine, etc.), or a pyridine compound (e.g. pyridine, lutidine, picoline, 4-N,N-dimethylaminopyridine, etc.), quinoline, and the like. The alkylation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (w), suitable halogenation reagents include, but are not limited to halogens treated by irradiation (sun lamp) for several hours (Heffner, R.; Safaryn, J. E.; Joullie, M. M.; *Tetrahedron Lett.* 1987, 28, 6539) or oxalyl chloride (Evans, D. A.; Dow, R. L.; Shih, T. L.; Takecs, J. M.; Zahler, R. *J. Am. Chem. Soc.* 1990, 112, 5290). The halogenation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (x), suitable oxidation reagents include, but are not limited to oxodiperoxymolybdenum(pyridine)-1,3-dimethyl-3,4,5,6-tetrahydro-2(1H)-pyrimidinone (Anderson, J. C.; Smith, S. C. *SYNLETT* 1990, 2, 107) and oxodiperoxymolybdenum(pyridine)-hexamethylphosphoramide (Vedejs, E. *J. Am. Chem. Soc.* 1974, 96, 5944; Vedejs, E.; Engler, D. A.; Telschow, J. E. *J. Org. Chem.* 1978, 43, 188). The oxidation may be carried out in a solvent which does not adversely affect the reaction (e.g. acetone, dichloromethane, tetrahydrofuran, pyridine, N,N-dimethylformamide, etc., or a mixture thereof). The reaction may be conducted above, at, or below ambient temperature.

In process (z), a compound of formulae I–VIII may be treated with a diazotization reagent. Suitable diazotization reagents include, but are not limited to azidotris(diethylamino)phosphonium bromide (McGuiness, M.; Shechter, H. *Tetrahedron Lett.* 1990, 31, 4987), p-carboxybenzenesulfonyl azide (Hendrickson, R. G.; Wolf, W. A. *J. Org. Chem.* 1968, 33, 3610; Williams, M. A.; Miller, M. J. *Tetrahedron Lett.* 1990, 31, 1807), polymer bound p-toluenesulfonyl azide (Roush, W. R.; Feitler, D.; Rebek, J. *Tetrahedron Lett.* 1974, 1391), p-toluenesulfonyl azide (Regitz, M. *Angew. Chem.* 1967, 79, 786), 2-azo-3-ethylbenzthiazolium tetrafluoroborate (Balli, H.; Kersting, F. *Justus Liebigs Ann. Chem.*, 1961 647, 1. Balli, H.; Low, R. *Tetrahedron Lett.* 1966, 5821), N,N-dimethylazidochloromethyleniminium chloride (Kokel, B.; Viehe, H. G; *Angew. Chem. Int. Ed. Engl.* 1980, 19, 716; Kokel, B.; Boussouira, N. *J. Heterocyclic Chem.* 1987, 24, 1493), and mesyl azide (Danheiser, R. L.; Miller, R. F.; Brisbois, R. G.; Park, S. Z. *J. Org. Chem.* 1990, 55, 1959). The diazotization may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (as), suitable olefination reagents include, but are not limited to Wittig reagents (Maecker, M., *Org. React.* 1965, 14,270; Johnson, A. W., "*Ylid Chemistry,*" Academic Press, New York, 1966) and $CH_2I_2$—Zn—$TiCl_4$[or $Ti(NEt_2)_4$] reagent (Hibino, J.; Okazoe, T.; Takai, K.; Nozaki, H. *Tetrahedron Lett.* 1985, 26, 5579; Okazoe, T.; Hibino, J.; Takai, K.; Nozaki, H. ibid. 1985, 26, 5581). The carbonyl olefination may be carried out in a solvent which does not adversely affect the reaction (e.g. acetone, dichloromethane, tetrahydrofuran, pyridine, N,N-dimethylformamide, etc., or a mixture thereof). The reaction may be conducted at room temperature.

In process (bb), suitable O-acylation reagents include, but are not limited to alkyl, aryl, or arylalkyl acyl halides (Lakhvich, F. A.; Khlebnicova, T. S.; Akhrem, A. A. *Synthesis* 1985, 8, 784). The O-acylation may be carried out in a solvent which does not adversely affect the reaction (e.g. acetone, dichloromethane, tetrahydrofuran, pyridine, N,N-dimethylformamide, etc., or a mixture thereof). The reaction may be conducted above, at, or below ambient temperature.

In process (cc), suitable amination reagents include, but are not limited to amino acid derivatives and lower alkyl, aryl, or arylalkyl amines (Winkler, J. D.; Hershberger, P. M.; Springer, J. P. *Tetrahedron Lett.* 1986, 27, 5177). The reaction may be carried out in refluxing in benzene, toluene or a solvent which does not adversely affect the reaction (e.g. tetrahydrofuran, pyridine, N,N-dimethylformamide, etc., or a mixture thereof). The reaction may be conducted at room temperature.

In process (dd), the alkylidene formation may be carried out using, but is not limited to aldehydes and ketones with active methylene compounds. (Schonberg, A.; Singer, E. *Chem. Ber.* 1970, 103, 3871; Chatterjee, S. *J. Chem. Soc. B*, 1969, 725). The alkylidene formation may be carried out in a solvent which does not adversely affect the reaction (e.g. acetone, dichloromethane, tetrahydrofuran, pyridine, N,N-dimethylformamide, etc., or a mixture thereof). The reaction may be conducted under cooling to heating.

In process (ee), L may be hydroxy, or a good leaving group (halogen, tosylate, mesylate or triflate, for example). When a precursor compound contains a C(OH)—$CH_2$—C=O group, the elimination of $H_2O$ may be carried out in a solvent which is inert under the reaction conditions (e.g.

toluene) with a trace of acid (e.g. toluenesulfonic acid), at a temperature selected from 50° to 100° C. When the precursor compound contains a good leaving group, the elimination may be carried out in the presence of a base (e.g. triethyl amine or potassium carbonate), at a temperature selected from 0° to 100° C.

In process (ff), suitable diamines include phenylene diamine and substituted 1,2-phenyl diamines, 2,3-diaminopyridine, 3,4-diaminopyridine, 4,5-diaminopyridazine, 4,5-diaminopyrimidine and their acid salts, preferably in the presence of tertiary amines (e.g. N-methylmorpholine). Suitable solvents include methanol, ethanol, propanol, acetonitrile, 2-butanone and N,N-dimethylformamide, and a reaction temperature selected from 50° to 100° C.

In process (gg), suitable reagents include sodium borohydride, zinc in acetic acid, sodium triacetoxyborohydride in acetic acid, lithium trialkoxyaluminum hydride in tetrahydrofuran, potassium or lithium tri-sec-butylborohydride in tetrahydrofuran, and borane/t-butylamine complex in a solvent such as methanol or ethanol. The reduction may be conducted at −70° C. to room temperature.

In process (hh), suitable 2-aminothiophenols include substituted 1,2-aminothiophenols, preferably in the presence of tertiary amine (e.g. N-methylmorpholine). Suitable solvents include methanol, ethanol and n-propanol; and the reaction may be conducted at a temperature selected from 50° to 100° C.

In process (ii), the reagent to be used in this reaction may include di(lower)alkyl sulfoxide (e.g. dimethyl sulfoxide, ethyl methyl sulfoxide, propyl methyl sulfoxide, isobutyl methyl sulfoxide, butyl methyl sulfoxide, isobutyl methyl sulfoxide, hexyl methyl sulfoxide, etc). This reaction is usually conducted in the presence of oxalyl chloride, acid chlorides, lower alkanoic anhydride such as acetic anhydride in a conventional solvent that does not adversely influence the reaction such as dichloromethane, acetone, ethyl acetate, tetrahydrofuran, pyridine, N,N-dimethylformamide, etc., followed by the addition of a tertiary amine (e.g. triethyl amine). The reaction may be conducted at −70° C. to room temperature.

In process (jj), the dithiols are lower alkyl dithiols (e.g. ethanedithiol, propanedithiol or butanedithiol) and 1,2-aryl dithiols (e.g. 1,2-benzenedithiol) in the presence of a Lewis acid (e.g. boron trifluoride etherate or lanthanum trichloride) in a conventional solvent that does not adversely influence the reaction such as dichloromethane, tetrahydrofuran or ether. The reaction may be conducted at −70° C. and room temperature.

In process (kk), suitable oxygen-substituted amines include hydroxyl amine, O-alkylhydroxyl amines, and O-arylalkyl hydroxyl amines, for example O-benzyl hydroxy amine. Suitable solvents include those that ethanol or methanol. The reaction is preferably carried out with one equivalent of hydroxyl amine, and at a temperature of 25° to 100° C., more preferably at the reflux temperature of the solvent.

In process (ll), suitable hydrazines include alkylhydrazines (e.g. butylhydrazine), arylhydrazines (e.g. phenylhydrazine), acylhydrazines (e.g. acetylhydrazine), semicarbazides (e.g. t-butyloxycarbonyl hydrazine) and sulfonyl hydrazines (e.g. tosyl hydrazine) in a conventional solvent that does not adversely affect the reaction such as tetrahydrofuran, methanol or ethanol. The reaction may be conducted at 20° to 100° C.

In process (mm), 2-substitutions on the pyrimidine may be hydrogen, alkyl, aryl, hydroxyl, alkoxy, thiol, amino, alkylamino, arylamino, acylamino, carbamylamino, and sulphonylamino groups. The appropriate pyrimidine containing compounds may be prepared according to the methods described in "The Chemistry of Heterocyclic Compounds, Vol. 16, supplement II, Chapter II, pp 21–60", D. J. Brown, John Wiley & Sons, 1985.

In process (nn), the furan containing compounds may be prepared according to the method described by Paulissen, R., et. al. in Tetrahedron Lett. 1974, 607.

In process (oo), one equivalent of hydroxyl amine hydrochloride and tertiary amine (e.g. N-methylmorpholine) in a conventional solvent that does not adversely affect the reaction such as tetrahydrofuran, methanol, ethanol or isopropanol is used to prepare the compound. The reaction is conducted at 20° to 100° C.

In process (pp), the pyridine containing compounds may be prepared according to the literature: Osman, A. N.; Ismail, M. M.; Barakat, M. A. Rev. Roum. Chim. 1986, 31, 615–624; Ried W.; Meyer, A., Ber. Deutsch. Chem. Ges. 1957, 90, 2841; Troschutz, R.; Troschultz, J.; Sollhuberkretzer, M. Arch Pharm. 1985, 318, 777–781.

In process (qq), a substituted 2-aminothiophenol, a 2-aminophenol or an aromatic 1,2-diamine is used in a conventional solvent that does not adversely affect the reaction such as tetrahydrofuran, ethanol, isopropanol, acetonitrile or N,N-dimethylformamide. The reaction may be conducted at 20° to 100° C.

In process (rr), the keto-substituted furan containing compound may be prepared according to the literature: Williams, P. H. et al, J. Am. Chem. Soc. 1960, 82, 4883; E. J. Corey et al., Chem. Lett. 1987, 223.

In process (ss), suitable 1-halo-2-nitroaromatics may be substituted 1-fluoro-2-nitrobenzene, o-fluoro-nitropyridines, or o-bromo-nitro-naphthalene, etc. The arylation may be carried out in a solvent which does not adversely affect the reaction (e.g. tetrahydrofuran, N,N-dimethylformamide, dimethoxyethane, diglyme, etc.).

The base used to generate the anion may be isopropyl magnesium chloride, lithium diisopropyl amine or sodium hydride. The reaction may be conducted at a temperature selected from −70° C. to 100° C.

In process (uu), a nitrile oxide may be formed either by oxidation of an aldoxime or dehydration of a nitro compound as described in the following references or literature cited therein: (1) Torssell, K. G. B. "Nitrile Oxides, Nitrones and Nitronates in Organic Synthesis"; VCH Publishers: New York, 1988, p 64; (2) Kim, J. N.; Ryu, E. K. Synthetic Communications 1990, 20, 1373; (3) Chow, Y. L.; Shy, Y. Y.; Bakker, B. H.; Pillay, K. S. Heterocycles 1989, 29, 2245. The nitrile oxide is placed in the presence of an alpha, beta-unsaturated enone in an inert solvent to yield an 2-isoxazolines. Any isomers may subsequently be chomatographically separated.

In process (zz), an isoxazoline may be transformed to the corresponding beta-hydroxy ketone using but is not limited to molybenum hexacarbonyl in wet acetonitrile according to: Baraldi, P. G.; Barco, A.; Benetti, S.; Manfredini, S.; Simoni, D. Synthesis 1987, 276. Alternatively, $Ti^{3+}$ may be employed to attain N—O bond cleavage: Das, N. B.; Torssell, K. B. G. Tetrahedron 1983, 39, 2227. Additionally, Raney-nickel may also selectively cleave the N—O bond without reducing the imino functionality as described in the following reference and literature cited therein: Torssell, K. G. B. "Nitrile Oxides, Nitrones and Nitronates in Organic Synthesis"; VCH Publishers: New York, 1988, p 16 and 290. During the course of this transformation, a significant amount of dehydration occurs to produce alpha-beta unsaturated enones which may be separated from the beta-hydroxy ketones.

In process (eee), an aryl- or alkylsulfonyl hydrazone may be formed by treatment of a ketone with an aryl- or alkylsulfonyl hydrazide in the presence of an acid catalyst in a solvent suitable for the reaction such as methanol or ethanol at temperatures ranging from ambient to the reflux temperature of the solvent.

In process (fff), a benzilic acid rearrangement to yield an alpha-hydroxy acid may be initiated in a tricarbonyl system by treatment with a slight excess of a hydroxylic base in THF-water initially between 0° C. and room temperature. The temperature may be permitted to rise to room temperature during the course of the reaction. Other nucleophiles such as methanol are also for this type of transformation at temperatures from ambient to the reflux temperature.

In process (ggg), an alpha-hydroxy acid may be oxidatively cleaved by treatment with lead tetraacetate in an inert solvent (e.g. benzene) to form a ketone.

In process (hhh), an allylic alcohol may be produced by selective reduction of an alpha-beta unsaturated enone. This is accomplished with but not limited to sodium borohydride in the presence of cerium(III) chloride heptahydrate in a suitable solvent such as methanol at or near 0° C.

In process (iii), an epoxide may be produced on the central carbonyl of a tricarbonyl moiety by but not limited to excess diazomethane as described in: Fisher, M. J.; Chow, K.; Villalobos, A.; Danishefsky, S. J. *J. Org. Chem.* 1991, 56, 2900–2907.

In process (jjj), liberation of the ester to the acid may be achieved by the cleavage of a suitably substituted ester function. Such a functional group may be benzyl, 2,2,2-trichloroethyl, 9-fluorenylmethyl and the like. These are cleaved by methods well known to those skilled in the art.

In process (kkk), condensation of an amine with the acid may be performed using the mixed or symmetrical anhydride of said acid, or an ester of the acid, preferably activated, such as the ester derived from hydroxybenzotriazole, or the corresponding acylcyanide, acylimidazole, or acylazide of the aforementioned acid.

In process (lll), selective protection of the 32-hydroxyl moiety may be achieved using one of a variety of trialkylsilyl groups. This then leaves exposed a lone secondary alcohol on C-24 for selective inversion, which may be accomplished by activation of the 24-hydroxy as a mesylate, tosylate, etc., followed by inversion with a suitable nucleophile such as water, benzoic acid, formic acid, etc. On the other hand inversion of the unactivated 24-hydroxy group may be achieved using well described Mitsunobu conditions. Liberation of the silyl ether and inverted C-24 acylated hydroxy (if carboxylic acids are used as the nucleophile) is accomplished using methods well known to those skilled in the art. Alternatively, inversion may be accomplished without protection of the 32-hydroxyl group if ascomycin, FK506, or similar compounds are treated with diethylaminosulfur trifluoride (DAST) in an inert solvent such as methylene chloride.

In-process (mmm), condensation of an alkyloxy or substituted alklyoxy carbonyl hydrazine with ascomycin, FK506, similar compounds, or a suitable derivative thereof wherein the C-22 is available as a reactive center, including but not limited to a carbonyl, is performed in an inert solvent such as methanol, ethanol, 2-propanol, etc., in the presence of a catalyst which may be an acid such as formic acid, p-toluenesulfonic acid, or camphorsulfonic acid.

In process (nnn), acylation at C-33 of 32-oxo-ascomycin or a suitable derivative thereof can be achieved, but is not limited to the process outlined in Danheiser, R. L.; Miller, R. F.; Brisbois, R. G.; Park, S. Z. *J. Org. Chem.* 1990, 55, 1959–1964.

In process (ooo), diazotization at C-33 of 32-oxo-ascomycin or a suitable derivative thereof can be achieved, but is not limited to the process outlined in Danheiser, R. L.; Miller, R. F.; Brisbois, R. G.; Park, S. Z. *J. Org. Chem.* 1990, 55, 1959–1964.

In process (ppp), L may be a hydroxyl group, or a good leaving group (halogen, tosylate, nitrobenzenesulfonate, mesylate or triflate, for example).

The condensation may be carried out in a solvent which does not adversely affect the reaction (e.g. isopropanol, acetonitrile, dioxane, N,N-dimethylformamide, tetrahydrofuran, etc.). The reaction may be carried out in the presence of base (e.g. triethylamine, 4-methylmorpholine or magnesium carbonate, etc.), at a temperature selected from 0° to 100° C. The appropriate thiazole containing compound may be prepared according to Hantzsch's synthesis described by: Katritzky, A. R.; Rees, C. W. "Comprehensive Heterocyclic Chemistry"; Pergamon Press: Oxford, 1984, Vol. 6, Part 4B, p. 294–299.

In process (qqq), L may be a hydroxyl group, or a good leaving group (halogen, tosylate, nitrobenzenesulfonate, mesylate or triflate, for example).

The condensation may be carried out in a solvent which does not adversely affect the reaction (e.g. isopropanol, t-butanol, acetonitrile, dioxane, N,N-dimethylformamide, tetrahydrofuran, etc.). The reaction may be carried out in the presence of base (e.g. triethylamine, 4-methylmorpholine, potassium carbonate or magnesium carbonate, etc.), at a temperature selected from 0° to 100° C.

Suitable amidines include formamidine, alkylamidines, arylamidines and alkylisoureas. Suitable guanidines include N-arylguanidines, N-acylated guanidines and N-sulfonylated guanidines.

In process (rrr), L may be a hydroxyl group, or a good leaving group (halogen, tosylate, nitrobenzenesulfonate, mesylate or triflate, for example).

The condensation may be carried out in a solvent which does not adversely affect the reaction (e.g. isopropanol, t-butanol, acetonitrile, dioxane, N,N-dimethylformamide, tetrahydrofuran, etc.). The reaction may be carried out in the presence of a base (e.g., triethylamine, 4-methylmorpholine, potassium carbonate or magnesium carbonate), at a temperature selected from 0° to 100° C.

The amides are primary amides such as formamide, alkylacylamides and arylacylamides.

In process (sss), the organometallic reagent may be a Grignard reagent, an alkyllithium, or an aryllithium reagents.

The selective addition may be carried out in a solvent which does not adversely affect the reaction (e.g., hexanes, ether, tetrahydrofuran, dimethoxyethane or 2-methoxyethyl ether). The reaction may be carried out in the presence of cerium (III) at a temperature selected from −100° C. to 0° C.

In process (ttt), the gamma amino alpha hydroxy carbonyl or a masked gamma amino alpha hydroxy carbonyl of a corresponding compound prepared by process (sss) may have substitutions (e.g. alkyl, aryl groups, etc.) at the alpha and/or beta positions. Furthermore, the amino group may have N-alkyl or aryl substitutions.

The condensation may be carried out in a solvent which does not adversely affect the reaction (e.g. isopropanol, t-butanol, acetonitrile, dioxane, N,N-dimethylformamide, tetrahydrofuran, etc.). The reaction may be carried out in the presence of a base (e.g. triethylamine, 4-methylmorpholine, potassium carbonate or magnesium carbonate, etc.), at a temperature selected from 0° to 100° C.

In process (uuu), the reaction is generally carried out in two steps: first the condensation of an alpha diketone or a masked alpha diketone with an 1,2-diaminoalkane gives a dihydropyrazine. Once the dihydropyrazine has been prepared, it may be oxidized by air in the presence of Pd/C, $PtO_2$ or other catalysts. Metal oxides (e.g. $MnO_2$ or CuO) may also be used for the aromatization.

The condensation and oxidation may be carried out in a solvent which does not adversely affect the reactions (e.g. isopropanol, acetonitrile, dioxane, benzene, toluene, etc.). The reaction may be carried out in the presence of drying agent such as magnesium sulfate or molecular sieves at a temperature selected from 0° C. to 100° C.

In process (vvv), a 1,5-dicarbonyl group or a masked 1,5-dicarbonyl group prepared by process (sss) may have substitutions (e.g. alkyl, aryl groups etc.) at the alpha and/or beta positions. The condensation may be carried out with anhydrous ammonia in a solvent which does not adversely affect the reactions (e.g. liquid ammonia, isopropanol, acetonitrile, dioxane, benzene, toluene, etc.). The reaction may be carried out at a temperature selected from –40° C. to 100° C.

In process (www), a 1,4-dicarbonyl group or a masked 1,4-dicarbonyl group prepared by process (sss) may have substitutions (e.g. alkyl, aryl groups, etc.) at the alpha position.

The condensation and oxidation may be carried out with anhydrous hydrazine in a solvent which does not adversely affect the reactions (e.g. isopropanol, acetonitrile, dioxane, benzene, toluene, etc.). The reaction may be carried out in the presence of a drying agent such as magnesium sulfate or molecular sieves at a temperature selected from 0° C. to 100° C.

In process (xxx), the thiocarbonate formation may be carried out in a solvent which does not adversely affect the reactions (e.g. toluene, acetone, methylene chloride, tetrahydrofuran or pyridine, etc.). The reaction may be carried out in the presence of a base such as triethylamine, pyridine, dimethylaminopyridine and sodium carbonate at a temperature selected from 0° C. to 100° C. The thiocarbonylating reagent may be N,N'-thiocarbonyldiimidazole, N,N'-thiocarbonylbis(2-pyridone), thiophosgene, or O-phenylthiochloroformate.

In process (yyy), the carbonate formation may be carried out in a solvent which does not adversely affect the reactions (e.g. toluene, acetone, butanone, methylene chloride, tetrahydrofuran or pyridine etc.). The reaction may be carried out in the presence of a base such as triethylamine, pyridine, dimethylaminopyridine and sodium carbonate at a temperature selected from 0° C. to 100° C.

The carbonylating reagent may be N,N'-carbonyldiimidazole, N,N'-carbonyl-bis(2-pyridone), phosgene, triphosgene, ethyl chloroformate, ethyl trichloroacetate, or o-phenylchloroformate.

In process (zzz), the cyclic phosphonate formation may be carried out by first reacting a diol from a selected compound with phosphorous trichloride followed by the addition of an appropriate alcohol and amine. The alcohol used may be an alkyl alcohol, or an aryl alcohol. The amine used may be primary or secondary. Alternatively, the cyclic phosphonate formation may be carried out by directly reacting the diol from a corresponding compound with an appropriate alkoxyphophoryl dichloride.

The phosphonate formation may be carried out in a solvent which does not adversely affect the reactions (e.g. carbon tetrachloride, chloroform, methylene chloride, toluene, tetrahydrofuran, etc.). The reaction may be carried out in the presence of a base such as triethylamine, pyridine, dimethylaminopyridine, and sodium carbonate at a temperature selected from 0° C. to 100° C.

In process (aaaa), the reduction of thiocarbonate may be carried out in a solvent which does not adversely affect the reactions (e.g., toluene or tetrahydrofuran) at a temperature selected from 0° C. to 100° C.

The reducing agent used may be trimethylphosphite, triethylphosphite, trialkylphosphite or tri-n-butyltin hydride.

In process (bbbb), the reduction of a 1,2-dicarbonyl group of a corresponding compound may be carried out in a solvent which does not adversely affect the reactions (e.g., methanol, ethanol, ethanol, pyridine or N,N-dimethylformamide).

The reducing agents used may be tin amalgam, aluminum amalgam with hydrogen chloride in ethanol, or may be hydrogen sulfide in pyridine or N,N-dimethylformamide.

In process (cccc), the reduction and condensation of a 2-(o-nitrophenyl)-1,3-diketone of a corresponding compound may be carried in a solvent which does not adversely affect the reactions (e.g. ethanol, tetrahydrofuran, ethyl acetate or benzene, etc.).

The reducing agents used may be hydrogen gas over Pd/C, or Pt/C, zinc dust with ammonium chloride, zinc dust with hydrochloric acid at a temperature selected from 0° C. to 100° C.

In process (dddd), triazole formation may be carried out using, but is not limited to an azide derivative with suitable acetylene analogues include diethylacetylene dicarboxylate, dimethylacetylene dicarboxylate, methyl cyanoacetylenecarboxylate, and the likes. The reaction may be conducted above, or below ambient temperature, more preferably from 0° to 50° C.

In process (eeee), pyrrole formation may be carried out using, but is not limited to amine compounds with 1,4-dicarbonyl analogues, such as acetonylacetone, and the likes. Suitable solvents include methanol, ethanol, n-propanol, isopropanol, acetonitrile and N,N-dimethylformamide. The reaction may be conducted above, or below ambient temperature, more preferably from 50° to 100° C.

In process (ffff), suitable reagents for vicinal hydroxylation include osmium tetraoxide, potassium permanganate, and iodine in conjunction with silver acetate. Osmium tetroxide is preferably used with a regenerating agent such as hydrogen peroxide, alkaline t-butyl hydroperoxide or N-methylmorpholine-N-oxide, and a solvent that does not adversely affect the reaction, for example diethyl ether or tetrahydrofuran. Potassium permanganate is preferably used in mild conditions, for example alkaline aqueous solution or suspensions. Co-solvents such as t-butanol or acetic acid may also be used. Iodine-silver acetate under 'wet' conditions yields ci-diols. Preferably, iodine is used in aqueous acetic acid in the presence of silver acetate. Iodine-silver acetate under 'dry' conditions yields trans-diols. Here, the initial reaction is carried out in the absence of water, and final hydrolysis yields the diol. In each case, the oxidation is preferably carried out at a temperature of 0° to 100° C.

Suitable reagents for the oxidative cleavage of the vicinal diol include lead tetraacetate, phenyliodoso acetate, periodic acid or sodium metaperiodate. Suitable solvents for the first two reagents include benzene and glacial acetic acid. The second two reagents are preferably used in aqueous solution. The reaction is preferably carried out at a temperature of 0° to 100° C.

In process (gggg), suitable reagents for the oxidation of an aldehyde of the corresponding compound may include silver oxide, chromic acid and potassium permanganate. In the presence of a variety of catalysts, oxygen may also be used in converting an aldehyde to a carboxylic acid of a corresponding compound. The catalysts may be palladium or platinum oxide. The air oxidation may be carried out in a solvent which does not adversely affect the reaction (e.g., ethanol, water, acetonitrile, aqueous acetone or pyridine) at a temperature of 0° to 100° C.

In process (hhhh), esters of a corresponding carboxylic acid may be prepared under neutral conditions at room temperature by the reaction of the carboxylic acid with alcohols in the presence of molar amounts of activating reagents such as triphenyl phosphine and diethyl azodicarboxylate, carbodiimides, N,N'-carbonyldiimidazole and 1-methyl-2-halopyridinium iodide. Esters may also be formed by reacting the corresponding carboxylic acid with diazoalkanes in a solvent which does not adversely affect the reaction (e.g., ether, tetrahydrofuran or methylene chloride) at a temperature of from 0° to 100° C.

In process (iiii), the cyclopropanation of the allyl group of a corresponding compound may be carried out with diazoalkanes in a solvent which does not adversely affect the reaction (e.g., ether, methylene chloride or tetrahydrofuran) in the presence of a catalyst such as palladium (II) acetate. The temperature of the reaction is of −15° to 5° C.

In process (jjjj), a pyrrole ring may be produced by reacting a 1,4-dicarbonyl group of a corresponding compound with ammonia, or a substituted amine such as benzylamine or 2-aminoethanol. Suitable solvents include those which do not adversely affect the reaction (e.g., methylene chloride, tetrahydrofuran or dioxane). The reaction is preferably carried out at a temperature of 0° to 100° C.

In process (kkkk), the cyclization of a 1,4-dicarbonyl group of a corresponding compound may be carried out in the presence of a catalytic amount of acid (e.g., acetic acid or arylsulfonic acid). The reaction may be carried out in a solvent which does not adversely affect the reaction (e.g., methylene chloride, ether, benzene or toluene). The reaction is preferably carried out at a temperature of 0° to 60° C.

In process (llll), suitable reagents include air, a palladium (II) halide (e.g. palladium (II) chloride), in conjunction with a cuprous halide (e.g. cupper (I) chloride). Suitable solvents include those that do not adversely affect the reaction (e.g. DMF and water). The reaction is preferably carried out at a temperature of 0° to 100° C.

In process (mmmm), the ketone of the alpha-methoxy cyclohexanone in a corresponding compound may be first converted to its oxime derivative with hydroxylamine. The derivatization is preferably carried out in a solvent which does not adversely affect the reaction (e.g., ethanol, isopropanol or tetrahydrofuran) at a temperature of 0° to 100° C.

The hydroxyl group of the oxime (=N—OH) may then be converted to a good leaving group (=N—OL) by reacting with an alkylsulfonyl chloride (e.g., methanesulfonyl chloride or trifluoromethanesulfonyl chloride), an arylsulfonyl chloride (e.g., bezenesulfonyl chloride or toluenesulfonyl chloride), a carboxylic acid anhydride (e.g., trifluoroacetic anhydride), phosphorous pentachloride, thionyl chloride or N-methyl 2-fluoropyridinium iodide. The activation of oxime is preferably carried out in a solvent that does not adversely affect the reaction (e.g., tetrahydrofuran or methylene chloride) at a temperature of −20° to 50° C.

The activated oxime of a corresponding compound may then be fragmented in a protic solvent such as ethanol or lower alkyl alcohol at a temperature of 0° to 100° C.

Alternatively, in process (mmmm), the Beckmann fragmentation may be carried out by reacting the alpha-methoxycyclohexanone directly with an o-alkylsulfonyl hydroxylamine or an o-arylsulfonyl hydroxylamine. The reaction may be carried out in a protic solvent (e.g., ethanol, propanol or benzyl alcohol) at a temperature of 0° to 100° C.

In process (nnnn), suitable reducing agents include but are not limited to sodium cyanoborohydride, lithium aluminum hydride, borane-pyridine, or hydrogen in the presence of such catalysts as Raney nickel, platinum, platinum oxide, or palladium. An acidic environment may promote the reduction in some cases, and acids such as hydrochloric acid or p-toluenesulfonic acid may be added for this purpose. The reduction may be carried out in a solvent which does not adversely affect the reaction (e.g. ethanol, ethyl acetate).

In process (oooo), reduction of an oxime to the corresponding amine may be accomplished with but not limited to hydrogenation with a suitable catalyst such as palladium on carbon in a solvent inert to the reaction conditions (e.g. ethanol) at temperatures ranging from 0° to 100° C.

In process (pppp), reduction of an enone to the corresponding saturated ketone may be accomplished with but not limited to hydrogenation with a suitable catalyst such as either palladium on carbon or rhodium on alumina in a solvent inert to the reaction conditions (e.g. methanol, ethanol, isopropanol, ethyl acetate) in a temperature range from −78° to 100° C.

In process (qqqq), isoxazoline formation is accomplished by but not limited to the following sets of reaction conditions involving a beta-hydroxy oxime. One possible method is to treat the beta-hydroxy oxime with Martin's sulfurane dehydrating reagent at or near room temperature in a solvent inert to the reaction conditions such as methylene chloride. Alternatively, the beta-hydroxy oxime may be treated with p-toluenesulfonyl chloride in a solvent such as pyridine at temperatures ranging from 0° to 100° C.

In process (rrrr), an intramolecular aldol reaction is may be accomplished by but is not limited to treatment of a carbonyl with a base such as potassium or sodium hydride in a solvent which is inert to the reaction conditions (e.g. tetrahydrofuran or N,N-dimethylformamide) at a temperature range from −78° to 150° C.

In process (ssss), a cyclic imine may be formed by but is not limited to treatment of an alpha,beta-unsaturated enone with the sodium enolate of a glycine ester imine in an inert solvent such as tetrahydrofuran in a temperature range from −78° to 100° C. Upon aqueous workup, the imine hydrolyzes and spontaneously cyclizes to form the cyclic imine.

In process (tttt), a substituted pyrrole may be formed by but is not limited to a 1,3-dipolar cycloaddition between an alpha,beta-unsaturated enone with a glycine ester imine in the presence of a suitable catalyst such as lithium bromide and triethylamine in a solvent inert to the reaction conditions (e.g. tetrahydrofuran) at or near room temperature.

In process (uuuu), alpha diazoketones can be decomposed by exposure to UV light or by heating. Wolff rearrangements often ensue yielding beta-keto carboxylic acids when run in a solvent mixture containing water, beta-keto esters when run in a solvent containing an alcohol, or beta-keto amides when run in a solvent containing ammonia, a primary or a secondary amine. Moreover [process (vvvv)], if a beta-keto carboxylic acid is formed, decarboxylation can occur spontaneously or by heating 0° to 100° C.

In process (xxxx), carbamate formations may be carried out by reacting CH—OH group with appropriate isocynates, or an appropriate compound containing an amino functional group derivative activated with N,N-carbonyldiimidazole, N,N-carbonyl-bis-(N-methylimidazole triflate), phosgene, diphosgene or triphosgene in the presence of a tert-amine. Alternatively, the CH—OH group may be activated with N,N-carbonyldiimidazole, phosgene, diphosgene or triphosgene in the presence of a tert-amine. The activated CH—OH group derivative may then reacted with appropriate amino-containing compound to produce the carbamate. The carbamate formation may be carried out in a solvent which does not adversely affect the reaction (e.g. acetone, toluene, dichloromethane, tetrahydrofuran, N,N-dimethylformamide, etc. or a mixture thereof). The reaction may be conducted above, at, or below room temperature. The literature for the preparation of carbamates may be found in volume 3 of *The Peptides*, Gross, E. and Meinhofer, J. Academic Press, 1981 and *Protective Groups in Organic Synthesis*, 2nd Ed., Greene, T. W. John Wiley & Sons, New York, P. 315, 1991.

In process (yyyy), aryl-, heterocyclic-, or alkyloxycarbonylation may be carried out using aryl-, heterocyclic-, or alkyl- chloroformate in the presence of amines like triethylamine, diisopropylethylamine, pyridine and the like. Alternatively, the reaction may be carried out by reacting the corresponding aryl-OH, heterocyclic-OH or alkyl-OH with —CHOC(O)Cl or —CHOC(O)—(p-nitrophenyl) in a corresponding compound in the presence of amine base. The reaction may be carried out in a solvent which does not adversely affect the reaction (e.g. acetone, dichloromethane, tetrahydrofuran, pyridine and N,N-dimethylformamide, or a mixture thereof). The reaction may be conducted above, at or below ambient temperature.

In process (zzzz) allylic oxidations may be carried out using selenium dioxide with or without a co-oxidant, such as tert-butyl hydroperoxide, in an inert solvent such as tetrahydrofuran, ether, ethylacetate, water, or a combination thereof. The reaction may be conducted at room temperature to 100° C.

The compounds, processes and uses of the present invention will be better understood in connection with the following examples, which are intended as an illustration of and certainly not a limitation upon the scope of the invention. Both below and throughout the specification, it is intended that citations to the literature are expressly incorporated by reference.

EXAMPLE 1a AND 1b

Formula I: R=ethyl; R'=R2=R3=H; n=1; $R^{1'}$=OCH$_3$; $R^1$=trifluoromethylsulfonyl (R Configuration) and Formula I: R=ethyl; R'=R2=R3=H; n=1; $R^1$=N$_3$ (S Configuration).

EXAMPLE 1a:

Ascomycin (4.748 g, 6 mmol) was dissolved in 60 mL of methylene chloride at 0° C. Pyridine (4.85 mL, 60 mmol), followed by trifluoromethanesulfonic acid anhydride (1.514 mL, 9 mmol) were carefully added to the reaction mixture. It was stirred at 0° C. for 10 min and allowed to warm to room temperature. After stirring for 2 hours, 40 mL of cold 10%-NaHCO$_3$ aqueous solution was carefully added to the cooled reaction mixture. Ethyl acetate (50 mL×3) was added to extract the compound. The combined organic layers were washed with brine, 10%-NaHCO$_3$, brine, 10%-KHSO$_4$, brine and dried over anhydrous magnesium sulfate. After the solvent was removed, the C32-triflate was obtained in quantitative yield.

EXAMPLE 1b:

Formula I: R=ethyl; R'=R2=R3=H; n=1; $R^1$=N$_3$ (S Configuration). Example 1a was dissolved in 40 mL of chloroform, and a chloroform solution containing n-tetrabutylammonium azide (14 mmol) (Hendrickson, J. B.; Judelson, D. A.; Chancellor, T. *Synthesis* 1984, 321) was added to the mixture and stirred at room temperature for 30 min. The solvent was removed, and the crude product was purified by silica gel column chromatography, eluting with 0.5%-methanol in chloroform to yield 2.043 g of the title compound. A small amount (100 mg) was purified further by recrystallization (3 mL of ether-8 mL of n-hexane) to yield 61.8 mg for characterization: mp. 153°–154° C.; MS (FAB) m/z: M+K=855; IR(KBr) 3490–3420, 2960, 2940, 2880, 2830, 2090, 1740, 1720, 1700, 1650, 1455, 1380, 1360, 1350, 1325, 1285, 1270, 1200, 1174, 1160, 1145, 1105, 1090, 1040, 1010 cm$^{-1}$.

EXAMPLE 2

Formula I: R=ethyl; R'=R2=R3=H; n=1; $R^{1'}$=OCH$_3$; $R^1$=NH$_2$ (S Configuration).

The product of Example 1b (1.632 g, 2 mmol) was dissolved in 40 mL of methanol:ethyl acetate (1:1). Lindlar catalyst (palladium on calcium carbonate poisoned with lead)(816 mg) was added. It was hydrogenated at 1 hydrogen atmosphere for 4 days. The catalyst was removed by filtration, more Lindlar catalyst (8 16 mg) was added, and hydrogenation was carried out for one more day at which time TLC analysis showed complete reaction. The catalyst was filtered over diatomaceous earth, and the filtrate was then evaporated to dryness to yield 1.560 g of the title compound. The product (200 mg) was recrystallized from ethyl acetate (0.75 mL) in n-hexane (1 mL) and ether (7 mL) for characterization. Yield: 138.4 mg, mp.141°–143° C.; MS (FAB) m/z: M+K=829; IR(KBr) 3440, 2960, 2940, 2880, 2830, 1740, 1705, 1645, 1500, 1455, 1450, 1380, 1350, 1325, 1280, 1245, 1200, 1170, 1140, 1100, 1040, 1015 cm$^{-1}$.

EXAMPLE 3

Formula I: R=ethyl; R'=R2=R3=H; n=1; $R^{1'}$=OCH$_3$; $R^1$=CH$_3$C(O)S (S Configuration).

The product of Example 1a (923 mg, 1 mmol) was dissolved in 3 mL of N,N-dimethylformamide (DMF), potassium thioacetate (571 mg, 5 mmol) was added, and the reaction was stirred at room temperature for 5 hours. Ethyl acetate (30 mL) was added to the reaction mixture, and the organic layer was washed with brine, 10%-NaHCO$_3$, brine, 10%-KHSO$_4$ and brine, and then dried over magnesium sulfate. Evaporation of the solvent gave 837 mg of crude product. This was purified twice by silica gel column chromatography, eluting with 0.5%-methanol in chloroform. Yield: 165 mg. MS (FAB) m/z: M+K=888; IR(KBr) 3440, 2960, 2930, 2880, 2820, 1740, 1690, 1645, 1455, 1450, 1380, 1355, 1325, 1280, 1245, 1195, 1170, 1160, 1140, 1105, 1035, 1020, 1010 cm$^{-1}$.

EXAMPLE 4

Formula I: R=ethyl; R'=R2=R3=H; n=1; $R^{1'}$=OCH$_3$; $R^1$=CH$_3$C(O)NH (S Configuration).

The resultant product from Example 2 (250 mg, 0.32 mmol) in 3 mL of pyridine at 0° C. was treated with acetyl chloride (27 mL, 0.38 mmol), and the mixture was stirred at 0° C. for 30 minutes and at room temperature overnight. Ethyl acetate (25 mL) was added, and the organic layer was washed with 10%-KHSO$_4$, brine, 10%-NaHCO$_3$, brine, and then dried over magnesium sulfate. The crude product (234 mg) obtained was purified by silica gel column chromatography, eluting with 0.5–1.5% methanol in chloroform. Yield: 68.7 mg. MS (FAB) m/z: M+K=871; IR(KBr) 3430, 2960, 2940, 2870, 2820, 1735, 1705, 1645, 1520, 1450, 1375, 1350, 1320, 1280, 1260, 1245, 1195, 1170, 1160, 1135, 1100, 1085, 1035, 1020 cm$^{-1}$.

EXAMPLE 5

Formula I: R=ethyl; R'=R2=R3=H; n=1; R$^{1'}$=OCH$_3$; R$^1$=C$_6$H$_5$C(O)NH (S Configuration).

The resultant product from Example 2 (250 mg, 0.32 mmol) was treated in the same fashion as mentioned in Example 4, except benzoyl chloride (44.1 mL, 0.30 mmol) was employed instead of acetyl chloride. After silica gel column chromatography, a white powder was obtained. Yield: 46.0 mg. MS (FAB) m/z: M+K=933; IR(KBr) 3440, 2960, 2940, 2880, 2830, 1740, 1720, 1705, 1645, 1575, 1515, 1480, 1450, 1445, 1375, 1360, 1345, 1320, 1280, 1260, 1245, 1195, 1170, 1160, 1140, 1100, 1090, 1035, 1020, 1010 cm$^{-1}$.

EXAMPLE 6

Formula I: R=ethyl; R'=R2=R3=H; n=1; R$^{1'}$=OCH$_3$; R$^1$=C$_6$H$_5$S(O)$_2$NH (S Configuration).

The resultant product from Example 2 (250 mg, 0.32 mmol) was treated in the same fashion as mentioned in Example 4, except benzenesulfonyl chloride (48.5 mL, 0.30 mmol) was employed instead of acetyl chloride. Yield: 84.6 mg. MS (FAB) m/z: M+K=969; IR(KBr) 3440, 2960, 2940, 2870, 2820, 1740, 1700, 1645, 1450, 1445, 1375, 1335, 1325, 1305, 1290, 1260, 1245, 1195, 1160, 1140, 1100, 1090, 1080, 1035, 1020, 1005 cm$^{-1}$.

EXAMPLE 7

Formula III: R=ethyl; R'=R2=R3=H; n=1; R$^{31}$=H; R$^{32}$=H; R$^{33}$=OH; R$^{34}$=H; R$^{35}$ and R$^{36}$ taken together form an oxime, =NR$^{38}$ where R$^{38}$=hydroxyl.

Ascomycin (1.187 g, 1.5 mmol) was dissolved in 30 mL of ethanol. After pyridine (1.215 mL, 15 mmol) and hydroxylamine hydrochloride (1.043 g, 15 mmol) were added to the reaction mixture, it was gently refluxed for 4 hours. Ethanol was removed by evaporation, and 50 mL of chloroform was added to the residue. The chloroform layer was washed with water, 10%-KHSO$_4$, water and dried over anhydrous magnesium sulfate. Evaporation to dryness yielded 1.175 g of the title compound. This was recrystallized from ethyl acetate (8 mL)-hexane (25 mL) to obtain 889 mg. MS (FAB) m/z: M+K=845, M+H=807; IR(KBr) 3440, 2950, 2920, 2870, 2820, 1740, 1705, 1645, 1450, 1375, 1350, 1330, 1280, 1260, 1230, 1195, 1170, 1160, 1100, 1090, 1045, 1035, 1010 cm$^{-1}$.

EXAMPLES 8a AND 8b

Formula I: R=ethyl; R'=R2=R3=H; n=1; R$^{1'}$=OCH$_3$; R$^1$=tert-butyldimethylsilyloxy (R Configuration) and Formula V: R=ethyl; R=ethyl; R'=R2=R3=H; n=1; R$^{1'}$=OCH$_3$; R$^1$=tert-butyldimethylsilyloxy; R$^{31}$=H; R$^{32}$=H; R$^{33}$ and R$^{34}$ taken together form an oxo group; R$^{35}$ and R$^{36}$ taken together form an oxo group.

EXAMPLE 8a:

Ascomycin (1.582 g, 2 mmol) was dissolved in 30 mL of methylene chloride, and tert-butyldimethylsilyl chloride (362 mg, 2.4 mmol) and imidazole (272 mg, 4 mmol) were added. It was then stirred at room temperature for 4 days. Saturated aqueous ammonium chloride solution (20 mL) was added, and the product was extracted with ethyl acetate (25 mL×3). The ethyl acetate layers were combined, washed with brine, dried over anhydrous magnesium sulfate, filtered and evaporated to dryness to yield 2.11 g of title compound.

EXAMPLE 8b:

To a −78° C. solution of oxalyl chloride (96 mL, 1.1 mmol) in 5 mL of methylene chloride was added a solution of dimethylsulfoxide (156 mL, 2.2 mmol) in 4 mL of methylene chloride and the mixture was stirred at −78° C. After 30 min a solution of example 8a (453 mg, 0.5 mmol) in 5 mL of methylene chloride was added. The reaction was carried out at −78° C. for 1.5 hours with stirring and then triethylamine (696.9 mL, 5 mmol) was added. After stirring at −78° C. for 5 min, the mixture was then allowed to stand at room temperature for 30 min. The reaction mixture was partitioned between 40 mL of ethylacetate and 10 mL of 10%-KHSO$_4$ solution. The separated organic layer was washed with 10%-KHSO$_4$ (3×), brine, and dried over anhydrous magnesium sulfate. Evaporation of the solvent gave 438 mg of the crude title compound. This was purified by silica gel column chromatography, eluting with 2.5% ethyl acetate in chloroform. Yield: 225.8 mg. MS (FAB) m/z: M+K=942; IR(KBr) 3500, 3440, 2950, 2935, 2880, 2860, 2820, 1740, 1720, 1650, 1630, 1580, 1460,1445, 1380, 1360, 1325, 1280, 1250, 1220, 1195, 1170, 1135, 1105, 1090, 1040, 1030, 1005 cm$^{-1}$.

EXAMPLE 9

Formula I: R=ethyl; R'=R2=R3=H; n=1; R$^{1'}$=OCH$_3$; R$^1$=iodo (S Configuration).

Ascomycin (3.164 g, 4 mmol) was dissolved in 20 mL of N,N-dimethylformamide (DMF), and methyltriphenoxyphosphonium iodide (2.713 g, 6 mmol) was added. The reaction was carried out under a nitrogen atmosphere at room temperature for 4 days. Approximately 100 mL of ethyl acetate was added to the reaction, and the organic mixture, was washed with brine, water, brine, and dried over anhydrous magnesium sulfate. After filtration, the filtrate was evaporated to dryness, and the crude product obtained was purified by silica gel column chromatography, eluting with 10%-ethyl acetate in chloroform. Yield: 1.86 g. MS (FAB) m/z: M+K=940; IR(KBr) 3500, 2960, 2940, 2870, 2820, 1740, 1720, 1690, 1670, 1650, 1620, 1500, 1490, 1450, 1440, 1405, 1385, 1360, 1350, 1320, 1280, 1250, 1205, 1195, 1170, 1155, 1140, 1100, 1090, 1070, 1035, 1000 cm$^{-1}$.

EXAMPLE 10

Formula VII: R=ethyl; R'=R2=R3=H; n=1; R$^{1'}$=OCH$_3$; R$^1$=iodo; R$^{21}$ and R$^{22}$ taken together form an oxo group; R$^{23}$=iodo; R$^{24}$=iodo; R$^{24}$=H; R$^{31}$ and R$^{33}$ taken together form a bond; R$^{32}$=H; R$^{34}$=H; R$^{35}$ and R$^{36}$ taken together form an oxo group.

The title compound was isolated as a by-product from the reaction described in Example 9. Yield: 166 mg. MS (FAB) m/z: M+K=1030, M−I=866; IR(KBr) 3420, 2980, 2930, 2870, 2820, 1740, 1690, 1645, 1625, 1590, 1485, 1450, 1380, 1360, 1345, 1320, 1280, 1260, 1245, 1210, 1190, 1170, 1140, 1100, 1090, 1075, 1020, 1010 cm$^{-1}$.

EXAMPLE 11

Formula I: R=ethyl; R'=R$^2$=R$^3$=H; n=1; R$^{1'}$OCH$_3$; R$^1$=C$_6$H$_5$OC(S)O (R Configuration).

Ascomycin (988.8 mg, 1.25 mmol) was dissolved in 10 mL of methylene chloride in an ice bath. Pyridine (404 uL, 5 mmol) followed by phenoxythiocarbonyl chloride (190 uL, 1.375 mmol) were added. The mixture was stirred at 0° C. for 5 min and allowed to stir at room temperature for 24 hours. Additional pyridine (404 uL, 5 mmol) and phenoxythiocarbonyl chloride (190 uL, 1.375 mmol) were added, and stirring was continued for 4 hours. Solvents were evaporated and 40 mL of ethyl acetate was added to the residue. The ethyl acetate layer was washed with 10%-KHSO4 (3×), brine, and dried over anhydrous magnesium sulfate. Evaporation of the solvent gave 1.400 g of crude product which was purified by silica gel column chromatography, eluting with 5%-ethyl acetate in chloroform. The title compound (730 mg) was obtained. MS (FAB) m/z: M+K=966; IR(KBr) 3420, 2980, 2930, 2870, 2825, 1740, 1705, 1645, 1630, 1590, 1490, 1450, 1375, 1365, 1320, 1280, 1260, 1230, 1200, 1175, 1140, 1100, 1090, 1080, 1035, 1020, 1005 cm$^{-1}$.

EXAMPLE 12

Formula III: R=ethyl; R'=R2=R3=H; n=1; $R^{31}$=H; $R^{32}$=H; $R^{33}$ and $R^{34}$ taken to ether form an oxo group; $R^{35}$ and $R^{36}$ taken together form an oxo group.

To a solution of acetonitrile (5 mL) and 48% hydrofluoric acid (100 uL) was added Example 8b (530 mg, 0.586 mmol) in acetonitrile (7 mL) dropwise, and the mixture was stirred at room temperature for 35 min. Ethyl acetate (60 mL) was added to the reaction mixture, and the organic layer was washed with brine, 10%-NaHCO$_3$, brine, and dried over anhydrous magnesium sulfate. Evaporation of the solvent gave 515 mg of crude title compound which was purified by silica gel column chromatography, eluting with 1%-methanol in chloroform. 304.8 mg of pure compound was obtained. MS (FAB) m/z: M+K=828; IR(KBr) 3420, 2960, 2930, 2870, 2820, 1740, 1720, 1645, 1620, 1580, 1450, 1380, 1345, 1325, 1280, 1260, 1245, 1220, 1195, 1170, 1140, 1115, 1100, 1090, 1050, 1035, 1010 cm$^{-1}$.

EXAMPLE 13

Formula V: R=ethyl; R'=R2=R3=H; n=1; $R^{1'}$=OCH$_3$; $R^1$=C$_6$H$_5$OC(S)O; $R^{31}$H; $R^{32}$=H; $R^{33}$=C$_6$H$_5$OC(S)O; $R^{34}$=H; $R^{35}$ and $R^{36}$ taken together form an oxo group.

The title compound (460 mg) was isolated from the reaction described in Example 11 as a minor product. MS (FAB) m/z: M+K=1103; IR(KBr) 3420, 2980, 2930, 2870, 2820, 1740, 1710, 1645, 1620, 1590, 1490, 1450, 1380, 1365, 1320, 1280, 1260, 1210, 1200, 1140, 1100, 1070, 1035, 1015, 1000 cm$^{-1}$.

EXAMPLE 14a

Formula V: R=ethyl; R'=R2=R3=H; n=1; $R^{1'}$=OCH$_3$; $R^{2a}$=H; $R^{2a'}$=H; $R^{3a}$ and $R^4$ taken together form an oxo group; $R^{31}$=H; $R^{32}$=H; $R^{33}$ and $R^{34}$ taken together form an oxo group; $R^{35}$ and $R^{36}$ taken together form an oxo group.

To a solution of oxalyl chloride (240 uL, 2.75 mmol), in methylene chloride (7 mL) was added dimethylsulfoxide (390 uL, 5.5 mmol) over 5 min at −78° C. The reaction mixture was aged for 30 min at −78° C. Ascomycin (988.8 mg, 1.25 mmol) in methylene chloride (8 mL) was added dropwise and stirred at −78° C. for 1.5 hours. Triethylamine (1.74 mL, 12.5 mmol) was carefully added and the mixture was stirred at −78° C. for an additional 5 min. It was then allowed to warm to room temperature for 30 min. Ethyl acetate (80 mL) was added to the reaction mixture, and the organic layer was washed with brine, 10%-KHSO$_4$, brine, 10%-NaHCO$_3$, brine and dried over anhydrous magnesium sulfate. Evaporation of the solvent yielded 920 mg of crude product. This was purified by silica gel column chromatography, eluting with 7%-ethyl acetate in chloroform. 648 mg of pure title compound was obtained. MS (FAB) m/z: M+K=826, M+H=788, M+H−H$_2$O=770; IR(KBr) 3420, 2960, 2930, 2870, 2820, 1725, 1645, 1625, 1450, 1380, 1340, 1325, 1280, 1260, 1245, 1220, 1195, 1170, 1130, 1115, 1100, 1090, 1040 cm$^{-1}$.

EXAMPLE 14b

Formula I: R=ethyl; R'=R2=R3=H; n=1; $R^{1'}$=OCH$_3$; $R^{2a}$=H; $R^{2a'}$=H; $R^{3a}$ and $R^4$ taken together form an oxo group.

(146 mg) was also isolated as a minor product from the above reaction. MS (FAB) m/z: M+K=828, IR(KBr) 3420, 2960; 2930, 2880, 2820, 1725, 1710, 1645, 1450, 1375, 1340, 1325, 1280, 1260, 1245, 1225, 1195, 1170, 1130, 1100, 1090, 1035. This compound was also produced by the procedure described in Example 48.

EXAMPLE 15

Formula VI: R=ethyl; R'=R2=R3=H; n=1; $R^{21}$ and $R^{22}$ taken together form an oxime, =NR$^{38}$ where R$^{38}$=hydroxyl; $R^{23}$=OH; $R^{24}$=H; $R^{31}$=H; $R^{32}$=H; $R^{33}$=OH; $R^{34}$=H; $R^{35}$ and $R^{36}$ taken together form an oxime, =NR$^{38}$ where R$^{38}$=hydroxyl.

To a solution of ascomycin (4.748 g, 6 mmol) in ethanol (70 mL) were added hydroxylamine hydrochloride (4.172 g, 60 mmol) and pyridine (4.86 mL, 60 mmol). The mixture was then gently refluxed for 4 hours and kept at room temperature overnight with stirring. After treating the mixture as described in Example 7, the crude material (4.85 g) obtained was purified by silica gel column chromatography, eluting with 1.5% to 4%-methanol in chloroform. 184 mg of pure title compound was isolated. MS (FAB) m/z: M+K= 860, M+H=822; IR(KBr) 3420, 2960, 2930, 2870, 2820, 1745, 1640, 1450, 1390, 1375, 1350, 1325, 1280, 1265, 1220, 1195, 1170, 1160, 1140, 1100, 1090, 1050, 1040, 1015 cm$^{-1}$.

EXAMPLE 16

Formula I: R=ethyl; R'=R2=R3=H; n=1; $R^{1'}$=OCH$_3$; $R^1$=H.

The title compound is prepared according to general literature procedures (Taylor, E. C.; Hawks, III, G. H.; McKillop, A. *J. Am. Chem. Soc.* 1968, 90, 2421; Corey, E. J.; Sachdev, H. S. *J. Am. Chem. Soc.* 1973, 95, 8483). To a solution of the product of Example 8b (1 mmol) in dry tetrahydrofuran is added thallous ethoxide (1 mmol) with stirring at 0° C. The mixture is stirred at room temperature for 30 min, and the solvent is removed to a yield powder which is dissolved in benzene, and to which benzylbromide (1 mmol) is added. The mixture is heated under reflux with stirring for several hours (until the reaction is judged to be complete by TLC analysis), cooled, and filtered. The filtrate is passed through a short column of Florisil to remove traces of thallium (I) bromide, concentrated, and purified on silica gel column chromatography to give the desired compound.

EXAMPLE 17

Formula V: R=ethyl; R'=R2=R3=H; n=1; $R^{1'}$=OCH$_3$; $R^1$=tert-butyldimethylsilyloxy; $R^{31}$=bromo; $R^{32}$=bromo; $R^{33}$ and $R^{34}$ taken together form an oxo group; $R^{35}$ and $R^{36}$ taken together form an oxo group.

The title compound is prepared by applying a general method described in the literature (Heffner, R.; Safaryn, J. E.; Joulie, M. M. *Tetrahedron Lett.* 1987, 28, 6539). A solution of bromine in dioxane is added dropwise to a solution of Example 8b in dioxane under irradiation with a sun lamp (150 watts, 120–125 Volt Duro Lite). After 2 hours of irradiation, ethyl acetate is added to the reaction mixture. The ethyl acetate layer is washed with brine, dried, evaporated, and purified by silica gel column chromatography to afford pure title compound.

EXAMPLE 18

Formula V: R=ethyl; R'=R2=R3=H; n=1; $R^{1'}$=OCH$_3$; $R^1$=tert-butyldimethylsilyloxy; one of $R^{31}$ and $R^{32}$ is OH; $R^{33}$ and $R^{34}$ taken together form an oxo group; $R^{35}$ and $R^{36}$ taken together form an oxo group.

The title compound is prepared by applying a general method described in the literature (Anderson, J. C.; Smith, S. C. *SYNLETT* 1990, 2, 107). A solution of lithio diisopropylamide in anhydrous tetrahydrofuran (THF) is added dropwise to a solution of Example 8b in THF at –78° C. under nitrogen atmosphere. The mixture is stirred at –78° C. for 30 min, then oxodiperoxymolybdenum(pyridine)-1,3-dimethyl-3,4,5,6-tetrahydro-2(1H)-pyrimidinone is added all at once. The mixture is stirred for an additional 30 min at –78° C., neutralized with 10% ammonium chloride and extracted with ethyl acetate. The ethyl acetate layer is washed with brine, dried, evaporated, and purified by silica gel column chromatography to afford pure title compound.

EXAMPLE 19

Formula II: R=ethyl; R'=R2=R3=H; n=1; $R^{21}$ and $R^{22}$ taken together form an oxo group; $R^{23}$=chloro; $R^{24}$=H.

To a suspension of thionyl chloride (260 uL, 3.52 mmol) and pyridine (400 uL, 4.9 mmol) in 20 mL of diethyether in an ice bath was added Example 54 (2.0, 1.96 mmol) in 50 mL of diethylether in periods of 10–15 min. It was stirred at 0° C. for 0.5 hours and evaporated to dryness. Ethyl acetate (50 mL) was added to the reaction mixture, and the organic layer was washed with brine (30 mL×3). It was then dried over anhydrous magnesium sulfate. Evaporation of the solvent gave 2.14 g of crude product which was dissolved in 60 mL of acetonitrile and 48%-hydrogen fluoride aqueous solution (300 uL) was added. It was then stirred at room temperature for 0.5 hours. The reaction was partitioned between ethyl acetate (60 mL) and 10%-sodium bicarbonate (20 mL), and the aqueous layer was washed with ethyl acetate (30 mL). The combined organic layers were washed with brine (30 mL×3) and dried over anhydrous magnesium sulfate. Evaporation of the solvent gave 1.70 g of crude product which was purified by silica gel (1t30 g) column chromatography, first eluting with 15%-acetone in hexane, followed by 30%-acetone-hexane. 290 mg of pure title compound was isolated.

MS (FAB) m/z: M+K=848. mp. 119°–120° C.

EXAMPLE 20

Formula V: R=ethyl; R'=R2=R3=H; n=1; $R^{1'}$=OCH$_3$; $R^{3a}$ and $R^4$ taken together form an oxo group; $R^{2a}$=H, $R^{2a'}$=H; $R^{31}$ and $R^{32}$ taken together form a diazo group; $R^{33}$ and $R^{34}$ taken together form an oxo group; $R^{35}$ and $R^{36}$ taken together form an oxo group.

The title compound was prepared by the method described in R. L. Danheiser, R. F. Miller, R. G. Brisbois, S. Z. Park *J. Org. Chem.* 1990, 55, 1959–1964. Accordingly Example 14a (1.0 mmol) in acetonitrile (20 mL) containing water (18 uL), triethylamine (0.21 mL, 1.5 mmol), and methanesulfonyl azide (0.28 mL, 3.0 mmol) was stirred at ambient temperature for 6 hours, whereupon the volatiles were removed in vacuo. The residue was purified by chromatography on silica gel eluting with a mixture of hexanes and acetone (4:1) which provided the desired product (610 mg) in 75% yield. MS (FAB) m/z: M+K–N$_2$=824. IR (CDCl$_3$) 2115 cm$^{-1}$.

EXAMPLE 21

Formula V: R=ethyl; R'=R2=R3=H; n=1; $R^{1'}$=OCH$_3$; $R^1$=tert-butyldimethylsilyloxy; $R^{31}$ and $R^{32}$ taken together form an methylene group; $R^{33}$ and $R^{34}$ taken together form an oxo group; $R^{35}$ and $R^{36}$ taken together form an oxo group.

The title compound is prepared by applying a general method described in the literature. To a stirred suspension of zinc in anhydrous tetrahydrofuran (THF) is added methylenediiodide at 25° C. under an argon atmosphere. After 30 min, a THF solution of Ti(OiPr)$_4$ is added. The resulting mixture is stirred at 25° C. for 30 min. A solution of Example 8b in THF is then added. After being stirred for 3 hours, the mixture is diluted with ethyl acetate, acidified, and extracted with ethyl acetate. The organic extracts are washed with brine, dried, and concentrated. The residue is then purified by silica gel column chromatography to yield pure title compound.

EXAMPLE 22

Formula V: R=ethyl; R'=R2=R3=H; n=1; $R^{1'}$=OCH$_3$; $R^1$=tert-butyldimethylsilyloxy; taken together with one of $R^{31}$ and $R^{32}$, one of $R^{33}$ and $R^{34}$ form a bond; one of $R^{31}$ and $R^{32}$ is H; one of $R^{33}$ and $R^{34}$ is CH$_3$C(O)O; $R^{35}$ and $R^{36}$ taken together form an oxo group.

The title compound is prepared by applying a general method described in the literature (Lakhvich, F. A.; Khlebnicova, T. S.; Akhrem, A. A. *Synthesis* 1985, 784. Akhrem, A. A.; Lakhvich, F. A.; Budai, S. I.; Khlebnicova, T. S.; Petrusevich, I. I. *Synthesis* 1978, 925). The product of Example 8b and a slight excess of acetyl chloride are dissolved in dry methylene chloride and pyridine, and the mixture is stirred at room temperature for 3–5 hours. The solvent is removed to give a residue that is dissolved in ethyl acetate and then washed with 10%-sodium hydrogen carbonate, 10%-potassium hydrogen sulfate, brine, and dried. The crude product obtained is purified by silica gel column chromatography to yield pure title compound.

EXAMPLE 23

Formula V: R=ethyl; R'=R2=R3=H; n=1; $R^{1'}$=OCH$_3$; $R^1$=tert-butyldimethylsilyloxy; taken together with one of $R^{31}$ and $R^{32}$, one of $R^{33}$ and $R^{34}$ form a bond; one of $R^{31}$ and $R^{32}$ is H; one of $R^{33}$ and $R^{34}$ is C$_6$H$_5$CH$_2$NH; $R^{35}$ and $R^{36}$ taken together form an oxo group.

The title compound is prepared by applying a general method described in the literature (Winkler, J. D.; Hershberger, P. M.; Springer, J. P. *Tetrahedron Lett.* 1986, 27, 5177). The product of Example 8b and a slight excess of benzylamine are dissolved in benzene and gently refluxed for 3–5 hours. The solvent is removed, and the residue obtained is purified by silica gel column chromatography to yield pure title compound.

EXAMPLE 24

Formula V: R=ethyl; R'=R2=R3=H; n=1; $R^{1'}$=OCH$_3$; $R^1$=tert-butyldimethylsilyloxy; taken together with one of $R^{31}$ and $R^{32}$, one of $R^{33}$ and $R^{34}$ form a bond; one of $R^{31}$ and $R^{32}$ is H; one of $R^{33}$ and $R^{34}$ is C$_6$H$_5$CH$_2$NH; $R^{35}$ and $R^{36}$ taken together form an oxo group.

Benzyl bromide and triethylamine are added to a solution of the product of Example 2 in acetonitrile. The reaction mixture is warmed to 35°–45° C. overnight. The solvent is removed, and the residue is dissolved in ethyl acetate. The ethyl acetate layer is washed with 10%-sodium hydrogen carbonate, brine, dried over magnesium sulfate, and evaporated. The crude product is purified by silica gel column chromatography.

EXAMPLE 25

Formula I: R=ethyl; R'=R2=R3=H; n=1; $R^{1'}$=OCH$_3$; $R^1$=NH$_2$C(O)NH (S Configuration).

The title compound is prepared by applying a general method described in the literature (Neville, R. G.; McGee, J. J. Can. J. Chem. 1963, 41, 2123). A solution of the product of Example 2 in anhydrous benzene is added, dropwise, to a solution of silicon tetraisocyanate in benzene in an ice bath. After the addition is over, the mixture is refluxed for 15 min and concentrated in vacuo. Aqueous isopropyl alcohol (i-propanol: water=9:1) is added to the residue, and the mixture is refluxed for 15 min. The mixture is filtered through a coarse-grade sintered-glass funnel and washed with acetone. Solvents are removed, and the residue is dissolved in ethyl acetate. The ethyl acetate layer is washed with 10%-sodium hydrogen carbonate, brine, and dried over magnesium sulfate. After the solvent is removed, the crude product is purified by silica gel column chromatography.

EXAMPLE 26

Formula I: R=ethyl; R'=R2=R3=H; n=1; $R^{1'}$=OCH$_3$; $R^1$=C$_6$H$_5$CH$_2$OCONH (S Configuration).

Benzyloxycarbonyl chloride and triethylamine are added to a solution of the product of Example 2 in anhydrous methylene chloride. The reaction mixture is stirred for 1 hour. The solvent is removed, and the residue is dissolved in ethyl acetate. The ethyl acetate layer is washed with 10%-sodium hydrogen carbonate, brine, dried over magnesium sulfate. After the solvent is removed, the crude product is purified on silica gel column chromatography.

EXAMPLE 27

Formula I: R=ethyl; R'=R2=R3=H; n=1; $R^{1'}$=OCH$_3$; $R^1$=NH$_2$C(NH)NH (S Configuration).

The title compound is prepared by applying a general method described in the literature (Van Nispen, J. W.; Tesser, G. L; Nivard, R. J. F. Int. J. Peptide Protein Res. 1977, 9, 193). The product of Example 2 is added to a freshly prepared methanolic solution of O-methyl-isourea. The solution is kept at 0° C. for 1 day, concentrated, and cooled. Water is added slowly to the residue, and the product is extracted with ethyl acetate. The ethyl acetate layer is washed with 10%-sodium hydrogen carbonate, brine, dried over magnesium sulfate. After the solvent is removed, the crude product is purified on silica gel column chromatography.

EXAMPLE 28

Formula I: R=ethyl; R'=R2=R3=H; n=1; $R^{1'}$=OCH$_3$; $R^1$=C$_6$H$_5$S(O)NH (S Configuration).

The title compound is prepared by applying a general method described in the literature (Kobayashi, T.; Iino, K.; Hiraoka, T. J. Am. Chem. Soc. 1977, 99, 5505). Benzenesulfenyl chloride is added dropwise to a solution of Example 2 and triethylamine in methylene chloride at 0° C. The solution is stirred at 0° C. for 1 hour and at room temperature for 1 day, concentrated and redissolved in ethyl acetate. The ethyl acetate layer is washed with 10%-sodium hydrogen carbonate, brine, dried over magnesium sulfate. After the solvent is removed, the crude product is purified by silica gel column chromatography.

EXAMPLE 29

Formula I: R=ethyl; R'=R2=R3=H; n=1; $R^{1'}$=OCH$_3$; $R^1$=(CH$_3$CH$_2$O)$_2$P(O).

The title compound is prepared by applying a general method described in the literature (Bauer, G.; Hagele, G. Angew. Chem. Int. Ed. Engl. 1977, 16, 477). The product of Example 9 is dissolved in dry diethylether under nitrogen and treated with triethylphosphite dropwise. After the exothermic reaction has subsided, the reaction mixture is warmed to gentle reflux for 1 hour. The solvent is removed, and the residue is dissolved in ethyl acetate. The ethyl acetate layer is washed with 10%-sodium hydrogen carbonate, brine, dried over magnesium sulfate. After the solvent is removed, the crude product is purified on silica gel column chromatography.

EXAMPLE 30

Formula I: R=ethyl; R'=R2=R3=H; n=1; $R^{1'}$=OCH$_3$; $R^1$=(C$_6$H$_5$O)$_2$P(O)O.

Ascomycin (100 mg, 0.126 mmol) was dissolved in 1 mL of benzene in an ice bath, and triethylamine (35 uL, 0.252 mmol) followed by diphenylchlorophosphate (53 uL, 0.252 mmol) in benzene (1 mL) was added dropwise. After 4-dimethylaminopyridine (DMAP) (10 mg, 0.08 mmol) was added,it was then stirred at room temperature for 2 hours. 10%-Sodium bisulfate was added to the cooled reaction mixture. After additional benzene (10 mL) was added, the organic layer was washed with 10%-NaHCO$_3$ (×3), brine (×5) and then dried over anhydrous magnesium sulfate. Evaporation of the solvent gave crude product which was purified by flash silica gel (25 g) column chromatography, eluting 15%-acetone in hexane. 73 mg of pure title compound was isolated. MS (FAB) m/z: M+K=1062.

EXAMPLE 31

Formula I: R=ethyl; R'=R2=R3=H; n=1; $R^{1'}$=OCH$_3$; $R^1$=C$_6$H$_5$S.

The title compound is prepared by applying a general method described in the literature (Guindon, Y.; Frenette, R.; Fortin, R.; Rokach, J. J. Org. Chem. 1983, 48, 1357). Dried zinc iodide is added to a solution of ascomycin in dry dichloroethane. To the suspension is added thiophenol, and the reaction mixture is stirred for 1 hour. The reaction is quenched with water, the solvent is removed, and the residue is dissolved in ethyl acetate. The ethyl acetate layer is washed with 10%-sodium hydrogen carbonate, brine, and dried over magnesium sulfate. After the solvent is removed, the crude product is purified on silica gel column chromatography.

EXAMPLE 32

Formula I: R=ethyl; R'=R2=R3=H; n=1; $R^{1'}$=OCH$_3$; $R^1$=C$_6$H$_5$CH$_2$O.

The title compound is prepared by applying a general method described in the literature (Onaka, M.; Kawai, M.; Izumi, Y. Chem. Lett. 1983, 1101). Benzyl chloride and powdered zeolite are added to a solution of ascomycin in tetrahydrofuran. The reaction mixture is vigorously stirred under gentle reflux for 5 hours, and then water is added and insoluble material is filtered. The filtrate is evaporated to dryness, and the residue is dissolved in ethyl acetate. The ethyl acetate layer is washed with 10%-sodium hydrogen carbonate, brine, and dried over magnesium sulfate. After the solvent is removed, the crude product is purified on silica gel column chromatography.

EXAMPLE 33

Formula I: R=ethyl; R'=R2=R3=H; n=1; $R^{1'}$=OCH$_3$; $R^1$=phthalimide (S Configuration).

The title compound is prepared by applying a general method described in the literature (Nefkens, G. H. L.; Tesser, G. I.; Nivard, R. J. F. *Rec. Trav. Chim.* 1960, 79, 688). Example 2 and sodium carbonate are suspended in a mixed solvent of tetrahydrofuran:water (1:1) and cooled in an ice bath. Powdered N-carboethoxy phthalimide is added to the reaction mixture which is then stirred at 0° C. for 5 min and at room temperature for 30 min. Insoluble material is filtered, the filtrate is acidified by 10% potassium hydrogen sulfate, and the product is extracted into ethyl acetate. The ethyl acetate layer is washed with 10%-sodium hydrogen carbonate, brine, and dried over magnesium sulfate. After the solvent is removed, the crude product is purified by silica gel column chromatography.

EXAMPLE 34

Formula I: R=ethyl; R'=R2=R3=H; n=1; $R^{1'}$=OCH$_3$; $R^1$=(C$_6$H$_5$)$_2$P(O)NH (S Configuration).

The title compound is prepared by applying a general method described in the literature (Kenner, G. W.; Moore, G. A.; Ramage, R. *Tetrahedron Lett.* 1976, 3623). The product of Example 2 and diphenylphosphinyl chloride are dissolved in dry tetrahedrofuran and cooled in an ice bath. N-methylmorpholine is added to the reaction mixture which is stirred at 0° C. for 5 min and at room temperature for 5 hours. Insoluble material is filtered, the filtrate is evaporated to dryness, and the product is extracted in ethyl acetate. The ethyl acetate layer is washed with 10%-sodium hydrogen carbonate, brine, and dried over magnesium sulfate. After the solvent is removed, the crude product is purified on silica gel column chromatography.

EXAMPLE 35

Formula I: R=ethyl; R'=R2=R3=H; n=1; $R^{1'}$=OCH$_3$; $R^1$=(C$_6$H$_5$O)$_2$P(O)NH (S Configuration).

The title compound is prepared by applying a general method described in the literature (Wolfrom, M. L.; Conigliaro, P. J.; Soltes, E. J. *J. Org. Chem.* 1967, 32,653). The product of Example 2 and diphenylphosphoryl chloride are dissolved in tetrahedrofuran and cooled in an ice bath. Triethylamine is added to the reaction mixture which is stirred at 0° C. for 5 min and at room temperature for 5 hours. Insoluble material is filtered, the filtrate is evaporated to dryness, and the product is extracted in ethyl acetate. The ethyl acetate layer is washed with 10%-sodium hydrogen carbonate, brine, and dried over magnesium sulfate. After the solvent is removed, the crude product is purified on silica gel column chromatography.

EXAMPLE 36

Formula III: R=ethyl; R'=R2=R3=H; n=1; $R^{31}$ and $R^{33}$ taken together form a bond; $R^{32}$=$R^{34}$=H; $R^{35}$ and $R^{36}$ taken together form an oxo group.

The title compound was prepared according to the methods described in the published European Patent Application No. 89192668 of Fisons, P.26, Example 11: mp 124°–125° C., MS (FAB) m/z: M+NH$_4$=791.

EXAMPLE 37

Formula III: R=ethyl; R'=R2=R3=H; n=1; $R^{31}$=H; $R^{32}$=H; $R^{33}$=OH; $R^{34}$=H; $R^{35}$ and $R^{36}$ taken together form =N—OCH$_2$C$_6$H$_5$.

A solution of ascomycin (0.791 g), O-benzylhydroxylamine hydrogen chloride (0.320 g) and dimethylaminopyridine (0.26 g) in absolute ethanol (10 mL) was refluxed under nitrogen overnight. After removal of solvent, the solid residue was purified by silica gel chromatography with ether elution. Yield: 0.6 g; mp 92°–98° C.; MS (FAB) m/z: M+H=897, M+NH$_4$=914.

EXAMPLE 38

Formula VI: R=ethyl; R'=R2=R3=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{31}$ and $R^{33}$ taken together form a bond; $R^{32}$=H; $R^{34}$=H; $R^{35}$ and $R^{36}$ taken together form an oxo group; $R^{60}$=OH (R configuration); $R^{65}$=H.

A solution of the product of Example 36 (0.338 g), o-phenylenediamine (0.05 g) and N-methylmorpholine (0.04 g) in absolute ethanol was refluxed under nitrogen overnight. Solvent was removed in vacuo and the product purified by silica gel chromatography (10 g) with methylene chloride/acetonitrile (5:2, v/v) elution, followed by ether. Yield: 0.3 g; MS (FAB) m/z: M+H=846, M+NH$_4$=863.

EXAMPLE 39

Formula II: R=ethyl; R'=R2=R3=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{60}$=OH (R configuration); $R^{65}$=H.

A solution of ascomycin (0.41 g), o-phenylenediamine (0.108 g) and N-methylmorpholine (0.072 g) in absolute ethanol (3 mL) was refluxed under nitrogen overnight. Solvent was removed in vacuo and the product purified on silica gel (10 g) with methylene chloride/acetonitrile (5:2, v/v) elution, followed by 40% acetone in hexanes. Yield: 0.396 g; mp 110°–120° C.; MS (FAB) m/z: M+NH$_4$=881.

EXAMPLE 40

Formula II: R=ethyl; R'=R2=R3=H; n=1; taken together with the carbon atoms to which they are attached, $R^{26}$, $R^{27}$, $R^{28}$ and $R^{29}$ form a 6',7'-dichloroquinoxaline with C-9 and C-10 becoming positions 2' and 3' of the heterocyclic system; $R^{60}$=OH (R configuration); $R^{65}$=H.

The title compound was prepared and purified by the procedure as described in Example 39 substituting 4,5-dichlorophenyl-1,2-diamine for o-phenylenediamine. mp: 107°–110° C.; MS (FAB) m/z: M+H=932, M+NH$_4$=949.

EXAMPLE 41

Formula II: R=ethyl; R'=R2=R3=H; n=1; taken together with the carbon atoms to which they are attached, $R^{26}$, $R^{27}$, $R^{28}$ and $R^{29}$ form a 6',7'-dichloroquinoxaline with C-9 and C-10 becoming positions 2' and 3' of the heterocyclic system; $R^{60}$=OH (R configuration); $R^{65}$=H.

The title compound was prepared and purified by the procedure as described in Example 39 substituting 4,5- dimethylphenyl-1,2-diamine for o-phenylenediamine. mp: 112°–115° C.; MS (FAB) m/z: M+H=892, M+NH$_4$=909.

EXAMPLES 42a AND 42b

Formula II: R=ethyl; R'=R2=R3=H; n=1; taken together with the carbon atoms to which they are attached, $R^{26}$, $R^{27}$, $R^{28}$ and $R^{29}$ form a 6'-methoxyquinoxaline with C-9 and C-10 becoming positions 2' and 3' of the heterocyclic system; $R^{60}$=OH (R configuration); $R^{65}$=H, and Formula II: R=ethyl; R'=R2=R3=H; n=1; taken together with the carbon atoms to which they are attached, $R^{26}$, $R^{27}$, $R^{28}$ and $R^{29}$ form a 7'-methoxyquinoxaline with C-9 and C-10 becoming positions 2' and 3' of the heterocyclic system; $R^{60}$=OH (R configuration); $R^{65}$=H.

The title compounds were prepared and purified by the procedure described in Example 39 substituting 4-methoxyphenyl-1,2-diamine for o-phenylenediamine. mp: 117°–126° C.; MS (FAB) m/z: M+H=894, M+NH$_4$=932.

EXAMPLE 43

Formula II: R=ethyl; R'=R2=R3=H; n=1; taken together with the carbon atoms to which they are attached, $R^{26}$, $R^{27}$, $R^{28}$ and $R^{29}$ form a benzo[g]quinoxaline with C-9 and C-10 becoming positions 2' and 3' of the heterocyclic system; $R^{60}$=OH (R configuration); $R^{65}$=H.

The title compound was prepared and purified by the procedure as described in Example 39 substituting 2,3-naphthalenediamine for o-phenylenediamine. mp: 115°–120° C.; MS (FAB) m/z: M+H=914, M+NH$_4$=931.

EXAMPLE 44

Formula II: R=ethyl; R'=R2=R3=H; n=1; taken together with the carbon atoms to which they are attached, $R^{26}$, $R^{27}$, $R^{28}$ and $R^{29}$ form a 6',7'-methylene-dioxy-quinoxaline with C-9 and C-10 becoming positions 2' and 3' of the heterocyclic system; $R^{60}$=OH (R configuration); $R^{65}$=H.

The title compound was prepared and purified by the procedure as described in Example 39 substituting 4,5-methylenedioxy-phenyl-1,2-diamine for o-phenylenediamine. mp: 190°–193° C.; MS (FAB) m/z: M+H=908, M+NH$_4$=946.

EXAMPLE 45

Formula II: R=ethyl; R'=R2=R3=H; n=1; taken together with the carbon atoms to which they are attached, $R^{26}$, $R^{27}$, $R^{28}$ and $R^{29}$ form a 6',7'-difluoroquinoxaline with C-9 and C-10 becoming positions 2' and 3' of the heterocyclic system; $R^{60}$=OH (R configuration); $R^{65}$=H.

The title compound was prepared and purified by the procedure as described in Example 39 substituting 4,5-difluorophenyl-1,2-diamine for o-phenylenediamine. mp: 112°–116° C.; MS (FAB) m/z: M+K=938.

EXAMPLE 46

Formula II: R=ethyl; R'=R2=R3=H; n=1; one of $R^{21}$ and $R^{22}$ is H and the other is OH; $R^{23}$=OH; $R^{24}$=H.

Zinc dust (5.4 g) was added portionwise into a stirred solution of ascomycin (5.4 g) in glacial acetic acid (50 mL) under nitrogen at room temperature. The reaction mixture was stirred vigorously at room temperature for 5 hours until TLC analysis (40% acetone in hexanes) showed the total disappearance of ascomycin. The solid was then filtered off and triturated with methylene chloride. The solvent was removed in vacuo and residue solid was redissolved in methylene chloride, filtered through silica gel eluting with 50% acetone in hexanes, and concentrated in vacuo. The solid was recrystallized from ether-hexanes. Yield: 4.9 g; mp 138°–140° C.; MS (FAB) m/z: M+NH$_4$=811.

EXAMPLE 47

Formula II: R=ethyl; R'=R2=R3=H; n=1; $R^{31}$=H; $R^{32}$=H; $R^{33}$=H; $R^{34}$=S; $R^{35}$ and $R^{36}$ taken together is N, the S and N is bridged by a phenyl ring to form a benzothiazepine.

A solution of the product of Example 36 (0.26 g) and 2-aminothiophenol (0.05 g) and N-methylmorpholine (0.07 g) in absolute ethanol (3 mL) was refluxed under nitrogen overnight. Solvent was removed in vacuo, and the product was purified on silica gel with ether elution. Yield: 0.23 g; mp: 133°–138° C; MS (FAB) m/z: M+H=881.

EXAMPLE 48

Formula II: R=ethyl; R'=R2=R3=H; n=1; $R^1$=OCH$_3$; $R^{2a}$=$R^{2a'}$=H; $R^{3a}$ and $R^4$ taken together form an oxo group.

Methylsulfide-chlorine complex was prepared by adding oxalyl chloride (0.32 g) into a stirred solution of dimethylsulfoxide (0.44 g) in methylene chloride (4 mL) and stirring at –70° C. for 0.5 hours. The solution of the complex was added in slow dropwise fashion into a stirring solution of ascomycin (1.6 g) in methylene chloride (5 mL) at –70° C. After stirring for 0.25 hours, triethylamine (1.4 g) was added at –70° C. Stirring was continued at –70° C. for 0.5 hours and then at room temperature for 1 hour. The reaction mixture was then diluted with ether (100 mL), washed with 1N HCl (aq) (2×30 mL), saturated brine (30 mL), dried over magnesium sulfate and solvent removed. The product was purified on silica gel (70 g) with ether elution. Yield: 0.95 g; MS (FAB) m/z: M+H=790.

EXAMPLE 49

Formula I: R=ethyl; R'=R2=R3=H; n=1; $R^1$=OCH$_3$; $R^{2a}$=$R^{2a'}$=H; $R^{3a}$ and $R^4$ taken together form an 1,3-ethylenethioketal group.

Triethyloxonium tetrafluoroborate (0.1 mL, 1M in CH$_2$Cl$_2$) was added into a stirred solution of ethanedithiol (0.01 mL) and the product of Example 48 (0.05 g) in dry methylene chloride (1 mL) at 0° C. After stirring at 0° C. and room temperature for 1 hour, potassium carbonate was added, and the product was purified by prep TLC (40% acetone in hexanes). Yield: 0.02 g; MS (FAB) m/z: M+H=866, M+Na=888, M+K=904.

EXAMPLE 50

Formula I: R=ethyl; R'=R2=R3=H; n=1; $R^1$=OCH$_3$; $R^{2a}$=$R^{2a'}$=H; $R^{3a}$ and $R^4$ taken together form =N—OH.

A solution of the product of Example 48 (0.25 g), hydroxylamine hydrochloride (0.03 g) and N-methylmorpholine (0.035 g) in absolute ethanol was refluxed under nitrogen for 1.5 hours. Solvent was removed in vacuo and the product was purified on silica gel with ether elution. Yield: 0.2 g; MS (FAB) m/z: M+H=805.

EXAMPLE 51

Formula I: R=ethyl; R'=R2=R3=H; n=1; $R^1$=OCH$_3$; $R^{3a}$=H; $R^{2a'}$=H; $R^4$=OH.

Lithium tri-t-butoxyaluminum hydride (0.2 mL, 1M in THF) was added slowly into a stirred solution of the product of Example 48 (0.056 g) in dry THF (1 mL) at –70° C. under nitrogen. After stirring at –70° C. for 3 hours, it was partitioned between ether (50 mL) and 1N HCl (10 mL). The organic phase was dried over magnesium sulfate, the solvent was removed and the product purified by prep TLC (35% acetone in hexanes). Yield: 0.025 g; MS (FAB) m/z: M+K= 830.

EXAMPLE 52

Formula III: R=ethyl; R'=R2=R3=H; n=1; $R^{31}$=H; taken together with the carbon atoms to which they are attached, $R^{33}$, $R^{34}$, $R^{35}$ and $R^{36}$ form a pyrrazole.

Hydrazine (0.014 g, in 2 mL of dry THF) was added into a stirred solution of the product of Example 12 (0.24 g) in dry THF (10 mL) at room temperature. After stirring at room temperature for 0.5 hours, the reaction mixture was refluxed for 2 hours. After removal of the solvent, the product was purified by silica gel chromatography (silica gel, 50 g) eluting with 50% acetone in hexanes. The solid was further purified by prep TLC (5% methanol in methylene chloride). Yield: 0.13 g; MS (FAB) m/z: M+H=786.

EXAMPLE 53

Formula II: R=ethyl; R'=R2=R3=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system, two of the quinoxalines form a carbon-carbon bond between either the 6' and 7' on each heterocyclic system; $R^{60}$=OH (R configuration); $R^{65}$=H.

A solution of ascomycin (0.6 g), N-methylmorpholine (0.153 g) and 3,3'-diaminobenzidine tetrahydrochloride (0.1 g) in absolute ethanol was refluxed overnight. The product was purified as described in Example 39. Yield: 0.31 g; mp: 128°–132° C.; MS (FAB) m/z: M+H=1725.

EXAMPLE 54

Formula V: R=ethyl; R'=R2=R3=H; n=1; $R^{1'}$=OCH$_3$; $R^1$=t-butyldimethylsilyloxy (R configuration); $R^{31}$=H; $R^{32}$=H; $R^{33}$=t-butyldimethylsilyloxy; $R^{34}$=H, $R^{35}$ and $R^{36}$ taken together form an oxo group.

Ascomycin (15 g) was dissolved in a solution of imidazole (3.75 g) in dry N,N-dimethylformamide (200 mL) and tert-butyldimethylchlorosilane (18.3 g) was added in portions and stirred at room temperature for 90 hours. N,N-dimethylformamide and excess tert-butyldimethylchlorosilane were removed by distillation (bath 30° C. at 0.8 torr.). The solid residue was extracted with anhydrous ether (4×50 mL). Ether was removed in vacuo and the solid residue was purified by silica gel chromatography eluting with 5% acetone in hexanes providing the title compound (17 g). MS (FAB) m/z: M+H= 1022.

EXAMPLE 55

Formula VII: R=ethyl; R'=R2=R3=H; n=1; $R^{1'}$=OCH$_3$; $R^1$=t-butyldimethylsilyloxy (R configuration); one of $R^{21}$ and $R^{22}$ is H and the other is OH; $R^{23}$=OH; $R^{24}$=H; $R^{31}$=$R^{32}$=H; $R^{33}$=t-butyldimethylsilyloxy; $R^{34}$=H; $R^{35}$ and $R^{36}$ taken together form an oxo group.

Zinc dust (5 g) was added into a stirred solution of the product of Example 54 (5 g) in glacial acetic acid (25 mL) and stirred at room temperature for 5 hours. The reaction mixture was diluted with methylene chloride (150 mL) and the solid was filtered off and extracted with additional methylene chloride (3×50 mL). Solvent was removed in vacuo, and the solid residue filtered through silica gel (20 g) and eluted with ether. Yield: 5 g; MS (FAB) m/z: M+H= 1024.

EXAMPLE 56

Formula VII: R=ethyl; R'=R2=R3=H; n=1; $R^{1'}$=OCH$_3$; $R^1$=t-butyldimethylsilyloxy (R configuration); one of $R^{21}$ and $R^{22}$ is H and the other is OAc; $R^{23}$=OH; $R^{24}$=H; $R^{31}$=$R^{32}$=H; $R^{33}$=t-butyldimethylsilyloxy; $R^{34}$=H; $R^{35}$ and $R^{36}$ taken together form an oxo group.

Acetic anhydride (1 mL) is added into a stirred solution of the product of Example 55 (1 g) and 4-dimethylaminopyridine (0.1 g) in dry pyridine (5 mL). The reaction mixture is stirred at room temperature for 1 hour. Solvent and excess acetic anhydride is removed in vacuo (0.1 torr) and the solid residue is purified by silica gel chromatography eluting with 2% ethanol in methylene chloride.

EXAMPLE 57

Formula V: R=ethyl; R'=R2=R3=H; n=1; $R^{1'}$=OCH$_3$; $R^1$=tri-isopropylsilyloxy (R configuration); one of $R^{31}$=$R^{32}$=H; $R^{33}$=tri-isopropylsilyloxy; $R^{34}$=H; $R^{35}$ and $R^{36}$ taken together form an oxo group.

Triisopropylsilyl trifluoromethanesulfonate (10 g) in dry methylene chloride (25 mL) was added dropwise into a stirred solution of ascomycin (7.8 g) and N-methylmorpholine (4 g) in dry methylene chloride (100 mL) at 0° C. and stirred at 0° C. for 3 hours. Methanol (3 mL) was added and stirring was continued for an additional hour. Solvent was removed in vacuo and the residue worked up with ether and 1N hydrochloric acid. The organic phase was dried over magnesium sulfate and solvent removed in vacuo. Purification by silica gel chromatography eluting with 10% ether in hexanes provided the title compound (9 g). MS (FAB) m/z: M+Na=1128.

EXAMPLE 58

Formula VII: R=ethyl; R'=R2=R3=H; n=1; $R^{1'}$=OCH$_3$; $R^1$=tri-isopropylsilyloxy (R configuration); one of $R^{21}$ and $R^{22}$ is H and the other is OH; $R^{23}$=OH; $R^{24}$=H; $R^{31}$=$R^{32}$=H; $R^{33}$=tri-isopropylsilyloxy; $R^{34}$=H; $R^{35}$ and $R^{36}$ taken together form an oxo group.

Zinc dust (5 g) was added into a stirred solution of the product of Example 57 (5 g) in glacial acetic acid (25 mL) and stirred at room temperature for 5 hours. The reaction mixture was diluted with methylene chloride (150 mL) and the solid was filtered off and extracted with methylene chloride (3×50 mL). The resulting solution was filtered through silica gel (20 g) and eluted with ether. Yield: 5 g; MS (FAB) m/z: M+Na=1130.

EXAMPLE 59

Formula VII: R=ethyl; R'=R2=R3=H; n=1; $R^{1'}$=OCH$_3$; $R^1$=tri-isopropylsilyloxy (R configuration); one of $R^{21}$ and $R^{22}$ is H and the other is OAc; $R^{23}$=OH; $R^{24}$=H; $R^{31}$=$R^{32}$=H; $R^{33}$=tri-isopropylsilyloxy; $R^{34}$=H; $R^{35}$ and $R^{36}$ taken together form an oxo group.

Acetic anhydride (1 mL) was added into a stirred solution of the product of Example 58 (1 g) and 4-dimethylaminopyridine (0.1 g) in dry pyridine (5 mL). The reaction mixture was stirred at room temperature for 1 hour. Solvent and excess acetic anhydride was removed in vacuo (0.1 torr) and the solid residue was purified by silica gel chromatography eluting with 2% ethanol in methylene chloride. Yield: 1 g; MS (FAB) m/z: M+Na=1172.

EXAMPLE 60

Formula II: R=ethyl; R'=R2=R3=H; n=1; one of $R^{21}$ and $R^{22}$ is H and the other is OAc; $R^{23}$=OH; $R^{24}$=H.

40% Aqueous hydrofluoric acid (0.5 mL, in 5 mL of acetonitrile) is added dropwise into a solution of the product of Example 59 (1.1 g) in acetonitrile (10 mL) at 0° C. The reaction mixture is stirred at room temperature for 2 hours. The reaction mixture is diluted with water (50 mL) and extracted with ethyl acetate (3×50 mL), dried over magnesium sulfate and the solvent removed in vacuo. The crude is purified by silica gel chromatography using 5% methanol in methylene chloride as eluent.

EXAMPLE 61

Formula II: R=ethyl; R'=R2=R3=H; n=1; taken together with the carbon atoms to which they are attached, $R^{26}$, $R^{27}$, $R^{28}$ and $R^{29}$ form a 2'-methyl-thiazole with C-9 and C-10 becoming positions 5' and 4' of the heterocyclic system; $R^{60}$=OH (R configuration); $R^{65}$=H.

A solution of the product of Example 60 (0.83 g), thioacetamide (0.15 g) and triethylamine (0.2 g) in isopropanol (5 mL) is refluxed under nitrogen for 16 hours. Solvent is removed in vacuo and the solid residue is purified by silica gel chromatography eluting first with 20% acetonitrile in methylene chloride followed by 7% methanol in methylene chloride.

EXAMPLE 62

Formula II: R=ethyl; R'=R2=R3=H; n=1; taken together with the carbon atoms to which they are attached, $R^{26}$, $R^{27}$, $R^{28}$ and $R^{29}$ form a 2'-amino-thiazole with C-9 and C-10 becoming positions 5' and 4' of the heterocyclic system; $R^{60}$=OH (R configuration); $R^{65}$=H.

A solution of the product of Example 60 (0.1 g), thiourea (0.015 g) and triethylamine (0.2 g) in acetonitrile (1 mL) is refluxed under nitrogen for 16 hours. Solvent is removed in vacuo and the solid residue is purified by silica gel chromatography eluting first with 20% acetonitrile in methylene chloride followed by 7% methanol in methylene chloride.

EXAMPLE 63

Formula II: R=ethyl; R'=R2=R3=H; n=1; taken together with the carbon atoms to which they are attached, $R^{26}$, $R^{27}$, $R^{28}$ and $R^{29}$ form a 2'-phenyl-imidazole with C-9 and C-10 becoming positions 5' and 4' of the heterocyclic system; $R^{60}$=OH (R configuration); $R^{65}$=H.

A solution of the product of Example 60 (0.83 g), benzamidine hydrochloride hydrate (0.3 g) and triethylamine (0.2 g) in isopropyl alcohol (5 mL) is refluxed under nitrogen for 24 hours. Solvent is removed in vacuo, and the solid residue is purified by silica gel chromatography eluting with 10% methanol in methylene chloride.

EXAMPLE 64

Formula II: R=ethyl; R'=R2=R3=H; n=1; taken together with the carbon atoms to which they are attached, $R^{26}$, $R^{27}$, $R^{28}$ and $R^{29}$ form a 2'-phenyl-oxazole with C-9 and C-10 becoming positions 5' and 4' of the heterocyclic system; $R^{60}$=OH (R configuration); $R^{65}$=H.

A solution of the product of Example 60 (0.83 g), benzamide (0.25 g) and triethylamine (0.2 g) in acetonitrile (5 mL) is refluxed under nitrogen for 24 hours. Solvent is removed in vacuo and the solid residue is purified by silica gel chromatography eluting with 10% methanol in methylene chloride.

EXAMPLE 65

Formula VII: R=ethyl; R'=R2=R3=H; n=1; $R^{1'}$=OCH$_3$; $R^1$=t-butyldimethylsilyloxy (R configuration); one of $R^{21}$ and $R^{22}$ is [1-(2'2',5',5'-tetramethyl-2'5'-disila-1'-azolidinyl)]-2-ethyl and the other is OH; $R^{23}$=OH; $R^{24}$=H; $R^{31}$=$R^{32}$=H; $R^{33}$=t-butyldimethylsilyloxy; $R^{34}$=H; $R^{35}$ and $R^{36}$ taken together form an oxo group.

To a solution of the product of Example 54 (1 g) in dry tetrahydrofuran (10 mL) is added with stirring at 0° C. 1-(2-ethyl)-2,2,5,5-tetramethyl-2,5-disila-1-azacyclopentane magnesium bromide (1M in THF, 1.5 mL). The reaction mixture is allowed to reach room temperature and stir for 4 hours. The reaction mixture is worked up with saturated ammonium chloride (50 mL) and extracted with ethyl acetate (3×50 mL). The combined organic phase is washed with water, brine and dried over magnesium sulfate. The product is purified by silica gel chromatography eluting with 3% methanol in methylene chloride.

EXAMPLE 66

Formula II: R=ethyl; R'=R2=R3=H; n=1; taken together with the carbon atoms to which they are attached, $R^{26}$, $R^{27}$, $R^{28}$ and $R^{29}$ form a pyrrole with C-9 and C-10 becoming positions 3' and 2' of the heterocyclic system; $R^{60}$=OH (R configuration); $R^{65}$=H.

40% Aqueous hydrofluoric acid (1 mL) is added dropwise into a solution of the product of Example 65 (1.1 g) in acetonitrile (10 mL) at 0° C. The reaction mixture is stirred at room temperature for 2 hours. The reaction mixture is diluted with water (50 mL), extracted with ethyl acetate (3×50 mL), dried over magnesium sulfate and the solvent is removed in vacuo. The crude is purified by silica gel chromatography using 5% methanol in methylene chloride as eluent.

EXAMPLE 67

Formula VII: R=ethyl; R'=R2=R3=H; n=1; $R^{1'}$=OCH$_3$; $R^1$=t-butyldimethylsilyloxy (R configuration); taken together with the carbon atoms to which they are attached, $R^{26}$, $R^{27}$, $R^{28}$ and $R^{29}$ form a pyrazine with C-9 and C-10 becoming positions 2' and 3' of the heterocyclic system; $R^{33}$=t-butyldimethylsilyloxy; $R^{31}$=H; $R^{32}$=H; $R^{34}$=H; $R^{35}$ and $R^{36}$ taken together form an oxo group; $R^{60}$=OH (R configuration);$R^{65}$=H.

Activated manganese dioxide (1.1 g) is added into a solution of the product of Example 54 (1.1 g) and ethylenediamine (0.1 g) in dry benzene, and the suspension is stirred at 50° C. for 24 hours. The solid is filmed off, and solvent is removed in vacuo. The product is purified by silica gel chromatography eluting with 3% methanol in methylene chloride.

EXAMPLE 68

Formula II: R=ethyl; R'=R2=R3=H; n=1; taken together with the carbon atoms to which they attached, $R^{26}$, $R^{27}$, $R^{28}$ and $R^{29}$ form a pyrazine with C-9 and C-10 becoming positions 2' and 3' of the heterocyclic system; $R^{60}$=OH (R configuration); $R^{65}$=H.

The product of Example 67 is deprotected to give the title compound and purified according to the procedure of Example 60.

EXAMPLE 69

Formula VII: R=ethyl; R'=R2=R3=H; n=1; $R^{1'}$=OCH$_3$; $R^1$=t-butyldimethylsilyloxy (R configuration); one of $R^{21}$ and $R^{22}$ is [2-(1,3-dioxolanyl)]-2-ethyl and the other is OH; $R^{23}$=OH; $R^{24}$=H; $R^{31}$=$R^{32}$=H; $R^{33}$=t-butyldimethylsilyloxy; $R^{34}$=H; $R^{35}$ and $R^{36}$ taken together form an oxo group.

To a solution of the product of Example 54 (1 g) in dry tetrahydrofuran (10 mL) is added under stirring at 0° C. 2-(2-ethyl)-1,3-dioxolane magnesium bromide (1M in THF, 1.5 mL). The reaction mixture is allowed to reach room temperature and stir for 4 hours. The reaction mixture is worked up with saturated ammonium chloride (50 mL) and extracted with ethyl acetate (3×50 mL). The combined organic phases are washed with water, brine and dried over magnesium sulfate. The product is purified by silica gel chromatography eluting with 3% methanol in methylene chloride.

EXAMPLE 70

Formula VII: R=ethyl; R'=R2=R3=H; n=1; $R^{1'}$=OCH$_3$; $R^1$=t-butyldimethylsilyloxy (R configuration); taken together with the carbon atoms to which they are attached, $R^{26}$, $R^{27}$, $R^{28}$ and $R^{29}$ form a pyradine with C-9 and C-10 becoming positions 3' and 2' of the heterocyclic system; $R^{33}$=t-butyldimethylsilyloxy; $R^{31}$=H; $R^{32}$32 H; $R^{34}$=H; $R^{35}$ and $R^{36}$ taken together form an oxo group; $R^{60}$=OH (R configuration); $R^{65}$=H.

A solution of the product of Example 69 (1 g), oxalic acid (0.2 g) and acetaldehyde (0.5 mL) in wet methylene chloride (5 mL) is stirred under nitrogen overnight. Solvent is removed in vacuo and the reaction crude is partitioned between ethyl acetate and aqueous sodium bicarbonate. The solution is dried over magnesium sulfate and the solvent is removed in vacuo. The residue is redissolved in isopropyl alcohol (5 mL) and ammonium hydroxide (0.5 mL) is added. The reaction mixture is allowed to stir at room temperature overnight. After removal of solvent in vacuo, the product is purified by silica gel chromatography eluting with 40% acetone in hexanes.

EXAMPLE 71

Formula II: R=ethyl; R'=R2=R3=H; n=1; taken together with the carbon atoms to which they are attached, $R^{26}$, $R^{27}$, $R^{28}$ and $R^{29}$ form a pyridine with C-9 and C-10 becoming positions 3' and 2' of the heterocyclic system; $R^{60}$=OH (R configuration); $R^{65}$=H.

The product of Example 70 is deprotected and purified according to the procedure of Example 60 to give the title compound.

EXAMPLE 72

Formula II: R=ethyl; R'=R2=R3=H; n=1; taken together with the carbon atoms to which they are attached, $R^{26}$, $R^{27}$, $R^{28}$ and $R^{29}$ form a pyridazine with C-9 and C-10 becoming positions 4' and 3' of the heterocyclic system; $R^{60}$=OH (R configuration); $R^{65}$=H.

A solution of the product of Example 69 (1 g), oxalic acid (0.2 g) and acetaldehyde (0.5 mL) in wet methylene chloride is stirred under nitrogen overnight. Solvent is removed and the reaction mixture is partitioned between ethyl acetate and aqueous sodium bicarbonate. After removal of the solvent, the residue is redissolved in isopropyl alcohol (5 mL) and hydrazine (0.035 g) is added. The reaction mixture is allowed to stir at room temperature overnight. After removal of solvent, the bis-silylated product is purified by silica gel chromatography and is deprotected according to the procedure of Example 60.

EXAMPLE 73

Formula II: R=ethyl; R'=R2=R3=H; n=1; taken together with the carbon atoms to which they are attached, $R^{26}$, $R^{27}$, $R^{28}$ and $R^{29}$ form a pyrazino[2,3-d]pyridazine with C-9 and C-10 becoming positions 2' and 3' of the heterocyclic system; $R^{60}$=OH (R configuration); $R^{65}$=H.

A solution of ascomycin (0.8 g), 4,5-diaminopyridazine (0.2 g) and N-methylmorpholine (0.2 g) in isopropyl alcohol (5 mL) is heated at 80° to 90° C. for 12 hours. Solvent is removed and product purified by silica gel chromatography eluting with 40% acetone in hexanes.

EXAMPLES 74a AND 74b

Formula II: R=ethyl; R'=R2=R3=H; n=1; taken together with the carbon atoms to which they are attached, $R^{26}$, $R^{27}$, $R^{28}$ and $R^{29}$ form a pyrido[3,4-b]pyrazine with C-9 and C-10 becoming positions 3' and 2' of the heterocyclic system; $R^{60}$=OH (R configuration); $R^{65}$=H and Formula II: R=ethyl; R'=R2=R3=H; n=1; taken together with the carbon atoms to which they are attached, $R^{26}$, $R^{27}$, $R^{28}$ and $R^{29}$ form a pyrido [3,4-b]pyrazine with C-9 and C-10 becoming positions 3' and 2' of the heterocyclic system; $R^{60}$=OH (R configuration); $R^{65}$=H A solution of ascomycin (0.8 g), 4,5-diaminopyridine (0.2 g) and N-methylmorpholine (0.2 g) in isopropyl alcohol (5 mL) is heated at 80 to 90° C. for 12 hours. Solvent is removed, and the products purified by silica gel chromatography eluting with 40% acetone in hexanes.

EXAMPLES 75a AND 75b

Formula II: R=ethyl; R'=R2=R3=H; n=1; taken together with the carbon atoms to which they are attached, $R^{26}$, $R^{27}$, $R^{28}$ and $R^{29}$ form a pyrido[2,3-b]pyrazine with C-9 and C-10 becoming positions 2' and 3' of the heterocyclic system; $R^{60}$=OH. (R configuration); $R^{50}$=H. and Formula II: R=ethyl; R'=R2=R3=H; n=1; taken together with the carbon atoms to which they are attached, $R^{26}$, $R^{27}$, $R^{28}$ and $R^{29}$ form a pyrido[2,3-b]pyrazine with C-9 and C-10 becoming positions 3' and 2' of the heterocyclic system; $R^{33}$=OH; $R^{31}$=H; $R^{60}$=OH (R configuration); $R^{65}$=H.

A solution of ascomycin (0.8 g), 2,3-diaminopyridine (0.2 g) and N-methylmorpholine (0.2 g) in isopropyl alcohol (5 mL) is heated at 80° to 90° C. for 12 hours. Solvent is removed, and the products are purified by silica gel chromatography eluting with 40% acetone in hexanes.

EXAMPLE 76a AND 76b

Formula II: R=ethyl; R'=R2=R3=H; n=1; taken together with the carbon atoms to which they are attached, $R^{26}$, $R^{27}$, $R^{28}$ and $R^{29}$ form a pteridine with C-9 and C-10 becoming positions 7' and 6' of the heterocyclic system; $R^{60}$=OH (R configuration); $R^{65}$=H and Formula II: R=ethyl; R'=R2=R3=H; n=1; taken together with the carbon atoms to which they are attached, $R^{26}$, $R^{27}$, $R^{28}$ and $R^{29}$ form a pteridine with C-9 and C-10 becoming positions 6' and 7' of the heterocyclic system; $R^{60}$=OH (R configuration); $R^{65}$=H.

A solution of ascomycin (0.8 g), 4,5-diaminopyrimidine (0.2 g) and N-methylmorpholine (0.2 g) in isopropyl alcohol (5 mL) is heated at 80° to 90° C. for 12 hours. Solvent is removed and products purified by silica gel chromatography eluting with 20% methanol in methylene chloride.

EXAMPLE 77

Formula V: R=ethyl; R'=R2=R3=H; n=1; $R^{1'}$=OCH$_3$; $R^1$=H; $R^{31}$=$R^{32}$=H; $R^{33}$=t-butyldimethylsilyloxy; $R^{34}$=H; $R^{35}$ and $R^{36}$ taken together form an oxo group.

To a solution of the product of Example 259 (15 g) and imidazole (3.75 g) in dry N,N-dimethylformamide (200 mL), tert-butyldimethylchlorosilane is added in portions and stirred at room temperature for 90 hours. N,N-dimethylformamide and excess tert-butyldimethylchlorosilane is removed by distillation (bath 30° C. at 0.8 torr.). The solid residue is extracted with anhydrous ether (4×50 mL). Ether is removed in vacuo and the solid residue is purified by silica gel chromatography eluting with 5% acetone in hexanes.

EXAMPLE 78

Formula VII: R=ethyl; R'=R2=R3=H; n=1; $R^{1'}$=OCH$_3$; $R^1$=H; one of $R^{21}$ and $R^{22}$ is n-butyl and the other is OH; $R^{23}$=OH; $R^{24}$=H; $R^{31}$=$R^{32}$=H; $R^{33}$=t-butyldimethylsilyloxy; $R^{34}$=H; $R^{35}$ and $R^{36}$ taken together form an oxo group.

The product of Example 77 (0.5 g) is dissolved in dry tetrahydrofuran (10 mL) and cooled to −78° C. n-Butyl lithium (1.6M in Hexanes, 0.5 mL) is added in slow dropwise. The reaction mixture is allowed to stir at −78° C. for 2 hours and worked up with saturated ammonium chloride and ether. Product is purified by silica gel chromatography eluting with ether.

EXAMPLE 79

Formula IV: R=ethyl; R'=R2=R3=H; n=1; $R^{1'}$=OCH$_3$; $R^1$=H; one of $R^{21}$ and $R^{22}$ is n-butyl and the other is OH; $R^{23}$=OH; $R^{24}$=OH; $R^{24}$=H.

The product of Example 78 is deprotected and purified according to the procedure of Example 60 to give the title compound.

EXAMPLE 80

Formula VII: R=ethyl; R'=R2=R3=H; n=1; $R^{1'}$=OCH$_3$; $R^1$=H; one of $R^{21}$ and $R^{22}$ is benzyl and the other is OH; $R^{23}$=OH; $R^{24}$=H; $R^{31}$=$R^{32}$=H; $R^{33}$=t-butyldimethylsilyloxy; $R^{34}$=H; $R^{35}$ and $R^{36}$ taken together form an oxo group.

The product of Example 77 (0.5 g) is dissolved in dry tetrahydrofuran (10 mL) and cooled to −78° C. Benzylmagnesium chloride (2M in tetrahydrofuran, 0.5 mL) is slowly added dropwise. The reaction mixture is allowed to stir at −78° C. for 1 hour, 0° C. for 4 hours and worked up with saturated ammonium chloride and ether. The product is purified by silica gel chromatography eluting with ether.

EXAMPLE 81

Formula IV: R=ethyl; R'=R2=R3=H; n=1; $R^{1'}$=OCH$_3$; $R^1$=H; one of $R^{21}$ and $R^{22}$ is n-benzyl and the other is OH; $R^{23}$=OH; $R^{24}$=H.

The product of Example 80 is deprotected and purified according to the procedure of Example 60 to give the title compound.

EXAMPLE 82

Formula VII: R=ethyl; R'=R2=R3=H; n=1; $R^{1'}$=OCH$_3$; $R^1$=H; one of $R^{21}$ and $R^{22}$ is hydrogen and the other is OH; $R^{23}$=OH; $R^{24}$=H; $R^{31}$=$R^{32}$=H; $R^{33}$=t-butyldimethylsilyloxy; $R^{34}$=H; $R^{35}$ and $R^{36}$ taken together form an oxo group.

The product of Example 82 is prepared from the product of Example 77 and purified according to procedure of Example 58.

EXAMPLE 83

Formula VII: R=ethyl; R'=R2=R3=H; n=1; $R^{1'}$=OCH$_3$; $R^1$=H; one of $R^{21}$ and $R^{22}$ is hydrogen and the other is O; which when taken together with $R^{23}$=O, both oxygens are connected with a thiocarbonyl bridge; $R^{24}$=H; $R^{31}$=$R^{32}$=H; $R^{33}$=t-butyldimethylsilyloxy; $R^{34}$=H; $R^{35}$ and $R^{36}$ taken together form an oxo group.

O-Phenyl chlorothioformate (0.07 g) is added into a stirred mixture of the product of Example 82 (0.3 g) and 4-dimethylaminopyridine (0.3 g) in anhydrous acetonitrile (5 mL). After stirring at room temperature for 1 hour, the solution is diluted with ether (30 mL) and washed with brine. The organic phase is dried over magnesium sulfate, and the solvent is removed in vacuo. The residue is purified by silica gel chromatography eluting with 20% acetone in hexanes.

EXAMPLE 84

Formula IV: R=ethyl; R'=R2=R3=H; n=1; $R^{1'}$=OCH$_3$; $R^1$=H; one of $R^{21}$ and $R^{22}$ is hydrogen and the other is O; which when taken together with $R^{23}$=O, both oxygens are connected with a thiocarbonyl bridge; $R^{24}$=H.

The product of Example 83 is deprotected and purified according to the procedure of Example 60 to give the title compound.

EXAMPLE 85

Formula VII: R=ethyl; R'=R2=R3=H; n=1; $R^{1'}$=OCH$_3$; $R^1$=H; one of $R^{21}$ and $R^{22}$ is hydrogen and the other is O; which when taken together with $R^{23}$=O, both oxygens are connected with a carbonyl bridge; $R^{24}$=H; $R^{31}$=$R^{32}$=H; $R^{33}$=t-butyldimethylsilyloxy; $R^{34}$=H; $R^{35}$ and $R^{36}$ taken together form an oxo group.

The product of Example 82 (1 g) is dissolved in 1,2-dichloroethane (15 mL) and N,N-carbonyldiimidazole (0.188 g) is added in portions to the mixture with stirring. After stirring at room temperature for 26 hours, the solvent is removed in vacuo and the residue is purified by silica gel chromatography eluting with 10% acetone in hexanes.

EXAMPLE 86

Formula IV: R=ethyl; R'=R2=R3=H; n=1; $R^{1'}$=OCH$_3$; $R^1$=H; one of $R^{21}$ and $R^{22}$ is hydrogen and the other is O; which when taken together with $R^{23}$=O, both oxygens are connected with a thiocarbonyl bridge; $R^{24}$=H.

The title compound is prepared from the product of Example 85 and purified according to the procedure of Example 60.

EXAMPLE 87

Formula VII: R=ethyl; R'=R2=R3=H; n=1; $R^{1'}$=OCH$_3$; $R^1$=H; one of $R^{21}$ and $R^{22}$ is hydrogen and the other is O; which when taken together with $R^{23}$=O, both oxygens are connected with a P(O)(OCH$_3$); $R^{24}$=H; $R^{31}$=$R^{32}$=H; $R^{33}$=t-butyldimethylsilyloxy; $R^{34}$=H; $R^{35}$ and $R^{36}$ taken together form an oxo group.

Methyl dichlorophosphate (0.15 g) in methylene chloride (10 mL) is added into a stirred mixture of the product of Example 82 (1 g) and 4-dimethylaminopyridine (0.5 g) in anhydrous methylene chloride (15 mL). After stirring at room temperature for 27 hours, solvent is removed in vacuo. The residue is diluted with ethyl ether (100 mL) and washed with brine, dried over magnesium sulfate and the solvent is removed in vacuo. The residue is purified by silica gel chromatography eluting with 20% acetone in hexanes.

EXAMPLE 88

Formula IV: R=ethyl; R'=R2=R3=H; n=1; $R^{1'}$=OCH$_3$; $R^1$=H; one of $R^{21}$ and $R^{22}$ is hydrogen and the other is O; which when taken together with $R^{23}$=O, both oxygens are connected with a P(O)(OCH$_3$); $R^{24}$=H.

The title compound is prepared from the product of Example 87 according to the procedure of Example 60.

EXAMPLE 89

Formula IV: R=ethyl; R'=R2=R3=H; n=1; $R^{1'}$=OCH$_3$; $R^1$=H; one of $R^{21}$ and $R^{22}$ is n-butyl and the other is O; which when taken together with $R^{23}$=O, both oxygens are connected with a thiocarbonyl bridge; $R^{24}$=H.

The title compound is prepared from the product of Example 78 by using the procedures described in Example 84.

EXAMPLE 90

Formula IV: R=ethyl; R'=R2=R3=H; n=1; $R^{1'}$=OCH$_3$; $R^1$=H; $R^{21}$ is n-butyl; $R^{22}$ and $R^{23}$ taken together form a bond; $R^{24}$=H.

To a mixture of the product of Example 89 (0.5 g) and 2,2'-azobisisobutyronitrile (catalytic amount) in anhydrous toluene (10 mL) is added tri-n-butyltin hydride (1 mL) over 0.5 hours. The solvent is removed in vacuo and the residue is purified by silica gel chromatography eluting with 10% acetone in hexanes.

EXAMPLE 91

Formula IV: R=ethyl; R'=R2=R3=H; n=1; $R^{1'}$=OCH$_3$; $R^1$=H; $R^{21}$=H; $R^{22}$ and $R^{23}$ taken together form a bond; $R^{24}$=H.

The title compound is prepared from the product of Example 84 using the procedure described in Example 90.

EXAMPLE 92

Formula IV: R=ethyl; R'=R2=R3=H; n=1; $R^{1'}$=OCH$_3$; $R^1$=H; $R^{21}$=$R^{22}$=H; $R^{23}$=OH; $R^{24}$=H.

Zinc dust (1 g) is added into a stirred solution of the product of Example 86 (0.5 g) in glacial acetic acid (5 mL) and stirred at room temperature for 35 hours. The reaction mixture is diluted with methylene chloride (150 mL) and the solid is filtered off and triturated with methylene chloride (3×50 mL). Solvent is removed in vacuo, and the residue is purified with silica gel chromatography (10 g) eluting with ether.

EXAMPLE 93

Formula IV: R=ethyl; R'=R2=R3=H; n=1; $R^{1'}$=OCH$_3$; $R^1$=H; one of $R^{21}$ and $R^{22}$ is n-butyl and the other is O; which when taken together with $R^{23}$=O, both oxygens are connected with a carbonyl bridge; $R^{24}$=H.

The title compound is prepared from the product of Example 78 according to the procedures used in Example 86.

EXAMPLE 94

Formula IV: R=ethyl; R'=R2=R3=H; n=1; $R^{1'}$=OCH$_3$; $R^1$=H; one of $R^{21}$ and $R^{22}$ is n-butyl and the other is H; $R^{23}$=OH; $R^{24}$=H.

The title compound is prepared from the product of Example 93 according to the procedures used in Example 92.

EXAMPLES 95a & 95b

Formula I: R=ethyl; R'=R2=R3=H; n=1; $R^{1'}$=OCH$_3$; (R configuration) $R^1$=$R^{33}$C$_6$H$_5$CH$_2$O— and Formula V: R=ethyl; R'=R2=R3=H; n=1; (both R configuration) $R^1$=C$_6$H$_5$CH$_2$O—; $R^{31}$=R$_{32}$=$R^{34}$=H; $R^{35}$ and $R^{36}$ taken together form an oxo group.

Ascomycin (2.00 g) and benzyl 2,2,2-trichloroacetimidate (1.88 mL) were combined in ether (100 mL) to which triflic acid (22 µL) was added dropwise. After stirring at ambient temperature overnight, the reaction mixture was diluted with more ether and sequentially washed with saturated aqueous sodium bicarbonate solution and brine. The organic layer was dried over sodium sulfate and freed of solvent. The title compounds were separated and purified by flash chromatography on silica gel using a step gradient of 15–30% acetone/hexane in steps of 5% to furnish the two products in yields of 355 and 850 mg respectively. MS (FAB) m/z: (M+K)=920 and 1010 respectively.

The products were also prepared as follows. Ascomycin (1.50 g) and benzyl bromide (1.57 mL) were dissolved in acetonitrile (2 mL), and the resultant solution was chilled to 0° C. in an ice bath. Silver(I) oxide (1.75 g) was introduced portionwise, and upon completion of this addition, the reaction mixture was permitted to warm to ambient temperature. After stirring for two days, the solids were removed by filtration through a plug of silica with ether elution. The filtrate was washed with saturated aqueous bicarbonate and brine prior to drying over sodium sulfate. The solvent was removed under reduced pressure to supply exude material which was purified by silica gel chromatography as described above to furnish the two products. ($^1$H NMR, $^{13}$C NMR, and mass spectral data consistent with the desired products.)

EXAMPLES 96a AND 96b

Formula III: R=ethyl; R'=R2=R3=H; n=1; $R^{31}$=$R^{34}$=H; taken together with the carbon atoms to which they are attached, $R^{32}$ and $R^{33}$ form a 3-phenyl-2-isoxazoline with C-23 and C-24 becoming positions 4' and 5' respectively of the heterocyclic system; $R^{35}$ and $R^{36}$ taken together form an oxo group; and formula III: R=ethyl; R'=R2=R3=H; n=1; $R^{31}$=$R^{34}$=H; taken together with the carbon atoms to which they are attached, $R^{32}$ and $R^{33}$ form a 3-phenyl-2-isoxazoline with C-23 and C-24 becoming positions 5' and 4' of the heterocyclic system; $R^{35}$ and $R^{36}$ taken together form an oxo group.

N-Chlorosuccinimide (2.67 g, 20 mmol) was suspended in chloroform (20 mL) with pyridine (0.1 mL). Benzaldehyde oxime (2.42 g, 20 mmol) was added to the suspension. Twenty minutes hence, the N-chlorosuccinimide had dissolved, and the resultant solution was stored under nitrogen. The product of Example 36 (1.006 g, 1.29 mmol) was dissolved in dry chloroform. The hydroxamic acid chloride solution (4 mL) prepared above was introduced, and the mixture was heated to 48° C. as triethylamine (0.4 mL) was slowly added. After 25 hours, the reaction mixture was cooled, and the volatiles were removed under reduced pressure. The crude material was purified by flash chromatography over silica gel (elution with hexanes:acetone 3:2) to supply the title compounds.

EXAMPLE 96a:

IR (CDCl$_3$) cm$^{-1}$ 3420, 2950, 1780, 1750, 1720, 1340, 1160; $^1$H NMR (CDCl$_3$, 500 MHz) delta 7.70–7.35 (m, 5H), 5.38 (s, 1H) & 5.15 (d, J=7.7 Hz, 1H), 4.73 (dd, J=6, 10 Hz, 1H) & 4.64 (coupling obscured), 4.16 (d, J=7 Hz, 1H) & 4.13 (d, J=7 Hz, 1H); MS (FAB) m/z: M+K=931.

EXAMPLE 96b:

IR (CDCl$_3$) cm$^{-1}$ 2930, 1750, 1720, 1700, 1650, 1450, 1090; $^1$H NMR (CDCl$_3$, 500 MHz) delta 5.37 (d, J=7 Hz, 1H) & 5.23 (d, J=3 Hz, 1H), 5.18 (br s, 1H) & 4.89 (d, J=7.7 Hz, 1H), 4.30 (m, 1H) & 4.05 (m, 1H); MS (FAB) m/z: M+K=931.

EXAMPLES 97a AND 97c

Formula III: R=ethyl; R'=R2=R3=H; n=1; R$^{31}$=H; R$^{32}$=—C(O)Ph; R$^{33}$=hydroxy; R$^{34}$=H; R$^{35}$ and R$^{36}$ taken together form an oxo group; and Formula III: R=ethyl; R'=R2=R3=H; n=1; R$^{31}$ and R$^{33}$ taken together form a bond; R$^{32}$=—C(O)Ph; R$^{34}$=H; R$^{35}$ and R$^{36}$ taken together form an oxo group.

EXAMPLE 97a:

The product of Example 96a (51.7 mg, 0.058 mmol) is dissolved in acetonitrile containing 1% water (5 mL) to which molybdenum hexacarbonyl (7.6 mg, 0.029 mmol) is added. The mixture is heated to reflux for several hours turning a darker blue throughout this time. The reaction mixture is cooled, and a small amount of silica gel is added prior to solvent removal under reduced pressure. The residue is applied to a silica gel column and the title product, the beta-hydroxy ketone, as well as the dehydration product Example 97c, are eluted with ether.

EXAMPLE 97b

Formula III: R=ethyl; R'=R2=R3=H; n=1; R$^{31}$=H; R$^{32}$=hydroxy; R$^{33}$=—C(O)Ph; R$^{34}$=H; R$^{35}$ and R$^{36}$ taken together form an oxo group.

The product of Example 96b is reduced in the presence of water using the methodology described above to furnish the title compound.

EXAMPLE 98

Formula I: R=ethyl; R'=R2=R3=H; n=1; R$^{1'}$=OCH$_3$; R$^1$=(4-NO$_2$)C$_6$H$_5$CH$_2$O— (R configuration).

Ascomycin (2.00 g), 4-nitrobenzyl bromide (1.63 g), and 2,6-lutidine (0.74 mL) were dissolved in methylene chloride (20 mL). The solution was cooled to 0° C., and silver triflate (1.94 g) was introduced portionwise. After stirring overnight at room temperature, the reaction mixture was diluted with additional methylene chloride and washed successively with water, 0.5M citric acid, and more water. The organic layer was dried over sodium sulfate and concentrated in vacuo. The product was purified by flash chromatography on silica gel using 25% acetone/hexane as fluent. Overlapped frations were further purified by radial chromatography on silica gel. The title compound was obtained as a colorless foam (0.66 g). MS (FAB) m/z: M+K=965. ($^1$H NMR and $^{13}$C NMR spectral data consistent with the desired product.).

EXAMPLE 99

Formula I: R=ethyl; R'=R2=R3=H; n=1; R$^{1'}$=OCH$_3$; R$^1$=(2-furan)CH$_2$O— (R configuration).

Furfuryl alcohol is reacted with trichloroacetonitrile in a mixture of pentane and methanol in the presence of sodium hydride to provide the corresponding trichloroacetimidate. The trichloroacetimidate and ascomycin are combined in a mixture of cyclohexane and methylene chloride and treated with triflic acid to furnish the desired ether using the methodology described in Example 95.

EXAMPLE 100

Formula I: R=ethyl; R'=R2=R3=H; n=1; R$^{1'}$=OCH$_3$; R$^1$=—OCH$_2$C(O)-(3'-benzo[B]thiophene) (R configuration).

3-Chloroacetylbenzo[B]thiophene is converted to its corresponding iodide with sodium iodide in acetone under standard Finkelstein conditions. This material is used to alkylate ascomycin using the conditions described in Example 346.

EXAMPLE 101

Formula I: R=ethyl; R'=R2=R3=H; n=1; R$^{1'}$=OCH$_3$; R$^1$=—OCH$_2$(5'-(methyl-2'-furancarboxylate) (R configuration).

Methyl 5-chloromethyl-2-furancarboxylate is converted to its corresponding iodide with sodium iodide in acetone under standard Finkelstein conditions. This material is used to alkylate ascomycin using the conditions described in Example 98.

EXAMPLE 102

Formula III: R=ethyl; n=1; R'=R2=R3=H; R$^{31}$=H; R$^{32}$=H; R$^{33}$=OH; R$^{34}$=H; R$^{35}$ and R$^{36}$ taken together is =NR$^{38}$; R$^{38}$=—OCH$_2$COOH.

Ascomycin (300 mg, 0.4 mmol), carboxymethoxylamine hemi-hydrochloride (250 mg, 1.2 mmol) and pyridine (100 uL, 1.2 mmol) in ethanol 10 mL were refluxed for 4 hours. The solvent was evaporated, and the residue was taken up in EtOAc, washed sequentially with H$_2$O, dilute acid (0.2M H$_3$PO$_4$), and brine and dried over Na$_2$SO$_4$. Concentration under vacuum gave 430 mg of crude material which was purified by reverse phase-HPLC (21.4 mm ID×25 cm, C18, 8 μm silica, DYNAMAX preparative HPLC (Rainin)). Elution (15 mL/min) was performed with a linear gradient from 55:45 (H$_2$O-CH$_3$CN containing 0.1% TFA) to 10:90 over 30 min. Combination of selected fractions, evaporation of CH$_3$CN and lyophilization gave 124 mg of the title compound. MS (FAB) m/z: (M+K)=903.

EXAMPLE 103a

Formula III: R=ethyl; n=1; R'=R2=R3=H; R$^{31}$=H; R$^{32}$=H; R$^{33}$=OH; R$^{34}$=H; R$^{35}$=OH (S-configuration); R$^{36}$=H:

To a solution of 48% aqueous HF (16 uL) in CH$_3$CN (1 mL) was added the product of Example 103c. below (S-isomer, 70 mg) in CH$_3$CN (1 mL). The mixture was stirred for 0.5 hours. The solvent was removed, and the crude material was purified by silica gel column chromatography using 2% MeOH/CH$_2$Cl$_2$, yielding 48 mg of the title compound. MS (FAB) m/z: M+K 814.

EXAMPLE 103b

Formula III: R=ethyl; n=1; R'=R2=R3=H; R$^{31}$=H; R$^{32}$=H; R$^{33}$=OH; R$^{34}$=H; R$^{35}$=H; R$^{36}$=OH (R-configuration).

The title compound was prepared using a procedure analogous to that of Example 103a, starting from the product of Example 103d, below.

EXAMPLES 103c AND 103d

Formula V: R=ethyl; n=1; R'=R2=R3=H; R$^{1'}$=OCH$_3$; R1=t-butyldimethylsilyloxy; R$^{31}$=H; R$^{32}$=H; R$^{33}$=OH; R$^{34}$=H; R$^{35}$=OH (S-configuration); R$^{36}$=H; and Formula V: R=ethyl; n=1; R'=R2=R3=H; R$^{1'}$=OCH$_3$; R$^1$=t- butyldimethylsilyloxy; $R^{31}$=H; $R^{32}$=H; $R^{33}$=OH; $R^{34}$=H; $R^{35}$=H; $R^{36}$=OH (R-configuration).

To a solution of the product of Example 8a (100 mg, 0.1 mmol) and sodium triacetoxyborohydride (25.7 mg, 0.11 mmol) in $CH_3CN$ (1 mL) at 0° C. was slowly added acetic acid (24 uL, 0.33 mmol). After stirring at 0° C. for 2 hours, the reaction mixture was quenched with water and stirred for an additional 0.5 hours. The solution was extracted with EtOAc, the organic phase was washed with $H_2O$, brine and dried over $Na_2SO_4$. Evaporation of the solvent gave 94 mg of the crude material which was chromatographed over silica gel using 20% $EtOAc/CHCl_3$ as an eluent. Unreacted starting material (10 mg), 18 mg of Example 103d, the silylated minor isomer (R), and 52 mg of Example 103c, the silylated major isomer (S), were collected.

EXAMPLE 104a

Formula V: R=ethyl; n=1; R'=R2=R3=H; $R^{1'}$=$OCH_3$; $R^1$=t-butyldimethylsilyloxy; $R^{31}$=H; $R^{32}$=H; $R^{33}$=OH; $R^{34}$=H; $R^{35}$=OSi (Me2)-t-Bu (S-configuration); $R^{36}$=H.

To a solution of the product of Example 103c, below (1.0 g, 1.1 mmol) in $CH_2Cl_2$ (20 mL) was added t-butyldimethylsilyl chloride (730 mg, 4.84 mmol) and imidazole (660 mg, 9.68 mmol). This was stirred at room temperature for 5.5 hours. The reaction mixture was quenched with saturated $NH_4Cl$, and diluted with EtOAc. The organic phase was washed with saturated $NH_4Cl_1$, saturated $NaHCO_3$, brine and dried over $Na_2SO_4$. The solvent was evaporated and 1.32 g of the crude material was chromatographed over silica gel column to give 868 mg of disilylated product and 140 mg of the recovered starting material.

EXAMPLE 104b

Formula V: R=ethyl; n=1; R'=R2=R3=H; $R^{1'}$=$OCH_3$; R1=OSi(Me2)-t-Bu; $R^{31}$=H; $R^{32}$=H; $R^{33}$ and $R^{34}$ taken together form an oxo group; $R^{35}$=t-butyldimethylsilyloxy (S-configuration); $R^{36}$=H.

To a −78° C. solution of oxalyl chloride (40 uL, 0.44 mmol) in 1 mL of methylene chloride was added a solution of dimethylsulfoxide (60 ul, 0.88 mmol) in 1 mL of methylene chloride and the mixture was aged at −78° C. for 30 min. A solution of the disilylated product of Example 104a (170 mg, 0.2 mmol) in methylene chloride (1 mL) was added. The reaction was carried out at −78° C. for 3 hours with stirring and triethylamine (270 uL, 2.0 mmol) was added. After stirring at −78° C. for 20 min, it was then allowed to stand to room temperature for 30 min. The reaction mixture was partitioned between 40 mL of ethylacetate and 10 mL of 10%-$NaHSO_4$ solution. The organic layer was washed with 10%-$NaHSO_4$, water (×3), brine, and dried over anhydrous magnesium sulfate. Evaporation of the solvent gave 160 mg of the crude material.

EXAMPLE 104c

Formula III: R=ethyl; n=1; R'=R2=R3=H; $R^{31}$=H; $R^{32}$=H; $R^{33}$ and $R^{34}$ taken together form an oxo group; $R^{35}$=OH (S-configuration); $R^{36}$=H.

Aqueous HF cleavage of the resultant product of Example 104b followed by silica gel column purification provided 85 mg of the title compound. MS (FAB) m/z: M+K=830.

EXAMPLE 105a

Formula II: R=allyl; R'=R2=R3=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{60}$=OH (R configuration); $R^{65}$=H.

A solution of FK-506 (0.41 g), o-phenylenediamine (0.108 g) and N-methylmorpholine (0.072 g) in absolute ethanol (3 mL) is refluxed under nitrogen overnight. Solvent is removed in vacuo and product is purified on silica gel (10 g) with methylene chloride/acetonitrile (5:2, v/v) elution, followed by 40% acetone in hexanes to give the desired compound.

EXAMPLE 105b

Formula II: R=propyl; R'=R2=R3=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{60}$=OH (R configuration); $R^{65}$=H.

The product of Example 105a (150 mg) and 10% Pd/C (30 mg) in ethylacetate (6 ml) are hydrogenated at room temperature for 20 min at 1 atm. The catalyst is filtered, the solvent is concentrated, and the resulting crude material is purified by silica gel column chromatography (eluting solvent, chloroform/acetone 5:1) to give the title compound.

EXAMPLES 106a AND 106b

Formula I: R=ethyl; R'=R2=R3=H; n=1; $R^{1'}$=$OCH_3$; $R^1$=$OCOCH_2CH_2$HN-FMOC, and Formula V: R=ethyl; R'=R2=R3=H; n=1; $R^{1'}$=$OCH_3$; $R^1$=$OCOCH_2CH_2$HN-FMOC; $R^{31}$=H; $R^{32}$=H; $R^{33}$=$OCOCH_2CH_2$HN-FMOC; $R^{34}$=H; $R^{35}$ and $R^{36}$ taken together form an oxo group.

To a stirred solution of ascomycin (142.5 mg, 0.180 mmol) and FMOC-beta-alanine (56.0 mg, 0.180 mmol) in dry dichloromethane (1.8 mL) were added 1-(3-dimethylamino propyl)-3-ethylcarbodiimide hydrochloride (38.0 mg, 0.198 mmol) and DMAP (2.2 mg, 0.018 mmol). After 2.5 days, more FMOC-beta-alanine (42.0 mg) and DMAP (1.5 mg) were added. After 6 hours, the mixture was evaporated, and the residue was chromatographed on silica gel using ether/dichloromethane (1/2) as eluent. Combination of selected fractions provided the less polar bis-acylated product Example 106b $^1$H NMR (500 MHz, $CDCl_3$) delta 2.55 (br, 4H), 3.32 (s, 3H), 4.37(br d, 2H),4.42 (br d, 2H), 7.32 (t, 4H), 7.39 (t, 4H), 7.59 (d, 2H), 7.61 (m, 2H), 7.76 (d, 4H).) as well as the mono-acylated product Example 106a (76 mg): $^1$H NMR (500 MHz, $CDCl_3$) delta 2.55 (br), 3.32 (s, 3H), 4.42 (br d), 5.49 (m, 1H), 7.32 (t, 2H), 7.39 (t, 2H), 7.59 (d, 2H), 7.76 (d, 2H).

EXAMPLE 107

Formula I: R=ethyl; R'=R2=R3=H; n=1; $R^{1'}$=$OCH_3$; $R^1$=$OCOCH_2CH_2NH_2$

To a stirred solution of the product of Example 106a (9.0 mg, 0.0082 mmol) in dry THF (0.8 mL) was added piperidine (4.0 uL, 0.041 mmol). After TLC showed complete reaction, the solvent was evaporated, and the solid residue was triturated 3 times with ether/hexane (1/2) to give the desired product as a white solid. Yield: 5.5 mg. MS (FAB) m/z: M+K=901.

EXAMPLE 108

Formula IV: R=propyl; R'=R2=R3=H; n=1; $R^{1'}$=$OCH_3$; $R^1$=benzoyloxy taken together with the carbon atoms to which they are attached, R26, R27, R28 and R29 form a quinoxaline with C-9 and C-10 becoming positions 2' and 3' of the heterocyclic system; $R^{60}$=OH (R configuration); $R^{65}$=H.

To a stirred 0° C. solution of the resultant compound of Example 105b (32 mg) in dry THF (200 uL) are added benzoyl chloride (20 uL) and pyridine (50 uL). After TLC shows consumption of the resultant compound of example 105b, the solvent is evaporated, and the residue is chromatographed on silica gel. Combination of selected fractions provides the mono-acylated product Example 108.

EXAMPLE 150

Formula III: R=ethyl; R'=R2=R3=H; n=1; $R^{31}$=$R^{32}$=$R^{33}$=H; $R^{34}$=OH; $R^{35}$ and $R^{36}$ taken together form an oxo group.

To a solution of ascomycin (2 g, 2.53 mmol) in dichloromethane (13.3 mL) at −78° C. was added diethylamino sulfurtrifluoride (3.4 mL, 25.3 mmol) and the reaction was stirred for 20 min. The reaction mixture was added dropwise to ice water (~75 mL), extracted with ethyl acetate (2×100 mL), dried ($Na_2SO_4$), filtered, and concentrated in vacuo to give a yellow foam (2.21 g). The mixture was purified by silica gel chromatography to give the title compound (0.23 g). mp 100°–105° C.; IR ($CDCl_3$) 3590, 3470, 2930, 1745, 1720, 1690, 1645, 1450 $cm^{-1}$; $^{13}C$ NMR (125 MHz) delta 9.3, 11.8, 14.3, 15.8, 16.3, 20.7, 21.0, 24.2, 24.4, 27.6, 27.6, 30.7, 31.2, 32.9, 32.9, 34.1, 34.7, 35.1, 39.1, 39.2, 41.8, 48.6, 55.7, 56.3, 56.3, 56.4, 56.9, 69.4, 73.6, 74.1, 74.3, 75.2, 75.3, 84.2, 96.9, 123.4, 128.0, 131.5, 140.4, 165.6, 169.4, 196.6, 213.3; MS (FAB) m/z: M+H=792, M+K=830. Anal. calc'd. for $C_{43}H_{69}NO_{12}$·0.6 hexane: C, 66.34; H, 9.25; N, 1.66. Found: C, 66.74; H, 8.88; N, 1.67.

EXAMPLE 151

Formula III: R=ethyl; R'=R2=R3=H; n=1; $R^{31}$=$R^{32}$=$R^{34}$=H; $R^{33}$=OH; $R^{35}$ and $R^{36}$ taken together=$NR^{38}$; $R^{38}$=—NHC(O)$OCH_3$.

Ascomycin (5.0 g), methylhydrazinocarboxylate (1.1 g), and p-toluenesulfonic acid monohydrate (1.2 g) in methanol (100 mL) were stirred at ambient temperature for 16 hours and concentrated to dryness. The mixture was purified by chromatography on silica gel eluting with hexane/acetone mixtures to give pure title compound (3.6 g). An analytical sample was recrystallized from methylene chloride and diethyl ether. mp 159°–164° C.; IR ($CDCl_3$) 3600, 3500, 3300, 2950, 1745, 1725, 1700, 1642, 1450 $cm^{-1}$; $^{13}C$ NMR (125 MHz) delta 10.2, 12.0, 14.7, 15.4, 15.7, 20.9, 21.2, 24.2, 26.9, 27.1, 28.0, 30.6, 31.1, 31.2, 32.1, 33.5, 34.6, 34.8, 34.9, 38.9, 41.1, 49.0, 49.1, 52.5, 56.2, 56.6, 56.8, 73.1, 73.5, 73.8, 73.9, 75.8, 76.0, 77.2, 84.1, 97.6, 126.3, 129.1, 132.6, 138.5, 155.7, 159.7, 165.0, 168.9, 196.5; MS (FAB) m/z: M+H=864, M+K=902. Anal. calc'd. for $C_{45}H_{73}N_3O_{13}$·2.0 $H_2O$: C, 60.05; H, 8.62; N, 4.67. Found: C, 60.17; H, 8.24; N, 4.55.

EXAMPLE 152

Formula III: R=ethyl; R'=R2=R3=H; n=1; $R^{31}$=$R^{32}$=$R^{34}$=H; $R^{33}$=OH; $R^{35}$ and $R^{36}$ taken together=$NR^{38}$; $R^{38}$=—NHC(O)$OCH_2CH_3$.

Example 151 is repeated using ascomycin and substituting ethylhydrazinocarboxylate for methylhydrazinocarboxylate to provide the title compound.

EXAMPLE 153

Formula III: R=ethyl; R'=R2=R3=H; n=1; $R^{31}$=$R^{32}$=$R^{34}$=H; $R^{33}$=OH; $R^{35}$ and $R^{36}$ taken together=$NR^{38}$; $R^{38}$=—NHC(O)$OCH_2C_6H_5$.

Example 151 is repeated using ascomycin and substituting benzylhydrazinocarboxylate for methylhydrazinocarboxylate to provide the title compound.

EXAMPLE 155

Formula V: R=ethyl; R'=R2=R3=H; n=1; $R^{1'}$=$OCH_3$; $R^{3a}$ and $R^4$ taken together form an oxo group; $R^{2a}$=—C(O)$CF_3$; $R^{31}$=$R^{32}$=$R^{34}$=H; $R^{33}$=t-butyldimethylsilyloxy; $R^{35}$ and $R^{36}$ taken together form an oxo group; $R^{2a'}$=H.

The product of Example 14b (0.8 g, 1.0 mmol) in dry DMF (5 mL) is treated with imidazole (0.1 g) and tert-butyldimethylsilyl chloride (0.18 g) until starting material is consumed. The mixture is then partitioned between water (20 mL) and EtOAc (20 mL). Organic layer is washed with brine (20 mL). Aqueous layers are extracted with EtOAc (2×10 mL), organics are combined, dried ($MgSO_4$), and concentrated to dryness. This residue is dissolved in THF (4 mL) and is added dropwise to a solution of lithium hexamethyldisilazide (2.2 mmol) in THF (5 mL) at −78° C. and the mixture is stirred for 30 minutes, whereupon 2,2,2-trifluoroethyl trifluoroacetate (0.17 mL, 1.3 mmol) is rapidly added in one portion. After 5 minutes the reaction mixture is partitioned between 5% aqueous HCl (15 mL) and $Et_2O$ (15 mL). The aqueous portion is extracted once more with $Et_2O$ and the organics are then washed with brine (2×10 mL), dried ($Na_2SO_4$), decanted from solids and concentrated to yield the title compound, which is used immediately in the following reaction. See Danheiser, R. L.; Miller, R. F.; Brisbois, R. G.; Park S. Z. *J. Org. Chem.* 1990, 55, 1959–1964.

EXAMPLE 156

Formula V: R=ethyl; R'=R2=R3=H; n=1; $R^{1'}$=$OCH_3$; $R^{3a}$ and $R^4$ taken together form an oxo group; $R^{2a}$ and $R^{2a'}$ taken together=$N_2$; $R^{31}$=$R^{32}$=$R^{34}$=H; $R^{33}$=t-butyldimethylsilyloxy; $R^{35}$ and $R^{36}$ taken together form an oxo group.

(See reference cited in Example 155.). The product isolated in Example 155 is dissolved in acetonitrile (4 mL) to which is added water (18 uL), triethylamine (0.21 mL, 1.5 mmol) and methanesulfonylazide (0.28 mL, 3.0 mmol). After stirring at ambient temperature for 4 hours, the mixture is concentrated to dryness. The residue is partitioned between EtOAc (20 mL) and water (20 mL). The aqueous layer is extracted again with EtOAc (20 mL), and the organics are washed with brine (2×10 mL), dried ($Na_2SO_4$) and concentrated to dryness. The residue is purified by chromatography on silica gel to provide the title compound.

EXAMPLES 157a AND 157b

Formula III: R=ethyl; R'=R2=R3=$R^{31}$=H; n=1; taken together with the carbon atoms to which they are attached, $R^{32}$, $R^{33}$, $R^{34}$, $R^{35}$ and $R^{36}$ form an isoxazole ring with C-24 and C-22 becoming positions 5' and 3' of the isoxazole ring; and Formula III: R=ethyl; R'=R2=R3=H; n=1; $R^{31}$=H; taken together with the carbon atoms to which they are attached, $R^{32}$, $R^{33}$, $R^{34}$, $R^{35}$ and $R^{36}$ form an isoxazole ring with C-24 and C-22 becoming positions 3' and 5' of the isoxazole ring.

A solution of the product of Example 12 (1 g), hydroxylamine hydrochloride (0.1 g) and N-methylmorpholine (0.14 g) in isopropanol was stirred at room temperature overnight, and then refluxed for 6 hours. The solvent was removed and the products were purified by silica gel chromatography eluting with 5% methanol in methylene chloride. Yield: 0.7 g; MS (FAB) m/z: M+K=825.

EXAMPLE 158

Formula II: R=ethyl; R'=R2=R3=H; n=1; taken together with the carbon atoms to which they are attached, $R^{26}$, $R^{27}$, $R^{28}$ and $R^{29}$ form a 6',9'-diaza-benzo[g]quinoxaline with C-9 and C-10 becoming positions 2' and 3' of the heterocyclic system; $R^{60}$=OH (R configuration); $R^{65}$=H.

A solution of ascomycin (0.5 g), 1,2,4,5-tetraaminobenzene tetrahydrochloride (0.9 g) and N-methylmorpholine (1.4 mL) in absolute ethanol (11 mL) was refluxed overnight. The solvent was removed, and the intermediate product was purified by silica gel chromatography. MS (FAB) m/z: M+K=932. The intermediate product (0.18 g) and glyoxal (40% in water, 0.06 g) in absolute ethanol (5 mL) was heated at 50° C. for 5 hours. After removal of solvent, the product was purified by silica gel chromatography eluting with 10% isopropanol in methylene chloride. Yield: 0.075 g; MS (FAB) m/z: M+NH$_4$=933.

EXAMPLES 159a, 159b AND 159c

Formula V: R=allyl; R'=R2=R3=H; n=1; $R^{1'}$=OCH$_3$; $R^{2a}$=$R^{31}$=$R^{32}$=$R^{2a'}$=H; $R^{3a}$ and $R^4$ taken together form an oxo group; $R^{33}$ and $R^{34}$ taken together form an oxo group; $R^{35}$ and $R^{36}$ taken together form an oxo group; Formula I: R=allyl; R'=R2=R3=H; n=1; $R^{1'}$=OCH$_3$; $R^{2a}$=$R^{2a'}$=H; $R^{3a}$ and $R^4$ taken together form an oxo group; and Formula III: R=allyl; R'=R2=R3=H; n=1; $R^{31}$=H; $R^{32}$=H; $R^{33}$ and $R^{34}$ taken together form an oxo group; $R^{35}$ and $R^{36}$ taken together form an oxo group.

FK-506 (2 g) was oxidized according to the procedure described in Example 48. The products were purified by silica gel chromatography eluting with 5% acetone in hexanes. Yield: Example 159a, 0.3 g; MS (FAB) m/z: M+K=838; Example 159b, 0.9 g; MS (FAB) m/z: M+K=840; Example 159c, 0.1 g; MS (FAB) m/z: M+H=840.

EXAMPLE 160

Formula IV: R=ethyl; R'=R2=R3=H; n=1; $R^{1'}$=OCH$_3$; $R^{2a}$=$R^{2a'}$=H; $R^{3a}$ and $R^4$ taken together form an oxo group; one of $R^{21}$ and $R^{22}$ is H and the other is OH; $R^{23}$=OH.

The title compound was prepared from the product of Example 48 according to the procedure described in Example 46. MS (FAB) m/z: M+H=792, M+K=830.

EXAMPLE 161

Formula VII: R=ethyl; R'=R2=R3=H; n=1; $R^{1'}$=OCH$_3$; $R^{2a}$=H; $R^{3a}$ and $R^4$ taken together form an oxo group; one of $R^{21}$ and $R^{22}$ is H and the other is OH; $R^{23}$=OH; $R^{24}$=H; $R^{31}$=H; $R^{32}$=H; $R^{33}$ and $R^{34}$ taken together form an oxo group; $R^{35}$ and $R^{36}$ taken together form an oxo group; $R^{2a'}$=H The title compound was prepared from the product of Example 14a according to the procedure described in Example 46. MS (FAB) m/z: M+K=828.

EXAMPLE 208

Formula I: R=ethyl; R'=R2=R3=H; n=1; $R^{1'}$=OCH$_3$; $R^1$=trichloroacetimidate (R configuration)

EXAMPLE 208a

Formula III: R=ethyl; R'=R2=R3=H; n=1; $R^{33}$=tert-butyldimethylsilyloxy; $R^{31}$=$R^{32}$=$R^{34}$=H; $R^{35}$, $R^{36}$ taken together forms an oxo group.

To a solution of 48% hydrogen fluoride aqueous solution (5 mL) was added Example 54 (32 g, 0.031 mol) in acetonitrile (500 mL), and the mixture was stirred at room temperature for 90 minutes. It was cooled to 0° C. in an ice bath, and solid NaHCO$_3$ was added to the reaction mixture. It was stirred for 1 hour and solid was removed by filtration. Acetonitrile was removed in vacuo and ethyl acetate (500 mL) was added to the residue, and the organic layer was washed with 10%-NaHCO$_3$ (300 mL×3), brine (250 mL), 10%-NaHSO$_4$ (300 mL×3), and brine (350 mL×3), and dried over anhydrous sodium sulfate. Evaporation of the solvent gave 35 g of crude title compound which was purified by silica gel column chromatography, followed by HPLC eluting with 25%-acetone in hexane. 24.28 g (85%) of pure compound was obtained. MS (FAB) m/z: M+K=844; In addition to the title compound, unreacted starting material (Example 54, 1.5 g) and ascomycin (500 mg) were isolated in pure form.

EXAMPLE 208b

Formula V: R=ethyl; R'=R2=R3=H; n=1; $R^{1'}$=OCH$_3$; $R^1$=trichloroacetimidate; $R^{33}$=tert-butyldimethylsilyloxy; $R^{31}$=$R^{32}$=$R^{34}$=H; $R^{35}$, $R^{36}$ taken together forms an oxo group.

The product of Example 208a (905 mg, 1 mmol) was dissolved in 20 mL of methylene chloride at room temperature. Glycerol formal trichloroimidate (1.243 g, 5 mmol) and boron trifluoride etherate (73.8 uL, 0.6 mmol) were added and stirred for one over night. Methylene chloride was removed by evaporation, and ethyl acetate (50 mL) was added to the residue. The ethyl acetate layer was washed with brine, 10% sodium bicarbonate (20 mL×3), brine, 10% potassium hydrogen sulfate (20 mL×3), brine and then dried over sodium sulfate. Solvent was removed to yield 2.24 g of crude product which was then purified by silica gel chromatography, eluting with 10% acetone in n-hexane. 800 mg of the title compound was isolated in 74% yield. MS (FAB) m/z: M+K=1090.

EXAMPLE 208

Formula I: R=ethyl; R'=R2=R3=H; n=1; $R^{1'}$=OCH$_3$; $R^1$=trichloroacetimidate (R configuration).

The product of Example 208b (800 mg, 0.73 mmol) was dissolved in 20 mL of acetonitrile at room temperature. 48% aqueous hydrogen fluoride solution (1 mL) was added and stirred for two hours. After being cooled in an ice bath, solid sodium hydrogen sulfate was added and stirred at 0° C. for an additional one hour. Solid was filtered and the filtrate was evaporated to dryness. The residue was re-dissolved in methylene chloride and passed through silica gel column, eluting with 15% acetone in n-hexane. The obtained crude product (680 mg) was finally purified by HPLC (column: microsorb, 1 inch diameter ×25 cm length; solvent: 20% acetone in n-hexane). The title compound (Example 208; 369.7 mg) was isolated in 57.4% yield. MS (FAB) m/z: M+K=976.

EXAMPLE 209

Formula V: R=ethyl; R'=R2=R3=H; n=1; $R^{1'}$=OCH$_3$; $R^1$=azido (S configuration); $R^{31}$=$R^{32}$=$R^{33}$=$R^{34}$=H; $R^{35}$, and $R^{36}$ taken together forms an oxo group.

EXAMPLE 209a

Formula III: R=ethyl; R'=R2=R3=H; n=1; $R^{31}$=$R^{33}$=H; $R^{32}$ and $R^{34}$ taken together forms a bond; $R^{35}$, $R^{36}$ taken together forms an oxo group.

Ascomycin (10 g, 12.6 mmol) and pyridinium p-toluene sulfonate (1 g, 3.98 mmol) were dissolved in 200 mL of toluene and stirred at 70° C. for one over night. Solvent was removed and the residue was purified by silica gel column chromatography, eluting with 5–10% acetone in hexane.

8.89 g of the title compound was isolated in 91% yield. MS (FAB) m/z: M+K=812.

EXAMPLE 209b

Formula III: R=ethyl; R'=R2=R3=H; n=1; $R^{31}=R^{32}=R^{33}=R^{34}$=H; $R^{36}$ taken together forms an oxo group.

The product of Example 209a (2.2 g, 2.8 mmol) was hydrogenated in the presence of 5% rhodium on alumina (220 mg) in 100 mL of ethanol at room temperature for 1 hour. After filtered, the filtrate was concentrated in vacuo to obtain the title compound in quantitative yield. The obtained product was then loaded on silica gel column, and eluted with 5–10% acetone in hexane to obtain the pure title compound in 80% yield. MS (FAB) m/z: M+K=814.

EXAMPLE 209

Formula V: R=ethyl; R'=R2=R3=H; n=1; $R^{1'}=OCH_3$; $R^1$=azido (S configuration); $R^{31}=R^{32}=R^{33}=R^{34}$=H; $R^{35}$, $R^{36}$ taken together forms an oxo group.

The product of Example 209b (1.16 g, 1.5 mmol) was reacted with trifluoromethane sulfonic anhydride (277.6 uL, 1.65 mmol) in 20 mL of methylene chloride at 0° C. for 20 minutes in the presence of pyridine (1.213 mL, 15 mmol). Ethyl acetate (60 mL) was added to the reaction mixture, and the organic layers were washed with brine, 10% potassium hydrogen sulfate, brine, and dried over anhydrous magnesium sulfate. Solvents were removed, and the residue was dried under high vacuum. 400 mole percent of n-tetrabutylammonium azide (in Example 1) in chloroform solution was added to a 5 mL of chloroform solution containing the above triflate, and it was then stirred at room temperature for 1.5 hours. Solvent was removed and the crude product obtained was purified by silica gel column chromatography eluting with 15% acetone in n-hexane to yield 982 mg of the product. The final purification was carried out by use of HPLC (column: microsorb, 1 inch diameter ×25 cm length; solvent: 20% acetone in n-hexane). 371.0 mg of the title compound was isolated in 31% yield. MS (FAB) m/z: M+K=839.

EXAMPLE 210

Formula I: R=ethyl; R'=R2=R3=H; n=1; $R^{1'}=OCH_3$; $R^1$=Bromo (S configuration);

The product of Example 209a (2.0 g, 2.2 mmol) was reacted with trifluoromethanesulfonic anhydride (372 uL, 2.2 mmol) according to the procedure described in Example 209 to yield 2.23 g in quantitative yield. The obtained triflate (1.16 g, 1.12 mmol) was reacted with 2.8 equivalent mole of triethylamine hydrobromide in 6 mL of methylene chloride at room temperature for one over night, followed by gently refluxed for 30 minutes. Solvent was evaporated to dryness and 50 mL of ethyl acetate was added to the residue. The ethyl acetate layer was washed with saturated sodium bicarbonate (20 mL×2), brine (20 mL×2), and dried over anhydrous magnesium sulfate. After the removal of solvent, 1.45 g of the crude product was isolated. This was purified by silica gel column chromatography, eluting with 30% acetone in n-hexane to obtain 619 mg of the pure compound in 57% yield. MS (FAB) m/z: M+K=1008.

The above product (500 mg, 0.52 mmol) was next treated with 48% aqueous hydrogen fluoride (150 mL) in 12 mL of acetonitrile, according to the procedure described in Example 209. This was then purified by HPLC (column: microsorb, 1 inch diameter ×25 cm length; solvent: 20% acetone in n-hexane). 250.0 mg of the title compound was isolated in 57% yield. MS (FAB) m/z: M+K=892. mp=103°–105° C.

EXAMPLE 211

Formula VI: R=ethyl; R'=R2=R3=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{31}$=H; taken together with the carbon atoms to which the are attached, $R^{32}$, $R^{33}$, $R^{34}$, and $R^{35}$ form a pyrazole; $R^{60}$=OH (R configuration); $R^{65}$=H.

A solution of the product of Example 52 (0.785 g) and o-phenylenediamine (0.2 g) in absolute ethanol is refluxed under nitrogen overnight. After removal of solvent, the product is purified by silica gel chromatography.

EXAMPLE 212

Formula VI: R=ethyl; R'=R2=R3=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{31}$=H; $R^{32}$=H; $R^{33}$ and $R^{34}$ taken together is nitrogen, $R^{35}$ and $R^{36}$ taken together in nitrogen, the two nitrogens are bridged by a phenyl ring to form a benzodiazepine ring; $R^{60}$=OH (R configuration); $R^{65}$=H.

A solution of the product of Example 12 (0.8 g) and o-phenylendiamine (0.4 g) in absolute ethanol (10 mL) is refluxed under nitrogen overnight. After removal of solvent, the product is purified by silica gel chromatography.

EXAMPLES 213a AND 213b

Formula III: R=ethyl; R'=R2=R3=H; n=1; $R^{31}$=H; $R^{36}$=O such that when taken together with $R^{32}$, $R^{33}$, $R^{34}$, $R^{35}$, and the carbon atoms to which they attached form a furan with a carboethoxy attached at the alpha position; and Formula III: R=ethyl; R'=R2=R3=H; n=1; $R^{31}$=H; $R^{33}$=O wuch that taken together with $R^{32}$, $R^{34}$, $R^{35}$, $R^{36}$ and the carbon atoms to which they attached form a furan with a carboethoxy attached at alpha position.

The title compounds are prepared from the product of Example 12, ethyl diazoacetate and rhodium acetate according to the methods described in the literature (Paulissen, R., et al, *Tetrahedron Lett.*, 1974, 607).

EXAMPLES 214a AND 214b

Formula III: R=ethyl; R'=R2=R3=H; n=1; $R^{31}$ and $R^{33}$ taken together form a bond; taken together with the carbon atoms to which they are attached $R^{34}$=O, and $R^{32}$ form a furan substituted with hydroxymethyl group at the alpha position; $R^{35}$ and $R^{36}$ taken together form an oxo group; and Formula III: R=ethyl; R'=R2=R3=H; n=1; $R^{31}$ and $R^{35}$ taken together form a bond; taken together with the carbon atoms to which they are attached, $R^{36}$=O and when taken together with $R^{32}$ forms a furan substituted with hydroxymethyl group at the alpha position; $R^{33}$ and $R^{34}$ taken together form an oxo group.

The title compounds are prepared from the product of Example 12 and epoxyacrolein according to the methods described in the literature (Williams, P. H., et al, *J. Am. Chem. Soc.* 1960, 82, 4883).

EXAMPLE 215

Formula III: R=ethyl; R'=R2=R3=H; n=1; $R^{31}$=H; $R^{33}$=N; $R^{32}$ and $R^{34}$ taken together form a bond, $R^{35}$ and $R^{36}$ taken together=N, such that taken together with the carbon atoms to which they attached $R^{31}$, $R^{32}$, $R^{33}$, $R^{34}$, $R^{35}$, $R^{36}$ form a pyrimidine with a phenyl group attached at a position 2'.

A solution of the product of Example 12 (0.8 g), benzamidine hydrochloride (0.4 g) and N-methylmorpholine (0.5 g) in isopropanol (10 mL) is refluxed for 2 hours. After removal of solvent, the product is partitioned between ethyl acetate and water. The organic phase is washed once with brine, dried over magnesium sulfate and the solvent is removed in vacuo. The product is purified by silica gel chromatography.

EXAMPLE 216

Formula III: R=ethyl; R'=R2=R3=H; n=1; $R^{33}$ and $R^{34}$ taken together form and oxo group; $R^{31}$=H; $R^{32}$=o-nitrophenyl; $R^{35}$ and $R^{36}$ taken together form an oxo group.

The title compound is prepared from the product of Example 12 and 1-fluoro-2-nitrobenzene according to the procedure described in Example 16.

EXAMPLES 217a AND 217b

Formula III: R=ethyl; R'=R2=R3=H; n=1; $R^{31}$ and $R^{33}$ taken together form a bond; taken together with the carbon atoms to which they are attached, $R^{34}$=NH, and $R^{32}$ form an indole; $R^{35}$ and $R^{36}$ taken together form an oxo group; and Formula III. R=ethyl; R'=R2=R3=H; n=1; $R^{31}$ and $R^{35}$ taken together form a bond; taken together with the carbon atoms to which they are attached, $R^{36}$=NH, and $R^{32}$ form an indole; $R^{33}$ and $R^{34}$ taken together form an oxo group.

The product of Example 216 and a catalytic amount of 5% Pd/C in ethanol is stirred under 1 atm of hydrogen. The reaction is followed by TLC analysis. The catalyst is then filtered off, solvent removed and product purified by silica gel chromatography.

EXAMPLES 218a AND 218b

Formula III: R=ethyl; R'=R2=R3=H; n=1; $R^{31}$=H; and $R^{32}$ and $R^{35}$ form a bond; $R^{36}$=N, $R^{33}$ and $R^{34}$, taken together with the carbon atoms to which they attached form a pyridine with amino group at position 2' and cyano group at position 3'; and Formula III: R=ethyl; R'=R2=R3=H; n=1; $R^{31}$=H; $R^{32}$ and $R^{34}$ form a bond; $R^{33}$=N, $R^{35}$, and $R^{36}$, taken together with the carbon atoms to which they attached form a pyridine with amino group at position 2' and cyano group at position 3'.

The title compounds are prepared from the product of Example 12 according to the methods described in the literature (Troschutz, R.; Troschutz, J.; Sollhuberkretzer, M. *Arch. Pharm.* 1985, 777–781).

EXAMPLES 219a and 219b

Formula I: R=ethyl; R'=R2=R3=H; n=1; $R^{1'}$=OCH$_3$; $R^{2a}$=H; $R^{3a}$=OH; $R^4$=methyl; $R^{2a'}$=H; and Formula I: R=ethyl; R'=R2=R3=H; n=1; $R^{2a}$=H; $R^4$=OH; $R^{3a}$=methyl; $R^{2a'}$=H.

Methylmagnesium chloride (0.3 mL, 3M in THF) is added into a stirred solution of the product of Example 12 (0.8 g) in dry THF (100 mL) at −70° C. After stirring at −70° C. for 8 hours, the reaction mixture is partitioned between ether and 1N HCl. The organic phase is washed once with brine and solvent removed. The products are purified by silica gel chromatography.

EXAMPLE 220

Formula I; R=ethyl; R'=R2=R3=H; n=1; $R^{1'}$=OCH$_3$; $R^4$ and $R^{2a}$ taken together form a bond; $R^{3a}$=methyl; $R^{2a'}$=H.

A solution containing the products of Examples 219a and 219b and silica gel in methylene chloride is stirred at room temperature overnight. The silica gel is filtered off, solvent removed and product purified by silica gel chromatography.

EXAMPLE 221

Formula III; R=ethyl; R'=R2=R3=H; n=1; $R^{31}$=$R^{32}$=$R^{34}$=H; $R^{33}$=hydroxy; $R^{35}$ and $R^{36}$ taken together form a hydrazone, =NR$^{38}$ where $R^{38}$=—NHS(O)$_2$R$^{40}$ and $R^{40}$=4-methylphenyl.

Ascomycin (1.00 g, 1.26 mmol) was dissolved in ethanol (125 mL) and treated at room temperature overnight with p-toluenesulfonyl hydrazide (235 mg, 1.26 mmol) and p-toluenesulfonic acid monohydrate (240 mg, 1.26 mmol). The solvent was removed under reduced pressure, and the crude material was purified by flash chromatography on silica gel eluting with 40% acetone in hexane. The title compound was obtained as a colorless solid (431 mg): mp 193°–194° C.; IR (CDCl$_3$) cm$^{-1}$ 3500, 2940, 1745, 1720, 1650, 1455, 1170, 1090; $^1$H NMR (CDCl$_3$, 500 MHz) delta (selected peaks) 9.21 & 9.18 (br s, 1H total), 7.83 (m, 2H), 7.30 (m, 2H), 3.44 (s, 3H), 3.36 (s, 3H), 3.27 (s, 3H); MS (FAB) m/e: M+K=999.

EXAMPLE 222

Formula IV: R=ethyl; R'=R2=R3=H; n=1; $R^{1'}$=OCH$_3$; $R^1$=—NR$^{17}$C(O)R$^{18}$ (S configuration) where $R^{17}$=H and $R^{18}$=phenyl; $R^{26}$, $R^{27}$ and the carbon to which they are attached are absent; one of $R^{28}$ and $R^{29}$ is hydroxy and the other is —COOH; C-8 is directly attached to C-10; $R^{60}$= hydroxy (R configuration; $R^{65}$=H.

The product of Example 5 (538 mg, 0.600 mmol) is dissolved in THF-H$_2$O (15 mL, 5:1) and treated at 0° C. with lithium hydroxide monohydrate (26 mg, 0.618 mmol) for 2 hours. The reaction is permitted to warm to ambient temperature and monitored by TLC (40% acetone in hexane) until complete. The reaction mixture is then quenched with 1N HCl (625 uL). This is diluted with additional water, and extracted with CH$_2$Cl$_2$. The combined organic washes are dried and freed of solvent to yield the title compound.

EXAMPLE 223

Formula IV: R=ethyl; R'=R2=R3=H; n=1; $R^{1'}$=OCH$_3$; $R^1$=—NR$^{17}$C(O)R$^{18}$ (S configuration) where $R^{17}$=H and $R^{18}$=phenyl; $R^{21}$, $R^{22}$ and the carbon to which they are attached are absent; C-8 is directly attached to C-10; $R^{23}$= hydroxy; $R^{24}$=H.

The material obtained in Example 222 (490 mg, 0.576 mmol) is dissolved in benzene to which lead tetraacetate (258 mg, 0.582 mmol) is added. After 2 hours, the mixture is quenched with NaHCO$_3$(aq) and extracted with CH$_2$Cl$_2$. The combined organic washes are washed with water, dried over magnesium sulfate, and concentrated in vacuo. The crude material is purified by flash chromatography with acetone-hexane as eluent.

EXAMPLES 224a AND 224b

Formula III: R=ethyl; R'=R2=R3=H; n=1; $R^{31}$ and $R^{33}$ taken together form a bond; $R^{32}$=H; $R^{34}$=H; $R^{35}$=H and $R^{36}$=OH; and Formula III: R=ethyl; R'=R2=R3=H; n=1; $R^{31}$ and $R^{33}$ taken together form a bond; $R^{32}$=H; $R^{34}$=H; $R^{35}$=OH and $R^{36}$=H The product of example 36 (861 mg, 1.11 mmol) was dissolved in methanol (75 mL) to which was added CeCl$_3$.7H$_2$O (456 mg, 1.22 mmol). The resultant mixture was chilled to 0° C., and sodium borohydride (46 mg, 1.22 mmol) was added portionwise. After 1 hour, the reaction was quenched by pouring the reaction mixture into 75 mL of water. This mixture was extracted with ether (2×50 mL). The combined organic extracts were dried over magnesium sulfate and freed of solvent. The isomeric allylic alcohols were purified and separated by silica gel chromatography using 25% acetone in hexane as eluent. Those fractions containing pure higher and lower Rf alcohols respectively were combined to furnish the less polar allylic alcohol (0.12 g) and the more polar allylic alcohol (0.23 g).

EXAMPLE 224a $^1$H NMR (CDCl$_3$, 500 MHz) delta (selected peaks) 5.65 (ddd, J=8.75, 16, 67.5 Hz, 1H), 3.43 (s, 3H), 3.38 (s, 3H), 3.32 (s, 3H), 1.67 (s, 3H), 1.63 (s, 3H), 1.06 (d, J=7.5 Hz, 3H), 0.84 (t, J=7.5 Hz, 3H).

EXAMPLE 224b

IR (CDCl$_3$) cm$^{-1}$ 3440, 2930, 1740, 1650, 1450, 1090; $^1$H NMR (CDCl$_3$, 500 MHz) delta (selected peaks) 5.45 (ddd, J=6.5, 17.5, 42.5 Hz, 1H), 1.66 (s, 3H), 1.64 (s, 3H), 1.04 (d, J=7.5 Hz, 3H), 0.99 (d, J=7.5 Hz, 3H), 0.87 (d, J=7.5 Hz, 3H), 0.83 (t, J=7.5 Hz, 3H); MS (FAB) m/e: M+K=814.

EXAMPLE 225

Formula VII: R=ethyl; R'=R2=R3=H; n=1; R$^{1'}$=OCH$_3$; R$^1$=t-butyldimethylsilyloxy (R configuration); R$^{21}$=H; R$^{22}$=R$^{23}$=OH; R$^{24}$=H; R$^{33}$=t-butyldimethylsilyloxy; R$^{31}$=R$^{32}$=R$^{34}$=H; R$^{35}$ and R$^{36}$ taken together form an oxo group.

The title compound is prepared according to the procedures described in the published European patent application of Sandoz, No.040293 1 A1, Example 1.

EXAMPLE 226

Formula VII: R=ethyl; R'=R2=R3=H; n=1; R$^{1'}$=OCH$_3$; R$^1$=t-butyldimethylsilyloxy (R configuration); R$^{22}$=H; R$^{21}$=R$^{23}$=OH; R$^{24}$=H; R$^{33}$=t-butyldimethylsilyloxy; R$^{31}$=R$^{32}$=R$^{34}$=H; R$^{35}$ and R$^{36}$ taken together form an oxo group.

The title compound is prepared according to the procedures described in the published European patent application of Sandoz, No.0402931 A1, Example 2.

EXAMPLE 227

Formula VII: R=ethyl; R'=R2=R3=H; n=1; R$^{1'}$=OCH$_3$; R$^1$=t-butyldimethylsilyloxy (R configuration); R$^{22}$=H; R$^{21}$=N$_3$; R$^{23}$=OH; R$^{24}$=H; R$^{33}$=t-butyldimethylsilyloxy; R$^{31}$=R$^{32}$=R$^{34}$=H; R$^{35}$ and R$^{36}$ taken together form an oxo group.

A solution of triphenylphosphine (0.131 g) and diethyl azodicarboxylate (0.09 g) in dry tetrahydrofuran (THF, 2 mL) is added to a stirred solution of the product of Example 225 (0.45 g) in THF (10 mL) followed by a solution of diphenylphosphorylazide (0.14 g in 1 mL of THF). The reaction mixture is stirred at 45° C. and the progress is monitored by TLC analysis. The reaction is quenched with water and extracted with ethyl acetate. Solvent is removed and the product is purified by silica gel chromatography.

EXAMPLE 228

Formula VII: R=ethyl; R'=R2=R3=H; n=1; R$^{1'}$=OCH$_3$; R$^1$=t-butyldimethylsilyloxy (R configuration); R$^{21}$=H; R$^{22}$=o-nitrobenzenesulfonate; R$^{23}$=OH; R$^{24}$=H; R$^{33}$=t-butyldimethylsilyloxy; R$^{31}$=R$^{32}$=R$^{34}$=H; R$^{35}$ and R$^{36}$ taken together form an oxo group.

o-Nitrobenzenesulfonyl chloride (0.115 g) in dry methylene chloride (1 mL) is added into a stirred solution of the product of Example 225 (0.5 g) and triethylamine (0.1 g) in methylene chloride (5 mL) at room temperature. After stirring at room temperature overnight the solvent is removed and the product purified by silica gel chromatography.

EXAMPLE 229

Formula VII: R=ethyl; R'=R2=R3=H; n=1; R$^{1'}$=OCH$_3$; R$^1$=t-butyldimethylsilyloxy (R configuration); R$^{21}$=N$_3$; R$^{22}$=H; R$^{23}$=OH; R$^{24}$=H; R$^{33}$=t-butyldimethylsilyloxy; R$^{31}$=R$^{32}$=R$^{34}$=H; R$^{35}$ and R$^{36}$ taken together form an oxo group.

Sodium azide (0.1 g) is added into a stirred solution of the product of Example 228 (0.12 g) in dry DMF (1 mL) at room temperature and heated at 60° C. for 5 hours. The reaction mixture is partitioned between ether and water. The organic phase is washed once with brine, dried over magnesium sulfate and the solvent is removed. The product is purified by silica gel chromatography.

EXAMPLE 230

Formula VII: R=ethyl; R'=R2=R3=H; n=1; R$^{1'}$=OCH$_3$; R$^1$=t-butyldimethylsilyloxy (R configuration); R$^{21}$=H; R$^{22}$=H; R$^{23}$=OH; R$^{24}$=H; R$^{33}$=t-butyldimethylsilyloxy; R$^{31}$=R$^{32}$=R$^{34}$=H; R$^{35}$ and R$^{36}$ taken together form an oxo group.

The title compound may be prepared according to the procedures described in Examples 227 or 229, but replacing the product of Example 225 with that of Example 226.

EXAMPLE 231

Formula II: R=ethyl; R'=R2=R3=H; n=1; R$^{22}$=H; R$^{21}$=N$_3$; R$^{23}$=OH; R$^{24}$=H.

40% Aqueous HF (0.1 mL) in acetonitrile (5 mL) is added into a stirred solution of the product of Example 227 (0.4 g) in acetonitrile (8 mL) at room temperature. The reaction mixture is diluted with water after stirring 2 hours at room temperature and extracted with ether. The organic phase is washed once with brine, dried over magnesium sulfate, and the solvent is removed. The product is purified by silica gel chromatography.

EXAMPLE 232

Formula II: R=ethyl; R'=R2=R3=H; n=1; R$^{21}$=H; R$^{22}$=N$_3$; R$^{23}$=OH; R$^{24}$=H.

The title compound may be prepared according to the procedure described in Example 231, but replacing the product of Example 227 with that of Example 230.

EXAMPLE 233

Formula II: R=ethyl; R'=R2=R3=H; n=1; R$^{22}$=H; R$^{21}$=NH$_2$; R$^{23}$=OH; R$^{24}$=H.

A solution of the product of Example 231 (0.25 g) and triphenylphosphine (0.09 g) in wet toluene (10 mL) is stirred at 70° C. for 8 hours. The solvent is removed and the product is purified by preparative TLC on silica.

EXAMPLE 234

Formula II: R=ethyl; R'=R2=R3=H; n=1; R$^{22}$=NH$_2$; R$^{21}$=H; R$^{23}$=OH; R$^{24}$=H.

The title compound may be prepared according to the procedure described in Example 233, but replacing the product of Example 231 with that of Example 232.

EXAMPLE 235

Formula II: R=ethyl; R'=R2=R3=H; n=1; $R^{22}$=H; $R^{21}$=NHAc; $R^{23}$=OH; $R^{24}$=H.

Acetic anhydride (0.15 g in 1 mL of dry methylene chloride) is added into a stirred solution of the product of Example 233 (0.4 g) containing triethylamine (0.15 g) in methylene chloride, (5 mL) and the mixture is stirred at room temperature for 1 hour. The reaction mixture is partitioned between ether and 1N HCl. The organic phase is washed once with brine, dried over magnesium sulfate and solvent removed. The product is purified by silica gel chromatography.

EXAMPLE 236

Formula II: R=ethyl; R'=R2=R3=H; n=1; $R^{21}$=H; $R^{22}$=NHAc; $R^{23}$=OH; $R^{24}$=H.

The title compound may be prepared according to the procedure described in Example 235, but replacing the product of Example 233 with that of Example 234.

EXAMPLE 237

Formula II: R=ethyl; R'=R2=R3=H; n=1; $R^{22}$=H; $R^{21}$=NH-adamantanecarbonyl $R^{23}$=OH; $R^{24}$=H.

The title compound may be prepared according to the procedure described in Example 235 by replacing acetic anhydride with 1-adamantane carbonyl chloride.

EXAMPLE 238

Formula II: R=ethyl; R'=R2=R3=H; n=1; $R^{21}$=H; $R^{22}$=NH-adamantanecarbonyl; $R^{23}$=OH; $R^{24}$=H.

The title compound may be prepared according to the procedure described in Example 236 by replacing acetic anhydride with 1-adamantane carbonyl chloride.

EXAMPLE 239

Formula II: R=ethyl; R'=R2=R3=H; n=1; $R^{22}$=H; $R^{21}$=benzoylamido; $R^{23}$=OH; $R^{24}$=H.

The title compound may be prepared according to the procedure described in Example 235 by replacing acetic anhydride with benzoyl chloride.

EXAMPLE 240

Formula II: R=ethyl; R'=R2=R3=H; n=1; $R^{21}$=H; $R^{22}$=benzoylamido; $R^{23}$=OH; $R^{24}$=H.

The title compound may be prepared according to the procedure described in Example 236 by replacing acetic anhydride with benzoyl chloride.

EXAMPLE 214

Formula II: R=ethyl; R'=R2=R3=H; n=1; $R^{22}$=H; $R^{21}$=N-benzylamino; $R^{23}$=OH; $R^{24}$=H.

Benzyl bromide (0.1 g) is added into a stirred solution of the product of Example 233 (0.4 g) in acetonitrile (5 mL) at 0° C. After being stored at 0° C. overnight, the reaction mixture is refluxed for an additional hour. The product is purified by silica gel chromatography.

EXAMPLE 242

Formula II: R=ethyl; R'=R2=R3=H; n=1; $R^{21}$=H; $R^{22}$=N-benzylamino; $R^{23}$=OH; $R^{24}$=H.

The title compound may be prepared from benzyl bromide according to the procedure described in Example 241, but replacing the product of Example 233 with that of Example 234.

EXAMPLE 243

Formula II: R=ethyl; R'=R2=R3=H; n=1; $R^{21}$=N-[(4',5'-biscarboethoxy)-triazole]; $R^{22}$=H; $R^{23}$=OH; $R^{24}$=H.

A mixture of the product of Example 231 (0.4 g) and diethylacetylene dicarboxylate (1 mL) is stirred at room temperature overnight. The triazole is purified by silica gel chromatography.

EXAMPLE 244

Formula II: R=ethyl; R'=R2=R3=H; n=1; $R^{21}$=H; $R^{22}$=N-[(4',5'-dicarboethoxy)-triazole]; $R^{23}$=OH; $R^{24}$=H.

The title compound may be prepared according to the procedure described in Example 243, but replacing the product of Example 231 with the that of Example 232.

EXAMPLE 245

Formula II: R=ethyl; R'=R2=R3=H; n=1; $R^{21}$=N-[(2',5'-dimethyl)-pyrrole]; $R^{22}$=H; $R^{23}$=OH; $R^{24}$=H.

A solution of acetonylacetone (0.5 g) and the product of Example 233 (0.5 g) in absolute ethanol (5 mL) is refluxed for 6 hours. After removal of solvent, the product is purified by silica gel chromatography.

EXAMPLE 246

Formula II: R=ethyl; R'=R2=R3=H; n=1; $R^{21}$=H; $R^{22}$=N-[(2',5'-dimethyl)-pyrrole]; $R^{23}$=OH; $R^{24}$=H.

The title compound may be prepared from acetonylacetone according to the procedure described in Example 245, but replacing the product of Example 233 with that of Example 234.

EXAMPLE 247

Formula VII: R=ethyl; R'=R2=R3=H; n=1; $R^{1'}$=OCH$_3$; $R^1$=t-butyldimethylsilyloxy (R configuration); $R^{22}$=H; $R^{21}$=iodo; $R^{23}$=OH; $R^{24}$=H; $R^{33}$=t-butyldimethylsilyloxy; $R^{31}$=$R^{32}$=$R^{34}$=H; $R^{35}$ and $R^{36}$ taken together form an oxo group.

Potassium iodide (0.1 g) is added into a stirred solution of the product of Example 228 (0.13 g) in dry DMF (1 mL) at room temperature and heated at 70° C. for 4 hours. The reaction mixture is partitioned between ether and water. The organic phase is washed once with brine, dried over magnesium sulfate and solvent removed. The product is purified by silica gel chromatography.

EXAMPLE 248

Formula II: R=ethyl; R'=R2=R3=H; n=1; $R^{21}$=iodo; $R^{22}$=H; $R^{23}$=OH; $R^{24}$=H.

The product of Example 247 may be deprotected according to the procedure of Example 231 to give the title compound.

EXAMPLE 249

Formula II: R=ethyl; R'=R2=R3=H; n=1; $R^{21}$=H; $R^{22}$=iodo; $R^{23}$=OH; $R^{24}$=H.

The title compound may be prepared according to the procedure of Examples 228, 247 and 248, but replacing the product of Example 225 with that of Example 226.

EXAMPLE 250

Formula II: R=ethyl; R'=R2=R3=H; n=1; $R^{21}$=bromo; $R^{22}$=H; $R^{23}$=OH; $R^{24}$=H.

The title compound may be prepared according to the procedure of Examples 247 and 248, but replacing potassium iodide with potassium bromide.

EXAMPLE 251

Formula II: R=ethyl; R'=R2=R3=H; n=1; $R^{21}$=H; $R^{22}$=bromo; $R^{23}$=OH; $R^{24}$=H.

The title compound may be prepared according to the procedure of Example 249, but replacing potassium iodide with potassium bromide.

EXAMPLE 252

Formula VII: R=ethyl; R'=R2=R3=H; n=1; $R^{1'}$=$OCH_3$; $R^1$=t-butyldimethylsilyloxy (R configuration); $R^{22}$=H; $R^{21}$=thiomethoxy; $R^{23}$=OH; $R^{24}$=H; $R^{33}$=t-butyldimethylsilyloxy; $R^{31}$=$R^{32}$=$R^{34}$=H; $R^{35}$ and $R^{36}$ taken together form an oxo group.

Sodium thiomethoxide (0.1 g) is added into a stirred solution of the product of Example 228 (0.12 g) in dry DMF (1 mL) at room temperature for 5 hours. The reaction mixture is partitioned between ether and water. The organic phase is washed once with brine, dried over magnesium sulfate and solvent removed. The product is purified by silica gel chromatography.

EXAMPLE 253

Formula II: R=ethyl; R'=R2=R3=H; n=1; $R^{22}$=H; $R^{21}$=thiomethoxy; $R^{23}$=OH; $R^{24}$=H.

The product of Example 252 is deprotected according to the procedure of Example 231 to give the title compound.

EXAMPLE 254

Formula II: R=ethyl; R'=R2=R3=H; n=1; $R^{21}$=H; $R^{22}$=thiomethoxy; $R^{23}$=OH; $R^{24}$=H.

The title compound may be prepared according to the procedure of Examples 228, 252 and 253, but replacing the product of Example 225 with that of Example 226.

EXAMPLE 255

Formula VII: R=ethyl; R'=R2=R3=H; n=1; $R^{1'}$=$OCH_3$; $R^1$=tert-butyldimethylsilyloxy (R configuration); $R^{21}$ and $R^{22}$ taken together form an oxo group; $R^{23}$ and $R^{24}$ taken together form a bond; $R^{31}$=H; $R^{32}$=H; $R^{33}$=tert-butyldimethylsilyloxy; $R^{34}$=H; $R^{35}$ and $R^{36}$ taken together form an oxo group.

The product of Example 54 (407.8 mg, 0.4 mmol) was dissolved in 4 mL of pyridine at 0° C., and thionyl chloride (46.8 uL, 0.6 mmol) was added. It was then stirred at 0° C. for 15 min and at room temperature for 72 hours. Ethyl acetate (40 mL) was added to the reaction mixture, and the organic layer was washed with brine, 10%-$KHSO_4$, brine and then dried over anhydrous magnesium sulfate. Evaporation of the solvent gave 364 mg of crude product which was purified by silica gel (50 g) column chromatography, eluting 2.5%-ethyl acetate in chloroform. Yield: 168.7 mg of pure title compound was isolated. MS (FAB) m/z: M+K=1040.

EXAMPLE 287

Formula II: R=ethyl; R'=R2=R3=H; n=1; $R^{21}$ and $R^{22}$ taken together form an oxo group; $R^{23}$ and $R^{24}$ taken together form a bond.

The product of Example 255 (120 mg, 0.12 mmol) was dissolved in 2.5 mL of acetonitrile and 48% hydrofluoric acid (100 uL) was added. It was then stirred at room temperature for 1 hour. Ethyl acetate (30 mL) was added to the reaction mixture, and the organic layer was washed with brine, 10%-$NaHCO_3$, brine and then dried over anhydrous magnesium sulfate. Evaporation of the solvent gave 98.2 mg of crude product which was purified by silica gel (25 g) column chromatography, eluting with 1.5%-methanol in chloroform. 63.4 mg of pure title compound was isolated. MS (FAB) m/z: M+K=812.

EXAMPLE 257

Formula I: R=ethyl; R'=R2=R3=H; n=1; $R^{1'}$=$OCH_3$; $R^1$=$(C_6H_5O)_2P(O)O$ (R configuration).

Ascomycin (500 mg, 0.632 mmol) was dissolved in 6 mL of benzene in an ice bath, and triethylamine (264 uL, 1.9 mmol) followed by diphenylchlorophosphate (393 uL, 1.9 mmol) in benzene (5 mL) was added dropwise. After 4-dimethylaminopyridine (DMAP) (100 mg, 0.82 mmol) was added, it was then stirred at room temperature for 1 hour. 10%-Sodium bisulfate (5 mL) was added to the cooled reaction mixture. After additional benzene (20 mL) was added, the organic layer separated was with 10%-$NaHCO_3$ (40 mL×3), brine (×5) and then dried over anhydrous magnesium sulfate. Evaporation of the solvent gave 860 mg of crude product which was purified by flash silica gel (120 g) column chromatography, eluting with 25%-acetone in hexane. 656 mg of pure title compound was isolated. MS (FAB) m/z: M+K=1294.

EXAMPLE 258

Formula II: R=ethyl; R'=R2=R3=H; n=1; $R^{21}$ and $R^{22}$ taken together form an oxo group; $R^{23}$=$C_6H_5CH_2O$; $R^{24}$=H.

The title compound is prepared from the product of Example 19 (85 mg, 0.1 mmol), silver trifluoromethanesulfonate (28.3 mg, 0.11 mmol) and disodium hydrogen phosphate (14.2 mg, 0.1 mmol) in 1 mL of benzene and 1 mL of benzyl alcohol. After 2 hours, the mixture is quenched with 10%-$NaHCO_3$ and extracted with ethyl acetate. The combined organic layers are washed with brine, dried over magnesium sulfate, and concentrated in vacuo. The crude material is purified by silica gel column chromatography eluting with 20% acetone-hexane.

EXAMPLE 259

Formula I: R=ethyl; R'=R2=R3=H; n=1; $R^{1'}$=$OCH_3$; $R^1$=H.

The product of Example 11 (447 mg, 0.48 mmol) was dissolved in toluene (6 mL) and deoxygenated with nitrogen for 10 min. 2,2'-azo-bis(2-methylpropanitrile)(15.8 mg, 0.096 mmol) and tributyltin hydride (196 uL, 0.72 mmol) were added, and the mixture was warmed to 75° C. for 3 hours with stirring. Ethyl acetate (40 mL) was added to the reaction mixture, and the organic layer was washed with brine, 10%-$KHSO_4$, brine, 10%-$NaHCO_3$, brine, and then dried over anhydrous magnesium sulfate. Evaporation of the solvent gave 421 mg of crude product. Purification was carried out using silica gel column chromatography, eluting 10%-ethyl acetate in chloroform. 28 mg of pure title compound was isolated. MS (FAB) m/z: M+K=814. IR(KBr); 3500, 3460, 2950, 2920, 2860, 2840, 2820, 1740, 1715, 1690, 1645, 1460, 1450, 1440, 1410, 1375, 1350, 1340, 1310, 1280, 1260, 1245, 1190, 1170, 1150, 1140, 1100, 1090, 1070, 1040, 1020, 1010.

EXAMPLE 262

Formula IV: R=ethyl; R'=R2=R3=H; n=1; $R^{1'}$=$OCH_3$; $R^1$=$C_6H_5C(O)NH$ (S configuration); $R^{21}$, $R^{22}$ and the carbon to which they are attached form a diastereomeric pair of epoxides; $R^{23}$=OH; R24=H.

The product of Example 5 (1.13 g, 1.26 mmol) is dissolved in methylene chloride (100 mL) and treated with diazomethane (8.4 mL, 2.5 mmol, ~0.3M in $Et_2O$) at ambient temperature. TLC analysis (acetone/hexane, 2:3) is used to monitor the progress of the reaction. An additional equivalent of diazomethane is added every few hours until the reaction was judged to be complete. Excess reagent is removed by gently bubbling a stream of nitrogen through the reaction mixture, and then the volatiles are removed under reduced pressure. The products are separated and purified by flash chromatography (ethyl acetate, 300 g silica) to supply the major and the minor diastereomers.

EXAMPLE 263

Formula I: R=allyl; R'=R2=R3=H; n=1; $R^{1'}$=$OCH_3$; $R^1$=H.

The title compound may be prepared according to the procedures described in Examples 11 and 259, using FK-506 in place of ascomycin.

EXAMPLE 264

Formula I: R=ethanalyl; R'=R2=R3=H; n=1; $R^{1'}$=$OCH_3$; $R^1$=H.

A solution of osmium tetroxide (1 mL of a 4% solution in water) is added into a stirred solution of the title compound of Example 263 (1.4 g) and 4-methylmorpholine N-oxide (1.4 g) in THF (25 mL) and water (15 mL) at room temperature. The reaction mixture is stirred at room temperature for an additional 4 hours. After addition of sodium metabisulfite, the reaction mixture is partitioned between water and ethyl acetate. The organic phase is washed with brine, dried over magnesium sulfate and solvent is removed. The residue is redissolved in benzene (40 mL) and lead tetraacetate (1.4 g) is added. After stirring at room temperature for 4 min., the reaction mixture is diluted with ether and the precipitate is filtered off. The solution is filtered through silica gel (5 g) with ether elution. After removal of solvent, the product is purified by silica gel chromatography.

EXAMPLE 265

Formula I: R=carboxymethyl; R'=R2=R3=H; n=1; $R^{1'}$=$OCH_3$; $R^1$=H.

A solution of the product of Example 264 (0.8 g) in ethanol (5 mL) is added into a suspension of 10% Pd/C (0.1 g) in ethanol (10 mL). Air is bubbled through the stirred reaction mixture for 96 hours, and the solid is removed by filtration. After removal of solvent, the product is purified by silica gel chromatography.

EXAMPLE 266

Formula I: R=methyl carboxymethyl; R'=R2=R3=H; n=1; $R^{1'}$=$OCH_3$; $R^1$=H.

A solution of diazomethane in ether is added into a stirred solution of the product of Example 265 (0.5 g) in methylene chloride (5 mL) until no starting material is present. A few drops of glacial acetic acid are added and the reaction mixture is stirred for 0.5 hours. Solvent is removed and the product is purified by silica gel chromatography.

EXAMPLE 267

Formula I: R=N-morpholine-amidomethyl; R'=R2=R3=H; n=1; $R^{1'}$=$OCH_3$; $R^1$=H.

A solution of the product of Example 265 (0.2 g), morpholine (0.06 g), 1-ethyl-3-(3-dimethylaminopropyl) carbodiimide hydrogen chloride (0.06 g) and 4-dimethylaminopyridine (0.06 g) in dry methylene chloride (4 mL) is stirred at room temperature overnight. The reaction mixture is partitioned between water and methylene chloride. After removal of solvent, the product is purified by silica gel chromatography.

EXAMPLE 268

Formula I: R=N-beta-hydroxyethylamidomethyl; R'=R2=R3=H; n=1; $R^{1'}$=$OCH_3$; $R^1$=H.

The title compound may be prepared from the product of Example 265 and ethanolamine according to the procedure described in Example 267.

EXAMPLE 269

Formula I: R=carboxymethyl; amide with glycine methyl ester; R'=R2=R3=H; n=1; $R^{1'}$=$OCH_3$; $R^1$=H.

The title compound may be prepared from the product of Example 265 and glycine methyl ester according to the procedure described in Example 267.

EXAMPLE 270

Formula I: R=N-piperidine-amidomethyl; R'=R2=R3=H; n=1; $R^{1'}$=$OCH_3$; $R^1$=H.

The title compound may be prepared from the product of Example 265 and piperidine according to the procedure described in Example 267.

EXAMPLE 271

Formula I: R=N-benzylamidomethyl; R'=R2=R3=H; n=1; $R^{1'}$=$OCH_3$; $R^1$=H.

The title compound may be prepared from the product of Example 265 and benzylamine according to the procedure described in Example 267.

EXAMPLE 272

Formula I: R=N-n-butylamidomethyl; R'=R2=R3=H; n=1; $R^{1'}$=$OCH_3$; $R^1$=H.

The title compound may be prepared from the product of Example 265 and n-butylamine according to the procedure described in Example 267.

EXAMPLE 273

Formula I: R=phenylcarboxymethyl; R'=R2=R3=H; n=1; $R^{1'}$=$OCH_3$; $R^1$=H.

The title compound may be prepared from the product of Example 265 and excess phenol according to the procedure described in Example 267.

EXAMPLE 274

Formula I: R=2-oxopropyl; R'=R2=R3=H; n=1; $R^{1'}$=$OCH_3$; $R^1$=H.

A mixture of palladium (II) chloride (0.05 g) and copper (I) chloride (0.1 g) in DMF (10 mL) and water (2 mL) is oxygenated by bubbling air through the mixture for 0.5 hours. A solution of the product of Example 263 (0.2 g) in DMF (2 mL) is added and the resulting reaction mixture is bubbled with air for 3 hours at room temperature. The reaction mixture is partitioned between ether and water. The organic phase is washed with dilute hydrochloric acid, brine and dried over magnesium sulfate. After removal of solvent, the product is purified by silica gel chromatography.

EXAMPLE 275

Formula I: R=cyclopropylmethyl; R'=R2=R3=H; n=1; $R^{1'}$=$OCH_3$; $R^1$=H.

Diazomethane (20 ml, 1M in ether) is added dropwise into a solution of the product of Example 263 (0.2 g) and palladium (II) acetate (0.02 g) in ether (5 mL) at −5° C. After stirring at −5° C. for 1 hour, the precipitate is filtered off and solvent removed in vacuo. The product is purified by silica gel chromatography.

EXAMPLE 276

Formula V: n=1; R2=R3=H; $R^{1'}$=OCH$_3$; $R^1$=H; $R^{31}$=H; $R^{32}$=H; $R^{33}$=OH; $R^{34}$=H; $R^{35}$, $R^{36}$, R and R' taken together with the carbon atoms to which they are attached for a pyrrole with C-22 and C-21 becoming positions 2' and 3' of the heterocyclic system.

A solution of the product of Example 264 (0.5 g) in methylene chloride (10 mL) is treated with ammonia (0.88M, aq., 0.4 mL). After stirring at room temperature for 0.25 hours, the reaction mixture is partitioned between ethyl acetate and water. The organic phase is washed once with brine, dried over magnesium sulfate and solvent removed. The product is purified by silica gel chromatography.

EXAMPLE 277

Formula V: n=1; R2=R3=H; $R^{1'}$=OCH$_3$; $R^1$=H; $R^{31}$=H; $R^{32}$=H; $R^{33}$=OH; $R^{34}$=H; $R^{35}$, $R^{36}$, R and R' taken together with the carbon atoms to which they are attached form a N-(beta-hydroxyethyl)-pyrrole with C-22 and C-21 becoming positions 2' and 3' of the heterocyclic system.

The title compound may be prepared from the product of Example 264 and 2-aminoethanol according to the procedure described in Example 276.

EXAMPLE 278

Formula V: n=1; R2=R3=H; $R^{1'}$=OCH$_3$; $R^1$=H; $R^{31}$=H; $R^{32}$=H; $R^{33}$=OH; $R^{34}$=H; $R^{35}$, $R^{36}$, R and R' taken together with the carbon atoms to which they are attached form a N-benzylpyrrole with C-22 and C-21 becoming positions 2' and 3' of the heterocyclic system.

The title compound may be prepared from the product of Example 264 and benzylamine according to the procedure described in Example 276.

EXAMPLE 279

Formula V: n=1; R2=R3=H; $R^{1'}$=OCH$_3$; $R^1$=H; $R^{31}$=H; $R^{32}$=H; $R^{33}$=OH; $R^{34}$=H; $R^{35}$, $R^{36}$, R and R' taken together with the carbon atoms to which they are attached form a N-phenylpyrrole with C-22 and C-21 becoming positions 2' and 3' of the heterocyclic system.

The title compound may be prepared from the product of Example 264 and aniline according to the procedure described in Example 276.

EXAMPLE 280

Formula V: n=1; R2=R3=H; $R^{1'}$=OCH$_3$; $R^1$=H; $R^{31}$=H; $R^{32}$=H; $R^{33}$=OH; $R^{34}$=H; $R^{35}$, $R^{36}$, R and R' taken together with the carbon atoms to which they are attached form a N-methylpyrrole with C-22 and C-21 becoming positions 2' and 3' of the heterocyclic system.

The title compound may be prepared from the product of Example 264 and methylamine according to the procedure described in Example 276.

EXAMPLE 281

Formula V: n=1; R2=R3=H; $R^{1'}$=OCH$_3$; $R^1$=H; $R^{31}$=H; $R^{32}$=H; $R^{33}$=OH; $R^{34}$=H; $R^{35}$, $R^{36}$, R and R' taken together with the carbon atoms to which they are attached form a furan with C-22 and C-21 becoming positions 2' and 3' of the heterocyclic system.

The product of Example 264 (0.2 g) and p-toluenesulfonic acid (0.005 g) in dry methylene chloride is refluxed under nitrogen for 1 hour. After removal of solvent, the product is purified by silica gel chromatography.

EXAMPLE 282

Formula III: R=ethyl; R'=R2=R3=H; n=1; $R^{31}$=H; $R^{32}$=H; $R^{33}$=t-butyldimethylsilyloxy; $R^{34}$=H; $R^{35}$ and $R^{36}$ taken together form an oxo group.

A solution of the product of Example 54 (1.0 g) in acetonitrile (10 mL) was added into a stirred solution of HF (0.1 mL, 40% aqueous) in acetonitrile (10 mL) and stirred at room temperature for 10 min. Saturated sodium bicarbonate (0.5 mL, aqueous) was added and stirred for 20 min. Solvent was removed in vacuo. Ether (50 mL) was added to the residue and the mixture dried over magnesium sulfate. Solid was removed by filtration and solvent removed in vacuo. The product was purified by silica gel (20 g) eluting with 20% (v/v) acetone in hexanes. Yield: 0.67 g; MS (FAB) m/z: M+K=944.

EXAMPLE 283

Formula V: R=ethyl; R'=R2=R3=H; n=1; $R^{1'}$=OCH$_3$; $R^{2a}$=H; $R^{2a'}$=H; $R^{3a}$ and $R^4$ taken together form an oxo group; $R^{31}$=H; $R^{32}$=H; $R^{33}$=t-butyldimethylsilyloxy; $R^{34}$=H; $R^{35}$ and $R^{36}$ taken together form an oxo group.

The title compound was prepared from the product of Example 282 according to the procedure described in Example 48. MS (FAB) m/z: M+K=942.

EXAMPLE 284

Formula V: R=ethyl; R'=R2=R3=H; n=1; $R^{1'}$=OCH$_3$; $R^{2a}$=H; $R^{2a'}$=H; $R^{3a}$ and $R^4$ taken together form an oxime; $R^{31}$=H; $R^{32}$=H; $R^{33}$=t-butyldimethylsilyloxy; $R^{34}$=H; $R^{35}$ and $R^{36}$ taken together form an oxo group.

N-methylmorpholine (0.1 mL) was added into a stirred solution of hydroxylamine hydrochloride (0.05 g) and the product of Example 283 (0.52 g) in absolute ethanol (3 mL) and stirred at room temperature for 1 hour. The reaction mixture was refluxed for 1 hour and solvent removed. The product was purified by silica gel (20 g) eluting with 20% acetone in hexanes. Yield: 0.5 g; MS (FAB) m/z: M+K=957.

EXAMPLE 285

Formula I: R=ethyl; R'=R2=R3=H; n=1; $R^{1'}$=—OCH$_3$; $R^1$=—OCH$_2$C(O) (R configuration); $R^{12}$=3-pyridyl Ascomycin and 3-(bromoacetyl)pyridine are stirred together in acetonitrile in the presence of Ag$_2$O to give the title compound after purification by chromatography.

EXAMPLE 286

Formula I: R=ethyl; R'=R2=R3=H; n=1; $R^{1'}$=—OCH$_3$; $R^1$=—OCH[C(O)$R^{12}$][C(O)$R^{12}$]; $R^{12}$=—OC$_2$H$_5$ (R configuration)

The title compound is prepared according to the procedure described in Example 346, substituting diethyl bromomalonate for ethyl iodoacetate.

EXAMPLE 287

Formula I: R=ethyl; R'=R2=R3=H; n=1; $R^{1'}$=—OCH$_3$; $R^1$=—OCH[C(O)$R^{12}$][C(O)$R^{12}$]; $R^{12}$=—OC$_2$H$_5$ (R configuration)

The title compound is prepared according to the procedure described in Example 346, substituting diethyl iodomalonate for ethyl iodoacetate.

EXAMPLE 288

Formula I: R=ethyl; R'=R2=R3=H; n=1; $R^{1'}$=—$OCH_3$; $R^1$=—$OCH[C(O)R^{12}][C(O)NR^{14}R^{15}]$; $R^{12}$=—$OC_2H_5$; $R^{14}$=H; $R^{15}$=p-fluorophenyl (R configuration)

The title compound is prepared according to the procedure described in Example 346, substituting ethyl N-(p-fluorophenyl)-bromomalonic ester amide for ethyl iodoacetate.

EXAMPLE 289

Formula I: R=ethyl; R'=R2=R3=H; n=1; $R^{1'}$=—$OCH_3$; $R^1$=—$OCH[C(O)R^{12}][C(O)NR^{14}R^{15}]$; $R^{12}$=—$OC_2H_5$; $R^{14}$=H; $R^{15}$=p-fluorophenyl (R configuration)

The title compound is prepared according to the procedure described in Example 346, substituting ethyl N-(p-fluorophenyl)-iodomalonic ester amide for ethyl iodoacetate.

EXAMPLE 314

Formula I: R=ethyl; R'=R2=R3=H; n=1; $R^{1'}$=$OCH_3$; $R^1$=benzenesulfonyloxy.

Ascomycin (791 mg, 1 mmol) was dissolved in 6 mL of pyridine in an ice bath and benzenesulfonyl chloride (153.1 uL, 1.2 mmol) was added. It was then stirred at 0° C. for 15 min and at room temperature for 24 hours. Ethyl acetate (40 mL) was added to the reaction mixture, and the organic layer was washed with brine, 10%-$KHSO_4$, brine and then dried over anhydrous magnesium sulfate. Evaporation of the solvent gave 961 mg of product. MS (FAB) m/z: M+K=970.

EXAMPLE 315

Formula V: R=ethyl; R'=R2=R3=H; n=1; $R^{1'}$=$OCH_3$; $R^1$=N-phenylcarbamate; $R^{31}$=H; $R^{32}$=H; $R^{33}$=t-butyldimethylsilyloxy; $R^{34}$=H; $R^{35}$ and $R^{36}$ take together form an oxo group.

A solution of the product of Example 282 in THF is added to a solution of phenyl isocyanate in THF. It is then gently refluxed until the total disappearance of starting material is observed. Catalytic amount of TEA is used ff necessary. Solvent is removed, and is purified by silica gel column chromatography to yield the title compound.

EXAMPLE 316

Formula I: R=ethyl; R'=R2=R3=H; n=1; $R^{1'}$=$OCH_3$; $R^1$=N-phenylcarbamate.

The product of Example 315 (200 mg) is dissolved in 2.5 mL of acetonitrile and 48% hydrofluoric acid (100 uL) is added. It is then stirred at room temperature for 4 hours. Ethyl acetate (30 mL) is added to the reaction mixture, and the organic layer is washed with brine, 10%-$NaHCO_3$, brine and then dried over anhydrous magnesium sulfate. Evaporation of the solvent gives crude product which is purified by silica gel (25 g) column chromatography, eluting 1.5%-methanol in chloroform.

EXAMPLE 317

Formula I: R=ethyl; R'=R2=R3=H; n=1; $R^{1'}$=$OCH_3$; $R^1$=phenylthio.

A solution of the product of Example 282 in methylene chloride is added to a solution of triflic anhydride in methylene chloride, according to the procedure described in Example 1a. To a solution of the obtained product in methylene chloride is added sodium phenylmercaptane in DMF. It is then gently warmed until the total disappearance of starting material is observed. Solvent is removed, and is purified by silica gel column chromatography to yield the title compound. C24-t-butyldimethylsilyl is removed according to the procedure described in Example 316 to give the title compound.

EXAMPLE 318

Formula I: R=ethyl; R'=R2=R3=H; n=1; $R^{1'}$=$OCH_3$; $R^1$=benzylthio.

The title compound may be prepared from the product of Example 282 and sodium benzylmercaptide, according to the procedure described in Example 317.

EXAMPLE 319

Formula I: R=ethyl; R'=R2=R3=H; n=1; $R^{1'}$=$OCH_3$; $R^1$=SH.

The product of Example 318 is carefully added to anhydrous liquid ammonia. Sodium metal is added until the reaction is completed. Solvent is removed, the residue is dissolved in degassed water, and is purified by high performance liquid chromatography to yield the title compound.

EXAMPLE 320

Formula I: R=ethyl; R'=R2=R3=H; n=1; $R^{1'}$=$OCH_3$; $R^1$=$C_2H_5SS$—.

The product of Example 319 is carefully dissolved in degassed water (or mixed solvent if necessary). Lithium thiocyanate hydrate and zinc chloride (II) are carefully added. After the total disappearance of starting material is observed, ethanethiol is added and stirred at room temperature for 5 hours. Solvent is removed, the residue is purified by silica gel column chromatography to yield the title compound.

EXAMPLE 321

Formula II: R=R2=R3=H; R'=allyl; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{60}$=OH (R configuration); $R^{65}$=H.

A solution of "17-epi-FK-506" (as described in published European Patent Application No. 0356399) (0.41 g), o-phenylenediamine (0.108 g) and N-methylmorpholine (0.072 g) in absolute ethanol (3 mL) is refluxed under nitrogen overnight. Solvent is removed in vacuo and product is purified on silica gel (10 g) with methylene chloride/ acetonitrile (5:2, v/v) elution, followed by 40% acetone in hexanes to give the desired compound.

EXAMPLE 322

Formula II: R=ethyl; R'=R2=R3=H; n=1; taken together with the carbon atoms to which they are attached, $R^{26}$, $R^{27}$, $R^{28}$ and $R^{29}$ form a fused naphthalene group wherein the atoms adjacent to C-9 and C-10 are substituted by cyano groups; $R^{60}$=OH (R configuration); $R^{65}$=H.

Ascomycin (1 mmol) is reacted with 1,2-phenylenediacetonitrile and piperidine according to published methods of ring formation (*Bull. Soc. Chim. Fr.* 1946, 106; *J. Am. Chem. Soc.* 1951, 73, 436). Solvent is removed in vacuo and product is purified on silica gel to give the desired compound.

EXAMPLE 323

Formula II: R=ethyl; R'=R2=R3=H; n=1; taken together with the carbon atoms to which they are attached, $R^{26}$ and $R^{28}$ are each OH; $R^{27}$ and $R^{29}$, taken together form —$CH_2$—$C(CH_2)$—$CH_2$— group; $R^{60}$=OH (R configuration)l $R^{65}$=H.

Ascomycin (1 mmol) is reacted with 1-trimethylsilyl-2-iodomethyl-prop-2-ene and $SnF_2$ according to published methods of ring formation (J. Am. Chem. Soc. 1986, 108, 4683). Solvent is removed in vacuo and product is purified on silica gel to give the desired compound.

EXAMPLE 324

Formula V: R=ethyl; R'=R2=R3=H; n=1; X=subformula Ia; $R^{1'}$=$OCH_3$; $R^1$=TBSO— (R-configuration); Y=subformula IIIa; $R^{31}$ and $R^{32}$ taken together form diazo; $R^{33}$ and $R^{34}$ taken together form an oxo; $R^{35}$ and $R^{36}$ taken together form an oxo.

The product of Example 8b (16.9 g, 18.7 mmol) in $CH_3CN$ containing water (0.34 mL, 18.7 mmol) and triethylamine (3.9 mL, 28.1 mmol, 1.5 eq) was treated with a portion of methanesulfonylazide (4.5 mL, 56.2 mmol) at ambient temperature (7 hours). The mixture was concentrated in vacuo and filtered through a plug of silica gel (300 mL, 70–230 mesh) eluting with hexane:EtOAc (1 L, 2:1). Fractions containing product were pooled and concentrated. This was purified further by HPLC on silica gel (50 mm×500 mm, 230–400 mesh) eluting with hexane:EtOAc (6 L, 5:1). The appropriate fractions were combined and concentrated to provide product as a yellow foam (13.8 g, 14.8 mmol) in 79% yield. IR ($CDCl_3$) 2130, 1743, 1645 $cm^{-1}$; MS (FAB) m/z 968 (M+K), 940 (M+K–$N_2$).

EXAMPLE 325

Formula V: R=ethyl; R'=R2=R3=$R^{35}$=$R^{36}$=H; n=1; X=subformula Ia; $R^{1'}$=$OCH_3$; $R^1$=TBSO— (R configuration); Y=subformula IIIa'; $R^{33}$ and $R^{34}$ taken together form an oxo.

The product of Example 324 (13.8 g, 14.8 mmol) in N-methylpyrollidone (600 mL) containing water (96 mL) was heated at 110° C. for 80 min after gas evolution commenced. The mixture was cooled and partitioned between EtOAc (1 L) and water (1 L). The aqueous layer was extracted with additional EtOAc (1 L). The organic layers were each washed sequentially with water (1 L) and brine (500 mL), and were then combined and dried ($NaSO_4$). The solvent was removed invacuo and the residue was passed through a silica gel column (300 mL, 70–230 mesh) eluting with a mixture of hexane:EtOAc (2:1, 2 L). The fractions containing product were combined and concentrated to a yellow oil (10 g) which was further purified by HPLC on silica gel (1 L, 230–400 mesh) eluting with hexane:EtOAc (5:1). This provided pure product (5.3 g, 6.1 mmol) in 41% yield. IR ($CDCl_3$) 1750, 1722, 1705 (sh), 1645 $cm^{-1}$; MS (FAB) m/z 914 (M+K).

Anal. Calcd. for $C_{48}H_{81}NO_{11}Si$: C, 65.79; H, 9.32; N, 1.60. Found: C, 65.57; H, 9.08; N, 1.56.

EXAMPLE 326

Formula V: R=ethyl; R'=$R^2$=$R^3$=$R^{2a}$=$R^{2a'}$=H; n=1; X=subformula Ib; $R^{1'}$=$OCH_3$; $R^{3a}$ and $R^4$ taken together form an oxo; Y=subformula IIIa; $R^{31}$ and $R^{32}$ taken together form a diazo; $R^{33}$ and $R^{34}$ taken together form an oxo; $R^{35}$ and $R^{36}$ taken together form an oxo.

The product of Example 14a (3.56 g, 4.5 mmol) in acetonitrile (89 mL) containing water (82 micro-L, 4.5 mmol) and triethylamine (0.95 mL, 6.8 mmol, 1.5 eq.) was treated with methanesulfonylazide (1.09 mL, 13.6 mmol, 3 eq.) for 6 h. Volatiles were immediately removed invacuo and the residue purified by MPLC on 230–400 mesh $SiO_2$ (2.54 cm×45 cm column) eluting with hexane:acetone (4:1) collecting 100 mL fractions throughout, which provided pure product (2.73 g, 3.35 mmol) in 75% yield. IR (film) 2930, 2115, 1725, 1645, 1455, 1200 $cm^{-1}$; MS (FAB) m/z (M+K+thioglycerol)=932, (M+K)=852, (M+K–$N_2$)=824.

EXAMPLE 327

Formula V: R=ethyl; R'=$R^2$=$R^3$=$R^{2a}$=$R^{2a'}$=H; n=1; X=subformula Ib; $R^{3a}$ and $R^4$ taken together form an oxo; Y=subformula IIIa'; $R^{1'}$=$OCH_3$; $R^{33}$ and $R^{34}$ taken together form an oxo.

The product of Example 326 (1.0 g, 1.23 mmol) in N-methylpyrollidone (50 mL) and water (8 mL) was heated at 110° C. (45 min). The reaction mixture was cooled and partitioned between water (500 mL) and EtOAc (300 mL). The aqueous layer was extracted with additional EtOAc (300 mL). The organic layers were washed with additional water (500 mL) and brine (500 mL), combined, and dried ($Na_2SO_4$). The extract was decanted from the drying agent and concentrated to a colorless foam (1.04 g), which was purified by silica gel chromatography (70–230 mesh, 300 mL) eluting with hexane:acetone (4:1, 2.5 L). The appropriate fractions were pooled and concentrated to provide pure product (0.55 g, 0.72 mmol) in 59% yield. IR ($CDCl_3$) 1743, 1721, 1643 $cm^{-1}$; MS (FAB) m/z 798 (M+K).

Anal. Calcd. for $C_{42}H_{65}NO_{11}$: C, 66.38; H, 8.62; N, 1.84. Found: C, 66.74; H, 8.29; N, 2.25.

EXAMPLE 328

Formula V: R=ethyl; R'=R2=R3=$R^{34}$=$R^{35}$=$R^{36}$=H; n=1; X=subformula Ia; $R^1$=TBSO— (R configuration); Y=subformula IIIa'; $R^{1'}$=$OCH_3$; $R^{33}$=OH.

A 1.0M solution of $LiAlH(Ot-Bu)_3$ in THF (4.0 mL, 4.0 mmol) was added dropwise to the product of Example 325 (877 mg, 1.0 mmol) in THF (4.0 mL) at –20° C. and allowed to stir at this temperature for 5 h, whereupon the reaction was quenched by the addition of acetone (0.5 mL) and then stirred vigorously at room temperature for 15 minutes with a saturated aqueous solution of sodium potassium tartrate (20 mL). The slurry was extracted with EtOAc (2×100 mL) and each extract was washed with 1N HCl (20 mL) and brine (2×30 mL). The organics were combined, dried ($Na_2SO_4$) and concentrated in vacuo. Purification by chromatography on 70–230 mesh silica gel (8 g) eluting with toluene:EtOAc (5:1) provided pure product (389 mg, 0.44 mmol) as a colorless foam in 44% yield. IR ($CDCl_3$) 1735, 1720 (sh), 1670, 1645 $cm^{-1}$; MS (FAB) m/z 918 (M+K).

EXAMPLE 329

Formula III: R=ethyl; R'=R2=R3=$R^{34}$=$R^{35}$=$R^{36}$=H; n=1; Y=subformula IIIa'; $R^{33}$=OH.

A 1M solution of HF (0.35 mL, 0.35 mmol (0.42 mL 48% aqueous HF in 9.58 mL $CH_3CN$ provides a 1M solution)) was added dropwise to a solution of the product of Example 328 (290 mg, 0.33 mmol) in acetonitrile (3.2 mL) at 0° C. The mixture was warmed to room temperature and stirred for 45 minutes, whereupon it was cooled to 0° C. and solid pulverized $NaHCO_3$ (244 mg, 2.9 mmol) was added. After 30 minutes anhydrous $MgSO_4$ (250 mg) was added and the mixture stirred for 15 minutes, when it was diluted with methylene chloride (15 mL), centrifuged and passed thru a plug of silica gel. The silica was eluted with hexane:acetone (1:1), and the fractions containing product were pooled, concentrated and purified by HPLC on silica gel eluting with hexane:acetone (2:1) providing desired product (163 mg, 0.21 mmol) in 64% yield. IR (CDCl$_3$) 1735, 1645 cm$^{-1}$; MS (FAB) m/z 802 (M+K).

Anal. Calcd. for $C_{42}H_{69}NO_{11}$: C, 66.03; H, 9.10; N, 1.83. Found: C, 65.92; H, 8.93; N, 1.76.

EXAMPLE 347

Formula I: R=ethyl; R'=R2=R3H; n=1; R$^{1'}$=OCH$_3$; R$^1$=—OC(O)-(ortho-NO$_2$)—C$_6$H$_4$ (R configuration).

Ascomycin (791 mg, 1.0 mmol) and triethylamine (0.28 mL, 2.0 mmol) in dichloromethane (10 mL) were cooled to 0° C. 2-Nitrobenzoylchloride (322 µL, 2.2 mmol) was added followed by DMAP (122 mg, 1.0 mmol). Warmed the mixture to room temperature and after 24 hours partioned the solution between 1N H$_3$PO$_4$ (30 mL) and EtOAc (30 mL). The aqueous layer was extracted again with EtOAc (30 mL). The organics were washed with brine (2×30 mL), combined, dried (Na$_2$SO$_4$) and concentrated in vacuo. The residue was purified by HPLC on silica gel eluting with hexane:acetone (2.5:1) providing the title compound in 40% yield. MS (FAB) m/z 979 (M+K).

EXAMPLE 348

Formula V; subformula IIIa: R=ethyl; R'=R2=R3=R$^{31}$=R$^{32}$=R$^{34}$H; n=1; R$^{1'}$=OCH$_3$; R$^1$=—OC(O)-(ortho-NO$_2$)—C$_6$H$_4$ (R configuration); R$^{33}$=—OC(O)-(ortho-NO$_2$)—C$_6$H$_4$; R$^{35}$=R$^{36}$=O.

Also isolated from the products of Example 347 was the title compound. MS (FAB) m/z 1128 (M+K).

EXAMPLE 349

Formula I: R=ethyl; R'=R2=R3=H; n=1; R$^{1'}$=OCH$_3$; R$^1$=—OC(O)-2-pyridyl (R configuration).

1-(3-Dimethylaminopropyl)-3-ethylcarbodiimide hydrochloride (700 mg, 3.7 mmol) was added at 0° C. to ascomycin (791 mg, 1.0 mmol), picolinic acid (381 mg, 3.1 mmol) and triethylamine (0.28 mL, 2.0 mmol) in dichloromethane (10 mL) followed by DMAP (122 mg, 1.0 mmol). The mixture was warmed to room temperature and stirred for 36 hours, whereupon it was partitioned between EtOAc (30 mL) and water (30 mL). Organics washed with brine (2×30 mL). Aqueous portions reextracted with EtOAc (30 mL), organics were combined, dried (Na$_2$SO$_4$) and concentrated in vacuo. Residue was purified by HPLC on silica gel eluting with hexane:acetone (1:1) to provide the title compound. MS (FAB) m/z 935 (M+K).

EXAMPLE 350

Formula V: subformula IIIa: R=ethyl; R'=R2=R3=R$^{31}$=R$^{34}$==H; n=1; R$^{1'}$=OCH$_3$; R$^1$=—OC(O)-2-pyridyl (R configuration); R$^{32}$ and R$^{33}$ taken together form a bond; R$^{35}$=R$^{36}$=O.

Also isolated from the products of Example 349 was the title compound. MS (FAB) m/z 917 (M+K).

EXAMPLE 351

Formula V: subformula IIIa: R=ethyl; R'=R2=R3=R$^{31}$=R$^{34}$=H; n=1; R$^{1'}$=OCH$_3$; R$^1$=—OC(O)-2-pyridyl (R configuration); R$^{33}$=—OC(O)-2-pyridyl; R$^{35}$=R$^{36}$=O.

Also isolated from the products of Example 349 was the title compound. MS (FAB) m/z 1040 (M+K).

EXAMPLE 352

Formula I: R=ethyl; R'=R2=R3=H; n=1; R$^{1'}$=OCH$_3$; R$^1$=—OC(O)-(ortho-NH$_2$)—C$_6$H$_4$ (R configuration).

The title compound is synthesized in the manner described in Example 111 substituting the product from Example 347 for the product from Example 110.

EXAMPLE 353

Formula V; subformula IIIa: R=ethyl; R'=R2=R3=R$^{31}$=R$^{32}$=R$^{34}$=H; n=1; R$^{1'}$=OCH$_3$; R$^1$=—OC(O)-(ortho-NH$_2$)—C$_6$H$_4$ (R configuration); R$^{33}$=—OC(O)-(ortho-NH$_2$)—C$_6$H$_4$; R$^{35}$=R$^{36}$=O.

The title compound is synthesized in the manner described in Example 111 substituting the product from Example 348 for the product from Example 110.

EXAMPLE 354

Formula III: R=ethyl; R'=R2=R3=H; n=1; R$^{31}$=R$^{32}$=H; one of R$^{33}$ and R$^{34}$=H and the other ==N-benzylpiperazinyl; R$^{35}$ and R$^{36}$ taken together form oxo.

The product of Example 36 (500 mg, 0.65 mmol) was dissolved in 5 mL of methylene chloride containing 1-benzyl-piperazine (337 mL, 1.95 mmol) and triethylamine (270 mL, 1.95 mmol). The mixture was stirred at room temperature for one over night Ethyl acetate (50 mL) and brine solution were added and partitioned. The ethyl acetate layer was washed with brine (×3), dried over anhydrous magnesium sulfate. Purification was carried out by silica gel column, followed by HPLC to obtain the title compound. Yield 159 mg (26%), MS (FAB) m/z: M+H=950, M+K=988.

EXAMPLE 355

Formula III: R=ethyl; R'=R2=R3=H; n=1; R$^{31}$=R$^{32}$=H; one of R$^{33}$ and R$^{34}$=H and the other ==N-methylpiperazinyl; R$^{35}$ and R$^{36}$ taken together form oxo.

The title compound was prepared from the product of Example 36 (700 mg, 0.91 mmol) and 1-methylpiperazine (507 mL, 4.55 mmol), according to the procedure described in Example 354. Yield 208 mg (26%), MS (FAB) m/z: M+H=874, M+K=912.

EXAMPLE 356

Formula III: R=ethyl; R'=R2=R3=H; n=1; R$^{31}$=R$^{32}$=H; one of R$^{33}$ and R$^{34}$=H and the other ==N-phenylpiperazinyl; R$^{35}$ and R$^{36}$ taken together form oxo.

The title compound was prepared from the product of Example 36 (500 mg, 0.65 mmol) and 1-phenylpiperazine (493 mL, 3.25 mmol), according to the procedure described in Example 354. Yield 248 mg (41%), MS (FAB) m/z: M+H=936, M+K=974.

EXAMPLE 357

Formula I: R=ethyl; R'=R2=R3=H; n=1; R$^{1'}$=OCH$_3$; R$^1$=azido (R Configuration).

To a stirred solution of the product of Example 9 (0.9 g, 1 mmol) in methylene chloride (2 mL) was added n-tetrabutylammonium azide (3.5 mmol) in chloroform (10 mL). After stirring at 45° C. overnight and at room temperature for 3 days, the reaction mixture was treated according to the procedure described in Example 1b and was further purified by HPLC (high performance liquid chromatography) to obtain the title compound (66.2 mg). m/z: M+K=855; IR(KBr) 3490–3420, 2960, 2940, 2875, 2820, 2100, 1740, 1720, 1705, 1650, 1455, 1380, 1350, 1285, 1245, 1200cm$^{-1}$.

EXAMPLE 358

Formula VII: R=ethyl; R'=R2=R3=H; n=1; R$^{1'}$=OCH$_3$; R$^1$=azido (S Configuration); R$^{21}$ and R$^{22}$ taken together form an oxo group; R$^{31}$ and R$^{33}$ taken together form a bond; R$^{32}$=H; R$^{34}$=H; R$^{35}$ and R$^{36}$ taken together form an oxo group.

The title compound was isolated as a by-product from the reaction described in Example 1b. Yield: 53.0 mg. MS (FAB) m/z: M+K=837; IR(KBr) 3430, 2960, 2930, 2870, 2825, 2090, 1735, 1715, 1670, 1650, 1625, 1590, 1450, 1375, 1360, 1345, 1325, 1280, 1270, 1250, 1235, 1200cm$^{-1}$.

EXAMPLE 359

Formula I: R=ethyl; R'=R2=R3=H; n=1; R$^{1'}$=OCH$_3$; R$^1$=ICH$_2$C(O)NH (S-Configuration).

The product of Example 2 (316.4 mg, 0.4 mmol) in 5 mL of methylene chloride at 0° C. was treated with iodoacetic anhydride (169.9 mg, 0.48 mmol), triethylamine (0.115 mL, 0.8 mmol) and DMAP (4 mg, 0.04 mmol), and the mixture was stirred at 0° C. for 2 hours and at room temperature for 6 hours. Ethyl acetate (25 mL) was added, and the organic layer washed with 10%-KHSO$_4$, brine, 10%-NaHCO$_3$, brine, and then dried over magnesium sulfate. The crude product (383.6 mg) obtained was purified by HPLC. Yield: 37.1 mg; MS (FAB) m/z: M+K=997.

EXAMPLE 360

Formula I: R=ethyl; R'=R2=R3=H; n=1; R$^{1'}$=OCH$_3$; R$^1$=Diethylphosphoryloxy (R-Configuration).

Ascomycin (474 mg, 0.6 mmol) was dissolved in 8 mL of benzene at 0° C. Triethylamine (250 mL, 1.8 mmol), diethylchlorophosphate (250 mL, 1.8 mmol), followed by DMAP (15 mg, 0.12 mmol) were added to the reaction mixture. It was stirred at 0° C. for 15 minutes and allowed to warm to room temperature. After stirring overnight, 20 mL of cold 10%-NaHSO$_4$ aqueous solution was carefully added to the cooled reaction mixture. Ethyl acetate (40 mL) was added to extract the compound. The organic layer was washed with 10%-NaHSO$_4$, brine, saturated NaHCO$_3$, brine and dried over anhydrous magnesium sulfate. After the solvent was removed, 632 mg of crude product was obtained. This was purified by reverse phase-HPLC to yield 140 mg of pure title compound in 25% yield. MS (FAB) m/z: M+K=966.

EXAMPLE 361

Formula IV: R=ethyl; R'=R2=R3=H; n=1; R$^{1'}$=OCH$_3$; R$^1$=H, R$^{21}$=OH, R$^{22}$=H.

The product of Example 11 (3.24 g, 3.5 mmol) was dissolved in 40 mL of benzene under nitrogen atmosphere. AIBN (2,2'-azobis[2-methylpropanenitrile], 29 mg) and tributyltin hydride (1.4 mL, 5.25 mmol) was added to the reaction mixture. The mixture was gently refluxed at 80° C. for 4 hours, and solvent was removed. The residue was dissolved in ethyl acetate (60 mL) and washed with brine (30 mL×2), 10% sodium bisulfate (30 mL×3), brine (30 mL×1), saturated sodium bicarbonate (30 mL×3), and brine (30 mL×3). It was then dried over anhydrous magnesium sulfate. Purification of the crude product (5.01 g) was carried out by silica gel column, followed by reverse phase HPLC to obtain the title compound. Yield 466 mg (17%), MS (FAB) m/z: M+K=816.

EXAMPLE 362

Formula I: R=ethyl; R'=R2=R3=H; n=1; R$^{1'}$=OCH$_3$; R$^{2a}$=H, R$^{3a}$=H, R$^{2a'}$ and R$^4$ taken together form a bond).

C-32-Trifluoromethanesulfonyl-C-24-tertbutyldimethylsilyl ascomycin (580 mg, 0.16 mmol) was dissolved in 4 mL of methylene chloride and triethylamine (684 ml, 1.68 mmol) was added. The mixture was stirred at 50° C. for 3 hours and at room temperature overnight. Methylene chloride was evaporated and ethyl acetate (40 mL) added to the residue, which was washed with 10% sodium hydrogen sulfate (20 mL×3), brine (20 mL), saturated sodium bicarbonate (20 mL×3) and brine (20 mL×3), and dried over magnesium sulfate. After deprotection according to the procedure of Example 60, the title compound was obtained by silica gel chromatography, followed by normal phase HPLC. Yield: 50 mg (12%); MS (FAB) m/z: M+K=812.

EXAMPLE 363

Formula V: R=ethyl; n=1; R'=R2=R3=H; R$^{1'}$=OCH$_3$; R$^1$=t-butyldimethylsilyloxy; R$^{31}$=H; R$_{32}$=H; R$^{33}$=OH; R$^{34}$=H; R$^{35}$=—O-benzoyl (S-configuration); R$^{36}$=H.

To a stirred solution of 32-TBDMS, 22-S-dihydro ascomycin (prepared according to the procedure of Example 103c, 0.14 g, 0.15 mmol) and triethylamine (0.10 mL, 0.75 mmol) in CH$_2$Cl$_2$ (3 mL) was added benzoyl chloride (0.052 mL, 0.45 mmol) followed by DMAP (0.002 g, 0.015 mmol). The reaction was stirred at room temperature overnight, and then diluted with ethyl acetate. The ethyl acetate layer was washed with 0.1M H$_3$PO$_4$, NaHCO$_3$, brine and dried over Na$_2$SO$_4$. Evaporation provided the title compound (0.13 g).

EXAMPLE 364

Formula III: R=ethyl; n=1; R'=R2=R3=H; R$^{31}$=H; R$^{32}$=H; R$^{33}$=OH; R$^{34}$=H; R$^{35}$=—O-benzoyl (S-Configuration); R$^{36}$=H.

The crude product derived from the procedure of Example 363 (0.13 g) was treated with HF according to the procedure of Example 60 and then purified by RP-HPLC (41.4 mm ID, Dynamax-60A 8 μm phenyl, 83-D41-C) to give 0.085 g of the title compound in 64% yield. FAB-MS (m/z) 936 (M+K).

EXAMPLES 365 AND 365a

Formula V: R=2-hydroxyethyl; n=1; R'=R2=R3=H; R$^{1'}$=OCH$_3$; R1=t-butyldimethylsilyloxy; R$^{31}$=H; R$^{32}$=H; R$^{33}$=t-butyldimethylsilyloxy; R$^{34}$=H; R$^{35}$ and R$^{36}$ taken together form an oxo group, and Formula VII: R=2-hydroxyethyl; n=1; R'=R2=R3=H; R$^{1'}$=OCH$_3$; R1=t-butyldimethylsilyloxy; one of R$^{21}$ and R$^{22}$ is H and the other is OH; R$^{23}$=OH; R$^{24}$=R$^{31}$=H; R$^{32}$H; R$^{33}$=t-butyldimethylsilyloxy; R$^{34}$=H; R$^{35}$ and R$^{36}$ taken together form an oxo group.

To a stirred solution of 32,24 -bisTBDMS, 21-ethanal ascomycin (0.50 g, 0.50 mmol, prepared according to the methods described in published PCT applications Nos. WO 89/05304 and WO 91/04025) and sodium triacetoxyborohydride (0.31 g, 1.45 mmol) in CH$_3$CN (15 mL) at 0° C. was added acetic acid (0.25 mL, 4.36 mmol). The reaction mixture was stirred at 0° for 2 hours, quenched with water, and stirred for another 0.5 hour while warming to room temperature. The reaction mixture was then partitioned between ethyl acetate and brine. The ethyl acetate layer was washed sequentially with aqueous NaHCO$_3$ and brine, dried over Na$_2$SO$_4$ and concentrated to give 0.56 g of crude product. Purification was done by silica gel column chromatography, eluting with 7.5% to 15% acetone in hexane. The desired product 32,24-bisTBDMS, 21-ethanol ascomycin (Example 365, 0.11 g) was collected along with the starting material (0.13 g) and the direduction product (Example 365a, 0.06 g) which was also reduced at position C-9.

EXAMPLE 366

Formula V: R=2-benzoyloxyethyl; n=1; R'=R2=R3=H; $R^{1'}$=OCH$_3$; R1=t-butyldimethylsilyloxy; $R^{31}$=H; $R^{32}$=H; $R^{33}$=t-butyldimethylsilyloxy; $R^{34}$=H; $R^{35}$ and $R^{36}$ taken together form an oxo group.

The product of Example 365 (32,24-bisTBDMS, 21-ethanol ascomycin, 110 mg) was reacted with benzoyl chloride using the same conditions used in Example 363. Purification of the titled bis-TBDMS protected benzoate was achieved using a silica gel column. Yield: 90 mg.

EXAMPLE 367

Formula III: R=2-benzoyloxyethyl; n=1; R'=R2=R3=H; $R^{31}$=H; $R^{32}$=H; $R^{33}$=OH; $R^{34}$=H; $R^{35}$ and $R^{36}$ taken together form an oxo group.

The product of Example 366 (32,24-bisTBDMS, 21-ethyl benzoate ascomycin, 90 mg) was treated with HF according to the procedure of Example 60 and purified by RP-HPLC to give 0.04 g of the title compound.

FAB-MS (m/z) 950 (M+K). Anal. Calcd. for $C_{50}H_{73}N_1O_{14}·H_2O$: C, 64.57; H, 8.13; N, 1.51. Found: C, 64.66; H, 8.02; N, 1.71.

EXAMPLES 368a AND 368b

Formula III: R=ethyl; n=1; R'=R2=R3=H; $R^{31}$=H; $R^{32}$=H; $R^{34}$=H; $R^{33}$ and $R^{35}$ (S-configuration) taken together form —O—C(CH$_3$)$_2$—O—; $R^{36}$=H, and Formula III: R=ethyl; n=1; R'=R2=R3=H; $R^{32}$=H; $R^{34}$=H; $R^{33}$ and $R^{35}$ (R-configuration) taken together form —O—C(CH$_3$)$_2$—O—; $R^{36}$=H.

To a stirred solution of ascomycin (0.5 g, 0.6 mmol) in CH$_3$CN (8 mL) at 0° C. was added acetic acid (0.12 mL, 2.1 mmol) followed by sodium triacetoxyborohydride (0.15 g, 0.7 mmol). The reaction was stirred at 0° C. for 2 hours and quenched with water. The ice bath was removed and the reaction mixture was stirred for another 0.5 hour while warming to room temperature. The reaction mixture was partitioned between ethyl acetate and brine. The organic layer was washed sequentially with aqueous NaHCO$_3$ and brine, and dried over Na$_2$SO$_4$. The solvent was concentrated to give 0.51 g of crude material containing both S and R isomers of C22-dihydro ascomycin along with the unreacted starting material. The above crude material was dissolved in DMF (5 mL) containing dimethoxypropane (5 mL). Pyridinium p-toluenesulfonate (0.05 g) was added, and the mixture was stirred at the room temperature overnight. The reaction mixture was diluted with ether and washed with brine. The ether was dried over Na$_2$SO$_4$ and evaporated to give 0.56 g of the crude C22,24-acetonides. Purification was done by RP-HPLC (41.4 mm ID, Dynamax-60A 8 um phenyl, 83-D41-C) to isolate 0.15 g of C22-S,24-acetonide and 0.025 g of C22-R,24-acetonide isomer along with 0.096 g of ascomycin and 0.03 g of C22-R-dihydro ascomycin. 1H-NMR d 1.3 (s, 6H) for 22,24-S-acetonide, d 1.42 (s, 6H) for 22,24-R-acetonide; FAB-MS (m/z) 872 (M+K)

EXAMPLE 369

Formula V: R=ethyl; n=1; R'=R2=R3=H; $R^{1'}$=OCH$_3$; R1=t-butyldimethylsilyloxy; $R^{31}$=H; $R^{32}$=H; $R^{33}$=OH; $R^{34}$=H; $R^{35}$=—O—CO$_2$Bn (S-configuration); $R^{36}$=H.

32-TBDMS, 22-S-dihydro ascomycin (0.5 g,0.63 mmol), prepared according to the procedure of Example 103c, N-(benzyloxycarbonyloxy)succinimide (0.27 g, 1.1 mmol) and DMAP (0.07 g, 0.63 mmol) in CH$_2$Cl$_2$ (10 mL) were stirred at room temperature for 7 days. Purification was done by silica gel column chromatography, eluting with 5/95 acetone/hexane to give 0.31 g of 32-TBDMS, 22-S-benzyl carbonate ascomycin in 54% yield.

EXAMPLE 370

Formula III: R=ethyl; n=1; R'=R2=R3=H; $R^{31}$=H; $R^{32}$=H; $R^{33}$=OH; $R^{34}$=H; $R^{35}$=—O—CO$_2$Bn (S-configuration); $R^{36}$=H.

The product of Example 369 is treated with HF according to the procedure of Example 60 and purified by RP-HPLC to give the title compound.

EXAMPLE 371

Formula VI: R=ethyl; R'=R2=R3=H; n=1; $R^{26}$, $R^{27}$ and the carbon to which they are attached are absent; one of $R^{28}$ and $R^{29}$ is hydroxy and the other is —COOCH$_3$; C-8 is directly attached to C-10; $R^{31}$=H; $R^{32}$=H; $R^{33}$=H; $R^{34}$=H; $R^{35}$ and $R^{36}$ taken together form an oxo group; $R^{60}$=hydroxy (R configuration); $R^{65}$=H.

To a stirred solution of 24-desoxy ascomycin, the product of Example 380 (0.155 g, 0.2 mmol) in 1 mL of methanolic ErCl$_3$·6H$_2$O (0.2M) was added trimethylorthoformate (0.15 mL, 1.4 mmol). After stirring at room temperature for 5 hours, the reaction mixture was poured into aqueous NaHCO$_3$ and extracted with ether. The ether layer was washed with brine, dried over Na$_2$SO$_4$, and evaporated to give the crude product. After purification by RP-HPLC, the title compound (0.11 g) was isolated in 69% yield. FAB-MS (m/z) 846 (M+K)

EXAMPLES 372a AND 372b

Formula II: R=ethyl; R'=R2=R3=H; n=1; $R^{26}$, $R^{27}$ and the carbon to which they are attached are absent; one of $R^{28}$ and $R^{29}$ is hydroxy and the other is —COOCH$_3$; C-8 is directly attached to C-10; $R^{60}$=hydroxy (R configuration); $R^{65}$=H, and Formula VI: R=ethyl; R'=R2=R3=H; n=1; $R^{26}$, $R^{27}$ and the carbon to which they are attached are absent; one of $R^{28}$ and $R^{29}$ is hydroxy and the other is —COOCH$_3$; C-8 is directly attached to C-10; $R^{31}$ and $R^{33}$ taken together form a bond; $R^{32}$=H; $R^{34}$=H; $R^{35}$=OCH$_3$; $R^{36}$=OCH$_3$; $R^{60}$=hydroxy (R configuration); $R^{65}$=H.

The procedure of Example 371, in which 24-desoxy ascomycin was replaced with ascomycin, produced the title compounds of Examples 372a and 372b as major and minor products FAB-MS (m/z) 890 (M+K).

EXAMPLE 373

Formula III: R=ethyl; R'=R2=R3=H; n=1; $R^{31}$=$R^{32}$=$R^{34}$=H; and $R^{33}$=hydroxy; $R^{35}$ or $R^{36}$=H and the other —NR$^{38}$ where $R^{38}$=—NHS(O)$_2$R$^{40}$ and $R^{40}$=4-methylphenyl.

The hydrazone obtained in Example 221 (1.00 g, 1.04 mmol), sodium cyanoborohydride (261 mg, 4.16 mmol) and p-toluenesulfonic acid monohydrate were combined in a mixture of N,N-dimethylformamide and sulfolane (1:1, 46 mL). This mixture was heated at 110° C. for 5.5 hours under a nitrogen atmosphere. The reaction mixture was diluted with water (200 mL) and extracted with ether (200 mL). Several washings of the organic phase were required to remove N,N-dimethylformamide and sulfolane. The ether layer was dried over sodium sulfate, and the solvent was removed under reduced pressure. The crude material was purified by flash chromatography on silica gel eluting with 40% acetone in hexane. The title compound was obtained as a solid (176 mg): mp 84°–87° C.; IR (CDCl$_3$) cm$^{-1}$3430, 2940, 1735, 1630, 1455, 1170, 1090; MS (FAB) m/e: M+K=1000.

EXAMPLE 374

Formula III: R=ethyl; R'=R2=R3=H; n=1; R$^{31}$=H; R$^{32}$=H; R$^{33}$=OH; R$^{34}$=H; one of R$^{35}$ or R$^{36}$=—NH$_2$ and the other is H.

The oximes obtained from Example 7 (50 mg, 0.062 mmol) were combined with 10% palladium on charcoal in ethanol (10 mL, 100%). The mixture was placed under a hydrogen atmosphere (1 atm) and stirred at ambient temperature overnight. The catalyst was removed by passing the mixture through a filter agent, and the filtrate was evaporated to dryness to provide the title compound in quantitative yield: MS (FAB) m/e: M+K=831.

EXAMPLE 375

Formula V: R=ethyl; R'=R2=R3=H; n=1; R$^{1'}$=OCH$_3$; R$^1$=H; R$^{31}$=R$^{32}$=R$^{33}$=R$^{34}$=H; R$^{35}$ and R$^{36}$ taken together form an oxo group.

The product of Example 259 is dehydrated as described in Example 36. This material is subsequently hydrogenated as described in Example 380 below to furnish the title compound after purification by flash chromatography on silica gel eluting with acetone and hexane.

EXAMPLE 376

Formula V: R=ethyl; R'=R2=R3=H; n=1; R$^{1'}$=OCH$_3$; R$^{2a}$=R$^{3a}$=H; R4 and R$^{2a'}$ taken together form a bond; R$^{31}$=R$^{32}$=R$^{33}$=H; R$^{35}$ and R$^{36}$ taken together form an oxo group.

The product of Example 380 is dehydrated according to the procedure described in Example 362.

EXAMPLE 377

Formula V: R=ethyl; R'=R2=R3=H; n=1; R$^{1'}$=OCH$_3$; R$^{2a}$=R$^{3a}$=R$^{2a'}$=H; R$^4$=OH, R$^{31}$=R$^{33}$=R$^{34}$=H; R$^{35}$ and R$^{36}$ taken together form an oxo group.

The product of Example 51 is dehydrated as described in Example 36. This material is subsequently hydrogenated as described in Example 380 below to furnish the title compound after purification by flash chromatography on silica gel eluting with acetone and hexane.

EXAMPLE 378

Formula VI: R=ethyl; R'=R2=R3=H; n=1; taken together with the carbon atoms to which they are attached, R$^{26}$, R$^{27}$, R$^{28}$ and R$^{29}$ form a quinoxaline with C-9 and C-10 becoming positions 2' and 3' of the heterocyclic system; R$^{31}$=R$^{32}$=R$^{33}$=R$^{34}$=H; R$^{35}$ and R$^{36}$ taken together form an oxo group; R$^{60}$=OH (R configuration); R$^{65}$=H.

The product of Example 38 is hydrogenated as described in Example 380 to supply the title compound after purification by flash chromatography on silica gel eluting with acetone and hexane.

EXAMPLE 380

Formula III: R=ethyl; R'=R2=R3=H; n=1; R$^{31}$=R$^{32}$=R$^{33}$=R$^{34}$=H; R$^{35}$ and R$^{36}$ taken together form an oxo group.

The enone obtained in Example 36 (1.00 g, 1.29 mmol) was combined with 10% palladium on carbon (100 mg) in methanol and reduced under a hydrogen (1 atm) environment for 4 hours. The catalyst is removed by passing the mixture through a filter agent and the filtrate is concentrated under reduced pressure. The crude material was purified by flash chromatography on silica gel eluting with 25% acetone in hexane to supply the title compound (348 mg) as a colorless foam: MS (FAB) m/e: M+K=814.

EXAMPLES 381a AND 381b

Formula III: R=ethyl; R'=R2=R3=H; n=1; R$^{33}$=H; R$^{34}$=—O—; R$^{31}$=R$^{32}$=H; R$^{35}$ and R$^{36}$ taken together form =N— which is attached to the —O— at R$^{34}$ to form an isoxazoline, and Formula III: R=ethyl; R'=R2=R3=H; n=1; R$^{33}$=—O—; R$^{34}$=H; R$^{31}$=R$^{32}$=H; R$^{35}$ and R$^{36}$ taken together form =N— which is attached to the —O— at R$^{33}$ to form an isoxazoline The oxime mixture obtained in Example 7 (250 mg, 0.310 mmol) was dissolved in methylene chloride (25 mL), and the solution was chilled to 0° C. Martin sulfurane dehyrating reagent (208 mg, 0.310 mmol) was added. Two more equivalents of dehydrating reagent were added after one and two hours of reaction respectively. The reaction was quenched with isopropanol (3 mL), and the mixture washed with saturated aqueous bicarbonate solution (80 mL). The organic phase was dried and freed of solvent. The products were separated and purified by flash chromatography on silica gel eluting with 30% acetone in hexane. Example 381a: MS (FAB) m/e: M+K=827. Example 381b: MS (FAB) m/e: M+K=827.

EXAMPLE 382

Formula III: R=ethyl; R'=R2=R3=H; n=1; R$^{31}$=R$^{32}$=R$^{34}$=H; R$^{33}$=OH; R$^{35}$ and R$^{36}$ taken together are =N$^{48}$ where R$^{48}$ is —OCH$_2$CH=CH$_2$.

Ascomycin (2.02 g, 2.54 mmol) was dissolved in 90% ethanol (40mL) To this solution was added O-allyl hydroxylamine hydrochloride (0.6275 g, 5.72 mmol) followed by pyridine (0.2 mL, 2.54 mmol). The reaction was stirred at room temperature for 23 hours. It was then poured into water (75 mL) and extracted with ethyl acetate (2×75 mL). The extracts were combined and washed with brine (50 mL) and dried over magnesium sulfate. Removal of the solvent gave crude material which was flash chromatographed on silica gel eluting with 30% acetone in hexane. Yield 1.97 g: MS (FAB) m/e: M+K=885; $^{13}$C NMR (75 MHz) delta (selected signals) 196.7, 161.6, 133.6, 118.5, 74.9; IR (KBr) cm$^{-1}$3450, 2930, 1745, 1720, 1650, 1450, 1100.

EXAMPLE 383

Formula VIII: R=ethyl; R'=R2=R3=H; n=1; R$^{31}$ and R$^{33}$ taken together form a bond; R$^{32}$=R$^{34}$=H; R$^{35}$ and R$^{36}$ taken together form an oxo group.

The product of Example 36 (502 mg, 0.646 mmol) was dissolved in anhydrous tetrahydrofuran (40 mL). Potassium hydride (193 mg, 1.61 mmol as a 35% suspension in mineral oil) was added and the reaction stirred at room temperature. After 19 hours, an additional aliquot of potassium hydride (76 mg, 0.646 mmol) was added followed by quenching 7 hours hence. The tetrahydrofuran was removed, and the material partitioned between 25 mL of 1N hydrochloric acid and 25 mL of ethyl acetate. The aqueous phase was washed with an additional 15 mL of ethyl acetate. The organic phases were combined, washed with 20 mL of brine, dried over magnesium sulfate and freed of solvent. This material was flash chromatographed on silica gel eluting with 30% acetone in hexane. Yield 59 mg: MS (FAB) m/e: M+K=812; $^{13}$C NMR (125 MHz) delta (selected signals) 96.4, 80.1, 75.2; IR (KBr) cm$^{-1}$3430, 2920, 1755, 1735, 1690, 1625, 1455, 1090.

EXAMPLE 384

Formula VIII: R=ethyl; R'=R2=R3=H; n=1; $R^{31}$ and $R^{33}$ taken together form a bond; $R^{32}$=$R^{34}$=H; one of $R^{35}$ or $R^{36}$=H and the other =—OH.

The product of Example 224 (102 mg, 0.128 mmol) was dissolved in tetrahydrofuran (10 mL). Potassium hydride (20 mg, 0.462 mmol) as a 35% suspension was added, and the reaction mixture was stirred at room temperature for 20 hours. The mixture was quenched with water (0.5 mL) and concentrated under reduced pressure. The residue was partitioned between 0.5N hydrochloric acid and ethyl acetate (50 mL). The aqueous phase was washed again with ethyl acetate (25 mL), and the combined organic washes were dried over magnesium sulfate and freed of solvent. The crude material was purified by flash chromatography silica gel eluting with 30% acetone in hexanes. Yield 50 mg: MS (FAB) m/e: M+K=814; 13 C NMR (125 MHz) (delta, selected signal) 202.8, 76.4, 75.8, 74.5, 71.8.

EXAMPLE 385

Formula V: R=ethyl; R'=R2=R3=H; n=1; $R^{1'}$=OCH$_3$; $R^1$=tert-butyldimethylsiloxy; $R^{31}$ and $R^{33}$ taken together form a bond; $R^{32}$=$R^{34}$=H; one of $R^{35}$ and $R^{36}$=H and the other is —OC(O)CH$_2$CH$_3$.

The product of Example 36 was dehydrated and the pendant cyclohexanol hydroxyl group protected as its t-butyldimethylsilyl ether as described in Example 8a. Propionic acid (50 microliters, 0.673 mmol) was dissolved in hexane (10 mL) and N,N-dimethylformamide (50 microliters). To this, oxalyl chloride (0.29mL, 3.37 mmol) was added, and the reaction mixture stirred at room temperature for 1 hour. The salts were then removed by filtration, and the solvent removed in vacuo. The freshly made acid chloride was taken into anhydrous methylene chloride (10 mL). The hydrated, protected ascomycin derivative described above (202 mg, 0.225 mmol) was added along with diisopropylethylamine (0.2 mL, 1.13 mmol). After 48 hours, the dichloromethane was removed and the material partitioned between 1N hydrochloric acid (30 mL) and ethyl acetate (30 mL). The aqueous layer was washed with an additional ethyl acetate (15 mL). The organics were combined, washed with brine and dried over magnesium sulfate. The solvent was then removed and the material flash chromatographed on silica gel eluting with 25% acetone in hexane. Yield 101 mg: MS (FAB) m/e: M+K=946.

EXAMPLE 386

Formula III: R=ethyl; R'=R2=R3=H; n=1; $R^{31}$=$R^{32}$=$R^{34}$=H; $R^{33}$=—CH(—)CO$_2$Et: $R^{35}$ and $R^{36}$ taken together are =N— which is attached to C22 and the unoccupied valence of the methine on $R^{33}$ to form a cyclic imine.

The 4-chlorobenzylimine of glycine ethyl ester (1.46 g, 6.46 mmol) was dissolved in 80 mL of anhydrous tetrahydrofuran. To this, 0.39 g (9.70 mmol) of sodium hydride as a 60% suspension in mineral oil was added. These were allowed to stir at room temperature for 15 min, before adding 2.00 g (2.58 mmol) of the product of Example 36. After 24 hours at room temperature, the reaction was quenched by the addition of 10 mL of water. The tetrahydrofuran was removed, and the residue loaded onto silica gel and eluted with 25% acetone in hexane. Yield 0.60 g: MS (FAB) m/e: M+K=897, M+H=859.

EXAMPLE 387

Formula III: R=ethyl; R'=R2=R3=H; n=1; $R^{31}$=—(CH(—)) p-chlorophenyl in which the unoccupied valence of the amine and the unoccupied valence on $R^{33}$ forming a pyrrolidine; $R^{32}$=$R^{34}$=H; $R^{33}$=—CH(—)CO$_2$Et: $R^{35}$ and $R^{36}$ taken together form. an oxo group.

The product of Example 36 (501 mg, 0.464 mmol) and the 4-chlorobenzylimine of glycine ethyl ester (218 mg, 0.97 mmol) were dissolved in 20mL anhydrous tetrahydrofuran. To this, 1.40 mL (9.69 mmol) of triethylamine and 265 mg (3.04 mmol) of lithium bromide were added. The reaction was stirred at room temperature under nitrogen. After 3 hours, the reaction was poured into 20 mL of 1N hydrochloric acid and 20 mL of ethyl acetate. The aqueous phase was washed with an additional 20 mL of ethyl acetate. The organic washes were combined and washed with 15 mL of brine. The organic layer was dried over magnesium sulfate and freed of solvent to give 0.70 g crude material. This material was recrystallized from 2:1 ethyl acetate/hexane to give 0.23 g of the title compound: MS (FAB) m/e: M+K= 1037, 1039, M+H=999, 1001; 13 C NMR (75 MHz) delta (selected signals) 167.6, 141.7, 135.8, 129.4, 128.9, 63.1, 62.9, 51.8, 50.4; IR (KBr) cm$^{-1}$ 3430, 2930, 1745, 1650, 1450, 1090.

EXAMPLES 388a AND 388b

Formula III: R=ethyl; R'=R2=R3=H; n=1; $R^{31}$=$R^{32}$=$R^{34}$=H; $R^{35}$ and $R^{36}$ taken together form =NMe(O) (E- and Z-Configurations)

Ascomycin (15 g), triethylamine (9.1 g) and N-methylhydroxylamine hydrogen chloride (7.5 g) in ethanol (60 mL) were stirred at 45° C. for 60 hours. Solvent was removed in vacuo and the product purified on silica gel eluting with 10% ethanol/dichloromethane.

Title compound of Example 388a: Yield: 10.2 g; MS(FAB) m/z: M+K=859.

Title compound of Example 388b: Yield: 3.5 g; MS(FAB) m/z: M+K=859.

EXAMPLE 391

Formula I: R=ethyl; R'=R2=R3=H; n=1; $R^{1'}$=OCH$_3$; $R^1$=— O-allyl (R-Configuration).

Silver (I) oxide (0.6 g) was added into a stirred solution of ascomycin (0.4 g) and allyl iodide (0.6 g) in acetonitrile (0.5 mL) at 0° C. After being stirred at room temperature overnight, the reaction mixture was poured over a column of silica gel (2 g) in ether and eluted with ether. The semi-pure product was purified by silica gel chromatography (10 g) eluting with 2% isopropanol/dichloromethane. Yield: 0.245 g; MS(FAB) m/z: M+NH$_4$=849.

EXAMPLE 392

Formula I: R=ethyl; R'=R2=R3=H; n=1; $R^{1'}$=OCH$_3$; $R^1$=4-(N-morpholino-2-trans-butenyl)-O— (R Configuration).

Silver (I) oxide (0.6 g) is added into a stirred solution of ascomycin (0.4 g) and 4-(N-morpholino-2-trans-butenyl)-bromide (0.6 g) in acetonitrile (0.5 mL) at 0° C. After being stirred at room temperature overnight, the reaction mixture is poured over a column of silica gel (2 g) in ether and eluted with ether. The semi-pure product is purified by silica gel chromatography (10 g) eluting with 2% isopropanol/ dichloromethane.

EXAMPLE 393

Formula I: R=ethyl; R'=R2=R3=H; n=1; $R^{1'}$=OCH$_3$; $R^1$=N-tetrazole (S-Configuration).

Trifluoromethanesulfonyl anhydride (0.28 g in dry dichloromethane 1 mL) was added into a stirred solution of ascomycin (0.8 g) and diisopropylethyl amine (0.5 g) in dichloromethane (2 mL) at −15° C., After being stirred for 0.5 hour, tetrazole (0.1 g) was added and stirred at room temperature for 24 hours. Solvent was removed in vacuo and the crude purified by silica gel (40 g) eluting with 40% acetone/hexanes. The product was further purified by silica gel (40 g) eluting with 3% isopropanol/dichloromethane. Yield: 0.3 g; MS(FAB) m/z: M+K=882.

EXAMPLE 394

Formula I: R=ethyl; R'=R2=R3=H; n=1; $R^{1'}$=OCH$_3$; $R^2$=$R^{2'}$=H; $R^3$=H, $R^4$=—S-2-(N-methylimidazole)

A solution of trifluoromethanesulfonyl anhydride (0.45 g in 1 mL dichloromethane) was added dropwise into a solution of ascomycin (0.8 g) and diisopropylethylamine (0.5 g) in dichloromethane (3 mL) cooled in dry-ice isopropanol bath. The reaction was allowed to stir at room temperature for 0.5 hour after the addition of triflic anhydride, 2-Mercapto-1-methylimidazole (0.23 g) was added to the reaction mixture and stirred at room temperature for 24 hours. Solvent was removed in vacuo and the product purified on silica gel with 30% acetone/hexanes elution. Yield: 0.7 g; MS(FAB) m/z: M+H=888.

EXAMPLE 395

Formula I: R=ethyl; R'=R2=R3=H; n=1; $R^{1'}$=OCH$_3$; $R^2$=$R^{2'}$=H; $R^3$=H, $R^4$=—S-3-(1H-1,2,3-triazole)

The title compound was prepared from ascomycin, trifluoromethanesulfonyl anhydride-diisopropylamine, and 1H-1,2,3-triazole-3-thiol according to the procedure described in Example 394. MS(FAB) m/z: M+H=875.

EXAMPLE 396

Formula I: R=ethyl; R'=R2=R3=H; n=1; $R^{1'}$=OCH$_3$; $R^2$=$R^{2'}$=H; $R^3$=H, $R^4$=—S-5-(1-methyl-tetrazole)

The title compound was prepared from ascomycin, trifluoromethanesulfonyl anhydride-diisopropylamine, and 5-mercapto-1-methyl-tetrazole according to the procedure described in Example 394. MS(FAB) m/z: M+NH$_4$=907.

EXAMPLE 397

Formula I: R=ethyl; R'=R2=R3=H; n=1; $R^{1'}$=OCH$_3$; $R^2$=$R^{2'}$=H; $R^3$=H, $R^4$=—S-2-(imidazole)

The title compound is prepared from ascomycin, trifluoromethanesulfonyl anhydride-diisopropylamine, and 2-mercaptoimidazole according to the procedure described in Example 394.

EXAMPLE 398

Formula I: R=ethyl; R'=R2=R3=H; n=1; $R^{1'}$=OCH$_3$; $R^2$=$R^{2'}$=H; $R^3$=H, $R^4$=—S-2-(4-methyl-pyrimidine)

The title compound is prepared from ascomycin, trifluoromethanesulfonyl anhydride-diisopropylamine, and 2-mercapto-4-methylpyrimidine according to the procedure described in Example 394.

EXAMPLE 399

Formula I: R=ethyl; R'=R2=R3=H; n=1; $R^{1'}$=OCH$_3$; $R^2$=$R^{2'}$=H; $R^3$=H, $R^4$=—S-6-(xanthine)

The title compound is prepared from ascomycin, trifluoromethanesulfonyl anhydride-diisopropylamine, and 6-thioxanthine according to the procedure described in Example 394.

EXAMPLE 400

Formula I: R=ethyl; R'=R2=R3=H; n=1; $R^{1'}$=OCH$_3$; $R^2$=$R^{2'}$=H; $R^3$=H, $R^4$=—S-5-(tetrazoleacetic acid)

The title compound is prepared from ascomycin, trifluoromethanesulfonyl anhydride-diisopropylamine, and 5-mercapto-tetrazoleacetic acid according to the procedure described in Example 394.

EXAMPLE 401

Formula I: R=ethyl; R'=R2=R3=H; n=1; $R^{1'}$=OCH$_3$; $R^2$=$R^{2'}$=H; $R^3$=H, $R^4$=—NH-4-(pyridine)

The title compound is prepared from ascomycin, trifluoromethanesulfonyl anhydride-diisopropylamine, and 4-aminopyridine according to the procedure described in Example 394.

EXAMPLE 402

Formula I: R=ethyl; R'=R2=R3=H; n=1; $R^{1'}$=OCH$_3$; $R^2$=$R^{2'}$=H; $R^3$=H, $R^4$=—O-4-(pyridine)

The title compound is prepared from ascomycin, trifluoromethanesulfonyl anhydride-diisopropylamine, and 4-hydroxypyridine according to the procedure described in Example 394.

EXAMPLE 403

Formula I: R=ethyl; R'=R2=R3=H; n=1; $R^{1'}$=OCH$_3$; $R^2$=$R^{2'}$=H; $R^3$=H, $R^4$=—S-2-(pyrimidine)

The title compound was prepared from ascomycin, trifluoromethanesulfonyl anhydride-diisopropylamine, and 2-mercaptopyrimidine according to the procedure described in Example 394. MS(FAB) m/z: M+NH$_4$=903.

EXAMPLE 404

Formula I: R=ethyl; R'=R2=R3=H; n=1; $R^{1'}$=OCH$_3$; R1=—O-{4-[(4'-pyridyl)NH]-2-butenyl} (R-Configuration)

The title compound is prepared from ascomycin and 4-(4'-pyridyl)NH-2-butenyl iodide in the presence of silver (I) oxide according to the procedure described in Example 391.

EXAMPLE 405

Formula I: R=ethyl; R'=R2=R3=H; n=1; $R^{1'}$=OCH$_3$; R1=—O-{4-[(2'-pyrimidinyl)-S]-2-butenyl} (R-Configuration)

The title compound is prepared from ascomycin and 4-[(2'-pyrimidinyl)-S]-2-butenyl bromide in the presence of silver (I) oxide according to the procedure described in Example 391.

EXAMPLE 406

Formula I: R=ethyl; R'=R2=R3=H; n=1; $R^{1'}$=OCH$_3$; R1=—O-{4-[(2'-pyridinyl)-O]-2-butenyl} (R-Configuration)

The title compound is prepared from ascomycin and 4-[(2'-pyridinyl)-O]-2-butenyl bromide in the presence of silver (I) oxide according to the procedure described in Example 391.

EXAMPLE 407

Formula I: R=ethyl; R'=R2=R3=H; n=1; $R^{1'}$=OCH$_3$; R1=—O-{4-(2'-pyrimidinyl)-2-butenyl} (R-Configuration)

The title compound is prepared from ascomycin and 4-(2'-pyrimidinyl)-2-butenyl bromide in the presence of silver (I) oxide according to the procedure described in Example 391.

EXAMPLE 408

Formula I: R=ethyl; R'=R2=R3=H; n=1; R¹'=OCH$_3$; R1=—O-{4-(2'-imidazoyl)-2-butenyl} (R-Configuration)

The title compound is prepared from ascomycin and 1,4-bis(2'-imidazoylcarbonyloxy)-2-butenyl-O(CO)Cl in the presence of palladium catalyst according to the procedure described in literature (Lakhmiri, R; Lhoste, P. and Sinou, Tetr. Lett., 1989 30, 4669).

EXAMPLE 409

Formula I: R=ethyl; R'=R2=R3=H; n=1; R¹'=OCH$_3$; R1=—O-{4-(2'-pyrazinyl)-2-butenyl} (R-Configuration)

The title compound is prepared from ascomycin and 4-(2'-pyrazinyl)-2-butenyl-O(CO)Cl in the presence of palladium catalyst according to the procedure described in literature [Lakhmiri, R; Lhoste, P. and Sinou, Tetr. Lett., 1989 30, 4669].

EXAMPLE 410

Formula I: R=ethyl; R'=R2=R3=H; n=1; R¹'=OCH$_3$; R1=—O-{4-(2'-thiophenyl)-2-butenyl} (R-Configuration)

The title compound is prepared from ascomycin and 4-(2'-thiophenyl)-2-butenyl bromide in the presence of Bu$_2$SnO according to the procedure described in literature [Sato S.; Nunomura S.; Nakano, T.; Ito, Y. and Ogawa, T., Tetr. Lett., 1988 29, 4097].

EXAMPLE 411

Formula I: R=ethyl; R'=R2=R3=H; n=1; R¹'=OCH$_3$; R1=—O-{4-(2'-pyridinyl)-2-butenyl} (R-Configuration)

The title compound is prepared from ascomycin and 4-(2'-pyridinyl)-2-butenyl-OC(=NH)CCl$_3$ in the presence of acid catalyst according to the procedure described in literature [Iversen T. and Bundle, D. R., J. Chem. Soc., Chem. Comm., 1981 1240].

EXAMPLE 412

Formula I: R=ethyl; R'=R2=R3=H; n=1; R¹'=OCH$_3$; R1=—O—C(=O)-Pyrrolidine (R-Configuration)

A solution of ascomycin (0.8 g in 1 mL dichloromethane) is added dropwise into a solution of triphosgene (0.1 g) in pyridine (3 mL) at room temperature. The reaction is flowed to stir at room temperature for 96 hours. Pyrrolidine (0.23 g) is added to the reaction mixture and stirred at room temperature for 24 hours. Solvent is removed in vacuo and the product purified on silica gel with 30% acetone/hexanes elution.

EXAMPLE 413

Formula I: R=ethyl; R'=R2=R3=H; n=1; R¹'=OCH$_3$; R1=—O—C(=O)—NH—NHC(=O)—NH$_2$ (R-Configuration)

The title compound is prepared from ascomycin, triphosgene-diisopropylamine, and semicarbazide according to the procedure described in Example 412.

EXAMPLE 414

Formula I: R=ethyl; R'=R2=R3=H; n=1; R¹'=OCH$_3$; R1=—O—C(=O)—NH—O-Benzyl (R-Configuration)

The title compound is prepared from ascomycin, triphosgene-diisopropylamine, and O-benzylhydroxylamine according to the procedure described in Example 412.

EXAMPLE 415

Formula I: R=ethyl; R'=R2=R3=H; n=1; R¹'=OCH$_3$; R1=—O—(=O)—NH—NH-Benzyl (R-Configuration)

The title compound is prepared from ascomycin, triphosgene-diisopropylamine, and benzylhydrazine according to the procedure described in Example 412.

EXAMPLE 416

Formula I: R=ethyl; R'=R2=R3=H; n=1; R¹'=OCH$_3$; R¹=—OC(O)—O(4-nitrophenyl) (R-Configuration)

4-Nitrophenyl chloroformate (3 g) was added into a solution of ascomycin (7.91 g) in pyridine (10 mL) and heated up to 40°–50° C. for 3 hours. The reaction mixture was cooled in iced-water bath and diluted with ether (150 mL). The ether mixture was partitioned with ice-cold ether (100 mL) and 1N hydrochloric acid (2×50 mL). The organic phase was washed once with saturated brine, dried over magnesium sulfate and solvent removed in vacuo. The solid residue was purified by silica gel (200 g) eluting with 25% acetone/hexanes. Yield: 8.5 g; MS (FAB) m/e: M+K=995.

EXAMPLE 417

Formula I: R=ethyl; R'=R2=R3=H; n=1; R¹=Morpholino-C(O)—O— (R-Configuration)

Morpholine (0.09 g) was added into a stirred solution of the title compound of Example 416 (0.5 g) in dichloromethane (1 mL) and stirred at room temperature for 12 hours. The reaction mixture was purified by silica gel chromatography (25 g) eluting with 25% acetone/hexanes. Yield: 0.4 g; MS (FAB) m/e: M+K=943.

EXAMPLE 418

Formula I: R=ethyl; R'=R2=R3=H; n=1; R¹=OCH$_3$; R¹=Morpholino-(CH$_2$)$_2$—NHC(O)—O— (R-Configuration)

4-(2-Aminoethyl)-morpholine (0.08 g) was added into a stirred solution of triethylamine (0.1 g) and the title compound of Example 416 (0.5 g) in dichloromethane (1 mL) and stirred at room temperature for 12 hours. The reaction mixture was purified by silica gel chromatography (25 g) eluting with 60% acetone/hexanes. Yield: 0.25 g; MS (FAB) m/e: M+K=986.

EXAMPLE 419

Formula I: R=ethyl; R'=R2=R3=H; n=1; R¹=OCH$_3$; R¹=Morpholino-(CH$_2$)$_3$—NHC(O)—O— (R-Configuration)

The title compound was prepared from 4-(3-aminopropyl) morpholine (0.08 g), triethylamine (0.1 g) and the title compound of Example 416 (0.5 g) according to the procedures of Example 18. Yield: 0.35 g.

EXAMPLE 420

Formula I: R=ethyl; R'=R2=R3=H; n=1; R¹'=OCH$_3$; R¹=—OC(O)—L-Ornithine(d-Cbz)—O-Bn (R-Configuration)

L-Ornithine(d-Cbz)—OBn.HCl (1 g) was added into a solution of the title compound of Example 416 (0.96 g) in pyridine (3 mL) and stirred at room temperature for 24 hours. The reaction mixture was partitioned between ether (2×100 mL) and 1N hydrochloric acid (2×50 mL). The organic phase was washed once with brine, dried over magnesium sulfate and solvent removed in vacuo. The solid residue was purified by silica gel (20 g) eluted with 30% acetone/hexanes. Yield: 1.1 g.

EXAMPLE 421

Formula I: R=ethyl; R'=R2=R3=H; n=1; R¹'=OCH$_3$; R¹=—OC(O)-Piperidine (R-Configuration)

The title compound was prepared from piperidine and the title compound of Example 416 in pyridine according to the procedures described in Example 420. MS (FAB) m/e: M+K=941.

EXAMPLE 422

Formula I: R=ethyl; R'=R2=R3=H; n=1; $R^{1'}$=OCH$_3$; $R^1$=—OC(O)—N(CH$_2$CH$_2$OH)$_2$ (R-Configuration)

The title compound was prepared from diethanol amine and the title compound of Example 416 in pyridine according to the procedures described in Example 420. MS (FAB) m/e: M+K=961.

EXAMPLE 423

Formula I: R=ethyl; R'=R2=R3=H; n=1; $R^{1'}$=OCH$_3$; $R^1$=4Pyridyl-NHC(O)—O— (R-Configuration)

The title compound was prepared from 4-aminopyridine and the title compound of Example 416 in dichloromethane according to the procedures described in Example 418. MS (FAB) m/e: M+K=950.

EXAMPLE 424

Formula I: R=ethyl; R'=R2=R3=H; n=1; $R^{1'}$=OCH$_3$; $R^1$=4-Hyroxypiperidyl-C(O)—O— (R-Configuration)

The title compound was prepared from 4-hydroxypiperidine and the title compound of Example 416 in dichloromethane according to the procedures described in Example 418. MS (FAB) m/e: M+K=957.

EXAMPLE 425

Formula I: R=ethyl; R'=R2=R3=H; n=1; $R^{1'}$=OCH$_3$; $R^1$=4-oxo-piperidyl-C(O)—O— (R-Configuration)

The title compound was prepared from 4-piperidone monohydrate hydrochloride, pyridine and the title compound of Example 416 in dichloromethane according to the procedures described in Example 418. MS (FAB) m/e: M+K=955.

EXAMPLE 426

Formula I: R=ethyl; R'=R2=R3=H; n=1; $R^{1'}$=OCH$_3$; $R^1$=4-Amindo-piperidyl-C(O)—O— (R-Configuration)

The title compound was prepared from isonipecotamide and the title compound of Example 416 in dichloromethane according to the procedures described in Example 418. MS (FAB) m/e: M+K=984.

EXAMPLE 427

Formula I: R=ethyl; R'=R2=R3=H; n=1; $R^{1'}$=OCH$_3$; $R^1$=4-Carboxypiperidyl-C(O)—O— (R-Configuration)

The title compound was prepared from isonipecotic acid and the title compound of Example 416 in dichloromethane according to the procedures described in Example 418. MS (FAB) m/e: M+K=985.

EXAMPLE 428

Formula I: R=ethyl; R'=R2=R3=H; n=1; $R^{1'}$=OCH$_3$; $R^1$=4-Phenylpiperidyl-C(O)—OC(O)— (R-Configuration)

The title compound was prepared from 4-phenylpiperidine and the title compound of Example 416 in dichloromethane according to the procedures described in Example 418. MS (FAB) m/e: M+K=1017.

EXAMPLE 429

Formula I: R=ethyl; R'=R2=R3=H; n=1; $R^{1'}$=OCH$_3$; $R^1$=4-Piperidinopiperidyl-C(O)—O— (R-Configuration)

The title compound was prepared from 4-piperidinopiperidine and the title compound of Example 416 in dichloromethane according to the procedures described in Example 418. MS (FAB) m/e: M+K=1024.

EXAMPLE 430

Formula I: R=ethyl; R'=R2=R3=H; n=1; $R^{1'}$=OCH$_3$; $R^1$=Piperazine-C(O)—O— (R-Configuration)

The title compound was prepared from piperazine and the title compound of Example 416 in dichloromethane according to the procedures described in Example 418. MS (FAB) m/e: M+K=942.

EXAMPLE 431

Formula I: R=ethyl; R'=R2=R3=H; n=1; $R^{1'}$=OCH$_3$; $R^1$=4-Methylpiperazine-C(O)—O— (R-Configuration)

The title compound was prepared from 4-methylpiperazine and the title compound of Example 416 in dichloromethane according to the procedures described in Example 418. MS (FAB) m/e: M+K=956.

EXAMPLE 432

Formula I: R=ethyl; R'=R2=R3=H; n=1; $R^{1'}$=OCH$_3$; $R^1$=(N,N-diethylaminoethyl)NMe-C(O)—O— (R-Configuration)

The title compound was prepared from N-(N,N-diethylaminoethyl)-N-methylamine and the title compound of Example 416 in dichloromethane according to the procedures described in Example 418. MS (FAB) m/e: M+K=986.

EXAMPLE 433

Formula I: R=ethyl; R'=R2=R3=H; n=1; $R^{1'}$=OCH$_3$; $R^1$=(MeO)NMe-C(O)—O— (R-Configuration)

The title compound was prepared from N,O-dimethylhydroxylamine and the title compound of Example 416 in dichloromethane according to the procedures described in Example 418. MS (FAB) m/e: M+K=917.

EXAMPLE 434

Formula I: R=ethyl; R'=R2=R3=H; n=1; $R^{1'}$=OCH$_3$; $R^1$=NMe(OH)—C(O)—O— (R-Configuration)

The title compound was prepared from N-methylhydroxylamine and the title compound of Example 416 in dichloromethane according to the procedures described in Example 418. MS (FAB) m/e: M+K=903.

EXAMPLE 435

Formula I: R=ethyl; R'=R2=R3=H; n=1; $R^{1'}$=OCH$_3$; $R^1$=N-(cyclohexyl)(OH)—C(O)—O— (R-Configuration)

The title compound was prepared from N-cyclohexylhydroxylamine and the title compound of Example 416 in dichloromethane according to the procedures described in Example 418. MS (FAB) m/e: M+K=971.

EXAMPLE 436

Formula I: R=ethyl; R'=R2=R3=H; n=1; $R^{1'}$=OCH$_3$; $R^1$=N—H(OH)—C(O)—O— (R-Configuration)

The title compound was prepared from hydroxylamine and the title compound of Example 416 in dichloromethane according to the procedures described in Example 418. MS (FAB) m/e: M+K=889.

EXAMPLE 437

Formula I: R=ethyl; R'=R2=R3=H; n=1; $R^{1'}$=OCH$_3$; $R^1$=N(CH$_2$CH$_2$OH)Et—C(O)—O— (R-Configuration)

The title compound was prepared from N-hydroxyethyl, N-ethylamine and the title compound of Example 416 in dichloromethane according to the procedures described in Example 418. MS (FAB) m/e: M+K=945.

EXAMPLE 438

Formula I: R=ethyl; R'=R2=R3=H; n=1; $R^{1'}$=OCH$_3$; $R^1$=N(Bn)ME—C(O)—O— (R-Configuration)

The title compound was prepared from N-methylbenzylamine and the title compound of Example 416 in dichloromethane according to the procedures described in Example 418. MS (FAB) m/e: M+K=977.

EXAMPLE 439

Formula I: R=ethyl; R'=R2=R3=H; n=1; $R^{1'}$=OCH$_3$; $R^1$=N(CH$_2$CH$_2$Ph)Me—C(O)—O— (R-Configuration)

The title compound was prepared from N-methylphenethylamine and the title compound of Example 416 in dichloromethane according to the procedures described in Example 418. MS (FAB) m/e: M+K=991.

EXAMPLE 440

Formula I: R=ethyl; R'=R2=R3=H; n=1; $R^{1'}$=OCH$_3$; $R^1$=N(CH$_2$CH$_2$-2-pyridine)Me—C(O)—O— (R-Configuration)

The title compound was prepared from 2-(2-methylaminoethyl)pyridine and the title compound of Example 416 in dichloromethane according to the procedures described in Example 418. MS (FAB) m/e: M+K=992.

EXAMPLE 441

Formula I: R=ethyl; R'=R2=R3=H; n=1; $R^{1'}$=OCH$_3$; $R^1$Ethyl-sarcosine-C(O)—O— (R-Configuration)

The title compound was prepared from ethyl sarcosine hydrochloride and the title compound of Example 416 in pyridine according to the procedures described in Example 418. MS (FAB) m/e: M+K=973.

EXAMPLE 442

Formula I: R=ethyl; R'=R2=R3=H; n=1; $R^{1'}$=OCH$_3$; $R^1$=N-methyl-D-glucamine-C(O)—O— (R-Configuration)

The title compound was prepared from N-methyl-D-glucamine and the title compound of Example 416 in pyridine according to the procedures described in Example 418. MS (FAB) m/e: M+K=1051.

EXAMPLE 443

Formula I: R=ethyl; R'=R2=R3=H; n=1; $R^{1'}$=OCH$_3$; $R^1$=O—C(O)—O-(4-nitrophenyl) (S-Configuration)

The title compound was prepared from the the compound of Example 51 and 4-nitrophenyl chloroformate in pyridine according to the procedure described in Example 416. MS (FAB) m/e: M+K=995.

EXAMPLE 444

Formula I: R=ethyl; R'=R2=R3=H; n=1; $R^{1'}$=OCH$_3$; $R^1$=Morpholino-C(O)—O— (S-Configuration)

The title compound was prepared from the tile compound of Example 443 and morpholine in dichloromethane according to the procedure described in Example 417. MS (FAB) m/e: M+K=943.

EXAMPLE 445

Formula I: R=ethyl; R'=R2=R3=H; n=1; $R^{1'}$=OCH$_3$; $R^1$=N-methylpiperazine-C(O)—O— (S-Configuration)

The title compound is prepared from the the compound of Example 443 and N-methylpiperazine in dichloromethane according to the procedure described in Example 417.

EXAMPLE 446

Formula I: R=ethyl; R'=R2=R3=H; n=1; $R^{1'}$=OCH$_3$; $R^1$=Piperidino-C(O)—O— (S-Configuration)

The title compound is prepared from the the compound of Example 443 and piperidine in dichloromethane according to the procedure described in Example 417.

EXAMPLE 447

Formula I: R=ethyl; R'=R2=R3=H; n=1; $R^{1'}$=OCH$_3$; $R^1$=N(OH)H—C(O)—O— (S-Configuration)

The title compound is prepared from the tile compound of Example 443 and hydroxylamine hydrochloride in pyridine according to the procedure described in Example 417.

EXAMPLE 448

Formula I: R=ethyl; R'=R2=R3=H; n=1; $R^{1'}$=OCH$_3$; $R^1$=4-pyridyl-NH—C(O)—O— (S-Configuration)

The title compound was prepared from the tile compound of Example 443 and 4-aminopyridine in dichloromethane according to the procedure described in Example 417. MS (FAB) m/e: M+K=950.

EXAMPLE 449

Formula I: R=ethyl; R'=R2=R3=H; n=1; $R^{1'}$=OCH$_3$; $R^1$=N-methyl-D-glucamine-C(O)—O— (S-Configuration)

The title compound was prepared from N-methyl-D-glucamine and the title compound of Example 443 in pyridine according to the procedures described in Example 418. MS (FAB) m/e: M+K=1051.

EXAMPLE 450

Formula I: R=ethyl; R'=R2=R3=H; n=1; $R^{1'}$=OCH$_3$; $R^1$=H$_2$NC(=O)NH—NH—C(O)—O— (S-Configuration)

The title compound is prepared from semicarbazide and the title compound of Example 443 in pyridine according to the procedures described in Example 418.

EXAMPLE 451

Formula I: R=ethyl; R'=R2=R3=H; n=1; $R^{1'}$=OCH$_3$; $R^1$=(HO—CH$_2$CH$_2$)2N—C(O)—O— (S-Configuration)

The title compound was prepared from bis(ethanol) amine and the title compound of Example 443 in dichloromethane according to the procedures described in Example 418. MS (FAB) m/e: M+K=961.

EXAMPLE 452

Formula I: R=ethyl; R'=R2=R3=H; n=1; $R^{1'}$=OCH$_3$; $R^1$=—OS(O)2-(8-quinoline) (R-Configuration)

8-Quinolinesulfonyl chloride (0.45 g) is added into a stirred solution of ascomycin (0.8 g) in pyridine (3 mL) at 0° C. After being stirred at room temperature overnight, the reaction mixture is partitioned between ether and dilute hydrochloric acid. The organic phase is dried over magnesium sulfate and solvent removed in vacuo. The product is purified by silica gel chromatography eluting with 40% acetone in hexanes.

EXAMPLE 453

Formula I: R=ethyl; R'=R2=R3=H; n=1; $R^{1'}$=OCH$_3$; $R^1$=—OS(O)2-(2-N-methyl-imidazole) (R-Configuration)

The title compound is prepared from 2-(N-methylimidazole)sulfonyl chloride and ascomycin in pyridine according to the procedure described in Example 452.

EXAMPLE 454

Formula I: R=ethyl; R'=R2=R3=H; n=1; $R^{1'}$=OCH$_3$; $R^1$=—N=C=O (S-Configuration)

The title compound is prepared from the title compound of Example 2 and triphosgene according to the procedure described in literature (*Aldrichimica Acta*, 21(2), 47, 1988).

EXAMPLE 455

Formula I: R=ethyl; R'=R2=R3=H; n=1; $R^{1'}$=OCH$_3$; $R^1$=N(OBn)H—C(O)—)— (S-Configuration)

The title compound was prepared from O-benzylhydroxylamie and the title compound of Example 416 in dichloromethane according to the procedures described in Example 418. MS (FAB) m/e: M+K=979.

EXAMPLE 456

Formula I: R=ethyl; R'=R2=R2a=R2a'=R3=H; n=1; $R^{1'}$=OCH$_3$; $R^{3a}$ and $R^4$ taken together form =N—OBn A solution of the title compound of Example 48 (0.5 g), O-benzylhydroxylamine hydrochloride (0.111 g) and triethylamine (0.11 mL) in absolute ethanol (4 mL) was stirred at room temperature for 1 hour. Ethanol was removed in vacuo and the crude purified by silica gel chromatography (30 g) eluting with 20% acetone in hexanes. Yield: 0.34 g. MS (FAB) m/e: M+K=933.

EXAMPLE 457

Formula I: R=ethyl; R'=R2=R2a=R2a'=R3=H; n=1; $R^{1'}$=OCH$_3$; $R^{3a}$ and $R^4$ taken together form =N—OMe A solution of the title compound of Example 48 (0.6 g), O-methylhydroxylamine hydrochloride (0.067 g) and triethylamine (0.13 mL) in absolute ethanol (4 mL) was stirred at room temperature for 1 hour. Ethanol was removed in vacuo and the crude purified by silica gel chromatography (30 g) eluting with 20% acetone in hexanes. Yield: 0.45 g. MS (FAB) m/e: M+K=857.

EXAMPLE 458

Formula I: R=ethyl; R'=R2=R2a=R2a'=R3=H; n=1; $R^{1'}$=OCH$_3$; $R^{3a}$ and $R^4$ taken together form =N—NH—C(=O)—NH$_2$.

A solution of the title compound of Example 48 (0.6 g), semicarbazide (0.09 g) and triethylamine (0.13 mL) in absolute ethanol (4 mL) was stirred at room temperature for 1 hour. Ethanol was removed in vacuo and the crude purified by silica gel chromatography (30 g) eluting with 20% acetone in hexanes. Yield: 0.33 g. MS (FAB) m/e: M+K=885.

EXAMPLE 459

Formula I: R=ethyl; R'=R2=R3=H; n=1; $R^{1'}$=OCH$_3$; $R^1$=NMe(OMe)—C(O)—O— (S-Configuration)

The title compound was prepared from the tile compound of Example 443 and N,O-diemthylhydroxylamine in dichloromethane according to the procedure described in Example 417. MS (FAB) m/e: M+K=917.

EXAMPLE 460

Formula I: R=ethyl; R'=R2=R3=H; n=1; $R^{1'}$=OCH$_3$; $R^1$=N[C(CH$_2$OH)$_3$]—C(O)—O— (S-Configuration)

The title compound was prepared from the tile compound of Example 443 and 2-amino-2hydroxymethyl-1,3-propanediol in dichloromethane according to the procedure described in Example 417. MS (FAB) m/e: M+K=977.

EXAMPLE 461

Formula V: R=ethyl; R'=R2=R3=H; n=1; $R^{1'}$=OCH$_3$; $R^1$=t-butyldimethylsilyloxy (R Configuration); $R^{31}$=$R^{32}$=H; $R^{33}$=iodoacetoxy; $R^{34}$=H; $R^{35}$ and $R^{36}$ taken together form an oxo group.

To a stirred solution of the resultant compound of example 8a (2.0 g, 2.2 mmol) and iodoacetic anhydride (0.78 g, 2.2 mmol) in CH$_2$Cl$_2$ (10 mL) was added DMAP (0.05 g, 0.44 mmol). After the reaction was stirred at room temperature for 18h more iodoacetic anhydride (0.1 g, 0.26 mmol) was added to the reaction, and stirring was continued for 24h. The reaction mixture was diluted with ethyl acetate, and then washed sequentially with 10% aqueous NaHSO$_4$, sat'd NaHCO$_3$ and brine to give 2.2 g of crude material. After purification (HPLC, Rainin microsorb column, eluting with 10% acetone: 90% hexane), 1.59 g of the titled compound was collected along with 0.23 g of the unreacted starting material.

EXAMPLE 462

Formula III: R=ethyl; R'=R2=R3=H; n=1; $R^{31}$=H; $R^{32}$=H; $R^{33}$=iodoacetoxy; $R^{34}$=H; $R^{35}$ and $R^{36}$ taken together form an oxo group.

The resultant compound of example 461 (1.59 g, 1.48 mmol) was treated with 48% aqueous HF (0.3 mL) in CH$_3$CN (50 mL) for 45 minutes to give 1.29 g of the semi-pure product from which 0.54 g was further purified by HPLC (Rainin microsorb column, eluting with 30% acetone: 70% hexane), and 0.41 g was collected as pure title compound. MS (FAB) m/z: M+K=998.

EXAMPLE 463

Formula V: R=ethyl; R'=R2=R3=H; n=1; $R^{1'}$=OCH$_3$; $R^1$=iodoacetoxy (R Configuration); $R^{31}$=$R^{32}$=H; $R^{33}$t-butyldimethylsilyloxy; $R^{34}$=H; $R^{35}$ and $R^{36}$ and taken together form an oxo group.

Following the procedure of example 461, but replacing the resultant compound of example 8a with the resultant compound of 208a provided the desired product.

EXAMPLE 464

Formula I: R=ethyl; R'=R2=R3=H; n=1; $R^{1'}$=OCH$_3$; $R^1$=iodoacetoxy (R Configuration)

Following the procedure of example 462, but replacing the resultant compound of example 461 with the resultant compound of example 463 provided the desired product. MS (FAB) m/z: M+K=998.

EXAMPLES 465

Formula V: R=ethyl; R'=R2=R3=H; n=1; $R^{1'}$=OCH$_3$; $R^1$=iodoacetoxy (R Configuration); $R^{31}$=$R^{32}$=H; $R^{33}$iodoacetoxy; $R^{34}$=H: $R^{35}$ and $R^{36}$ taken together form an oxo group.

To a stirred solution of ascomycin (0.500 g, 0.632 mmol) and iodoacetic anhydride (0.28 g, 0.79 mmol) in CH$_2$Cl$_2$ (0.63 mL) was added DMAP (7.7 mg, 0.063 mmol). After the reaction was stirred at room temperature for 50 h, more iodoacetic anhydride (0.112 g, 0.316 mmol) was added to the reaction, and stirring was continued for 48 h. The reaction mixture was evaporated and chromatographed to give the desired product. MS (FAB) m/z: M+K=1114.

EXAMPLE 466

Formula III: R=ethyl; R'=R2=H; n=1; $R^3$=OH; $R^{31}$=H; $R^{32}$=H; $R^{33}$=iodoacetoxy; $R^{34}$H; $R^{35}$ and $R^{36}$ taken together form an oxo group.

To a stirred solution of selenium (IV) oxide (0.26 g, 2.3 mmol) in THF (8 mL) and water (1 mL) was added a 3M solution of tert-butyl hydroperoxide in 2,2,4-trimethylpentane (2.08 mL, 6.2 mmol). After stirring at room temperature for 10 minutes, the resultant product of example 462 (0.75 g, 0.78 mmol) was added to the reaction. The stirring was continued and the reaction was monitored by TLC. After the reaction was close to completion (7 days), it was partitioned between ethyl acetate and brine. The organic layer was separated and dried over $Na_2SO_4$. Filtration and evaporation of the solvent gave 0.67 g of the crude product which was purified by HPLC (microsorb column, eluting 35% acetone: 65% hexane) to give 0.24 g of the title compound in 32% yield. MS (FAB) m/z: M+K=1014.

EXAMPLE 467

Formula I: R=ethyl; R'=R2=H; n=1; $R^{1'}$=$OCH_3$; $R^1$=iodoacetoxy (R Configuration); $R^3$=OH.

Following the procedure of example 466, but replacing the resultant compound of example 462 with the resultant compound of example 464 provided the desired product. MS (FAB) m/z: M+K=1014.

EXAMPLE 500

Formula I: R=ethyl; R'=R2=R3=H; n=1; $R^{1'}$=$OCH_3$; $R^1$=1-(1,2,3-triazolyl)

EXAMPLE 500a

Formula V: R=ethyl; n=1; R'=R2=R3=H; $R^{1'}$=$OCH_3$; $R^1$=O-trifluoromethanesulfonyl; $R^{31}$=H; $R^{32}$=H; $R^{33}$=t-butyldimethylsilyloxy; $R^{34}$=H; $R^{35}$ and $R^{36}$ taken together form an oxo group.

The product of Example 208a (4.0 g, 4.42 mmol) was dissolved in 20 mL of methylene chloride at 0° C. pyridine (3.57 mL, 44.2 mmol), followed by trifluoromethanesulfonic acid anhydride (0.74 mL, 4.42 mmol) were carefully added to the reaction mixture. It was stirred at 0° C. for 20 minutes and the solvent was removed. Ethyl acetate (50 mL) was added to the residue. The organic layers were washed with brine, saturated $NaHCO_3$ (20 mL×3), brine (20 mL), 10%-$NaHSO_4$ (20 mL×3), brine (20 mL×3) and dried over anhydrous sodium sulfate. After the solvent was removed, the title compound was obtained in quantitative yield (4.2 g). This compound was used for the displacement reaction without further purification and characterization.

EXAMPLE 500b

Formula V: R=ethyl; n=1; R'=R2=R3=H; $R^{1'}$=$OCH_3$; $R^1$=1-(1,2,3-triazolyl); $R^{31}$=H; $R^{32}$=H; $R^{33}$=t-butyldimethylsilyloxy; $R^{34}$=H; $R^{35}$ and $R^{36}$ taken together form an oxo group.

The product of Example 500a (2.1 g, 2.03 mmol) was dissolved in 10 mL of fleshly distilled methylene chloride, (1H)-1,2,3-triazole (0.42 g, 6.08 mmol) and triethylamine (0.565 mL, 4.05 mmol) were added, and the reaction was then stirred at room temperature for three days. The reaction mixture was passed through silica gel, using 10–25% acetone in hexane as an elutant to obtain semi-pure title compound (1.25 g) in 65% yield. MS (FAB) m/z: M+K=995.

EXAMPLE 500c

Formula I: R=ethyl; R'=R2=R3=H; n=1; $R^{1'}$=$OCH_3$; $R^1$=1-(1,2,3-triazolyl) (S Configuration).

The product of Example 500b (1.25 g, 1.307 mmol) was dissolved in 35 mL of acetonitrile, 48% hydrogen fluoride aqueous solution (4 mL) was added, and the reaction was then stirred at room temperature for 4 hours. It was cooled to 0° C. in an ice bath, and solid $NaHCO_3$ was added to the reaction mixture. It was stirred for an additional 2 hours and solid was removed by filtration. Acetonitrile was removed in vacuo and the residue was purified by high performance liquid chromatography (HPLC), eluting with 30% acetone in hexane. 263.6 mg of pure title compound was obtained in 24% yield. MS (FAB) m/z: M+K=881; mp=110°–113° C. (dec.); $^1$H-NMR (ppm in pyridine): 3.25 (s, 3H, $R^1$—OMe)

EXAMPLE 501

Formula I: R=ethyl: R'=R2=R3=H; n=1; $R^{1'}$=1-(1,2,3-triazolyl) $R^1$=$OCH_3$;

The title compound (85 mg) was isolated from the reaction described in Example 500 as a minor product in 8% yield. MS (FAB) m/z: M+K=881; mp=103°–105° C.; $^1$H-NMR (ppm in pyridine): 3.05 (s, 3H, $R^1$—OMe)

EXAMPLE 502

Formula I: R=ethyl; R'=R2=R3=H; n=1; $R^{1'}$=$OCH_3$; $R^1$=1-(1,2,3-benzotriazolyl)

Following the procedure of Example 500, but replacing (1H)-1,2,3-triazole with (1H)-1,2,3-benzotriazole, provided the desired compound. The product of Example 500a (2.1 g, 2.03 mmol), (1H)-1,2,3-benzotriazole (0.724 g, 6.08 mmol), and triethylamine (0.565 mL, 4.05 mmol) in 10 mL of methylene chloride were used and stirred at room temperature for three days. 1.45 g of pure compound was isolated after silica gel column chromatography, followed by normal phase HPLC purification in 71% yield. MS (FAB) m/z: M+H=1007. M+K=1045. The obtained product (1.4 g, 1.39 mmol) was treated with 48%-HF (4 mL) in 40 mL of acetonitrile in the procedure described in Example 500c. After a normal phase-HPLC purification, 422 mg of the pure title compound was isolated in 34% yield. MS (FAB) m/z: M+K=931. mp=120° C.; $^1$H-NMR (ppm in pyridine): 3.15 (s, 3H, $R^1$—OMe)

EXAMPLE 530

Formula I: R=ethyl; R'=R2=R3=H; n=1; $R^{1'}$=1-(1,2,3-benzotriazolyl) $R^1$=$OCH_3$;

The title compound (60 mg) was isolated from the reaction described in Example 502 as a minor product in 5% yield. MS (FAB) m/z: M+K=931; mp=115°–16° C.; $^1$H-NMR (ppm in pyridine): 2.95 (s, 3H, $R^1$—OMe)

EXAMPLE 504

Formula I: R=ethyl; R'=R2=R3=H: n=1: $R^{1'}$=$OCH_3$; $R^1$=1-(5-nitro-1,2,3-benzotriazolyl)

Following the procedure of Example 500, but replacing (1H)-1,2,3-triazole with 5-nitro-(1H)-1,2,3-benzotriazole, provided the desired compound. The product of Example 500a (2.1 g, 2.03 mmol), 5-nitro-(1H)-1,2,3-benzotriazole (0.997 g, 6.08 mmol), and triethylamine (0.565 mL, 4.05 mmol) in 10 mL of methylene chloride were used and stirred at room temperature for three days. 2.0 g of semi-pure compound was isolated after silica gel column chromatography, followed by normal phase HPLC purification. MS (FAB) m/z: M+H=1090. The obtained product (2.0 g, 1.90 mmol) was treated with 48%-HF (4 mL) in 40 mL of acetonitrile in the procedure described in Example 500c. After a normal phase-HPLC purification, 146.5 mg of the pure title compound was isolated in 8% yield. MS (FAB) m/z: M+K=976. mp=125°–130° C.; $^1$H-NMR (ppm in pyridine): 3.20 (s, 3H, $R^{1'}$—OMe), 7.99(d, 1H, aromatic), 8.40 (d. 1H, aromatic).

EXAMPLE 505

Formula I; R=ethyl; R'=R2=R3=H; n=1; $R^{1'}$=OCH$_3$; $R^1$=1-(6-nitro-1,2,3-benzotriazolyl)

The title compound (80 mg) was isolated from the reaction described in Example 504 as a minor product in 4% yield. MS (FAB) m/z: M+K=976. mp=120° C. (dec.); $^1$H-NMR (ppm in pyridine): 3.19 (s, 3H, $R^{1'}$—OMe), 8.20 (s, 1H, aromatic), 8.40 (br. d. 1H, aromatic), 8.99 (s, 1H, aromatic).

EXAMPLE 506

Formula I; R=ethyl; R'=R2=R3=H; n=1; $R^{1'}$=1-(5-nitro-1,2,3-benzotriazolyl) $R^1$=OCH$_3$.

The title compound (78 mg) was isolated from the reaction described in Example 504 as a minor product in 4% yield. m/z: M+K=976. mp=110°–117° C. (dec.); $^1$H-NMR (ppm in pyridine): 2.99 (s, 3H, $R^{1'}$—OMe), 7.95–8.02 (br. m. aromatic), 8.20 (m, aromatic).

EXAMPLE 507

Formula: R=ethyl; R'=R2=R3=H; n=1; $R^{1'}$=1-(6-nitro-1,2,3-benzotriazolyl) $R^1$=OCH$_3$;

The title compound (78 mg) was isolated from the reaction described in Example 504 as a minor product in 4% yield. m/z: M+K=976. mp=115° C. (dec.); $^1$H-NMR (ppm in pyridine): 2.99 (s, 3H, $R^{1'}$—OMe), 8.23 (m, aromatic).

EXAMPLE 508

Formula I; R=ethyl; R'=R2=R3=H; n=1; $R^{1'}$=OCH$_3$; $R^1$=1-(1,2,4-triazolyl)

Following the procedure of Example 500, but replacing (1H)-1,2,3-triazole with (1H)-1,2,4-triazole, provided the desired compound. The product of Example 500a (1.7 g, 1.67 mmol), (1H)-1,2,4-triazole (0.288 g, 4.18 mmol), and triethylamine (0.58 mL, 4.18 mmol) in 10 mL of methylene chloride were used and stirred at room temperature for one over night and at 40° C. for an additional day. After silica gel column chromatography eluting with 10%-acetone in hexane, followed by normal phase HPLC purification using 40% acetone in hexane as an elutant, 1.057 g of pure major isomer was isolated in 67% yield. MS (FAB) m/z: M+K= 995, M+H=957. An additional 0.28 g of minor isomer was isolated as a pure form in 18% yield. MS (FAB) m/z M+H=957. This minor isomer was used to prepare an example 509. The obtained major product (1.05 g, 1.106 mmol) was treated with 48%-HF (4 mL) in 35 mL of acetonitrile in the procedure described in Example 500c. After a reverse phase-HPLC purification, 190 mg of the pure title compound was isolated in 18% yield. MS (FAB) m/z: M+K=881, M+H=843. mp=110°–114° C.; $^1$H-NMR (ppm in pyridine): 8.20 (s, 1H, triazole), 8.80 (s. 1H, triazole). $^{13}$C-NMR (ppm in pyridine): 142.7 (t, CH, triazole), 143.2 (t. CH, triazole).

EXAMPLE 509

Formula I; R=ethyl; R'=R2=R3=H; n=1; $R^1$=OCH$_3$; $R^1$=4-(1,2,4-triazolyl)

The above minor product (example 508) (0.28 g, 0.292 mmol) was treated with 48%-HF (1 mL) in 10 mL of acetonitrile in the procedure described in Example 500c, except the reaction time was three hours. After a reverse phase-HPLC purification, 52 mg of the pure title compound was isolated in 22% yield. MS (FAB) m/z: M+K=881, M+H=843. mp=92°–98° C.; $^1$H-NMR (ppm in pyridine): 8.25 (s, 2H, triazole). $^{13}$C-NMR (ppm in pyridine): 145.0 (t, 2-CH, triazole).

EXAMPLE 510

Formula I: R=ethyl: R'=R2=R3=H; n=1; $R^{1'}$=OCH$_3$; $R^1$=1-(3-nitro-1,2,4-triazolyl)

Following the procedure of Example 500, but replacing (1H)-1,2,3-triazole with 3-nitro-1,2,4-triazole, provided the desired compound. The product of Example 500a (2.0 g, 1.93 mmol), 3-nitro-1,2,4-triazole (0.66 g, 5.79 mmol), and triethylamine (0.538 mL, 3.86 mmol) in 10 mL of methylene chloride were used and stirred at room temperature for three days. 1.59 g of semi-pure compound was isolated after silica gel column chromatography, initially eluting with 10%-acetone in hexane, followed by 10% methanol in methylene chloride in 82% yield. MS (FAB) m/z: M+K=1040. The obtained product (1.58 g, 1.78 mmol) was treated with 48%-HF (4 mL) in 35 mL of acetonitrile in the procedure described in Example 500c. After a normal phase-HPLC purification, 219 mg of the pure title compound was isolated in 16% yield. MS (FAB) m/z: M+K=926. mp=110°–112° C.; $^1$H-NMR (ppm in pyridine): 3.24 (s, 3H, $R^{1'}$—OMe)

EXAMPLE 511

Formula I; R=ethyl; R'=R2=R3=H; n=1; $R^{1'}$=1-(3-nitro-1,2,4-triazolyl) $R^1$=OCH$_3$;

The title compound (98 mg) was isolated from the reaction described in Example 510 as a minor product in 7% yield. MS (FAB) m/z: M+K=926; mp=121°–127° C.; $^1$H-NMR (ppm in pyridine): 3.01 (s, 3H, $R^1$—OMe)

EXAMPLE 600

In Vivo Assay of Biological Activity

The immunosuppressant activity of the compounds of the present invention was determined using the human mixed lymphocyte reaction (MLR) assay described by Kino, T. et al. in *Transplantation Proceedings*, XIX(5):36–39, Suppl. 6 (1987). The results of the assay,

TABLE 1

| Ex. # | IC$_{50}$(M) | Ex. # | IC$_{50}$(M) |
|---|---|---|---|
| 1b | <1 × 10$^{-6}$ | 106a | <1 × 10$^{-6}$ |
| 2 | <1 × 10$^{-6}$ | 107 | <1 × 10$^{-6}$ |
| 3 | <1 × 10$^{-6}$ | 150 | <1 × 10$^{-6}$ |
| 4 | <1 × 10$^{-6}$ | 151 | <1 × 10$^{-6}$ |
| 5 | <1 × 10$^{-6}$ | 159a | <1 × 10$^{-6}$ |
| 6 | <1 × 10$^{-6}$ | 159b | <1 × 10$^{-6}$ |
| 7 | <1 × 10$^{-6}$ | 159c | <1 × 10$^{-6}$ |
| 8b | <1 × 10$^{-6}$ | 160 | <1 × 10$^{-6}$ |
| 9 | <1 × 10$^{-6}$ | 161 | <1 × 10$^{-6}$ |
| 10 | <1 × 10$^{-6}$ | 170 | <1 × 10$^{-6}$ |
| 11 | <1 × 10$^{-6}$ | 172 | <1 × 10$^{-6}$ |
| 12 | <1 × 10$^{-6}$ | 173 | <1 × 10$^{-6}$ |
| 13 | <1 × 10$^{-6}$ | 174 | <1 × 10$^{-6}$ |

TABLE 1-continued

| Ex. # | IC$_{50}$(M) | Ex. # | IC$_{50}$(M) |
|---|---|---|---|
| 14a | <1 × 10$^{-6}$ | 178 | >1 × 10$^{-6}$ |
| 14b/48 | <1 × 10$^{-6}$ | 182 | <1 × 10$^{-6}$ |
| 15 | <1 × 10$^{-6}$ | 208 | <1 × 10$^{-6}$ |
| 30 | <1 × 10$^{-6}$ | 209 | <1 × 10$^{-6}$ |
| 36 | <1 × 10$^{-6}$ | 221 | <1 × 10$^{-6}$ |
| 37 | <1 × 10$^{-6}$ | 255 | >1 × 10$^{-6}$ |
| 38 | <1 × 10$^{-6}$ | 256 | <1 × 10$^{-6}$ |
| 39 | <1 × 10$^{-6}$ | 257 | <1 × 10$^{-6}$ |
| 40 | <1 × 10$^{-6}$ | 393 | <1 × 10$^{-6}$ |
| 41 | <1 × 10$^{-6}$ | 394 | <1 × 10$^{-6}$ |
| 42a/b | <1 × 10$^{-6}$ | 462 | <1 × 10$^{-6}$ |
| 43 | <1 × 10$^{-6}$ | 464 | <1 × 10$^{-6}$ |
| 44 | <1 × 10$^{-6}$ | 466 | <1 × 10$^{-6}$ |
| 45 | <1 × 10$^{-6}$ | 467 | <1 × 10$^{-6}$ |
| 46 | <1 × 10$^{-6}$ | 500c | <1 × 10$^{-6}$ |
| 47 | <1 × 10$^{-6}$ | 501 | <1 × 10$^{-6}$ |
| 49 | <1 × 10$^{-6}$ | 502 | >1 × 10$^{-6}$ |
| 50 | <1 × 10$^{-6}$ | 503 | <1 × 10$^{-6}$ |
| 51 | <1 × 10$^{-6}$ | 504 | <1 × 10$^{-6}$ |
| 52 | <1 × 10$^{-6}$ | 505 | <1 × 10$^{-6}$ |
| 53 | <1 × 10$^{-6}$ | 506 | <1 × 10$^{-6}$ |
| 96 | <1 × 10$^{-6}$ | 507 | >1 × 10$^{-6}$ |
| 102 | <1 × 10$^{-6}$ | 508 | <1 × 10$^{-6}$ |
| 103a | <1 × 10$^{-6}$ | 509 | <1 × 10$^{-6}$ |
| 103b | <1 × 10$^{-6}$ | 510 | <1 × 10$^{-6}$ |
| 104c | <1 × 10$^{-6}$ | 511 | <1 × 10$^{-6}$ | shown above in Table 1, demonstrate that the compounds tested are effective immunomodulators at sub-micromolar concentrations.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

We claim:

1. A compound of the formula:

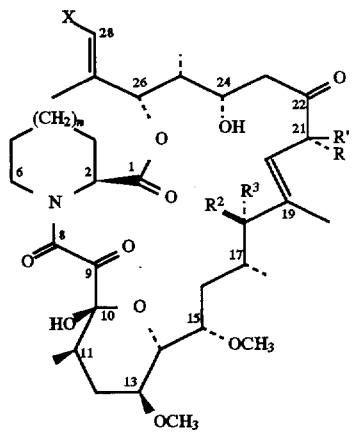

(I)

wherein X is

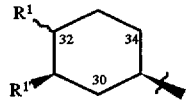

and (a) R=ethyl; R'=R2=R3=H; n=1; R$^{1'}$=—OCH$_3$; and R$^1$=CH$_3$C(O)S— (S Configuration); or
(b) R=ethyl; R'=R2=R3=H; n=1; R$^{1'}$=—OCH$_3$; and R$^1$=C$_6$H$_5$S—; or
(c) R=ethyl; R'=R2=R3=H; n=1; R$^{1'}$=—OCH$_3$; and R$^1$=benzylthio; or
(d) R=ethyl; R'=R2=R3=H; n=1; R$^{1'}$=—OCH$_3$; and R$^1$=—SH;

or a pharmaceutically acceptable salt, ester, amide or prodrug thereof.

2. The compound according to claim 1 wherein R=ethyl; R'=R2=R3=H; n=1; R$^{1'}$=—OCH$_3$; and R$^1$=—SH.

3. A compound of the formula:

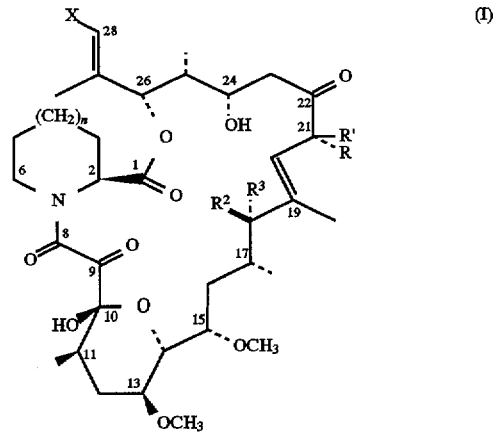

(I)

wherein X is

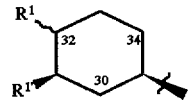

and R=ethyl; R'=R2=R3=H; n=1; R$^{1'}$=—OCH$_3$; R$^1$=N-tetrazole (S-Configuration); or a pharmaceutically acceptable salt, ester, amide or prodrug thereof.

4. A method for providing immunomodulatory treatment comprising administering to a patient in need thereof a therapeutically effective amount of a compound of claim 1.

5. A method for providing immunomodulatory treatment comprising administering to a patient in need thereof a therapeutically effective amount of a compound of claim 3.

6. A pharmaceutical composition for immunomodulatory treatment comprising a therapeutically effective amount of a compound of claim 1 in combination with a pharmaceutically acceptable carrier.

7. A pharmaceutical composition for immunomodulatory treatment comprising a therapeutically effective amount of a compound of claim 3 in combination with a pharmaceutically acceptable carrier.

* * * * *